US010245302B2

(12) United States Patent
Cload et al.

(10) Patent No.: US 10,245,302 B2
(45) Date of Patent: *Apr. 2, 2019

(54) FIBRONECTIN BASED SCAFFOLD DOMAIN PROTEINS THAT BIND TO MYOSTATIN

(71) Applicant: BRISTOL-MYERS SQUIBB COMPANY, Princeton, NJ (US)

(72) Inventors: Sharon Cload, Cambridge, MA (US); Linda Engle, Framingham, MA (US); Dasa Lipovsek, Cambridge, MA (US); Malavi Madireddi, West Windsor, NJ (US); Ginger Chao Rakestraw, Somerville, MA (US); Joanna Swain, Concord, MA (US); Wenjun Zhao, Montgomery, NJ (US); Hui Wei, Princeton Junction, NJ (US); Aaron P. Yamniuk, Lawrenceville, NJ (US); Vidhyashankar Ramamurthy, Bangalore (IN); Alexander T. Kozhich, Princeton, NJ (US); Martin J. Corbett, Mount Holly, NJ (US); Stanley Richard Krystek, Jr., Ringoes, NJ (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 18 days.

This patent is subject to a terminal disclaimer.

(21) Appl. No.: 15/282,277

(22) Filed: Sep. 30, 2016

(65) Prior Publication Data
US 2017/0088602 A1    Mar. 30, 2017

Related U.S. Application Data

(60) Division of application No. 14/481,641, filed on Sep. 9, 2014, now Pat. No. 9,493,546, which is a continuation of application No. 14/025,307, filed on Sep. 12, 2013, now Pat. No. 8,853,154.

(60) Provisional application No. 61/780,005, filed on Mar. 13, 2013, provisional application No. 61/700,697, filed on Sep. 13, 2012.

(51) Int. Cl.
| | |
|---|---|
| *C12P 21/02* | (2006.01) |
| *C07K 14/78* | (2006.01) |
| *A61K 38/39* | (2006.01) |
| *C07K 16/46* | (2006.01) |
| *A61K 45/06* | (2006.01) |
| *G01N 33/74* | (2006.01) |
| *C07K 14/435* | (2006.01) |
| *C07K 14/765* | (2006.01) |
| *C07K 14/79* | (2006.01) |
| *C07K 16/18* | (2006.01) |
| *A61K 38/17* | (2006.01) |
| *A61K 47/64* | (2017.01) |
| *A61K 47/60* | (2017.01) |
| *A61K 47/48* | (2006.01) |
| *A61K 38/00* | (2006.01) |

(52) U.S. Cl.
CPC .............. *A61K 38/39* (2013.01); *A61K 38/17* (2013.01); *A61K 38/1709* (2013.01); *A61K 45/06* (2013.01); *A61K 47/48215* (2013.01); *A61K 47/60* (2017.08); *A61K 47/642* (2017.08); *C07K 14/435* (2013.01); *C07K 14/765* (2013.01); *C07K 14/78* (2013.01); *C07K 14/79* (2013.01); *C07K 16/18* (2013.01); *C07K 16/46* (2013.01); *G01N 33/74* (2013.01); *A61K 38/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,514,581 | A | 5/1996 | Ferrari et al. |
| 5,545,620 | A | 8/1996 | Wahl et al. |
| 5,641,648 | A | 6/1997 | Ferrari et al. |
| 5,770,697 | A | 6/1998 | Ferrari et al. |
| 5,792,742 | A | 8/1998 | Gold et al. |

(Continued)

FOREIGN PATENT DOCUMENTS

| | | |
|---|---|---|
| EP | 1075272 B1 | 2/2001 |
| EP | 1266025 B1 | 11/2006 |

(Continued)

OTHER PUBLICATIONS

Koide et al. (Koide I), "Target-Binding Proteins Based on the 10th Human Fibronectin Type III Domain (10Fn3)" 503 Methods in Enzymology 135-156 (Jan. 19, 2012).*

(Continued)

*Primary Examiner* — Nancy J Leith
(74) *Attorney, Agent, or Firm* — Nelson Mullins Riley & Scarborough LLP; Jane E. Remillard, Esq.; Cynthia L. Kanik

(57) ABSTRACT

The present invention relates to fibronectin-based scaffold domain proteins that bind to myostatin. The invention also relates to the use of these proteins in therapeutic applications to treat muscular dystrophy, cachexia, sarcopenia, osteoarthritis, osteoporosis, diabetes, obesity, COPD, chronic kidney disease, heart failure, myocardial infarction, and fibrosis. The invention further relates to cells comprising such proteins, polynucleotides encoding such proteins or fragments thereof, and to vectors comprising the polynucleotides encoding the proteins.

17 Claims, 17 Drawing Sheets

Specification includes a Sequence Listing.

(56) References Cited

U.S. PATENT DOCUMENTS

| | | |
|---|---|---|
| 5,827,733 A | 10/1998 | Lee et al. |
| 5,994,618 A | 11/1999 | Lee et al. |
| 6,018,030 A | 1/2000 | Ferrari et al. |
| 6,096,506 A | 8/2000 | Lee et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,368,597 B1 | 4/2002 | Strassmann et al. |
| 6,462,189 B1 | 10/2002 | Koide |
| 6,465,239 B1 | 10/2002 | Lee et al. |
| 6,468,535 B1 | 10/2002 | Lee et al. |
| 6,500,664 B1 | 12/2002 | Lee et al. |
| 6,518,018 B1 | 2/2003 | Szostak et al. |
| 6,607,884 B1 | 8/2003 | Lee et al. |
| 6,673,534 B1 | 1/2004 | Lee et al. |
| 6,818,418 B1 | 11/2004 | Lipovsek et al. |
| 6,858,208 B2 | 2/2005 | Lee et al. |
| 7,115,396 B2 | 10/2006 | Lipovsek et al. |
| 7,179,884 B2 | 2/2007 | Lee et al. |
| 7,320,789 B2 | 1/2008 | Dunham et al. |
| 7,332,575 B2 | 2/2008 | Lee et al. |
| 7,381,528 B2 | 6/2008 | Lee et al. |
| 7,393,682 B1 | 7/2008 | Lee et al. |
| 7,399,848 B2 | 7/2008 | Lee et al. |
| 7,534,432 B2 | 5/2009 | Lee et al. |
| 7,556,925 B2 | 7/2009 | Koide et al. |
| 7,598,352 B2 | 10/2009 | Koide |
| 7,632,499 B2 | 12/2009 | Davies et al. |
| 7,635,760 B2 | 12/2009 | Han et al. |
| 7,655,763 B2 | 2/2010 | Veldman et al. |
| 7,731,961 B1 | 6/2010 | Aghajanian et al. |
| 7,745,583 B2 | 6/2010 | Han et al. |
| 7,807,159 B2 | 10/2010 | Chin et al. |
| 7,847,062 B2 | 12/2010 | Chen et al. |
| 7,858,739 B2 | 12/2010 | Chen et al. |
| 7,888,486 B2 | 2/2011 | Walsh et al. |
| 7,910,107 B2 | 3/2011 | Walsh et al. |
| 8,066,995 B2 | 11/2011 | Davies et al. |
| 8,067,201 B2 | 11/2011 | Morin et al. |
| 8,092,798 B2 | 1/2012 | Aghajanian et al. |
| 8,221,765 B2 | 7/2012 | Camphausen et al. |
| 8,258,265 B2 | 9/2012 | Koide |
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 8,343,501 B2 | 1/2013 | Emanuel et al. |
| 8,470,332 B2 | 6/2013 | Camphausen et al. |
| 8,524,244 B2 | 9/2013 | Camphausen et al. |
| 8,609,613 B2 | 12/2013 | Chen et al. |
| 8,728,483 B2 | 5/2014 | Camphausen et al. |
| 8,853,154 B2 | 10/2014 | Cload et al. |
| 8,933,199 B2 | 1/2015 | Cload et al. |
| 8,969,289 B2 | 3/2015 | Gosselin et al. |
| 8,993,265 B2 | 3/2015 | Cload et al. |
| 9,017,655 B2 | 4/2015 | Emanuel et al. |
| 9,234,028 B2 | 1/2016 | Camphausen et al. |
| 9,328,157 B2 | 5/2016 | Chen et al. |
| 9,493,546 B2 | 11/2016 | Cload et al. |
| 9,540,424 B2 | 1/2017 | Gosselin et al. |
| 9,562,089 B2 | 2/2017 | Camphausen et al. |
| 9,605,039 B2 | 3/2017 | Lipovsek et al. |
| 9,662,373 B2 | 5/2017 | Cload et al. |
| 9,771,411 B2 | 9/2017 | Emanuel et al. |
| 9,862,758 B2 | 1/2018 | Chen et al. |
| 9,902,762 B2 | 2/2018 | Camphausen et al. |
| 9,920,108 B2 | 3/2018 | Camphausen et al. |
| 2002/0019517 A1 | 2/2002 | Koide |
| 2002/0157125 A1 | 10/2002 | Lee et al. |
| 2003/0074680 A1 | 4/2003 | Lee et al. |
| 2003/0082181 A1 | 5/2003 | Lee et al. |
| 2003/0120058 A1 | 6/2003 | Lee et al. |
| 2003/0170753 A1 | 9/2003 | Koide |
| 2004/0048307 A1 | 3/2004 | Lee et al. |
| 2004/0055027 A1 | 3/2004 | Lee et al. |
| 2005/0175612 A1 | 8/2005 | Lee et al. |
| 2005/0216962 A1 | 9/2005 | Lee et al. |
| 2005/0255548 A1 | 11/2005 | Lipovsek et al. |
| 2006/0210604 A1 | 9/2006 | Dadey et al. |
| 2006/0246059 A1 | 11/2006 | Lipovsek et al. |
| 2007/0082365 A1 | 4/2007 | Lipovsek et al. |
| 2007/0178095 A1 | 8/2007 | Smith et al. |
| 2007/0185321 A1 | 8/2007 | Lee et al. |
| 2008/0108798 A1 | 5/2008 | Lipovsek et al. |
| 2008/0178310 A1 | 7/2008 | Lee et al. |
| 2008/0213426 A1 | 9/2008 | Lee et al. |
| 2008/0220049 A1 | 9/2008 | Chen et al. |
| 2008/0299126 A1 | 12/2008 | Han et al. |
| 2008/0311584 A1 | 12/2008 | Lee et al. |
| 2009/0017045 A1 | 1/2009 | Lee et al. |
| 2009/0017522 A1 | 1/2009 | Lee et al. |
| 2009/0148436 A1 | 6/2009 | LaVallie et al. |
| 2009/0176654 A1 | 7/2009 | Cappuccilli et al. |
| 2009/0285827 A1 | 11/2009 | Walsh et al. |
| 2010/0087631 A1 | 4/2010 | Han et al. |
| 2010/0144601 A1 | 6/2010 | Jacobs et al. |
| 2010/0152063 A1 | 6/2010 | Cappuccilli et al. |
| 2010/0166764 A1 | 7/2010 | Sayers et al. |
| 2010/0273216 A1 | 10/2010 | Morin et al. |
| 2010/0298541 A1 | 11/2010 | Wu et al. |
| 2010/0322930 A1 | 12/2010 | Kolbinger et al. |
| 2011/0021746 A1 | 1/2011 | Cappuccilli et al. |
| 2011/0038866 A1 | 2/2011 | Hastewell et al. |
| 2011/0053787 A1 | 3/2011 | Brulliard et al. |
| 2011/0091455 A1 | 4/2011 | Chin et al. |
| 2011/0123545 A1 | 5/2011 | Marsh et al. |
| 2011/0124527 A1 | 5/2011 | Cappuccilli et al. |
| 2011/0243953 A1 | 10/2011 | Veldman et al. |
| 2011/0256132 A1 | 10/2011 | Ashman et al. |
| 2011/0274623 A1 | 11/2011 | Jacobs |
| 2011/0275535 A1 | 11/2011 | Loew |
| 2011/0293630 A1 | 12/2011 | Stitt et al. |
| 2012/0003212 A1 | 1/2012 | Walsh et al. |
| 2012/0016106 A1 | 1/2012 | Walsh et al. |
| 2012/0107928 A1 | 5/2012 | Aghajanian et al. |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0210703 A1 | 8/2013 | Camphausen et al. |
| 2013/0217625 A1 | 8/2013 | Walker et al. |
| 2013/0237684 A1 | 9/2013 | Koide |
| 2013/0267676 A1 | 10/2013 | Koide |
| 2013/0310317 A1 | 11/2013 | Camphausen et al. |
| 2014/0038893 A1 | 2/2014 | Camphausen et al. |
| 2014/0057807 A1 | 2/2014 | Loew et al. |
| 2014/0094595 A1 | 4/2014 | Lipovsek et al. |
| 2014/0179896 A1 | 6/2014 | Chen et al. |
| 2014/0349929 A1 | 11/2014 | Camphausen et al. |
| 2015/0072919 A1 | 3/2015 | Cload et al. |
| 2015/0152147 A1 | 6/2015 | Gosselin et al. |
| 2015/0231211 A1 | 8/2015 | Cload et al. |
| 2015/0252097 A1 | 9/2015 | Camphausen et al. |
| 2015/0259398 A1 | 9/2015 | Emanuel et al. |
| 2016/0152688 A1 | 6/2016 | Camphausen et al. |
| 2016/0297869 A1 | 10/2016 | Chen et al. |
| 2017/0088602 A1 | 3/2017 | Cload et al. |
| 2017/0145464 A1 | 5/2017 | Gosselin et al. |
| 2017/0166627 A1 | 6/2017 | Camphausen et al. |
| 2017/0190761 A1 | 7/2017 | Camphausen et al. |
| 2017/0334958 A1 | 11/2017 | Lipovsek et al. |
| 2017/0354718 A1 | 12/2017 | Cload et al. |
| 2018/0037631 A1 | 2/2018 | Emanuel et al. |
| 2018/0162926 A1 | 6/2018 | Chen et al. |

FOREIGN PATENT DOCUMENTS

| | | |
|---|---|---|
| EP | 1137941 B1 | 8/2009 |
| EP | 2141243 A2 | 1/2010 |
| EP | 2274331 B1 | 1/2011 |

(56) References Cited

FOREIGN PATENT DOCUMENTS

| | | |
|---|---|---|
| EP | 2385067 A1 | 11/2011 |
| EP | 2439212 A1 | 4/2012 |
| EP | 2379718 B1 | 3/2013 |
| WO | 9831700 A1 | 7/1998 |
| WO | 9856915 A2 | 12/1998 |
| WO | 9951773 A1 | 10/1999 |
| WO | 0034784 A1 | 6/2000 |
| WO | 0164942 A1 | 9/2001 |
| WO | 02/04523 A2 | 1/2002 |
| WO | 0232925 A2 | 4/2002 |
| WO | 02081497 A2 | 10/2002 |
| WO | 03027248 A2 | 4/2003 |
| WO | 03104418 A2 | 12/2003 |
| WO | 2004037861 A2 | 5/2004 |
| WO | 2005056764 A2 | 6/2005 |
| WO | 2005094446 A2 | 10/2005 |
| WO | 2006083183 A1 | 8/2006 |
| WO | 2006116269 A2 | 11/2006 |
| WO | 2007044411 A2 | 4/2007 |
| WO | 2007047112 A2 | 4/2007 |
| WO | 2008030706 A2 | 3/2008 |
| WO | 2008031098 A1 | 3/2008 |
| WO | 2008066752 A2 | 6/2008 |
| WO | 2008097497 A2 | 8/2008 |
| WO | 2009023184 A2 | 2/2009 |
| WO | 2009025806 A2 | 2/2009 |
| WO | 2009058346 A1 | 5/2009 |
| WO | 2009058379 A2 | 5/2009 |
| WO | 2009073115 A1 | 6/2009 |
| WO | 2009083804 A2 | 7/2009 |
| WO | 2009086116 A2 | 7/2009 |
| WO | 2009102421 A2 | 8/2009 |
| WO | 2009133208 A1 | 11/2009 |
| WO | 2009142773 A2 | 11/2009 |
| WO | 2010051274 A2 | 5/2010 |
| WO | 2010051310 A2 | 5/2010 |
| WO | 2010060095 A1 | 5/2010 |
| WO | 2010069913 A1 | 6/2010 |
| WO | 2010070094 A1 | 6/2010 |
| WO | 2010093627 A2 | 8/2010 |
| WO | 2010093771 A1 | 8/2010 |
| WO | 2011020033 A2 | 2/2011 |
| WO | 2011035202 A2 | 3/2011 |
| WO | 2011051333 A1 | 5/2011 |
| WO | 2011051466 A1 | 5/2011 |
| WO | 2011092233 A1 | 8/2011 |
| WO | 2011100700 A2 | 8/2011 |
| WO | 2011103105 A1 | 8/2011 |
| WO | 2011130324 A1 | 10/2011 |
| WO | 2011130328 A1 | 10/2011 |
| WO | 2011130354 A1 | 10/2011 |
| WO | 2011137319 A2 | 11/2011 |
| WO | 2011140086 A2 | 11/2011 |
| WO | 2011150008 A1 | 12/2011 |
| WO | 2011150133 A2 | 12/2011 |
| WO | 2012016245 A2 | 2/2012 |
| WO | 2012024242 A1 | 2/2012 |
| WO | 2012088006 A1 | 6/2012 |
| WO | 2012142515 A2 | 10/2012 |
| WO | 2012158678 A1 | 11/2012 |
| WO | 2012158739 A1 | 11/2012 |
| WO | 2013049275 A1 | 4/2013 |
| WO | 2013186719 A1 | 12/2013 |
| WO | 2013188448 A2 | 12/2013 |
| WO | 2014043344 A1 | 3/2014 |

OTHER PUBLICATIONS

Koide et al. (Koide II), "The Fibronectin Type III Domain as a Scaffold for Novel Binding Proteins" 284 Journal of Molecular Biology 1141-1151 (1998).*
U.S. Appl. No. 15/491,271, filed Apr. 19, 2017, Sharon Cload.
U.S. Appl. No. 15/583,561, filed May 1, 2017, Dasa Lipovsek.
U.S. Appl. No. 15/440,730, filed Feb. 23, 2017, Dasa Lipovsek.
U.S. Appl. No. 15/826,196, filed Nov. 29, 2017, Yan Chen.
U.S. Appl. No. 15/404,749, filed Jan. 12, 2017 Ray Camphausen.
U.S. Appl. No. 15/684,595, filed Aug. 23, 2017 Stuart Emanuel.
U.S. Appl. No. 14/229,415, filed Jun. 16, 2017.
U.S. Appl. No. 14/229,415, filed Jan. 9, 2017.
U.S. Appl. No. 14/229,415, filed Aug. 1, 2016.
U.S. Appl. No. 14/229,415, filed Feb. 9, 2016.
U.S. Appl. No. 14/632,436, filed Jan. 20, 2017.
U.S. Appl. No. 14/664,290, filed May 23, 2017.
U.S. Appl. No. 14/664,290, filed Jan. 13, 2017.
U.S. Appl. No. 14/954,596, filed Nov. 2, 2017.
U.S. Appl. No. 14/954,596, filed Jul. 27, 2017.
U.S. Appl. No. 15/070,572, filed Aug. 31, 2017.
U.S. Appl. No. 15/070,572, filed May 22, 2017.
U.S. Appl. No. 15/684,595, filed Nov. 24, 2017.
Baron, Martin et al., "H NMR Assignment and Secondary Structure of the Cell Adhesion Type III Module of Fibronectin," Biochemistry, vol. 31:2068-2073(1992).
Breitbart, Astrid et al., "Myostatin from the heart: local and systemic actions in cardiac failure and muscle wasting," Am. J. Physiol. Circ. Physiol., vol. 300:H1973-H1982 (2011).
Campbell, Iain D. et al., "Building proteins with fibronectin type III modules, Fibronectin type III modules are versatile components of many proteins. Recent structures of module pairs show how these modules are joined together," Structure, vol. 2:333-337 (1994).
Clarke, Jane et al., "Folding and Stability of a Fibronectin Type III Domain of Human Tenascin," J. Mol. Biol., vol. 270:771-778 (1997).
Connelly, Roberta et al., "Mitogenic properties of a bispecific single-chain Fv-Ig fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Ely, Kathryn R. et al., "Common molecular scaffold for two unrelated RGD molecules," Protein Engineering, vol. 8 (8):823-827 (1995).
Emanuel, Stuart L. et al., "A fibronectin scaffold approach to bispecific inhibitors of epidermal growth factor receptor and insulin-like growth factor-I receptor," mAbs, vol. 3(1):38-48 (2011).
GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages, (1996).
GenBank Accession No. ABB78921, Lipovsek, D. et al., "New non-antibody proteins having an immunoglobulin fold, useful in research, therapeutic or diagnostic fields, particularly as scaffolds for designing proteins with specific properties, e.g. forbinding any antigen of interest," 33 pages (2005).
GenBank Accession No. CAA26536, Komblihtt, A.R. et al., "Primary structure of human fibronectin: differential splicing may generate at least 10 polypeptides froma single gene," EMBO J., vol. 4(7):1755-1759 (1985), 7 pages, (1996).
GenBank Accession No. P07589, Skorstengaard, K. et al., "Complete primary structure of bovine plasma fibronectin," Eur J. Biochem., vol. 161(2):441-453 (1986), 9 pages, (1997).
GenBank Accession No. X02761, Komblihtt, A.R. et al., "Primary structure of human fibronectin: differential splicing may generate at least 10 polypeptides from a single gene," EMBO J., vol. 4(7):1755-1759 (1985), 4 pages, (1996).
Gonzalez-Cadavid, Nestor F. et al., "Organization of the human myostatin gene and expression in healthy men and HIV-infected men with muscle wasting," Proc. Natl. Acad. Sci. USA, vol. 95:14938-14943 (1998).

(56) References Cited

OTHER PUBLICATIONS

Hamrick, M.W. et al., "Bone Mineral Content and Density in the Humerus of Adult Myostatin-Deficient Mice," Caclif. Tissue Int., vol. 71:63-68 (2002).
International Preliminary Report on Patentability for Application No. PCT/US2013/059458, 6 pages, dated Dec. 13, 2013.
International Search Report for Application No. PCT/US2013/059458, 5 pages, dated Dec. 13, 2013.
King, Catherine et al., "DNA vaccines with single-chain Fv fused to fragment C of tetanus toxin induce protective immunity against lymphoma and myeloma," Nature Medicine, vol. 4(11):1281-1286 (1998).
Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Shohei et al., "Directed Evolution of Fibronectin Type III Domain to Novel Ligand Binding Proteins," FASEB J., vol. 11(9 Suppl.), Poster No. M40, p. A837, (1997).
Koide, Shohei et al., "Directed Evolution of Fibronectin Type III Domain to Novel Ligand Binding Proteins," The Faseb Journal, vol. 11(9):A1155, Poster No. 1739 (1997).
Leahy, Daniel J. et al., "2.0 A Crystal Structure of a Four-Domain Segment of Human Fibronectin Encompassing the RGD Loop and Synergy Region," Cell, vol. 84:155-164 (1996).
Leahy, Daniel J. et al., "Structure of a Fibronectin Type III Domain from Tenascin Phased by MAD Analysis of the Selenomethionyl Protein," Science, vol. 258:987-991 (1992).
Lee, Se-Jin, "Extracellular Regulation of Myostatin: A Molecular Rheostat for Muscle Mass," Immunol. Endocr. Metabl. Agents Med. Chem., vol. 10:183-194 (2010).
Lipovsek, D., "Adnectins: engineered target binding protein therapeutics," Protein Engineering, Design & Selection, vol. 24(1-2):3-9 (2011).
Lipovsek, Dasa et al., "In-vitro protein evolution by ribosome display and mRNA display," Journal of Immunological Methods, vol. 290:51-67 (2004).
Litvinovich, Sergei V. et al., "Interactions Between Type III Domains in the 110 kDa Cell-binding Fragments of Fibronectin," J. Mol. Biol., vol. 248:611-626 (1995).
Lombardo, A. et al., "Conformational flexibility and crystallization of tandemly linked type III modules of human fibronectin," Protein Science, vol. 5:1934-1938 (1996).
Main, Alison L. et al., "The Three-Dimensional Structure of the Tenth Type III Module of Fibronectin: An Insight into RGD-Mediated Interactions," Cell, vol. 71:671-678 (1992).
Mao, Yong et al., "Fibronectin fibrillogenesis, a cell-mediated matrix assembly process," Matrix Biology, vol. 24:389-399 (2005).
McPherron, Alexandra C. et al., "Double muscling in cattle due to mutations in the myostatin gene," Proc. Natl. Acad. Sci. USA, vol. 94:12457-12461 (1997).
McPherron, Alexandra C. et al., "Redundancy of myostatin and growth/differentiation factor II function," BMC Developmental Biology, vol. 9(24):1-9 doi:10.1186/1471-213X-9-24 (2009).
McPherron, Alexandra C. et al., "Suppression of body fat accumulation in myostatin-deficient mice," The Journal of Clinical Investigation, vol. 109(5):595-601 (2002).
Plaxco, Kevin W. et al., "A Comparison of the Folding Kinetics and Thermodynamics of Two Homologous Fibronectin Type III Modules," J. Mol. Biol., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Potts, Jennifer R. et al., "Fibronectin structure and assembly," Current Biology, vol. 6:648-655 (1994).
Potts, Jennifer R. et al., "Structure and Function of Fibronectin Modules," Matrix Biology, vol. 15:313-320 (1996).
Rebbapragada, A. et al., "Myostatin Signals through a Transforming Growth Factor beta-Like Signaling Pathway to Block Adipogenesis," Molecular and Cellular Biology, vol. 23(20):7230-7242 (2003).
Richards, Julie et al., "Engineered Fibronectin Type III Domain with a RGDWXE Sequence Binds with Enhanced Affinity and Specificity to Human alphavbeta3 Integrin," J. Mol. Biol., vol. 326:1475-1488 (2003).
Sako, Dianne et al., "Characterization of the Ligand Binding Functionality of the Extracellular Domain of Activin Receptor Type IIB," The Journal of Biological Chemistry, vol. 285(27):21037-21048 (2010).
Thies, R. Scott et al., "GDF-8 Propeptide Binds to GDF-8 and Antagonizes Biological Activity by Inhibiting GDF-8 Receptor Binding," Growth Factors, vol. 18:251-259 (2001).
Vuento, Matti et al., "Purification of Fibronectin from Human Plasma by Affinity Chromatography under Non-Denaturing Conditions," Biochem. J., vol. 183:331-337 (1979).
Wolfman, Neil M. et al., "Activation of latent myostatin by the BMP-1/tolloid family of metalloproteinases," PNAS, vol. 100(26):15842-15846 (2003).
Yen, Terence T. et al., "Obesity, diabetes, and neoplasia in yellow Avy/-mice: ectopic expression of the agouti gene," FASEB J., vol. 8:479-488 (1994).
Zimmers, Teresa A. et al., "Induction of Cachexia in Mice by Systemically Administered Myostatin," Science, vol. 296:1486-1488 (2002).
U.S. Appl. No. 14/481,641, filed Sep. 9, 2014, Sharon Cload.
U.S. Appl. No. 14/025,253, filed Sep. 12, 2013, Sharon Cload.
U.S. Appl. No. 14/275,542, filed May 12, 2014, Sharon Cload.
U.S. Appl. No. 14/632,436, filed Feb. 26, 2015, Sharon Cload.
U.S. Appl. No. 14/025,307, filed Sep. 12, 2013, Sharon Cload.
U.S. Appl. No. 09/515,260, filed Feb. 29, 2000, Dasa Lipovsek.
U.S. Appl. No. 10/728,078, filed Dec. 3, 2003, Dasa Lipovsek.
U.S. Appl. No. 11/483,918, filed Jul. 7, 2006, Dasa Lipovsek.
U.S. Appl. No. 11/890,627, filed Aug. 6, 2007, Dasa Lipovsek.
U.S. Appl. No. 11/543,316, filed Oct. 3, 2006, Dasa Lipovsek.
U.S. Appl. No. 14/022,827, filed Sep. 10, 2013, Dasa Lipovsek.
U.S. Appl. No. 11/448,171, filed Jun. 5, 2006, Yan Chen.
U.S. Appl. No. 11/482,641, filed Jul. 7, 2006, Yan Chen.
U.S. Appl. No. 12/788,240, filed May 26, 2010, Yan Chen.
U.S. Appl. No. 13/552,398, filed Jul. 18, 2012, Yan Chen.
U.S. Appl. No. 14/071,069, filed Nov. 4, 2013, Yan Chen.
U.S. Appl. No. 15/070,572, filed Mar. 15, 2016, Yan Chen.
U.S. Appl. No. 12/312,725, filed Jan. 20, 2010, Ray Camphausen.
U.S. Appl. No. 13/892,418, filed May 13, 2013, Ray Camphausen.
U.S. Appl. No. 14/659,028, filed Mar. 16, 2015, Ray Camphausen.
U.S. Appl. No. 12/867,406, filed Oct. 29, 2010, Ray Camphausen.
U.S. Appl. No. 13/956,952, filed Aug. 1, 2013, Ray Camphausen.
U.S. Appl. No. 14/954,596, filed Nov. 30, 2015, Ray Camphausen.
U.S. Appl. No. 12/470,989, filed May 22, 2009, Ray Camphausen.
U.S. Appl. No. 13/533,382, filed Jun. 26, 2012, Ray Camphausen.
U.S. Appl. No. 14/229,415, filed Mar. 28, 2014, Ray Camphausen.
U.S. Appl. No. 12/625,217, filed Nov. 24, 2009, Stuart Emanuel.
U.S. Appl. No. 13/692,555, filed Dec. 3, 2012, Stuart Emanuel.
U.S. Appl. No. 14/664,290, filed Mar. 20, 2015, Stuart Emanuel.
U.S. Appl. No. 13/098,851, filed May 2, 2011, Michael L. Gosselin.
U.S. Appl. No. 14/552,823, filed Nov. 25, 2014, Michael L. Gosselin.
U.S. Appl. No. 15/363,724, filed Nov. 29, 2016, Michael L. Gosselin.
U.S. Appl. No. 14/481,641, filed Jul. 1, 2016, Z. Miknis.
U.S. Appl. No. 14/481,641, filed Nov. 20, 2015, Z. Miknis.
U.S. Appl. No. 14/481,641, filed Aug. 27, 2015, Z. Miknis.
U.S. Appl. No. 14/025,253, filed Sep. 2, 2014, M. Haddad.
U.S. Appl. No. 14/025,253, filed Jun. 25, 2014, M. Haddad.
U.S. Appl. No. 14/275,542, filed Nov. 21, 2014, M. Haddad.
U.S. Appl. No. 14/275,542, filed Aug. 6, 2014, M. Haddad.
U.S. Appl. No. 14/025,307, filed Aug. 27, 2014, Z. Miknis.
U.S. Appl. No. 14/025,307, filed Jul. 15, 2014, Z. Miknis.
U.S. Appl. No. 14/025,307, filed Feb. 27, 2014, Z. Miknis.
U.S. Appl. No. 09/515,260, filed Mar. 11, 2003, M. Audet.
U.S. Appl. No. 09/515,260, filed Jun. 18, 2002, H. Schnizer.
U.S. Appl. No. 09/515,260, filed Sep. 7, 2001, H. Schnizer.
U.S. Appl. No. 09/515,260, filed Jun. 1, 2001, H. Schnizer.
U.S. Appl. No. 10/728,078, filed Mar. 10, 2006, M. Audet.
U.S. Appl. No. 10/728,078, filed Jul. 1, 2005, M. Audet.

(56) References Cited

OTHER PUBLICATIONS

U.S. Appl. No. 10/728,078, filed Feb. 9, 2005, M. Audet.
U.S. Appl. No. 11/483,918, filed Dec. 29, 2009, M. Audet.
U.S. Appl. No. 11/483,918, filed Jun. 16, 2009, M. Audet.
U.S. Appl. No. 11/483,918, filed Jun. 12, 2009, M. Audet.
U.S. Appl. No. 11/483,918, filed Dec. 15, 2008, M. Audet.
U.S. Appl. No. 11/483,918, filed Mar. 24, 2008, M. Audet.
U.S. Appl. No. 11/483,918, filed Sep. 10, 2007, M. Audet.
U.S. Appl. No. 11/483,918, filed Apr. 11, 2007, M. Audet.
U.S. Appl. No. 11/890,627, filed Nov. 16, 2009, M. Audet.
U.S. Appl. No. 11/890,627, filed Apr. 2, 2009, M. Audet.
U.S. Appl. No. 11/543,316, filed Nov. 16, 2016, M. Audet.
U.S. Appl. No. 11/543,316, filed Feb. 12, 2016, M. Audet.
U.S. Appl. No. 11/543,316, filed Jul. 10, 2015, M. Audet.
U.S. Appl. No. 11/543,316, filed Apr. 20, 2011, M. Audet.
U.S. Appl. No. 11/543,316, filed Aug. 4, 2010, M. Audet.
U.S. Appl. No. 11/543,316, filed Nov. 12, 2009, M. Audet.
U.S. Appl. No. 11/543,316, filed Apr. 3, 2009, M. Audet.
U.S. Appl. No. 14/022,827, filed Jul. 21, 2016, A. Bunker.
U.S. Appl. No. 14/022,827, filed Jan. 13, 2016, A. Bunker.
U.S. Appl. No. 14/022,827, filed Jul. 13, 2015, A. Bunker.
U.S. Appl. No. 14/022,827, filed Sep. 30, 2014, M. Audet.
U.S. Appl. No. 14/022,827, filed Feb. 11, 2014, M. Audet.
U.S. Appl. No. 11/448,171, filed Feb. 26, 2010, Z. Howard.
U.S. Appl. No. 11/448,171, filed Sep. 25, 2009, Z. Howard.
U.S. Appl. No. 11/448,171, filed Feb. 2, 2009, Z. Howard.
U.S. Appl. No. 11/448,171, filed Jun. 12, 2008, Z. Howard.
U.S. Appl. No. 11/482,641, filed Jan. 28, 2010, Z. Howard.
U.S. Appl. No. 11/482,641, filed Jun. 8, 2009, Z. Howard.
U.S. Appl. No. 11/482,641, filed Oct. 28, 2008, Z. Howard.
U.S. Appl. No. 11/482,641, filed Mar. 27, 2008, Z. Howard.
U.S. Appl. No. 11/482,641, filed Nov. 28, 2007, Z. Howard.
U.S. Appl. No. 12/788,240, filed Apr. 4, 2012, Z. Howard.
U.S. Appl. No. 12/788,240, filed Oct. 27, 2011, Z. Howard.
U.S. Appl. No. 12/788,240, filed Aug. 2, 2011, Z. Howard.
U.S. Appl. No. 13/552,398, filed Aug. 5, 2013, Z. Howard.
U.S. Appl. No. 13/552,398, filed Mar. 15, 2013, Z. Howard.
U.S. Appl. No. 13/552,398, filed Nov. 21, 2012, Z. Howard.
U.S. Appl. No. 13/552,398, filed Sep. 21, 2012, Z. Howard.
U.S. Appl. No. 14/071,069, filed Dec. 16, 2015, Z. Howard.
U.S. Appl. No. 14/071,069, filed Jul. 30, 2015, Z. Howard.
U.S. Appl. No. 14/071,069, filed Apr. 16, 2015, Z. Howard.
U.S. Appl. No. 14/071,069, filed Dec. 12, 2014, Z. Howard.
U.S. Appl. No. 14/071,069, filed Sep. 18, 2014, Z. Howard.
U.S. Appl. No. 15/070,572, filed Nov. 9, 2016, Z. Howard.
U.S. Appl. No. 15/070,572, filed Jul. 21, 2016, Z. Howard.
U.S. Appl. No. 12/312,725, filed Feb. 13, 2013, B. Bunner.
U.S. Appl. No. 12/312,725, filed Sep. 27, 2012, B. Bunner.
U.S. Appl. No. 12/312,725, filed Apr. 19, 2012, B. Bunner.
U.S. Appl. No. 12/312,725, filed Feb. 3, 2012, B. Bunner.
U.S. Appl. No. 13/892,418, filed Dec. 15, 2014, B. Bunner.
U.S. Appl. No. 13/892,418, filed Sep. 24, 2014, B. Bunner.
U.S. Appl. No. 14/659,028, filed Oct. 12, 2016, B. Bunner.
U.S. Appl. No. 14/659,028, filed Jul. 1, 2016, B. Bunner.
U.S. Appl. No. 12/867,406, filed May 3, 2013, B. Bunner.
U.S. Appl. No. 12/867,406, filed Nov. 6, 2012, B. Bunner.
U.S. Appl. No. 12/867,406, filed Aug. 24, 2012, B. Bunner.
U.S. Appl. No. 13/956,952, filed Sep. 1, 2015, B. Bunner.
U.S. Appl. No. 13/956,952, filed Mar. 18, 2015, B. Bunner.
U.S. Appl. No. 13/956,952, filed Jan. 2, 2015, B. Bunner.
U.S. Appl. No. 12/470,989, filed Mar. 16, 2012, B. Bunner.
U.S. Appl. No. 12/470,989, filed Sep. 1, 2011, B. Bunner.
U.S. Appl. No. 12/470,989, filed Mar. 18, 2011, B. Bunner.
U.S. Appl. No. 13/533,382, filed Jan. 2, 2014, B. Bunner.
U.S. Appl. No. 13/533,382, filed May 24, 2013, B. Bunner.
U.S. Appl. No. 13/533,382, filed Dec. 10, 2012, B. Bunner.
U.S. Appl. No. 12/625,217, filed Aug. 22, 2012, B. Bunner.
U.S. Appl. No. 12/625,217, filed Apr. 2, 2012, B. Bunner.
U.S. Appl. No. 12/625,217, filed Jan. 19, 2012, B. Bunner.
U.S. Appl. No. 13/692,555, filed Dec. 23, 2014, B. Bunner.
U.S. Appl. No. 13/692,555, filed Jul. 25, 2014, B. Bunner.
U.S. Appl. No. 13/692,555, filed Mar. 3, 2014, B. Bunner.
U.S. Appl. No. 14/664,290, filed Sep. 20, 2016, B. Bunner.
U.S. Appl. No. 13/098,851, filed Aug. 27, 2014, A. Desai.
U.S. Appl. No. 13/098,851, filed May 20, 2014, A. Desai.
U.S. Appl. No. 13/098,851, filed Dec. 4, 2013, A. Desai.
U.S. Appl. No. 13/098,851, filed Mar. 18, 2013, A. Desai.
U.S. Appl. No. 14/552,823, filed Aug. 31, 2016, A. Desai.
U.S. Appl. No. 14/552,823, filed Mar. 24, 2016, A. Desai.
Koide, S. et al. (Koide I), "Target-Binding Proteins Based on the 10th Human Fibronectin Type III Domain (10Fn3)" Methods in Enzymology, vol. 503:135-156 (Jan. 19, 2012).
Koide, S. et al. (Koide II), "The Fibronectin Type III Domain as a Scaffold for Novel Binding Proteins," Journal of Molecular Biology, vol. 284: 1141-1151 (1998).
U.S. Appl. No. 15/886,118, filed Feb. 1, 2018, Ray Camphausen.
U.S. Appl. No. 15/866,919, filed Jan. 10, 2018, Ray Camphausen.
U.S. Appl. No. 14/022,827, filed Jan. 31, 2017, A. Bunker.
U.S. Appl. No. 14/229,415, filed Oct. 11, 2017, B. Bunner.
U.S. Appl. No. 15/404,749, filed Apr. 2, 2018, B. Bunner.
U.S. Appl. No. 15/404,749, filed Dec. 1, 2017, B. Bunner.
U.S. Appl. No. 15/684,595, filed Apr. 10, 2018, B. Bunner.

* cited by examiner

Fig. 1

FIBRONECTIN BASED SCAFFOLD DOMAIN PROTEINS THAT BIND TO MYOSTATIN

REFERENCE TO RELATED APPLICATIONS

This application is a divisional of U.S. patent application Ser. No. 14/481,641, filed on Sep. 9, 2014, which is a continuation of U.S. patent application Ser. No. 14/025,307, filed on Sep. 12, 2013, which claims priority to United States Provisional Application No. 61/700,697, filed on Sep. 13, 2012, and United States Provisional Application No. 61/780,005, filed Mar. 13, 2013, the entirety of each of which is hereby incorporated by reference.

SEQUENCE LISTING

The instant application contains a Sequence Listing which has been submitted via EFS-Web and is hereby incorporated by reference in its entirety. Said ASCII copy, created on Sep. 30, 2016, is named MXI_514BCNDV_Sequence_Listing.txt and is 252,507 bytes in size.

FIELD OF THE INVENTION

The present invention relates to fibronectin-based scaffold domain proteins that bind myostatin. The invention also relates to the use of the innovative proteins in therapeutic applications to treat muscle-wasting diseases and metabolic disorders. The invention further relates to cells comprising such proteins, polynucleotides encoding such proteins or fragments thereof, and to vectors comprising the polynucleotides encoding the innovative proteins.

BACKGROUND OF THE INVENTION

Myostatin, also known as growth and differentiation factor-8 (GDF-8), is a member of the transforming growth factor-β (TGF-β) superfamily of secreted growth factors. Myostatin has all of the structural features common to the TGF-β family proteins: a hydrophobic amino-terminus that acts as a secretory signal, nine invariant cysteine residues, and an "RXXR" furin-type proteolytic processing site. Proteolytic cleavage of the protein gives rise to a C-terminal domain which forms a homodimer that is the biologically active form of myostatin (Thies et al., *Growth Factors* 2001; 18(4):251-9). Alignments of the C-terminal fragment of myostatin amino acid sequences from multiple vertebrate species reveal that the protein is highly conserved (100% identity) between human, monkey, cow, dog, mouse, rat, turkey and chicken (McPherron, et al. PNAS, 94:12457-61, 1997).

Myostatin expression is limited primarily to skeletal muscle and adipose tissue, where it has been shown to be a negative regulator of skeletal muscle development (Lee L S, *Immunol Endocr Metab Agents Med Chem.* 2010; 10:183-194). In mammals, skeletal muscle appears to be the principal target tissue of myostatin, where it binds to cell-surface receptors, leading to muscle loss. Mice and cattle with genetic deficiencies in myostatin exhibit dramatic increases in skeletal muscle mass, i.e., the "double muscling" phenotype, therefore supporting the role of myostatin in suppressing muscle growth (McPherron and Lee, *Proc Natl Acad Sci USA.* 2003 Dec. 23; 100(26):15842-6). Muscle hypertrophy in Belgian Blue and Piedmontese cattle breeds is due to a mis sense mutation within the third exon of the bovine myostatin gene (Bass et. al., *Domest Anim Endocrinol.* 1999; 17(2-3):191-7). Transgenic overexpression of myostatin inhibitors also results in hyper-muscularity. Enhanced muscle growth in these animals is due to an increase in both cell number, or hyperplastic growth, and cell size, or hypertrophic growth, which results in larger and heavier myofibers. Increased skeletal muscle mass due to a myostatin mutation has also been reported in humans. Myostatin inhibition effectively increases skeletal muscle mass and strength, both in the postnatal period and in adults.

Increases in skeletal muscle mass and strength are also associated with metabolic adaptations which positively affect body composition, energy expenditure, glucose homeostasis and insulin requirements. Both genetic and pharmacological findings indicate that myostatin regulates energy metabolism and that its inhibition can significantly attenuate the progression of metabolic diseases, including obesity and diabetes. For example, myostatin null mice exhibit decreased body fat accumulation (McPherron & Lee, J. JCI 109:595, 2002) when compared with wild type mice of the same age. This reduction in body fat is a manifestation of reduced adipocyte number and size, implicating a significant role of myostatin in adipogenesis as well as in myogenesis.

Accordingly, myostatin is a desirable target for therapeutic or prophylactic intervention for the treatment of disorders or conditions which would benefit from an increase in muscle mass, muscle strength and/or metabolism (e.g., muscular dystrophy, frailty, disuse atrophy and cachexia), disorders associated with muscle wasting (e.g., renal disease, cardiac failure or disease, and liver disease), and metabolic disorders (e.g., Type II diabetes, metabolic syndrome, obesity and osteoarthritis).

Accordingly, it would be advantageous to obtain improved fibronectin domain scaffold proteins that bind myostatin for the therapeutic treatment of, e.g., metabolic disorders, muscle wasting disorders, and muscle loss due to inactivity.

SUMMARY OF THE INVENTION

The present invention is based, at least in part, on the discovery of Adnectins that bind to and antagonize myostatin. Specifically, the anti-myostatin Adnectins of the present invention inhibit myostatin activity, thereby affecting downstream SMAD signaling. One mechanism accounting for altered SMAD signaling of some of the anti-myostatin Adnectins of the invention involves the inhibition of Alk4 recruitment to the myostatin-ActRIIb complex, the physiological consequences of which are increased muscle volume and body weight.

In one aspect, the invention provides a polypeptide comprising a fibronectin tenth type III domain ($^{10}$Fn3) wherein the $^{10}$Fn3 has at least one loop selected from loop BC, DE, and FG with an altered amino acid sequence relative to the sequence of the corresponding loop of the human $^{10}$Fn3 domain, and wherein the polypeptide binds myostatin. In certain embodiments, the polypeptide binds myostatin with a $K_D$ of less than 500 nM.

In some embodiments, the BC loop of the polypeptide of the invention comprises an amino acid sequence according to the formula $X_1$-L-P-$X_2$-$X_3$-$X_4$-$X_5$-$X_6$-$X_7$, wherein (a) $X_1$ is selected from the group consisting of S, T and Y; (b) $X_2$ is selected from the group consisting of H, Y, N, R, F, G, S and T; (c) $X_3$ is selected from the group consisting of A, P, Q, S, F, H, N and R; (d) $X_4$ is selected from the group consisting of G and A; (e) $X_5$ is selected from the group consisting of H, L, R, V, N, D, F, I and K; (f) $X_6$ is selected from the group consisting of A, L, G, M, F, I and V; and (g) $X_7$ is selected from the group consisting of H and N. In certain embodiments, $X_1$ is S, and/or $X_2$ is H or Y, and/or $X_3$ is A or P, and/or $X_4$ is G, and/or $X_5$ is H, L or R, and/or $X_6$ is A or L., and/or $X_7$ is H.

In other embodiments, the BC loop comprises an amino acid sequence according to the formula $X_{19}$-$X_{20}$-P-$X_{21}$-G-$X_{22}$-A, wherein (a) $X_{19}$ is selected from the group consisting of D, E, V and W; (b) $X_{20}$ is selected from the group consisting of A, S and V; (c) $X_{21}$ is selected from the group consisting of R, A, G, K and L; and (d) $X_{22}$ is selected from the group consisting of L and R. In certain embodiments, $X_{19}$ is D, and/or $X_{20}$ is A, S or V, and/or $X_{22}$ is L.

In some embodiments, the DE loop comprises an amino acid sequence according to the formula G-R-G-$X_8$, wherein $X_8$ is V or L.

In some embodiments, the DE loop comprises an amino acid sequence according to the formula $X_{23}$-G-R-G-$X_{24}$, wherein (a) $X_{23}$ is selected from the group consisting of V, P, F, I and L; and (b) $X_{24}$ is selected from the group consisting of S, N and T.

In some embodiments, the FG loop of the polypeptide of the invention comprises an amino acid sequence according to the formula $X_9$-$X_{10}$-$X_{11}$-$X_{12}$-$X_{13}$-$X_{14}$-$X_{15}$-$X_{16}$-$X_{17}$-$X_{18}$, wherein (a) $X_9$ is selected from the group consisting of L, V and I; (b) $X_{10}$ is selected from the group consisting of T and S; (c) $X_{11}$ is selected from the group consisting of K, R, A, G, S, D, H, N, T and P; (d) $X_{12}$ is selected from the group consisting of S, T, A, E, H, K and N; (e) $X_{13}$ is selected from the group consisting of K, G, Q, D, E, N, T and S; (f) $X_{14}$ is selected from the group consisting of V, I, F, L, M, P, T and Y; (g) $X_{15}$ is selected from the group consisting of I, L and Y; (h) $X_{16}$ is selected from the group consisting of H, I, V, K, L, R, F, G, S and T; (i) $X_{17}$ is selected from the group consisting of Y and H; and (j) $X_{18}$ is selected from the group consisting of K, M, L, R and V.

In certain embodiments, $X_9$ is L or V, and/or $X_{10}$ is T, $X_{11}$ is K or R, and/or $X_{12}$ is S or T, and/or $X_{13}$ is K, G or Q, and/or $X_{14}$ is V or I, and/or $X_{15}$ is I, and/or $X_{16}$ is H, I or V, and/or $X_{17}$ is Y and/or $X_{18}$ is K or M.

In other embodiments, the FG loop comprises an amino acid sequence according to the formula $X_{25}$-$X_{26}$-R-$X_{27}$-G-$X_{28}$-$X_{29}$-$X_{30}$-$X_{31}$-$X_{32}$, wherein (a) $X_{25}$ is selected from the group consisting of I and V; (b) $X_{26}$ is selected from the group consisting of F, D and Y; (c) $X_{27}$ is selected from the group consisting of D and T; (d) $X_{28}$ is selected from the group consisting of P, M, V and T; (e) $X_{29}$ is selected from the group consisting of V, L, N, R and S; (f) $X_{30}$ is selected from the group consisting of H, T, L, N, Q and S; (g) $X_{31}$ is selected from the group consisting of F, W, Y, H and L; and (h) $X_{32}$ is selected from the group consisting of D, A and G.

In certain embodiments, $X_{25}$ is I, and/or $X_{26}$ is F, and/or $X_{27}$ is D, and/or $X_{28}$ is P, and/or $X_{29}$ is V, and/or $X_{30}$ is H or T, and/or $X_{31}$ is F or W, and/or $X_{32}$ is D.

In some embodiments, the polypeptide comprises a BC loop and a DE loop, or a BC loop and FG loop, or a DE loop and an FG loop, or a BC loop, a DE loop and an FG loop.

In some embodiments, the BC loop of the polypeptide comprises an amino acid sequence selected from the group consisting of SEQ ID NOs: 7-38. In other embodiments, the DE loop comprises an amino acid selected from the group consisting of SEQ ID NOs: 39-45. In yet other embodiments, the FG loop comprises an amino acid sequence selected from the group consisting of SEQ ID NOs: 46-79. In some embodiments, the BC, DE, or FG loop amino acid sequence is at least 80% identical to any one of SEQ ID NOs: 7-38, 39-45, and 46-79, respectively. In other embodiments, the polypeptide comprises an amino acid sequence that is at least 80%, 85%, 90%, 95%, 98%, or 99% identical to any one of SEQ ID NOs: 80-123, 228-239, and 252-273. In yet other embodiments, the polypeptide comprises an amino acid sequence selected from the group consisting of SEQ ID NOs: 80-123, 228-239, and 252-273.

In some embodiments, the polypeptides comprise the BC, DE, and FG loop combinations as shown in Table 1. In one embodiment, the polypeptide has the BC, DE, and FG loops as set forth in SEQ ID NOs: 34, 39, and 75, respectively.

In some embodiments, the polypeptide comprises the BC, DE, and FG loops as set forth in SEQ ID NOs: 34, 39, and 75, respectively, wherein the BC loop has 1, 2, 3, 4, 5, or 6 amino acid substitutions, such as conservative amino acid substitutions. In some embodiments, the BC loop has an amino acid sequence according to the formula $X_{33}$-L-P-$X_{34}$-$X_{35}$-$X_{36}$-$X_{37}$-$X_{38}$-$X_{39}$, wherein $X_{33}$ is T or Y; $X_{34}$ is Y, N, R, F, G, S, or T; $X_{35}$ is A, P, S, F, H, N, or R; $X_{36}$ is A; $X_{37}$ is H, L, R, V, N, D, F, or I; $X_{38}$ is L, G, M, F, I, or V; and $X_{39}$ is H.

In some embodiments, the polypeptide comprises the BC, DE, and FG loops as set forth in SEQ ID NOs: 34, 39, and 75, respectively, wherein the DE loop has 1 amino acid substitution, such as a conservative amino acid substitution. In some embodiments, the DE loop has an amino acid sequence according to the formula G-R-G-$X_{40}$, wherein $X_{40}$ is L.

In some embodiments, the polypeptide comprises the BC, DE, and FG loops as set forth in SEQ ID NOs: 34, 39, and 75, respectively, wherein the FG loop has 1, 2, 3, 4, 5, 6, 7, or 8 amino acid substitutions, such as conservative amino acid substitutions. In some embodiments, the FG loop has an amino acid sequence according to the formula $X_{41}$-$X_{42}$-$X_{43}$-$X_{44}$-$X_{45}$-$X_{46}$-$X_{47}$-$X_{48}$-$X_{49}$-$X_{50}$, wherein $X_{41}$ is L or I; $X_{42}$ is S; $X_{43}$ is K, R, A, G, S, H, N, T, or P; $X_{44}$ is S, A, E, H, K, or N; $X_{45}$ is K, Q, D, E, N, T, or S; $X_{46}$ is V, I, F, L, M, P, or T; $X_{47}$ is I or Y; $X_{48}$ is H, I, V, L, R, F, G, S, or T; $X_{49}$ is H; and $X_{50}$ is M, L, R, or V.

In some embodiments, the polypeptide comprises the BC, DE, and FG loops as set forth in SEQ ID NOs: 34, 39, and 75, respectively, wherein the BC loop has 1, 2, 3, 4, 5, or 6 amino acid substitutions, such as conservative amino acid substitutions, and the DE loop has 1 amino acid substitution, such as a conservative amino acid substitution. In some embodiments, the BC loop has an amino acid sequence according to the formula $X_{33}$-L-P-$X_{34}$-$X_{35}$-$X_{36}$-$X_{37}$-$X_{38}$-$X_{39}$, wherein $X_{33}$ is T or Y; $X_{34}$ is Y, N, R, F, G, S, or T; $X_{35}$ is A, P, S, F, H, N, or R; $X_{36}$ is A; $X_{37}$ is H, L, R, V, N, D, F, or I; $X_{38}$ is L, G, M, F, I, or V; and $X_{39}$ is H, and the DE loop has an amino acid sequence according to the formula G-R-G-$X_{40}$, wherein $X_{40}$ is L.

In some embodiments, the polypeptide comprises the BC, DE, and FG loops as set forth in SEQ ID NOs: 34, 39, and 75, respectively, wherein the BC loop has 1, 2, 3, 4, 5, or 6 amino acid substitutions, such as conservative amino acid substitutions, and the FG loop has 1, 2, 3, 4, 5, 6, 7, or 8 amino acid substitutions, such as conservative amino acid substitutions. In some embodiments, the BC loop has an amino acid sequence according to the formula $X_{33}$-L-P-$X_{34}$-$X_{35}$-$X_{36}$-$X_{37}$-$X_{38}$-$X_{39}$, wherein $X_{33}$ is T or Y; $X_{34}$ is Y, N, R, F, G, S, or T; $X_{35}$ is A, P, S, F, H, N, or R; $X_{36}$ is A; $X_{37}$ is H, L, R, V, N, D, F, or I; $X_{38}$ is L, G, M, F, I, or V; and $X_{39}$ is H, and the FG loop has an amino acid sequence according to the formula $X_{41}$-$X_{42}$-$X_{43}$-$X_{44}$-$X_{45}$-$X_{46}$-$X_{47}$-$X_{48}$-$X_{49}$-$X_{50}$, wherein $X_{41}$ is L or I; $X_{42}$ is S; $X_{43}$ is K, R, A, G, S, H, N, T, or P; $X_{44}$ is S, A, E, H, K, or N; $X_{45}$ is K, Q, D, E, N, T, or S; $X_{46}$ is V, I, F, L, M, P, or T; $X_{47}$ is I or Y; $X_{48}$ is H, I, V, L, R, F, G, S, or T; $X_{49}$ is H; and $X_{50}$ is M, L, R, or V.

In some embodiments, the polypeptide comprises the BC, DE, and FG loops as set forth in SEQ ID NOs: 34, 39, and 75, respectively, wherein and the DE loop has 1 amino acid substitution, such as a conservative amino acid substitution, and the FG loop has 1, 2, 3, 4, 5, 6, 7, or 8 amino acid substitutions, such as conservative amino acid substitutions. In some embodiments, the DE loop has an amino acid sequence according to the formula G-R-G-$X_{40}$, wherein $X_{40}$ is L, and the FG loop has an amino acid sequence according to the formula $X_{41}$-$X_{42}$-$X_{43}$-$X_{44}$-$X_{45}$-$X_{46}$-$X_{47}$-$X_{48}$-$X_{49}$-$X_{50}$, wherein $X_{41}$ is L or I; $X_{42}$ is S; $X_{43}$ is K, R, A, G, S, H, N, T, or P; $X_{44}$ is S, A, E, H, K, or N; $X_{45}$ is K, Q, D, E, N, T, or S; $X_{46}$ is V, I, F, L, M, P, or T; $X_{47}$ is I or Y; $X_{48}$ is H, I, V, L, R, F, G, S, or T; $X_{49}$ is H; and $X_{50}$ is M, L, R, or V.

In some embodiments, the polypeptide comprises the BC, DE, and FG loops as set forth in SEQ ID NOs: 34, 39, and 75, respectively, wherein the BC loop has 1, 2, 3, 4, 5, or 6 amino acid substitutions, such as conservative amino acid substitutions, and the DE loop has 1 amino acid substitution, such as a conservative amino acid substitution, and the FG loop has 1, 2, 3, 4, 5, 6, 7, or 8 amino acid substitutions, such as conservative amino acid substitutions. In some embodiments, the BC loop has an amino acid sequence according to the formula $X_{33}$-L-P-$X_{34}$-$X_{35}$-$X_{36}$-$X_{37}$-$X_{38}$-$X_{39}$, wherein $X_{33}$ is T or Y; $X_{34}$ is Y, N, R, F, G, S, or T; $X_{35}$ is A, P, S, F, H, N, or R; $X_{36}$ is A; $X_{37}$ is H, L, R, V, N, D, F, or I; $X_{38}$ is L, G, M, F, I, or V; and $X_{39}$ is H; the DE loop has an amino acid sequence according to the formula G-R-G-$X_{40}$, wherein $X_{40}$ is L; and the FG loop has an amino acid sequence according to the formula $X_{41}$-$X_{42}$-$X_{43}$-$X_{44}$-$X_{45}$-$X_{46}$-$X_{47}$-$X_{48}$-$X_{49}$-$X_{50}$, wherein $X_{41}$ is L or I; $X_{42}$ is S; $X_{43}$ is K, R, A, G, S, H, N, T, or P; $X_{44}$ is S, A, E, H, K, or N; $X_{45}$ is K, Q, D, E, N, T, or S; $X_{46}$ is V, I, F, L, M, P, or T; $X_{47}$ is I or Y; $X_{48}$ is H, I, V, L, R, F, G, S, or T; $X_{49}$ is H; and $X_{50}$ is M, L, R, or V.

In some embodiments, the polypeptide comprises the BC, DE, and FG loops as set forth in SEQ ID NOs: 34, 39, and 75, respectively, and has amino acid substitutions in the BC, DE, and FG loops which allow the polypeptide to maintain binding to myostatin. Such amino acid substitutions can be determined by, e.g., deep mutational scanning as described in Example 8. Accordingly, in some embodiments, the polypeptide has a BC loop comprising an amino acid sequence according to the formula $X_{51}$-$X_{52}$-$X_{53}$-$X_{54}$-$X_{55}$-$X_{56}$-$X_{57}$-$X_{58}$-$X_{59}$, wherein: $X_{51}$ is selected from the group consisting of A, C, D, F, H, I, K, L, N, Q, R, S, T, V, W, and Y; $X_{52}$ is selected from the group consisting of L, M, and V; $X_{53}$ is selected from the group consisting of A, C, D, E, I, K, L, M, N, P, Q, R, S, T, V, and Y; $X_{54}$ is selected from the group consisting of A, C, D, E, F, G, H, I, K, L, M, N, Q, R, S, T, V, W, and Y; $X_{55}$ is selected from the group consisting of A, C, D, E, F, G, H, I, K, L, M, N, P, Q, R, S, T, V, W, and Y; $X_{56}$ is selected from the group consisting of G and S; $X_{57}$ is selected from the group consisting of A, C, D, E, F, G, H, I, K, L, M, N, Q, R, S, T, V, W, and Y; $X_{58}$ is selected from the group consisting of A, C, G, L, M, S, and T; and $X_{59}$ is selected from the group consisting of A, C, F, H, N, P, Q, R, S, and Y. In a preferred embodiment, $X_{51}$ is selected from the group consisting of C, F, I, S, V, W, and Y; $X_{52}$ is selected from the group consisting of L; $X_{53}$ is selected from the group consisting of P; $X_{54}$ is selected from the group consisting of C, D, E, F, G, H, I, K, L, M, N, Q, R, S, T, V, W, and Y; $X_{55}$ is selected from the group consisting of A, C, D, E, F, G, H, I, K, L, M, N, P, Q, R, S, T, V, W, and Y; $X_{56}$ is selected from the group consisting of G; $X_{57}$ is selected from the group consisting of A, C, G, H, I, K, L, M, N, Q, R, S, V, W, and Y; $X_{58}$ is selected from the group consisting of A, G, L, M, and S; and $X_{59}$ is selected from the group consisting of C, H, N, Q, S, and Y. In a more preferred embodiment, $X_{51}$ is selected from the group consisting of F, S, and W; $X_{52}$ is selected from the group consisting of L; $X_{53}$ is selected from the group consisting of P; $X_{54}$ is selected from the group consisting of C, F, G, I, K, L, M, N, R, S, T, V, W, and Y; $X_{55}$ is selected from the group consisting of A, C, E, F, H, I, K, L, M, P, Q, R, S, T, V, and Y; $X_{56}$ is selected from the group consisting of G; $X_{57}$ is selected from the group consisting of A, C, H, K, L, M, N, R, V, W, and Y; $X_{58}$ is selected from the group consisting of A, G, and L; and $X_{59}$ is selected from the group consisting of H, N, and Q. In a specific embodiment, $X_{51}$ S; $X_{52}$ is L; $X_{53}$ is P; $X_{54}$ is H; $X_{55}$ is Q; $X_{56}$ is G; $X_{57}$ is K; $X_{58}$ is A; $X_{59}$ is N.

In some embodiments, the polypeptide comprises a DE loop comprising an amino acid sequence according to the formula G-R-G-$X_{60}$, wherein $X_{60}$ is A, C, D, E, F, I, K, L, M, N, Q, S, T, and V. In a preferred embodiment, $X_{60}$ is C, E, I, L, M, Q, T, and V. In a more preferred embodiment, $X_{60}$ is C, E, I, L, M, and V. In a specific embodiment, $X_{60}$ is V.

In some embodiments, the polypeptide comprises an FG loop comprising an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is selected from the group consisting of A, C, F, I, L, M, Q, T, V, W, and Y; $X_{62}$ is selected from the group consisting of A, C, F, G, H, I, K, L, M, N, Q, R, S, T, V, W, and Y; $X_{63}$ is selected from the group consisting of A, C, D, E, F, G, H, I, K, L, M, N, P, Q, R, S, T, V, W, and Y; $X_{64}$ is selected from the group consisting of A, C, D, E, F, G, H, I, K, L, M, N, P, Q, R, S, T, V, W, and Y; $X_{65}$ is selected from the group consisting of A, C, D, E, F, G, H, I, K, L, M, N, Q, R, S, T, V, W, and Y; $X_{66}$ is selected from the group consisting of A, C, F, H, I, L, M, N, P, S, T, V, W, and Y; $X_{67}$ is selected from the group consisting of A, C, E, F, H, I, K, L, M, N, Q, R, S, T, V, W, and Y; $X_{68}$ is selected from the group consisting of A, C, D, E, F, G, H, I, K, L, M, N, P, Q, R, S, T, V, W, and Y; $X_{69}$ is selected from the group consisting of F, W, and Y; and $X_{70}$ is selected from the group consisting of A, C, D, E, F, G, H, I, K, L, M, N, P, Q, R, S, T, V, W, and Y. In a preferred embodiment, $X_{61}$ is selected from the group consisting of A, C, I, L, M, and V; $X_{62}$ is selected from the group consisting of C, F, H, I, L, M, Q, R, S, T, V, W, and Y; $X_{63}$ is selected from the group consisting of A, C, D, E, F, G, H, I, L, M, N, P, Q, S, T, V, W, and Y; $X_{64}$ is selected from the group consisting of A, C, D, E, F, G, H, I, K, L, M, N, Q, R, S, T, V, W, and Y; $X_{65}$ is selected from the group consisting of A, D, E, F, G, H, I, L, M, N, Q, S, T, V, W, and Y; $X_{66}$ is selected from the group consisting of C, F, I, L, M, P, T, V, W, and Y; $X_{67}$ is selected from the group consisting of C, F, H, I, K, L, M, N, Q, R, T, V, W, and Y; $X_{68}$ is selected from the group consisting of A, C, E, F, G, I, K, L, M, N, P, Q, R, S, T, V, W, and Y; $X_{69}$ is selected from the group consisting of W and Y; and $X_{70}$ is selected from the group consisting of A, C, D, E, G, H, K, L, M, N, P, Q, R, S, T, and V. In a more preferred embodiment, $X_{61}$ is selected from the group consisting of I and V; $X_{62}$ is selected from the group consisting of C, F, I, L, M, T, V, W, and Y; $X_{63}$ is selected from the group consisting of A, C, D, E, F, G, H, I, L, M, N, Q, S, T, and V; $X_{64}$ is selected from the group consisting of A, C, D, F, G, I, L, M, N, Q, S, T, V, W, and Y; $X_{65}$ is selected from the group consisting of A, G, S, T, and W; $X_{66}$ is selected from the group consisting of F, I, V, W, and Y; $X_{67}$ is selected from the group consisting of F, H, I, L, M, V, W, and Y; $X_{68}$ is selected from the group consisting of A, C, F, G, I, K, L, M, T, V, and W; $X_{69}$ is selected from the group consisting of W and Y; and $X_{70}$ is selected from the group consisting of A, G, K, L, M, P, Q, and R. In a specific embodiment, $X_{61}$ is V; $X_{62}$ is T; $X_{63}$ is D; $X_{64}$ is T; $X_{65}$ is G; $X_{66}$ is Y; $X_{67}$ is L; $X_{68}$ is K; $X_{69}$ is Y; and $X_{70}$ is K.

In some embodiments, the polypeptide of the invention comprises BC, DE, and FG loops, wherein the BC loop comprises an amino acid sequence according to the formula $X_{51}$-$X_{52}$-$X_{53}$-$X_{54}$-$X_{55}$-$X_{56}$-$X_{57}$-$X_{58}$-$X_{59}$, wherein, $X_{51}$ is selected from the group consisting of A, C, D, F, H, I, K, L, N, Q, R, S, T, V, W, and Y; $X_{52}$ is selected from the group consisting of L, M, and V; $X_{53}$ is selected from the group consisting of A, C, D, E, I, K, L, M, N, P, Q, R, S, T, V, and Y; $X_{54}$ is A, C, D, E, F, G, H, I, K, L, M, N, Q, R, S, T, V, W, and Y; $X_{55}$ is selected from the group consisting of A, C, D, E, F, G, H, I, K, L, M, N, P, Q, R, S, T, V, W, and Y; $X_{56}$ is selected from the group consisting of G and S; $X_{57}$ is A, C, D, E, F, G, H, I, K, L, M, N, Q, R, S, T, V, W, and Y; $X_{58}$ is A, C, G, L, M, S, and T; and $X_{59}$ is A, C, F, H, N, P, Q, R, S, and Y; the DE loop comprises an amino acid sequence according to the formula G-R-G-$X_{60}$, wherein $X_{60}$ is selected from the group consisting of A, C, D, E, F, I, K, L, M, N, Q, S, T, and V; and the FG loop comprises an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is selected from the group consisting of A, C, F, I, L, M, Q, T, V, W, and Y; $X_{62}$ is A, C, F, G, H, I, K, L, M, N, Q, R, S, T, V, W, and Y; $X_{63}$ is selected from the group consisting of A, C, D, E, F, G, H, I, K, L, M, N, P, Q, R, S, T, V, W, and Y; $X_{64}$ is selected from the group consisting of A, C, D, E, F, G, H, I, K, L, M, N, P, Q, R, S, T, V, W, and Y; $X_{65}$ is selected from the group consisting of A, C, D, E, F, G, H, I, K, L, M, N, Q, R, S, T, V, W, and Y; $X_{66}$ is selected from the group consisting of A, C, F, H, I, L, M, N, P, S, T, V, W, and Y; $X_{67}$ is selected from the group consisting of A, C, E, F, H, I, K, L, M, N, Q, R, S, T, V, W, and Y; $X_{68}$ is selected from the group consisting of A, C, D, E, F, G, H, I, K, L, M, N, P, Q, R, S, T, V, W, and Y; $X_{69}$ is selected from the group consisting of F, W, and Y; and $X_{70}$ is selected from the group consisting of A, C, D, E, F, G, H, I, K, L, M, N, P, Q, R, S, T, V, W, and Y.

In a preferred embodiment, the polypeptide of the invention comprises BC, DE, and FG loops, wherein the BC loop comprises an amino acid sequence according to the formula $X_{51}$-$X_{52}$-$X_{53}$-$X_{54}$-$X_{55}$-$X_{56}$-$X_{57}$-$X_{58}$-$X_{59}$, wherein, $X_{51}$ is selected from the group consisting of C, F, I, S, V, W, and Y; $X_{52}$ is L; $X_{53}$ is P; $X_{54}$ is selected from the group consisting of C, D, E, F, G, H, I, K, L, M, N, Q, R, S, T, V, W, and Y; $X_{55}$ is selected from the group consisting of A, C, D, E, F, G, H, I, K, L, M, N, P, Q, R, S, T, V, W, and Y; $X_{56}$ is G; $X_{57}$ is selected from the group consisting of A, C, G, H, I, K, L, M, N, Q, R, S, V, W, and Y; $X_{58}$ is selected from the group consisting of A, G, L, M, and S; and $X_{59}$ is selected from the group consisting of C, H, N, Q, S, and Y; the DE loop comprises an amino acid sequence according to the formula G-R-G-$X_{60}$, wherein $X_{60}$ is selected from the group consisting of C, E, I, L, M, Q, T, and V; and the FG loop comprises an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is selected from the group consisting of A, C, I, L, M, and V; $X_{62}$ is C, F, H, I, L, M, Q, R, S, T, V, W, and Y; $X_{63}$ is selected from the group consisting of A, C, D, E, F, G, H, I, L, M, N, P, Q, S, T, V, W, and Y; $X_{64}$ is selected from the group consisting of A, C, D, E, F, G, H, I, K, L, M, N, Q, R, S, T, V, W, and Y; $X_{65}$ is selected from the group consisting of A, D, E, F, G, H, I, L, M, N, Q, S, T, V, W, and Y; $X_{66}$ is selected from the group consisting of C, F, I, L, M, P, T, V, W, and Y; $X_{67}$ is selected from the group consisting of C, F, H, I, K, L, M, N, Q, R, T, V, W, and Y; $X_{68}$ is selected from the group consisting of A, C, E, F, G, I, K, L, M, N, P, Q, R, S, T, V, W, and Y; $X_{69}$ is selected from the group consisting of W and Y; and $X_{70}$ is selected from the group consisting of A, C, D, E, F, G, H, I, K, L, M, N, P, Q, R, S, T, V, W, and Y.

In a more preferred embodiment, the polypeptide of the invention comprises BC, DE, and FG loops, wherein the BC loop comprises an amino acid sequence according to the formula $X_{51}$-$X_{52}$-$X_{53}$-$X_{54}$-$X_{55}$-$X_{56}$-$X_{57}$-$X_{58}$-$X_{59}$, wherein, $X_{51}$ is selected from the group consisting of F, S, and W; $X_{52}$ is L; $X_{53}$ is P; $X_{54}$ is selected from the group consisting of C, F, G, I, K, L, M, N, R, S, T, V, W, and Y; $X_{55}$ is selected from the group consisting of A, C, E, F, H, I, K, L, M, P, Q, R, S, T, V, and Y; $X_{56}$ is G; $X_{57}$ is selected from the group consisting of A, C, H, K, L, M, N, R, V, W, and Y; $X_{58}$ is selected from the group consisting of A, G, and L; and $X_{59}$ is selected from the group consisting of H, N, and Q; the DE loop comprises an amino acid sequence according to the formula G-R-G-$X_{60}$, wherein $X_{60}$ is selected from the group consisting of C, E, I, L, M, and V; and the FG loop comprises an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is selected from the group consisting of I and V; $X_{62}$ is C, F, I, L, M, T, V, W, and Y; $X_{63}$ is selected from the group consisting of A, C, D, E, F, G, H, I, L, M, N, Q, S, T, and V; $X_{64}$ is selected from the group consisting of A, C, D, F, G, I, L, M, N, Q, S, T, V, W, and Y; $X_{65}$ is selected from the group consisting of A, G, S, T, and W; $X_{66}$ is selected from the group consisting of F, I, V, W, and Y; $X_{67}$ is selected from the group consisting of F, H, I, L, M, V, W, and Y; $X_{68}$ is selected from the group consisting of A, C, F, G, I, K, L, M, T, V, and W; $X_{69}$ is selected from the group consisting of W and Y; and $X_{70}$ is selected from the group consisting of A, G, K, L, M, P, Q, and R.

In a specific embodiment, the polypeptide of the invention comprises BC, DE, and FG loops, wherein the BC loop comprises an amino acid sequence according to the formula $X_{51}$-$X_{52}$-$X_{53}$-$X_{54}$-$X_{55}$-$X_{56}$-$X_{57}$-$X_{58}$-$X_{59}$, wherein, $X_{51}$ is S; $X_{52}$ is L; $X_{53}$ is P; $X_{54}$ is H; $X_{55}$ is Q; $X_{56}$ is G; $X_{57}$ is K; $X_{58}$ is A; $X_{59}$ is N; the DE loop comprises an amino acid sequence according to the formula G-R-G-$X_{60}$, wherein $X_{60}$ is V; and the FG loop comprises an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is V; $X_{62}$ is T; $X_{63}$ is D; $X_{64}$ is T; $X_{65}$ is G; $X_{66}$ is Y; $X_{67}$ is L; $X_{68}$ is K; $X_{69}$ is Y; and $X_{70}$ is K.

In another embodiment, the polypeptide comprises an amino acid sequence at least 80%, 85%, 90%, 95%, 96%, 97%, 98%, 99% or 100% identical to the amino acid sequence set forth in SEQ ID NO: 273 [PRD-1474], SEQ ID NO: 118 [3116_A06], SEQ ID NO: 281 [core Adnectin sequence of PRD-1474 and 3116_A06 preceded by N-terminal extension sequence (GVSDVPRDL) and followed by a C-terminal tail (EI)] or SEQ ID NO: 331 [core Adnectin sequence of PRD-1474 and 3116_A06 without an N-terminal leader sequence or C-terminal tail]. In yet another embodiment, the polypeptide comprises an amino acid sequence at least 80%, 85%, 90%, 95%, 98%, 99% or 100% identical to the non-BC, DE, and FG loop regions of SEQ ID NO: 118, 273, 281, or 331.

In another aspect, the invention provides for polypeptides which bind to a discontinuous Adnectin binding site on myostatin. In some embodiments, the polypeptides bind a region within amino acids 55-66 of myostatin (SEQ ID NO: 3). In some embodiments, the polypeptides bind a region within amino acids 85-101 of myostatin (SEQ ID NO: 3). In yet other embodiments, the polypeptides binds within two regions, amino acids 85-101 and 55-66, of myostatin (SEQ ID NO: 3).

In some embodiments, the polypeptides of the invention do not compete for binding to myostatin with ActRIIB In some embodiments, the polypeptides of the invention compete for binding to myostatin with ALK4 and/or ALK5.

In some embodiments, the polypeptides described above may comprise one or more pharmacokinetic (PK) moieties such as polyethylene glycol, sialic acid, Fc, Fc fragment, transferrin, serum albumin, a serum albumin binding protein, and a serum immunoglobulin binding protein. In one embodiment, the PK moiety is a serum albumin binding protein that comprises an $^{10}$Fn3 domain which binds to, for example, HSA. In another embodiment, the PK moiety is Fc and can be on either the N- or C-terminus of the polypeptide, and optionally form a dimer. In yet other embodiments, the PK moiety is polyethylene glycol. In some embodiments, the PK moiety and polypeptide are linked via at least one disulfide bond, a peptide bond, a polypeptide, a polymeric sugar or a polyethylene glycol moiety.

In another aspect, the invention provides a pharmaceutical composition comprising a polypeptide described above, which is optionally endotoxin-free.

In another aspect, the invention provides an isolated nucleic acid molecule encoding a polypeptide described above, an expression vector comprising a nucleotide sequence, and a cell comprising the nucleic acid encoding the polypeptide. In another aspect, the invention provides a method of producing the anti-myostatin polypeptide by culturing the cell.

In another aspect, the invention provides a method of attenuating or inhibiting a myostatin-related disease or disorder in a subject by administering an effective amount of the polypeptide or composition comprising a polypeptide described above. In some embodiments, the disease to be treated is muscular dystrophy, amyotrophic lateral sclerosis, inclusion body myositis (IBM), congestive obstructive pulmonary disease, chronic heart failure, cancer, AIDs, renal failure, chronic kidney disease, uremia, rheumatoid arthritis, sarcopenia, muscle wasting due to prolonged bedrest, spinal cord injury, stroke, bone fracture, aging, diabetes, obesity, hyperglycemia, cachexia, osteoarthritis, osteoporosis, myocardial infarction, or fibrosis.

In another aspect, the invention provides a method of attenuating or inhibiting a disorder associated with degeneration or wasting of muscle in a subject.

In another aspect, the invention provides a method of administering the polypeptide to increase muscle mass, increase the number of muscle cells, increase the size of muscle cells, increase muscle strength, physical performance and/or endurance in the subject.

In another aspect, the invention provides a method of attenuating or inhibiting a metabolic disorder in a subject. In some embodiments, the metabolic disorder is diabetes (e.g., type II diabetes), hyperglycemia, hyperinsulinaemia, hyperlipidaemia, insulin resistance, impaired glucose metabolism, lipodystrophy, obesity, or metabolic syndrome. In some embodiments, a second therapeutic composition can be administered. In other embodiments, administration of the polypeptide results in increased insulin sensitivity, increased glucose uptake by cells, decreased blood glucose levels, and/or decreased body fat.

In another aspect, the invention provides a method for enhancing lean muscle mass in a subject comprising administering an effective amount of a polypeptide or composition described above.

In another aspect, the invention provides a method for increasing the ratio of lean muscle mass to fat in a subject comprising administering an effective amount of a polypeptide or composition described above.

In another aspect, the invention provides kits comprising a polypeptide or composition described above, and instructions for use.

In another aspect, the invention provides methods of detecting or measuring myostatin in a sample comprising contacting the sample with a polypeptide described above, and detecting or measuring binding of the polypeptide to myostatin.

In another aspect, the invention relates to anti-myostatin binding Adnectins for use in attenuating or inhibiting a myostatin-related disease or disorder, attenuating or inhibiting a disorder associated with degeneration or wasting of muscle, increasing muscle mass, increasing the number of muscle cells, increasing the size of muscle cells, increasing muscle strength, physical performance and/or endurance, attenuating or inhibiting a metabolic disorder, enhancing lean muscle mass, and/or increasing the ratio of lean muscle mass to fat, in a subject. In some embodiments, the anti-myostatin Adnectins are those described herein, e.g., the anti-myostatin Adnectins set forth in SEQ ID NOs: 80-123, 228-239, and 252-273.

In another aspect, the invention relates to the use of the anti-myostatin binding Adnectins for preparing a medicament for attenuating or inhibiting a myostatin-related disease or disorder, attenuating or inhibiting a disorder associated with degeneration or wasting of muscle, increasing muscle mass, increasing the number of muscle cells, increasing the size of muscle cells, increasing muscle strength, physical performance and/or endurance, attenuating or inhibiting a metabolic disorder, enhancing lean muscle mass, and/or increasing the ratio of lean muscle mass to fat, in a subject. In some embodiments, the anti-myostatin Adnectins are those described herein, e.g., the anti-myostatin Adnectins set forth in SEQ ID NOs: 80-123, 228-239, and 252-273.

BRIEF DESCRIPTION OF THE FIGURES

Figure 1:
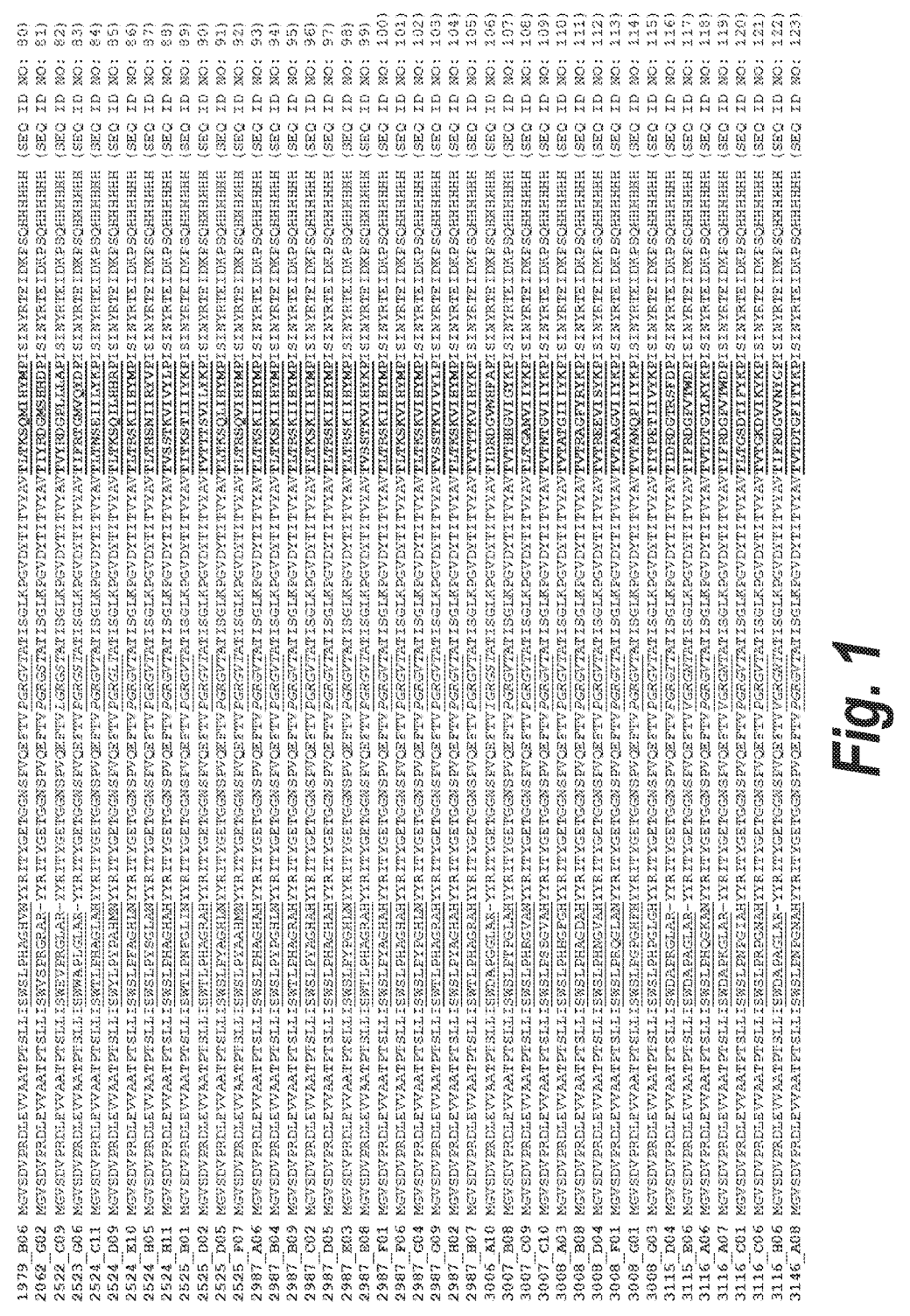

FIG. 1 shows an alignment of exemplary anti-myostatin Adnectin amino acid sequences. The BC, DE, and FG loop amino acid sequences are identified by underlining, italics/underlining or bold/underlining, respectively.

FIG. 13A shows the structure of myostatin alone (grey), with the ALK4 binding sites and ActRIIB binding sites indicated. The regions where 3116_A06 binds to myostatin (i.e., Regions 1 and 2) are indicated in black, as determined from experiments described in Example 11. FIG. 13B shows a preferred complex of 3116_A06 (black) and myostatin (grey) derived from a docking protocol as described in Example 12. Myostatin regions 1 and 2 as identified by HDX-MS (Example 11) are represented in space-fill on one side of the molecule only, and the BC, DE, and FG loops of 3116_A06 are represented in stick rendering. Although this figure shows one Adnectin bound to one of the two Adnectin binding sites, it should be noted that either individual Adnectin binding site, or both Adnectin binding sites, could be occupied.

DETAILED DESCRIPTION OF THE INVENTION

Definitions

Figure 2:
FIG. 2 depicts a WebLogo-based analysis of the varied residues of the BC loop of the 1979_B06 family of anti-myostatin Adnectins. Indicated is the frequency of amino acids in each position of the BC loop that were varied during PROfusion. The image was created using WebLogo (Crooks G E, Hon G, Chandonia J M, Brenner S E. WebLogo: A sequence logo generator. *Genome Research* 2004; 14:1188-1190).
Figure 3:
FIG. 3 depicts a WebLogo-based analysis of the varied residues of the DE loop of the 1979_B06 family of anti-myostatin Adnectins. Indicated is the frequency of amino acids in each position of the DE loop that were varied during PROfusion.
Figure 4:
FIG. 4 depicts a WebLogo-based analysis of the varied residues of the FG loop of the 1979_B06 family of anti-myostatin Adnectins. Indicated is the frequency of amino acids in each position of the FG loop that were varied during PROfusion.
Figure 5:
FIG. 5 depicts a WebLogo-based analysis of the varied residues of the BC loop of the 2062_G02 family of anti-myostatin Adnectins. Indicated is the frequency of amino acids in each position of the BC loop that were varied during PROfusion.
Figure 6:
FIG. 6 depicts a WebLogo-based analysis of the varied residues of the DE loop of the 2062_G02 family of anti-myostatin Adnectins. Indicated is the frequency of amino acids in each position of the DE loop that were varied during PROfusion.
Figure 7:
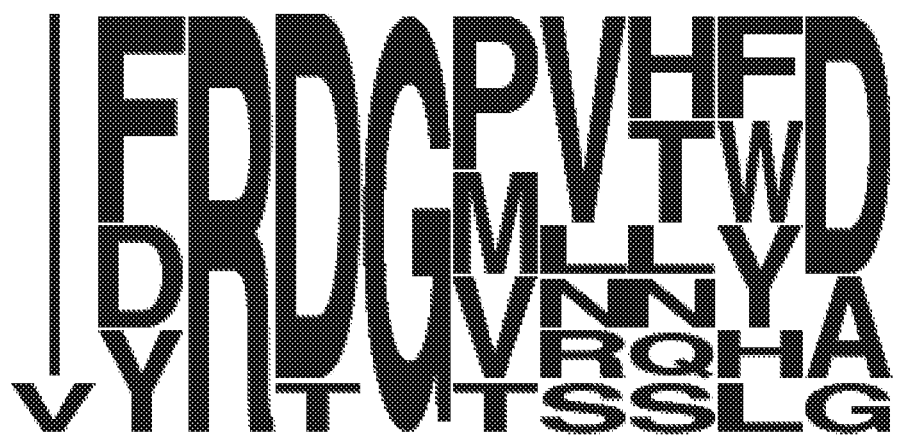
FIG. 7 depicts a WebLogo-based analysis of the varied residues of the FG loop of the 2062_G02 family of anti-myostatin Adnectins. Indicated is the frequency of amino acids in each position of the FG loop that were varied during PROfusion.
Figure 8:
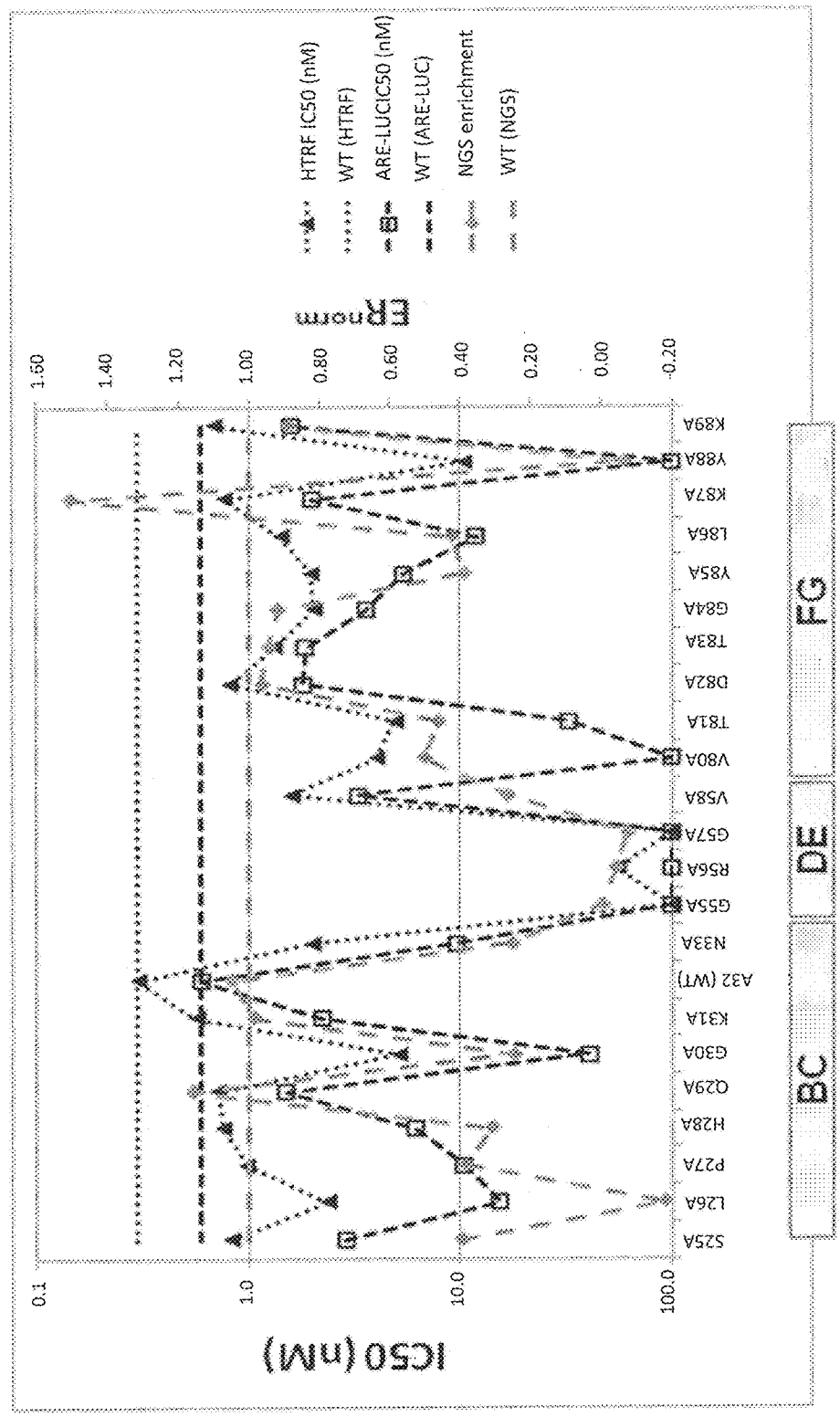
FIG. 8 depicts a graph showing the correlation of biochemical and cell-based data for discrete alanine mutant proteins of Adnectin 3116_A06, with their relative fitness in deep mutational scanning according to sequence position.
Figure 9:
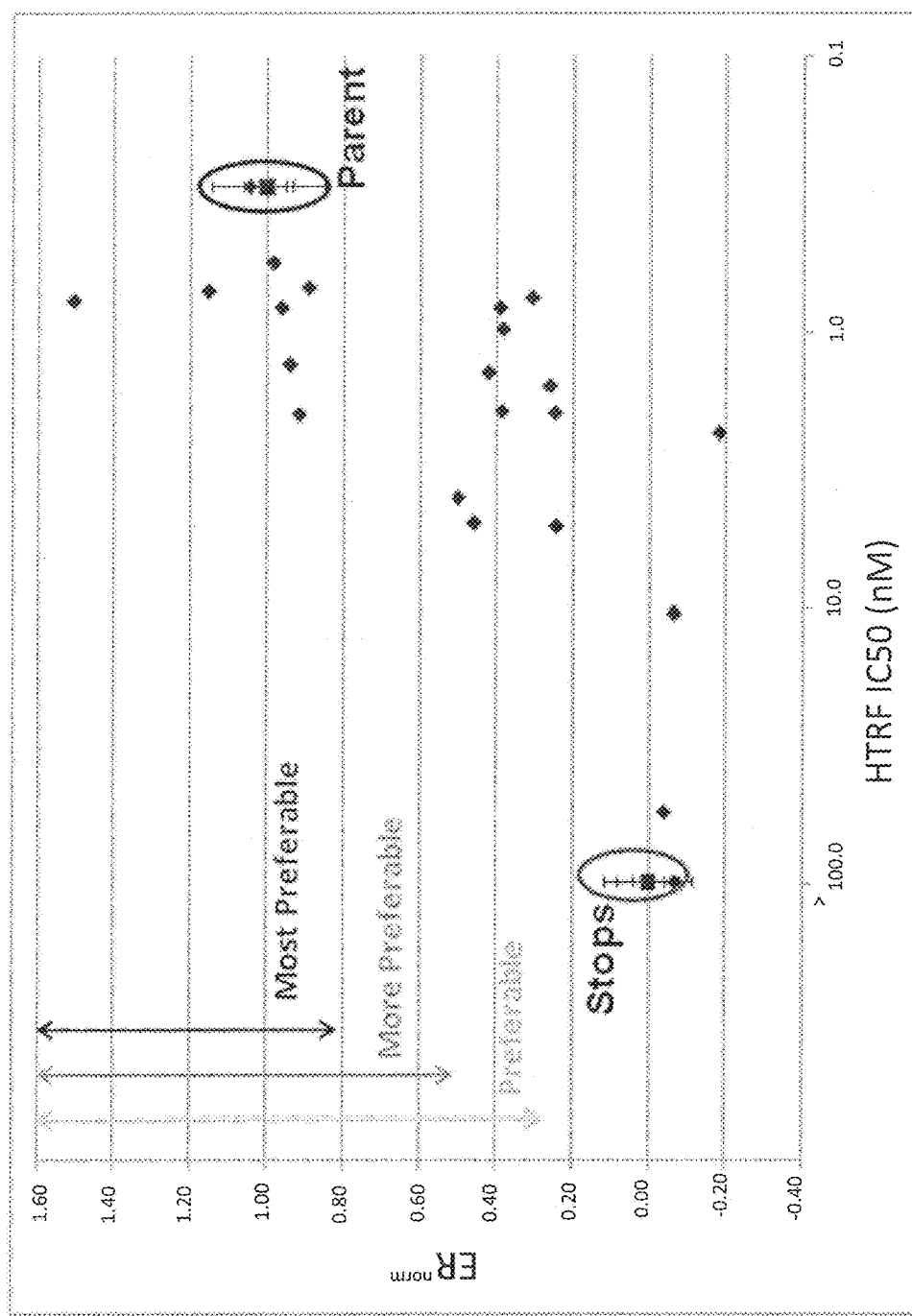
FIG. 9 depicts a graph showing the correlation of $ER^{norm}$ from NGS deep mutational scanning of alanine mutations of Adnectin 3116_A06 with the IC50 measured by HTRF. Bins for preferable, more preferable, and most preferable single site mutations for binding to myostatin are indicated.

Unless defined otherwise, all technical and scientific terms used herein have the same meaning as commonly understood by the skilled artisan. Although any methods and compositions similar or equivalent to those described herein can be used in practice or testing of the present invention, the preferred methods and compositions are described herein.

"Full-length myostatin" as used herein refers to the full length polypeptide sequence described in McPherron et al. (1997), supra, as well as related full-length polypeptides including allelic variants and interspecies homologs. The term "myostatin" or "mature myostatin" refers to fragments of the biologically active mature myostatin, as well as related polypeptides including allelic variants, splice variants, and fusion peptides and polypeptides. The mature C-terminal protein has been reported to have 100% sequence identity among many species including human, mouse, chicken, porcine, turkey, and rat (Lee et al., PNAS 2001; 98:9306). The sequence for human prepromyostatin is:

```
                                          (SEQ ID NO: 1)
MQKLQLCVYIYLFMLIVAGPVDLNENSEQKENVEKEGLCNACTWRQNTKS

SRIEAIKIQILSKLRLETAPNISKDVIRQLLPKAPPLRELIDQYDVQRDD

SSDGSLEDDDYHATTETIITMPTESDFLMQVDGKPKCCFFKFSSKIQYNK

VVKAQLWIYLRPVETPTTVFVQILRLIKPMKDGTRYTGIRSLKLDMNPGT

GIWQSIDVKTVLQNWLKQPESNLGIEIKALDENGHDLAVTFPGPGEDGLN

PFLEVKVTDTPKRSRRDFGLDCDEHSTESRCCRYPLTVDFEAFGWDWIIA

PKRYKANYCSGECEFVFLQKYPHTHLVHQANPRGSAGPCCTPTKMSPINM

LYFNGKEQIIYGKIPAMVVDRCGCS
```

The sequence for human pro-myostatin is:

(SEQ ID NO: 2)
NENSEQKENVEKEGLCNACTWRQNTKSSRIEAIKIQILSKLRLETAPNIS

KDVIRQLLPKAPPLRELIDQYDVQRDDSSDGSLEDDDYHATTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS

The sequence for mature myostatin (conserved in human, murine, rat, chicken, turkey, dog, horse, and pig) is:

(SEQ ID NO: 3)
DFGLDCDEHSTESRCCRYPLTVDFEAFGWDWIIAPKRYKANYCSGECEFV

FLQKYPHTHLVHQANPRGSAGPCCTPTKMSPINMLYFNGKEQIIYGKIPA

MVVDRCGCS.

"Polypeptide" as used herein refers to any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D). The peptides of the invention are proteins derived from the tenth type III domain of fibronectin that have been modified to bind to myostatin and are referred to herein as, "anti-myostatin Adnectin" or "myostatin Adnectin."

A "polypeptide chain", as used herein, refers to a polypeptide wherein each of the domains thereof is joined to other domain(s) by peptide bond(s), as opposed to non-covalent interactions or disulfide bonds.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or nonreducing condition using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR™) software. Those skilled in the art can readily determine appropriate parameters for measuring alignment, including any algorithms needed to achieve maximal alignment over the full-length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, "conservative substitution" denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. By "substituted" or "modified" the present invention includes those amino acids that have been altered or modified from naturally occurring amino acids. As such it should be understood that in the context of the present invention a conservative substitution is recognized in the art as a substitution of one amino acid for another amino acid that has similar properties.

As used herein, the term "Adnectin binding site" refers to the site or portion of a protein (e.g., myostatin) that interacts or binds to a particular Adnectin (e.g., as an epitope is recognized by an antibody). Adnectin binding sites can be formed from contiguous amino acids or noncontiguous amino acids juxtaposed by tertiary folding of a protein. Adnectin binding sites formed by contiguous amino acids are typically retained on exposure to denaturing solvents, whereas Adnectin binding sites formed by tertiary folding are typically lost on treatment of denaturing solvents.

An Adnectin binding site for an anti-myostatin Adnectin of the invention may be determined by application of standard techniques typically used for epitope mapping of antibodies including, but not limited to protease mapping and mutational analysis. Alternatively, an Adnectin binding site can be determined by competition assay using a reference Adnectin or antibody which binds to the same polypeptide, e.g., myostatin (as further described infra in the section "Cross-Competing Adnectins and/or Adnectins that Bind to the Same Adnectin Binding Site." If the test Adnectin and reference molecule (e.g., another Adnectin or antibody) compete, then they bind to the same Adnectin binding site or to Adnectin binding sites sufficiently proximal such that binding of one molecule interferes with the other.

The terms "specifically binds," "specific binding," "selective binding," and "selectively binds," as used interchangeably herein refers to an Adnectin that exhibits affinity for a myostatin, but does not significantly bind (e.g., less than about 10% binding) to a different polypeptide as measured by a technique available in the art such as, but not limited to, Scatchard analysis and/or competitive binding assays (e.g., competition ELISA, BIACORE assay). The term is also applicable where e.g., a binding domain of an Adnectin of the invention is specific for myostatin.

The term "preferentially binds" as used herein refers to the situation in which an Adnectin of the invention binds myostatin at least about 20% greater than it binds a different polypeptide as measured by a technique available in the art such as, but not limited to, Scatchard analysis and/or competitive binding assays (e.g., competition ELISA, BIACORE assay).

As used herein, the term "cross-reactivity" refers to an Adnectin which binds to more than one distinct protein having identical or very similar Adnectin binding sites.

The term "$K_D$," as used herein, is intended to refer to the dissociation equilibrium constant of a particular Adnectin-protein (e.g., myostatin) interaction or the affinity of an Adnectin for a protein (e.g., myostatin), as measured using a surface plasmon resonance assay or a cell binding assay. A "desired $K_D$," as used herein, refers to a $K_D$ of an Adnectin that is sufficient for the purposes contemplated. For example, a desired $K_D$ may refer to the $K_D$ of an Adnectin required to elicit a functional effect in an in vitro assay, e.g., a cell-based luciferase assay.

The term "$k_{ass}$", as used herein, is intended to refer to the association rate constant for the association of an Adnectin into the Adnectin/protein complex.

The term "$k_{diss}$", as used herein, is intended to refer to the dissociation rate constant for the dissociation of an Adnectin from the Adnectin/protein complex.

The term "$IC_{50}$", as used herein, refers to the concentration of an Adnectin that inhibits a response, either in an in vitro or an in vivo assay, to a level that is 50% of the maximal inhibitory response, i.e., halfway between the maximal inhibitory response and the untreated response.

The term "myostatin activity" as used herein refers to one or more of growth-regulatory or morphogenetic activities associated with the binding of active myostatin protein to ActRIIb and the subsequent recruitment of Alk4 or Alk5 For example, active myostatin is a negative regulator of skeletal muscle mass. Active myostatin can also modulate the production of muscle-specific enzymes (e.g., creatine kinase), stimulate myoblast proliferation, and modulate preadipocyte differentiation to adipocytes. Myostatin activity can be determined using art-recognized methods, such as those described herein.

The phrases "inhibit myostatin activity" or "antagonize myostatin activity" or "antagonize myostatin" are used interchangeably to refer to the ability of the anti-myostatin Adnectins of the present invention to neutralize or antagonize an activity of myostatin in vivo or in vitro. The terms "inhibit" or "neutralize" as used herein with respect to an activity of an Adnectin of the invention means the ability to substantially antagonize, prohibit, prevent, restrain, slow, disrupt, eliminate, stop, reduce or reverse e.g., progression or severity of that which is being inhibited including, but not limited to, a biological activity or property, a disease or a condition. The inhibition or neutralization is preferably at least about 10%, 20%, 30%, 40%, 50%, 60%, 70%, 80%, 90%, 95% or higher.

For example, an anti-myostatin Adnectin of the invention may reduce circulating levels of biologically active myostatin normally found in a vertebrate subject, or a reduction of circulating levels of biologically active myostatin in subjects with disorders that result in elevated circulating levels of myostatin. A reduction of myostatin activity may be determined using in vitro assays, e.g., binding assays, as described herein. Alternatively, a reduction in myostatin activity may result in an increase in body weight, enhanced muscle mass, increased muscle strength, an alteration in the ratio of muscle to fat, an increase in fat-free muscle mass, an increase in the size and/or number of muscle cells, and/or a reduction in body fat content.

The term "PK" is an acronym for "pharmacokinetic" and encompasses properties of a compound including, by way of example, absorption, distribution, metabolism, and elimination by a subject. A "PK modulation protein" or "PK moiety" as used herein refers to any protein, peptide, or moiety that affects the pharmacokinetic properties of a biologically active molecule when fused to or administered together with the biologically active molecule. Examples of a PK modulation protein or PK moiety include PEG, human serum albumin (HSA) binders (as disclosed in U.S. Publication Nos. 2005/0287153 and 2007/0003549, PCT Publication Nos. WO 2009/083804 and WO 2009/133208), human serum albumin, Fc or Fc fragments and variants thereof, and sugars (e.g., sialic acid).

The "half-life" of an amino acid sequence or compound can generally be defined as the time taken for the serum concentration of the polypeptide to be reduced by 50%, in vivo, for example due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may for example generally involve the steps of suitably administering to a subject a suitable dose of the amino acid sequence or compound of the invention; collecting blood samples or other samples from the subject at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Reference is, for example, made to the standard handbooks, such as Kenneth, A. et al., Chemical Stability of Pharmaceuticals: A Handbook for Pharmacists and in Peters et al., Pharmacokinete Analysis: A Practical Approach (1996). Reference is also made to Gibaldi, M. et al., Pharmacokinetics, 2nd Rev. Edition, Marcel Dekker (1982).

Half-life can be expressed using parameters such as the $t_{1/2}$-alpha, $t_{1/2}$-beta, HL_Lambda_z, and the area under the curve (AUC). In the present specification, an "increase in half-life" refers to an increase in any one of these parameters, any two of these parameters, any three of these parameters or all four of these parameters. An "increase in half-life" in particular refers to an increase in the $t_{1/2}$-beta, and/or HL_Lambda_z, either with or without an increase in the $t_{1/2}$-alpha and/or the AUC or both.

The notations "mpk", "mg/kg", or "mg per kg" refer to milligrams per kilogram. All notations are used interchangeably throughout the present disclosure.

The terms "individual," "subject," and "patient," used interchangeably herein, refer to an animal, preferably a mammalian (including a nonprimate and a primate) or avian species, including, but not limited to, murines, simians, humans, mammalian farm animals (e.g., bovine, porcine, ovine), mammalian sport animals (e.g., equine), and mammalian pets (e.g., canine and feline); preferably the term refers to humans. The term also refers to avian species, including, but not limited to, chickens and turkeys. In a certain embodiment, the subject, preferably a mammal, preferably a human, is further characterized with a disease or disorder or condition that would benefit from a decreased level or decreased bioactivity of myostatin. In another embodiment the subject, preferably a mammal, preferably a human, is further characterized as being at risk of developing a disorder, disease or condition that would benefit from a decreased level of myostatin or a decreased bioactivity of myostatin.

The term "therapeutically effective amount" refers to at least the minimal dose, but less than a toxic dose, of an agent which is necessary to impart a therapeutic benefit to a subject. For example, a therapeutically effective amount of an anti-myostatin Adnectin of the invention is an amount which in mammals, preferably humans, results in one or more of the following: an increase in muscle volume and/or muscle strength, a decrease in body fat, an increase in insulin sensitivity, or the treatment of conditions wherein the presence of myostatin causes or contributes to an undesirable pathological effect or a decrease in myostatin levels results in a beneficial therapeutic effect.

The term "frail" or "frailty" as used herein refers to a condition that can be characterized by two or more symptoms from weakness, weight loss, slowed mobility, fatigue, low activity levels, poor endurance, and impaired behavioral response to sensory cues. One hallmark of frailty is "sarcopenia," or the age-related loss of muscle mass.

The term "cachexia" as used herein refers to the condition of accelerated muscle wasting and loss of lean body mass that can result from various diseases.

Overview

The present invention provides novel polypeptides that bind to and antagonize myostatin (herein referred to as "anti-myostatin Adnectins"). In order to identify myostatin antagonists, myostatin was presented to large synthetic libraries of Adnectins. Adnectins that bound to myostatin were screened for myostatin binding, for biophysical properties, and for myostatin inhibitory activity. The anti-myostatin Adnectins were mutated and subjected to further selective pressure by lowering the target concentration and selecting for anti-myostatin Adnectins with slow off-rates. From this optimization process, a family of Adnectins was identified as myostatin specific inhibitors with favorable biochemical and biophysical activity. The anti-myostatin Adnectins disclosed in the present application are useful for the treatment of disorders, diseases, and conditions for which inhibition of myostatin activity is known to be beneficial, including, but not limited to, the treatment of muscle wasting diseases, metabolic disorders, and muscle atrophy due to inactivity.

As disclosed in Rebbapragada et al. (*MCB* 2003; 23:7230-42), the myostatin signaling pathway involves binding of myostatin to ActRIIb, followed by recruitment of activin receptor-like kinase 4 (ALK4) or ALK5. Binding to the ALKs induces Smad2/Smad3 phosphorylation, followed by activation of the TGFβ-like signaling pathway (see, e.g., Rebbapragada et al., *MCB* 2003; 23:7230-42).

I. Fibronectin Based Scaffolds

One aspect of the application provides anti-myostatin Adnectins comprising an Fn3 domain in which one or more of the solvent accessible loops has been randomized or mutated. In some embodiments, the Fn3 domain is an Fn3 domain derived from the wild-type tenth module of the human fibronectin type III domain ($^{10}$Fn3):

(SEQ ID NO: 4)
VSDVPRDLEVVAATPTSLLI<u>SWDAPAVTVR</u>YYRITYGETGGNSPVQEFTV

<u>PGSKSTATISGLKPGVDYTITVYAVTGRGDSPASSKP</u>ISINYRT (BC,
DE, and FG loops are underlined).

In other embodiments, the non-ligand binding sequences of $^{10}$Fn3, i.e., the "$^{10}$Fn3 scaffold", may be altered provided that the $^{10}$Fn3 retains ligand binding function and/or structural stability. A variety of mutant $^{10}$Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (see, e.g., PCT Publication No. WO 02/04523). A variety of additional alterations in the $^{10}$Fn3 scaffold that are either beneficial or neutral have been disclosed. See, for example, Batori et al., Protein Eng., 15(12):1015-1020 (December 2002); Koide et al., Biochemistry, 40(34):10326-10333 (Aug. 28, 2001).

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO:4, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87 (Xu et al., *Chemistry & Biology*, 9:933-942, 2002).

Accordingly, in some embodiments, the anti-myostatin Adnectin is an $^{10}$Fn3 polypeptide that is at least 40%, 50%, 60%, 65%, 70%, 75%, 80%, 85%, or 90% identical to the human $^{10}$Fn3 domain, shown in SEQ ID NO:4. Much of the variability will generally occur in one or more of the loops. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO:4, provided that such variation does not disrupt the stability of the polypeptide in physiological conditions.

In some embodiments, the invention provides an anti-myostatin Adnectin comprising a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain. In some embodiments, the anti-myostatin Adnectins of the present invention comprise an $^{10}$Fn3 domain comprising an amino acid sequence at least 80%, 85%, 90%, 95%, 98%, 99% or 100% identical to the non-loop regions of SEQ ID NO:4, wherein at least one loop selected from BC, DE, and FG is altered. In some embodiments, the BC and FG loops are altered, and in some embodiments, the BC, DE, and FG loops are altered, i.e., the $^{10}$Fn3 domains comprise non-naturally occurring loops. In some embodiments, the AB, CD and/or the EF loops are altered. By "altered" is meant one or more amino acid sequence alterations relative to a template sequence (corresponding human fibronectin domain) and includes amino acid additions, deletions, substitutions or a combination thereof. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In some embodiments, one or more loops selected from BC, DE, and FG may be extended or shortened in length relative to the corresponding human fibronectin loop. In some embodiments, the length of the loop may be extended by 2-25 amino acids. In some embodiments, the length of the loop may be decreased by 1-11 amino acids. To optimize antigen binding, therefore, the length of a loop of $^{10}$Fn3 may be altered in length as well as in sequence to obtain the greatest possible flexibility and affinity in antigen binding.

In some embodiments, the polypeptide comprises a Fn3 domain that comprises an amino acid sequence at least 80, 85, 90, 95, 98, 99, or 100% identical to the non-loop regions of SEQ ID NO: 4, wherein at least one loop selected from BC, DE, and FG is altered. In some embodiments, the altered BC loop has up to 1, 2, 3, 4, 5, 6, 7, 8, 9, or 10 amino acid substitutions, up to 1, 2, 3, or 4 amino acid deletions, up to 1, 2, 3, 4, 5, 6, 7, 8, 9, or 10 amino acid insertions, or a combination thereof. In some embodiments, the altered DE loop has up to 1, 2, 3, 4, 5, or 6 amino acid substitutions, up to 1, 2, 3, or 4 amino acid deletions, up to 1, 2, 3, 4, 5, 6, 7, 8, 9, 10, 11, 12, or 13 amino acid insertions, or a combination thereof. In some embodiments, the FG loop has up to 1, 2, 3, 4, 5, 6, 7, 8, 9, 10, 11, or 12 amino acid substitutions, up to 1, 2, 3, 4, 5, 6, 7, 8, 9, 10, or 11 amino acid deletions, up to 1, 2, 3, 4, 5, 6, 7, 8, 9, 10, 11, 12, 13, 14, 15, 16, 17, 18, 19, 20, 21, 22, 23, 24, or 25 amino acid insertions, or a combination thereof.

The anti-myostatin Adnectins of the invention are based on an $^{10}$Fn3 scaffold and are defined generally by the following sequence:

(SEQ ID NO: 5)
EVVAAT(Z)$_a$SLLI(Z)$_x$YYRITYGE(Z)$_b$QEFTV(Z)$_y$ATI(Z)$_c$DYTI

TVYAV(Z)$_z$ISINYRT, wherein the AB loop is represented by (Z)$_a$, the CD loop is represented by (Z)$_b$, the EF loop is represented by (Z)$_e$, the BC loop is represented by (Z)$_x$, the DE loop is represented by (Z)$_y$, and the FG loop is represented by (Z)$_z$. Z represents any amino acid and the subscript following the Z represents an integer of the number of amino acids. In particular, a may be anywhere from 1-15, 2-15, 1-10, 2-10, 1-8, 2-8, 1-5, 2-5, 1-4, 2-4, 1-3, 2-3, or 1-2 amino acids; and b, c, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, a is 2 amino acids, b is 7 amino acids, c is 7 amino acids, x is 11 amino acids, y is 6 amino acids, and z is 12 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 4. In certain embodiments, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 4. In certain embodiments, the core amino acid residues are fixed and any substitutions, conservative substitutions, deletions or additions occur at residues other than the core amino acid residues.

Alternatively, the anti-myostatin Adnectins of the invention are based on an $^{10}$Fn3 scaffold and are defined generally by the sequence:

(SEQ ID NO: 6)
EVVAATPTSLLI(Z)$_x$YYRITYGETGGNSPVQEFTV(Z)$_y$ATISGLKPGV

DYTITVYAV(Z)$_z$ISINYRT wherein the BC loop is represented by (Z)$_x$, the DE loop is represented by (Z)$_y$, and the FG loop is represented by (Z)$_z$. Z represents any amino acid and the subscript following the Z represents an integer of the number of amino acids. In particular, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, x is 11 amino acids, y is 6 amino acids, and z is 12 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In certain embodiments, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 4. In certain embodiments, the core amino acid residues are fixed and any substitutions, conservative substitutions, deletions or additions occur at residues other than the core amino acid residues.

In certain embodiments, an anti-myostatin Adnectin described herein may comprise the sequence as set forth in SEQ ID NO: 5 or 6, wherein at least one of BC, DE, and FG loops as represented by (Z)$_x$, (Z)$_y$, and (Z)$_z$, respectively, are altered. As described above, amino acid residues corresponding to residues 21-30, 51-56, and 76-87 of SEQ ID NO: 4 define the BC, DE, and FG loops, respectively. However, it should be understood that not every residue within the loop region needs to be modified in order to achieve a $^{10}$Fn3 binder having strong affinity for a desired target (e.g., myostatin).

For example, residues 21 (S) and 22 (W) of the BC loop as shown in SEQ ID NO: 1 do not need to be modified for binding to myostatin. That is, $^{10}$Fn3 domains with high affinity binding to myostatin may be obtained by modifying only residues 23-30 of loop BC as shown in SEQ ID NO: 4. This is demonstrated in the BC loops exemplified in Table 1, which indicates that only the underlined positions are modified.

Similarly, positions 51 (P) and 56 (T) of loop DE as shown in SEQ ID NO: 4 do not need to be modified for binding myostatin. That is, $^{10}$Fn3 domains with high affinity binding to myostatin may be obtained by modifying only residues 52-55 of loop DE as shown in SEQ ID NO: 4. This is demonstrated in the DE loops exemplified in Table 1, which indicates that only resides spanning the underlined positions were altered.

Likewise, positions 76 (T) and 87 (P) of the FG loop as shown in SEQ ID NO: 1 do not need to be modified for binding myostatin. That is, $^{10}$Fn3 domains with high affinity binding to myostatin may be obtained by modifying only residues 77-86 of loop FG as shown in SEQ ID NO: 4. This is demonstrated in the FG loops exemplified in Table 1, which indicates that only the residues spanning the underlined positions were altered.

Accordingly, in some embodiments, the BC, DE, and FG loop regions of the anti-myostatin Adnectins of the invention can be described according to consensus sequences. These consensus sequences are exemplified by the BC, DE, and FG loops shown in Table 1, and as determined by WebLogo analysis (FIGS. 2-7) (Crooks G E, Hon G, Chandonia J M, Brenner S E. WebLogo: A sequence logo generator. *Genome Research* 2004; 14:1188-1190, herein incorporated by reference in its entirety). WebLogo analysis generates an amino acid signature reflecting the frequency of amino acids in each altered position of the BC, DE, or FG loop.

For example, in some embodiments, the BC loop, $(Z)_x$, is defined by the consensus sequence $X_1$-L-P-$X_2$-$X_3$-$X_4$-$X_5$-$X_6$-$X_7$, wherein, $X_1$ is S, T or Y; $X_2$ is H, Y, N, R, F, G, S or T; $X_3$ is A, P, Q, 5, F, H, N or R; $X_4$ is G or A; $X_5$ H, L, R, V, N, D, F, I or K; $X_6$ is A, L, G, M, F, I or V; and $X_7$ is H or N. In certain preferred embodiments, the BC loop comprises an amino acid sequence selected from SEQ ID NOs: 7, 11-21, 23-31, 34, and 36-38. In one embodiment, the BC loop comprises the amino acid set forth in SEQ ID NO. 34.

In some embodiments, the DE loop, $(Z)_y$, is defined by the consensus sequence G-R-G-$X_8$, wherein $X_8$ is V or L. In certain preferred embodiments, the DE loop comprises an amino acid selected from SEQ ID NOs: 39 and 42. In one embodiment, the DE loop comprises the amino acid set forth in SEQ ID NO. 39.

In some embodiments, the FG loop, $(Z)_z$, is defined by consensus sequence $X_9$-$X_{10}$-$X_{ii}$-$X_{12}$-$X_{13}$-$X_{14}$-$X_{15}$-$X_{16}$-$X_{17}$-$X_{18}$, wherein $X_9$ is L, V or I; $X_{10}$ is T or S; $X_{11}$ is K, R, A, G, S, D, H, N, T or P; $X_{12}$ is S, T, A, E, H, K or N; $X_{13}$ is K, G, Q, D, E, N, T or S; $X_{14}$ is V, I, F, L, M, P, T or Y; $X_{15}$ is I, L or Y; $X_{16}$ is H, I, V, K, L, R, F, G, S or T; $X_{17}$ is Y or H; and $X_{18}$ is K, M, L, R or V. In certain preferred embodiments, the FG loop comprises an amino acid sequence selected from SEQ ID NOs: 46, 50-62, 64-72, 75-77, and 79. In one embodiment, the FG loop comprises the amino acid set forth in SEQ ID NO. 75.

In other embodiments, the BC loop, $(Z)_x$, is defined by the consensus sequence $X_{19}$-$X_{20}$-P-$X_{21}$-G-$X_{22}$-A, wherein $X_{19}$ is D, E, V or W; $X_{20}$ is A, S or V; $X_{21}$ is R, A, G, K or L; and $X_{22}$ is L or R. In certain preferred embodiments, the BC loop comprises an amino acid sequence selected from SEQ ID NOs: 8-10, 22, 32, 33, and 35.

In other embodiments, the DE loop, $(Z)_y$, is defined by the consensus sequence $X_{23}$-G-R-G-$X_{24}$, wherein $X_{23}$ is V, P, F, I or L; and $X_{24}$ is S, N or T. In certain preferred embodiments, the DE loop comprises and amino acid sequence selected from SEQ ID NOs: 40, 41, and 43-45.

In other embodiments, the FG loop, $(Z)_z$, is defined by the consensus sequence $X_{25}$-$X_{26}$-R-$X_{27}$-G-$X_{28}$-$X_{29}$-$X_{30}$-$X_{31}$-$X_{32}$, wherein $X_{25}$ is I or V; $X_{26}$ is F, D or Y; $X_{27}$ is D or T; $X_{28}$ is P, M, V or T; $X_{29}$ is V, L, N, R or S; $X_{30}$ is H, T, L, N, Q or S; $X_{31}$ is F, W, Y, H or L; and $X_{32}$ is D, A or G. In certain preferred embodiments the FG loop comprises an amino acid sequence selected from SEQ ID NOs: 47-49, 63, 73, 74, and 78.

Accordingly, in certain embodiments the invention provides an anti-myostatin Adnectin comprising a BC loop, $(Z)_x$, having the sequence $X_1$-L-P-$X_2$-$X_3$-$X_4$-$X_5$-$X_6$-$X_7$ and a DE loop, $(Z)_y$, having the sequence G-R-G-$X_8$, as defined above. In certain embodiments, the BC loop comprises an amino acid sequence selected from SEQ ID NOs: 7, 11-21, 23-31, 34, and 36-38, and the DE loop comprises an amino acid sequence selected from SEQ ID NOs: 39 and 42. In one embodiment, the BC and DE loops comprise the amino acid sequences set forth in SEQ ID NOs: 34 and 39, respectively.

In certain embodiments, the anti-myostatin Adnectin comprises a BC loop, $(Z)_x$, having the sequence $X_1$-L-P-$X_2$-$X_3$-$X_4$-$X_5$-$X_6$-$X_7$ and an FG loop, $(Z)_z$, having the sequence $X_9$-$X_{10}$-$X_{ii}$-$X_{12}$-$X_{13}$-$X_{14}$-$X_{15}$-$X_{16}$-$X_{17}$-$X_{18}$, as defined above. In certain embodiments, the BC loop comprises an amino acid sequence selected from SEQ ID NOs: 7, 11-21, 23-31, 34, and 36-38, and the FG loop comprises an amino acid sequence selected from SEQ ID NOs: 46, 50-62, 64-72, 75-77, and 79. In one embodiment, the BC and FG loops comprise the amino acid sequences set forth in SEQ ID NOs: 34 and 75, respectively.

In certain embodiments the anti-myostatin Adnectin comprises a DE loop, $(Z)_y$, having the sequence G-R-G-$X_8$ and an FG loop, $(Z)_z$, having the sequence $X_9$-$X_{10}$-$X_{ii}$-$X_{12}$-$X_{13}$-$X_{14}$-$X_{15}$-$X_{16}$-$X_{17}$-$X_{18}$, as defined above. In certain embodiments, the DE loop comprises an amino acid sequence selected from SEQ ID NOs: 39 and 42, and the FG loop comprises an amino acid sequence selected from SEQ ID NOs: 46, 50-62, 64-72, 75-77, and 79. In one embodiment, the DE and FG loops comprise the amino acid sequences set forth in SEQ ID NOs: 39 and 75, respectively.

In certain embodiments, the anti-myostatin Adnectin comprises a BC loop, $(Z)_x$, having the sequence $X_1$-L-P-$X_2$-$X_3$-$X_4$-$X_5$-$X_6$-$X_7$, a DE loop, $(Z)_y$, having the sequence G-R-G-$X_8$ and an FG loop, $(Z)_z$, having the sequence $X_9$-$X_{10}$-$X_{11}$-$X_{12}$-$X_{13}$-$X_{14}$-$X_{15}$-$X_{16}$-$X_{17}$-$X_{18}$, as defined above. In certain embodiments, the BC loop comprises an amino acid sequence selected from SEQ ID NOs: 7, 11-21, 23-31, 34, and 36-38, the DE loop comprises an amino acid sequence selected from SEQ ID NOs: 39 and 42, and the FG loop comprises an amino acid sequence selected from SEQ ID NOs: 46, 50-62, 64-72, 75-77, and 79. In one embodiment, the BC, DE, and FG loops comprise the amino acid sequences set forth in SEQ ID NOs: 34, 39, and 75, respectively.

In other embodiments, the invention provides an anti-myostatin Adnectin comprising a BC loop, $(Z)_x$, having the sequence $X_{19}$-$X_{20}$-P-$X_{21}$-G-$X_{22}$-A and a DE loop, $(Z)_y$, having the sequence $X_{23}$-G-R-G-$X_{24}$, as defined above. In certain embodiments, the BC loop comprises an amino acid sequence selected from SEQ ID NOs: 8-10, 22, 32, 33, and 35 and the DE loop comprises an amino acid sequence selected from SEQ ID NOs: 40, 41, and 43-45.

In other embodiments, the anti-myostatin Adnectin comprises a BC loop, $(Z)_x$, having the sequence $X_{19}$-$X_{20}$-P-$X_{21}$-G-$X_{22}$-A and an FG loop, $(Z)_z$, having the sequence $X_{25}$-$X_{26}$-R-$X_{27}$-G-$X_{28}$-$X_{29}$-$X_{30}$-$X_{30}$-$X_{32}$, as defined above. In certain embodiments, the BC loop comprises an amino acid sequence selected from SEQ ID NOs: 8-10, 22, 32, 33, and 35 and the FG loop comprises an amino acid sequence selected from SEQ ID NOs: 47-49, 63, 73, 74, and 78.

In other embodiments, the anti-myostatin Adnectin comprises a DE loop, $(Z)_y$, having the sequence $X_{23}$-G-R-G-$X_{24}$ and an FG loop, $(Z)_z$, having the sequence $X_{25}$-$X_{26}$-R-$X_{27}$-G-$X_{28}$-$X_{29}$-$X_{30}$-$X_{30}$-$X_{32}$, as defined above. In certain embodiments, the DE loop comprises an amino acid sequence selected from SEQ ID NOs: 40, 41, and 43-45 and the FG loop comprises an amino acid sequence selected from SEQ ID NOs: 47-49, 63, 73, 74, and 78.

In other embodiments, the anti-myostatin Adnectin comprises a BC loop, $(Z)_x$, having the sequence $X_{19}$-$X_{20}$-P-$X_{21}$-G-$X_{22}$-A, comprises a DE loop, $(Z)_y$, having the sequence $X_{23}$-G-R-G-$X_{24}$ and an FG loop, $(Z)_z$, having the sequence $X_{25}$-$X_{26}$-R-$X_{27}$-G-$X_{28}$-$X_{29}$-$X_{30}$-$X_{30}$-$X_{32}$, as defined above. In certain embodiments, the BC loop comprises an amino acid sequence selected from SEQ ID NOs: 8-10, 22, 32, 33, and 35, the DE loop comprises an amino acid sequence selected from SEQ ID NOs: 40, 41, and 43-45, and the FG loop comprises an amino acid sequence selected from SEQ ID NOs: 47-49, 63, 73, 74, and 78.

In certain preferred embodiments, an anti-myostatin Adnectin of the invention comprises the sequence set forth in SEQ ID NO: 5 or 6, wherein BC, DE and FG loops as represented by $(Z)_x$, $(Z)_y$, and $(Z)_z$, respectively, are replaced with a respective set of BC, DE, and FG loops having the consensus sequences of SEQ ID NOs: 7-38, 39-45, and 46-79, respectively.

In other preferred embodiments, an anti-myostatin Adnectin of the invention comprises the sequence set forth in SEQ ID NO: 5 or 6, wherein BC, DE and FG loops as represented by $(Z)_x$, $(Z)_y$, and $(Z)_z$, respectively, are replaced with a respective set of BC, DE, and FG loops having sequences at least 75%, 80%, 85%, 90%, 95%, 97%, 98%, or 99% identical to the BC, DE or FG loop sequences of the clones listed in Table 1.

In exemplary embodiments, an anti-myostatin Adnectin as described herein is defined by SEQ ID NO: 5 and has a respective set of BC, DE and FG loop sequences from any of the clones listed in Table 1. For example, clone 1979_B06 in Table 1 comprises BC, DE, and FG loops as set forth in SEQ ID NOs: 7, 39, and 46, respectively. Therefore, an anti-myostatin Adnectin based on these loops may comprise SEQ ID NO: 5 or 6, wherein $(Z)_x$ comprises SEQ ID NO: 7, $(Z)_y$ comprises SEQ ID NO: 39, and $(Z)_z$ comprises SEQ ID NO: 46. Similar constructs are contemplated utilizing the set of BC, DE and FG loops from the other clones in Table 1, or the consensus sequences of SEQ ID NOs: 7-38, 39-45, and 46-79, respectively. The scaffold regions of such anti-myostatin Adnectins may comprise anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acids residues of SEQ ID NO: 4. Such scaffold modifications may be made, so long as the anti-myostatin Adnectin is capable of binding myostatin with a desired $K_D$.

In preferred embodiments, the BC loop of the anti-myostatin Adnectin of the invention comprises an amino acid sequence selected from the group consisting of: SWSLPHAGHVN (SEQ ID NO: 7), SWVSPRGRAR (SEQ ID NO: 8), SWEVPRGLAR (SEQ ID NO: 9), SWWAPLGLAR (SEQ ID NO: 10), SWTLPHAGLAH (SEQ ID NO: 11), SWYLPYPAHMN (SEQ ID NO: 12), SWSLPFAGHLN (SEQ ID NO: 13), SWSLPYSGLAN (SEQ ID NO: 14), SWSLPHAGHAH (SEQ ID NO: 15), SWTLPNFGLIN (SEQ ID NO: 16), SWTLPHAGRAH (SEQ ID NO: 17), SWSLPYAGHLN (SEQ ID NO: 18), SWSLPYAAHMN (SEQ ID NO: 19), SWSLPYPGHLN (SEQ ID NO: 20), SWSLPYAGHAH (SEQ ID NO: 21), SWDAPGGLAR (SEQ ID NO: 22), SWSLPTPGLAH (SEQ ID NO: 23), SWSLPHRGVAN (SEQ ID NO: 24), SWSLPSSGVAH (SEQ ID NO: 25), SWSLPHHGFGH (SEQ ID NO: 26), SWSLPHAGDAH (SEQ ID NO: 27), SWSLPHNGVAH (SEQ ID NO: 28), SWSLPRQGLAN (SEQ ID NO: 29), SWSLPGPGHFH (SEQ ID NO: 30), SWSLPHPGLGH (SEQ ID NO: 31), SWDAPRGLAR (SEQ ID NO: 32), SWDAPAGLAR (SEQ ID NO: 33), SWSLPHQGKAN (SEQ ID NO: 34), SWDAPKGLAR (SEQ ID NO: 35), SWSLPNPGIAH (SEQ ID NO: 36), SWSLPRPGNAH (SEQ ID NO: 37), and SWSLPNPGNAH (SEQ ID NO: 38).

In some embodiments, the BC loop of the anti-myostatin Adnectin of the invention comprises the underlined portion of any one of SEQ ID NOs: 7-38, as shown in Table 1. In one embodiment, the BC loop comprises the underlined portion of SEQ ID NO: 34.

In some embodiments, the DE loop of the anti-myostatin Adnectin of the invention comprises an amino acid sequence selected from the group consisting of: PGRGVT (SEQ ID NO: 39), PGRGST (SEQ ID NO: 40), LGRGST (SEQ ID NO: 41), PGRGLT (SEQ ID NO: 42), IGRGST (SEQ ID NO: 43), FGRGTT (SEQ ID NO: 44), and VGRGNT (SEQ ID NO: 45). In some embodiments, the DE loop of the anti-myostatin Adnectin of the invention comprises the underlined portion of any one of SEQ ID NOs: 39-45, as shown in Table 1. In one embodiment, the DE loop comprises the underlined portion of SEQ ID NO: 39.

In some embodiments, the FG loop of the anti-myostatin Adnectin of the invention comprises an amino acid sequence selected from the group consisting of: TLTKSQMIHYMP (SEQ ID NO: 46), TIYRDGMSHHDP (SEQ ID NO: 47), TVYRDGPLLLAP (SEQ ID NO: 48), TIFRTGMVQYDP (SEQ ID NO: 49), TLTNSEIILYKP (SEQ ID NO: 50), TLTKSQILHHRP (SEQ ID NO: 51), TLTRSKIIHYMP (SEQ ID NO: 52), TLTHSNIIRYVP (SEQ ID NO: 53), TVSSTKVIVYLP (SEQ ID NO: 54), TITKSTIIIYKP (SEQ ID NO: 55), TVTTTSVILYKP (SEQ ID NO: 56), TLTKSQLIHYMP (SEQ ID NO: 57), TLTRSQVIHYMP (SEQ ID NO: 58), TLTKSKIIHYMP (SEQ ID NO: 59), TVSSTKVIHYKP (SEQ ID NO: 60), TLTKSKVIHYMP (SEQ ID NO: 61), TVTTTKVIHYKP (SEQ ID NO: 62), TIDRDGVNHFAP (SEQ ID NO: 63), TVTHHGVIGYKP (SEQ ID NO: 64), TLTGANVIIYKP (SEQ ID NO: 35), TVTNTGVIIYKP (SEQ ID NO: 66), TVTATGIIIYKP (SEQ ID NO: 67), TVTRAGFYRYKP (SEQ ID NO: 68), TVTREEVISYKP (SEQ ID NO: 69), TVTAAGVIIYKP (SEQ ID NO: 70), TVTANQPIIYKP (SEQ ID NO: 71), TITPETIIVYKP (SEQ ID NO: 72), TIDRDGTRSFDP (SEQ ID NO: 73), TIFRDGPVTWDP (SEQ ID NO: 74), TVTDTGYLKYKP (SEQ ID NO: 75), TLTGSDTIFYKP (SEQ ID NO: 76), TVTGKDVIKYKP (SEQ ID NO: 77), TIFRDGVVNYGP (SEQ ID NO: 78), and TVTDTGFITYKP (SEQ ID NO: 79).

In some embodiments, the FG loop of the anti-myostatin Adnectin of the invention comprises the underlined portion of any one of SEQ ID NOs: 46-79, as shown in Table 1. In one embodiment, the FG loop comprises the underlined portion of SEQ ID NO: 75.

In some embodiments, the anti-myostatin Adnectin of the invention comprises one BC loop sequence selected from the BC loop sequences having SEQ ID NOs: 7-38, or the underlined portion of any one of SEQ ID NOs: 7-38, as shown in Table 1; one DE loop sequence selected from the DE loop sequences having SEQ ID NOs: 39-45, or the underlined portion of any one of SEQ ID NOs: 39-45 as shown in Table 1; and one FG loop sequence selected from the FG loop sequences having SEQ ID NOS: 46-79, or the underlined portion of any one of SEQ ID NOS: 46-79 as shown in Table 1. In some embodiments, the anti-myostatin Adnectin of the invention comprises a BC, DE and FG loop amino acid sequence at least 70%, 75%, 80%, 85%, 90%, 95%, 98%, 99% or 100% identical to of any one of SEQ ID NOs: 7-38, 39-45, and 46-79, respectively. In other embodiments, the anti-myostatin Adnectin of the invention comprises a BC, DE and FG loop amino acid sequence at least 70%, 75%, 80%, 85%, 90%, 95%, 98%, 99% or 100% identical to the underlined portion of any one of SEQ ID NOS: 7-38, 39-45, and 46-79, respectively, as shown in Table 1.

In some embodiments, the anti-myostatin Adnectin comprises the amino acid sequence of any one of SEQ ID NOs: 80-123, 228-239, and 252-273 (full length sequences from Tables 2, 5, and 6). In one embodiment, the anti-myostatin Adnectin comprises the amino acid sequence of SEQ ID NO: 273.

In some embodiments, the anti-myostatin Adnectin comprises an amino acid sequence at least 70%, 75%, 80%, 85%, 90%, 95%, 98%, 99% or 100% identical to any one of SEQ ID NOS: 80-123, 228-239, and 252-273. In other embodiments, the anti-myostatin Adnectin comprise an amino acid sequence at least 80%, 85%, 90%, 95%, 98%, 99% or 100% identical to the non-BC, DE, and FG loop regions of SEQ ID NOs: 80-123, 228-239, and 252-273.

In one embodiment, the anti-myostatin Adnectin of the invention comprises the BC, DE, and FG loops as set forth in SEQ ID NOs: 34, 39, and 75, respectively. In another embodiment, the anti-myostatin Adnectin comprises an amino acid sequence at least 80%, 85%, 90%, 95%, 96%, 97%, 98%, 99% or 100% identical to the amino acid sequence set forth in SEQ ID NO: 273 [PRD-1474], SEQ ID NO: 118 [3116_A06], SEQ ID NO: 281 [core Adnectin sequence shared by PRD-1474 and 3116_A06, preceded by a N-terminal extension sequence (GVSDVPRDL) and followed by a C-terminal tail (EI)] or SEQ ID NO: 331 [core Adnectin sequence of PRD-1474 and 3116_A06 without an N-terminal leader sequence or C-terminal tail]. The core Adnectin sequence of PRD-1474 and 3116_A06 is set forth below:

```
                                      (SEQ ID NO: 331)
EVVAATPTSLLISWSLPHQGKANYYRITYGETGGNSPVQEFTVPGRGVTA

TISGLKPGVDYTITVYAVTVTDTGYLKYKPISINYRT
```

In yet another embodiment, the anti-myostatin Adnectin of the present invention comprises an amino acid sequence at least 80%, 85%, 90%, 95%, 98%, 99% or 100% identical to the non-BC, DE, and FG loop regions of SEQ ID NO: 118, 273, 281, or 331.

In one embodiment, the anti-myostatin Adnectin of the invention and disclosed herein can be described in relation to the anti-myostatin Adnectin comprising BC, DE, and FG loops as set forth in SEQ ID NOs: 34, 39, and 75.

Accordingly, in some embodiments, the anti-myostatin Adnectin of the invention comprises the BC, DE, and FG loops as set forth in SEQ ID NOs: 34, 39, and 75, respectively, wherein the BC loop comprises 1, 2, 3, 4, 5, or 6 amino acid substitutions, such as conservative amino acid substitutions. Accordingly, in some embodiments, the BC loop is defined by the consensus sequence $X_{33}$-L-P-$X_{34}$-$X_{35}$-$X_{36}$-$X_{37}$-$X_{38}$-$X_{39}$, wherein $X_{33}$ is T or Y; $X_{34}$ is Y, N, R, F, G, S, or T; $X_{35}$ is A, P, S, F, H, N, or R; $X_{36}$ is A; $X_{37}$ is H, L, R, V, N, D, F, or I; $X_{38}$ is L, G, M, F, I, or V; and $X_{39}$ is H.

In some embodiments, the anti-myostatin Adnectin of the invention comprises the BC, DE, and FG loops as set forth in SEQ ID NOs: 34, 39, and 75, respectively, wherein the DE loop comprises 1 amino acid substitution, such as a conservative amino acid substitution. Accordingly, in some embodiments, the DE loop is defined by the consensus sequence G-R-G-$X_{40}$, wherein $X_{40}$ is L.

In some embodiments, the anti-myostatin Adnectin of the invention comprises the BC, DE, and FG loops as set forth in SEQ ID NOs: 34, 39, and 75, respectively wherein the FG loop comprises 1, 2, 3, 4, 5, 6, 7, or 8 amino acid substitutions, such as conservative amino acid substitutions. Accordingly, in some embodiments, the FG loop is defined by the consensus sequence $X_{41}$-$X_{42}$-$X_{43}$-$X_{44}$-$X_{45}$-$X_{46}$-$X_{47}$-$X_{48}$-$X_{49}$-$X_{50}$, wherein $X_{41}$ is L or I; $X_{42}$ is S; $X_{43}$ is K, R, A, G, S, H, N, T, or P; $X_{44}$ is S, A, E, H, K, or N; $X_{45}$ is K, Q, D, E, N, T, or S; $X_{46}$ is V, I, F, L, M, P, or T; $X_{47}$ is I or Y; $X_{48}$ is H, I, V, L, R, F, G, S, or T; $X_{49}$ is H; and $X_{50}$ is M, L, R, or V.

In some embodiments, the anti-myostatin Adnectin of the invention comprises the BC, DE, and FG loops as set forth in SEQ ID NOs: 34, 39, and 75, respectively, wherein the BC loop has 1, 2, 3, 4, 5, or 6 amino acid substitutions, such as conservative amino acid substitutions, and the DE loop has 1 amino acid substitution, such as a conservative amino acid substitution. In some embodiments, the BC loop has an amino acid sequence according to the formula $X_{33}$-L-P-$X_{34}$-$X_{35}$-$X_{36}$-$X_{37}$-$X_{38}$-$X_{39}$, wherein $X_{33}$ is T or Y; $X_{34}$ is Y, N, R, F, G, S, or T; $X_{35}$ is A, P, S, F, H, N, or R; $X_{36}$ is A; $X_{37}$ is H, L, R, V, N, D, F, or I; $X_{38}$ is L, G, M, F, I, or V; and $X_{39}$ is H, and the DE loop has an amino acid sequence according to the formula G-R-G-$X_{40}$, wherein $X_{40}$ is L.

In some embodiments, the anti-myostatin Adnectin of the invention comprises the BC, DE, and FG loops as set forth in SEQ ID NOs: 34, 39, and 75, respectively, wherein the BC loop has 1, 2, 3, 4, 5, or 6 amino acid substitutions, such as conservative amino acid substitutions, and the FG loop has 1, 2, 3, 4, 5, 6, 7, or 8 amino acid substitutions, such as conservative amino acid substitutions. In some embodiments, the BC loop comprises an amino acid sequence according to the formula $X_{33}$-L-P-$X_{34}$-$X_{35}$-$X_{36}$-$X_{37}$-$X_{38}$-$X_{39}$, wherein $X_{33}$ is T or Y; $X_{34}$ is Y, N, R, F, G, S, or T; $X_{35}$ is A, P, S, F, H, N, or R; $X_{36}$ is A; $X_{37}$ is H, L, R, V, N, D, F, or I; $X_{38}$ is L, G, M, F, I, or V; and $X_{39}$ is H, and the FG loop comprises an amino acid sequence according to the formula $X_{41}$-$X_{42}$-$X_{43}$-$X_{44}$-$X_{45}$-$X_{46}$-$X_{47}$-$X_{48}$-$X_{49}$-$X_{50}$, wherein $X_{41}$ is L or I; $X_{42}$ is S; $X_{43}$ is K, R, A, G, S, H, N, T, or P; $X_{44}$ is S, A, E, H, K, or N; $X_{45}$ is K, Q, D, E, N, T, or S; $X_{46}$ is V, I, F, L, M, P, or T; $X_{47}$ is I or Y; $X_{48}$ is H, I, V, L, R, F, G, S, or T; $X_{49}$ is H; and $X_{50}$ is M, L, R, or V.

In some embodiments, the anti-myostatin Adnectin of the invention comprises the BC, DE, and FG loops as set forth in SEQ ID NOs: 34, 39, and 75, respectively, wherein and the DE loop has 1 amino acid substitution, such as a conservative amino acid substitution, and the FG loop has 1, 2, 3, 4, 5, 6, 7, or 8 amino acid substitutions, such as conservative amino acid substitutions. In some embodiments, the DE loop comprises an amino acid sequence according to the formula G-R-G-$X_{40}$, wherein $X_{40}$ is L, and the FG loop has an amino acid sequence according to the formula $X_{41}$-$X_{42}$-$X_{43}$-$X_{44}$-$X_{45}$-$X_{46}$-$X_{47}$-$X_{48}$-$X_{49}$-$X_{50}$, wherein $X_{41}$ is L or I; $X_{42}$ is S; $X_{43}$ is K, R, A, G, S, H, N, T, or P; $X_{44}$ is S, A, E, H, K, or N; $X_{45}$ is K, Q, D, E, N, T, or S; $X_{46}$ is V, I, F, L, M, P, or T; $X_{47}$ is I or Y; $X_{48}$ is H, I, V, L, R, F, G, S, or T; $X_{49}$ is H; and $X_{50}$ is M, L, R, or V.

In some embodiments, the anti-myostatin Adnectin of the invention comprises the BC, DE, and FG loops as set forth in SEQ ID NOs: 34, 39, and 75, respectively, wherein the BC loop has 1, 2, 3, 4, 5, or 6 amino acid substitutions, such as conservative amino acid substitutions, and the DE loop has 1 amino acid substitution, such as a conservative amino acid substitution, and the FG loop has 1, 2, 3, 4, 5, 6, 7, or 8 amino acid substitutions, such as conservative amino acid substitutions. In some embodiments, the BC loop comprises an amino acid sequence according to the formula $X_{33}$-L-P-$X_{34}$-$X_{35}$-$X_{36}$-$X_{37}$-$X_{38}$-$X_{39}$, wherein $X_{33}$ is T or Y; $X_{34}$ is Y, N, R, F, G, S, or T; $X_{35}$ is A, P, S, F, H, N, or R; $X_{36}$ is A; $X_{37}$ is H, L, R, V, N, D, F, or I; $X_{38}$ is L, G, M, F, I, or V; and $X_{39}$ is H; the DE loop comprises an amino acid sequence according to the formula G-R-G-$X_{40}$, wherein $X_{40}$ is L; and the FG loop has an amino acid sequence according to the formula $X_{41}$-$X_{42}$-$X_{43}$-$X_{44}$-$X_{45}$-$X_{46}$-$X_{47}$-$X_{48}$-$X_{49}$-$X_{50}$, wherein $X_{41}$ is L or I; $X_{42}$ is S; $X_{43}$ is K, R, A, G, S, H, N, T, or P; $X_{44}$ is S, A, E, H, K, or N; $X_{45}$ is K, Q, D, E, N, T, or S; $X_{46}$ is V, I, F, L, M, P, or T; $X_{47}$ is I or Y; $X_{48}$ is H, I, V, L, R, F, G, S, or T; $X_{49}$ is H; and $X_{50}$ is M, L, R, or V.

In one embodiment, the anti-myostatin Adnectin of the invention comprises the BC, DE, and FG loops as set forth in SEQ ID NOs: 34, 39, and 75, respectively, and has amino acid substitutions in the BC, DE, and FG loops which allow the anti-myostatin Adnectin to maintain binding to myostatin. Such amino acid substitutions can be determined by, e.g., deep mutational scanning, as described in Example 8.

Accordingly, in some embodiments, the anti-myostatin Adnectin of the invention comprises a BC loop comprising an amino acid sequence according to the formula $X_{51}$-$X_{52}$-$X_{53}$-$X_{54}$-$X_{55}$-$X_{56}$-$X_{57}$-$X_{58}$-$X_{59}$, wherein: $X_{51}$ is selected from the group consisting of A, C, D, F, H, I, K, L, N, Q, R, S, T, V, W, and Y; $X_{52}$ is selected from the group consisting of L, M, and V; $X_{53}$ is selected from the group consisting of A, C, D, E, I, K, L, M, N, P, Q, R, S, T, V, and Y; $X_{54}$ is selected from the group consisting of A, C, D, E, F, G, H, I, K, L, M, N, Q, R, S, T, V, W, and Y; $X_{55}$ is selected from the group consisting of A, C, D, E, F, G, H, I, K, L, M, N, P, Q, R, S, T, V, W, and Y; $X_{56}$ is selected from the group consisting of G and S; $X_{57}$ is selected from the group consisting of A, C, D, E, F, G, H, I, K, L, M, N, Q, R, S, T, V, W, and Y; $X_{58}$ is selected from the group consisting of A, C, G, L, M, S, and T; and $X_{59}$ is selected from the group consisting of A, C, F, H, N, P, Q, R, S, and Y. In a preferred embodiment, $X_{51}$ is selected from the group consisting of C, F, I, S, V, W, and Y; $X_{52}$ is selected from the group consisting of L; $X_{53}$ is selected from the group consisting of P; $X_{54}$ is selected from the group consisting of C, D, E, F, G, H, I, K, L, M, N, Q, R, S, T, V, W, and Y; $X_{55}$ is selected from the group consisting of A, C, D, E, F, G, H, I, K, L, M, N, P, Q, R, S, T, V, W, and Y; $X_{56}$ is selected from the group consisting of G; $X_{57}$ is selected from the group consisting of A, C, G, H, I, K, L, M, N, Q, R, S, V, W, and Y; $X_{58}$ is selected from the group consisting of A, G, L, M, and S; and $X_{59}$ is selected from the group consisting of C, H, N, Q, S, and Y. In a more preferred embodiment, $X_{51}$ is selected from the group consisting of F, S, and W; $X_{52}$ is selected from the group consisting of L; $X_{53}$ is selected from the group consisting of P; $X_{54}$ is selected from the group consisting of C, F, G, I, K, L, M, N, R, S, T, V, W, and Y; $X_{55}$ is selected from the group consisting of A, C, E, F, H, I, K, L, M, P, Q, R, S, T, V, and Y; $X_{56}$ is selected from the group consisting of G; $X_{57}$ is selected from the group consisting of A, C, H, K, L, M, N, R, V, W, and Y; $X_{58}$ is selected from the group consisting of A, G, and L; and $X_{59}$ is selected from the group consisting of H, N, and Q.

In some embodiments, the anti-myostatin Adnectin of the invention comprises a DE loop comprising an amino acid sequence according to the formula G-R-G-$X_{60}$, wherein $X_{60}$ is A, C, D, E, F, I, K, L, M, N, Q, S, T, and V. In a preferred embodiment, $X_{60}$ is C, E, I, L, M, Q, T, and V. In a more preferred embodiment, $X_{60}$ is C, E, I, L, M, and V.

In some embodiments, the anti-myostatin Adnectin of the invention comprises an FG loop comprising an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is selected from the group consisting of A, C, F, I, L, M, Q, T, V, W, and Y; $X_{62}$ is selected from the group consisting of A, C, F, G, H, I, K, L, M, N, Q, R, S, T, V, W, and Y; $X_{63}$ is selected from the group consisting of A, C, D, E, F, G, H, I, K, L, M, N, P, Q, R, S, T, V, W, and Y; $X_{64}$ is selected from the group consisting of A, C, D, E, F, G, H, I, K, L, M, N, P, Q, R, S, T, V, W, and Y; $X_{65}$ is selected from the group consisting of A, C, D, E, F, G, H, I, K, L, M, N, Q, R, S, T, V, W, and Y; $X_{66}$ is selected from the group consisting of A, C, F, H, I, L, M, N, P, S, T, V, W, and Y; $X_{67}$ is selected from the group consisting of A, C, E, F, H, I, K, L, M, N, Q, R, S, T, V, W, and Y; $X_{68}$ is selected from the group consisting of A, C, D, E, F, G, H, I, K, L, M, N, P, Q, R, S, T, V, W, and Y; $X_{69}$ is selected from the group consisting of F, W, and Y; and $X_{70}$ is selected from the group consisting of A, C, D, E, F, G, H, I, K, L, M, N, P, Q, R, S, T, V, W, and Y. In a preferred embodiment, $X_{61}$ is selected from the group consisting of A, C, I, L, M, and V; $X_{62}$ is selected from the group consisting of C, F, H, I, L, M, Q, R, S, T, V, W, and Y; $X_{63}$ is selected from the group consisting of A, C, D, E, F, G, H, I, L, M, N, P, Q, S, T, V, W, and Y; $X_{64}$ is selected from the group consisting of A, C, D, E, F, G, H, I, K, L, M, N, Q, R, S, T, V, W, and Y; $X_{65}$ is selected from the group consisting of A, D, E, F, G, H, I, L, M, N, Q, S, T, V, W, and Y; $X_{66}$ is selected from the group consisting of C, F, I, L, M, P, T, V, W, and Y; $X_{67}$ is selected from the group consisting of C, F, H, I, K, L, M, N, Q, R, T, V, W, and Y; $X_{68}$ is selected from the group consisting of A, C, E, F, G, I, K, L, M, N, P, Q, R, S, T, V, W, and Y; $X_{69}$ is selected from the group consisting of W and Y; and $X_{70}$ is selected from the group consisting of A, C, D, E, G, H, K, L, M, N, P, Q, R, S, T, and V. In a more preferred embodiment, $X_{61}$ is selected from the group consisting of I and V; $X_{62}$ is selected from the group consisting of C, F, I, L, M, T, V, W, and Y; $X_{63}$ is selected from the group consisting of A, C, D, E, F, G, H, I, L, M, N, Q, S, T, and V; $X_{64}$ is selected from the group consisting of A, C, D, F, G, I, L, M, N, Q, S, T, V, W, and Y; $X_{65}$ is selected from the group consisting of A, G, S, T, and W; $X_{66}$ is selected from the group consisting of F, I, V, W, and Y; $X_{67}$ is selected from the group consisting of F, H, I, L, M, V, W, and Y; $X_{68}$ is selected from the group consisting of A, C, F, G, I, K, L, M, T, V, and W; $X_{69}$ is selected from the group consisting of W and Y; and $X_{70}$ is selected from the group consisting of A, G, K, L, M, P, Q, and R.

In some embodiments, the anti-myostatin Adnectin of the invention comprises BC, DE, and FG loops, wherein the BC loop comprises an amino acid sequence according to the formula $X_{51}$-$X_{52}$-$X_{53}$-$X_{54}$-$X_{55}$-$X_{56}$-$X_{57}$-$X_{58}$-$X_{59}$, wherein, $X_{51}$ is selected from the group consisting of A, C, D, F, H, I, K, L, N, Q, R, S, T, V, W, and Y; $X_{52}$ is selected from the group consisting of L, M, and V; $X_{53}$ is selected from the group consisting of A, C, D, E, I, K, L, M, N, P, Q, R, S, T, V, and Y; $X_{54}$ is A, C, D, E, F, G, H, I, K, L, M, N, Q, R, S, T, V, W, and Y; $X_{55}$ is selected from the group consisting of A, C, D, E, F, G, H, I, K, L, M, N, P, Q, R, S, T, V, W, and Y; $X_{56}$ is selected from the group consisting of G and S; $X_{57}$ is A, C, D, E, F, G, H, I, K, L, M, N, Q, R, S, T, V, W, and Y; $X_{58}$ is A, C, G, L, M, S, and T; and $X_{59}$ is A, C, F, H, N, P, Q, R, S, and Y; the DE loop comprises an amino acid sequence according to the formula G-R-G-$X_{60}$, wherein $X_{60}$ is selected from the group consisting of A, C, D, E, F, I, K, L, M, N, Q, S, T, and V; and the FG loop comprises an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is selected from the group consisting of A, C, F, I, L, M, Q, T, V, W, and Y; $X_{62}$ is A, C, F, G, H, I, K, L, M, N, Q, R, S, T, V, W, and Y; $X_{63}$ is selected from the group consisting of A, C, D, E, F, G, H, I, K, L, M, N, P, Q, R, S, T, V, W, and Y; $X_{64}$ is selected from the group consisting of A, C, D, E, F, G, H, I, K, L, M, N, P, Q, R, S, T, V, W, and Y; $X_{65}$ is selected from the group consisting of A, C, D, E, F, G, H, I, K, L, M, N, Q, R, S, T, V, W, and Y; $X_{66}$ is selected from the group consisting of A, C, F, H, I, L, M, N, P, S, T, V, W, and Y; $X_{67}$ is selected from the group consisting of A, C, E, F, H, I, K, L, M, N, Q, R, S, T, V, W, and Y; $X_{68}$ is selected from the group consisting of A, C, D, E, F, G, H, I, K, L, M, N, P, Q, R, S, T, V, W, and Y; $X_{69}$ is selected from the group consisting of F, W, and Y; and $X_{70}$ is selected from the group consisting of A, C, D, E, F, G, H, I, K, L, M, N, P, Q, R, S, T, V, W, and Y.

In a preferred embodiment, the anti-myostatin Adnectin of the invention comprises BC, DE, and FG loops, wherein the BC loop comprises an amino acid sequence according to the formula $X_{51}$-$X_{52}$-$X_{53}$-$X_{54}$-$X_{55}$-$X_{56}$-$X_{57}$-$X_{58}$-$X_{59}$, wherein, $X_{51}$ is selected from the group consisting of C, F, I, S, V, W, and Y; $X_{52}$ is L; $X_{53}$ is P; $X_{54}$ is selected from the group consisting of C, D, E, F, G, H, I, K, L, M, N, Q, R, S, T, V, W, and Y; $X_{55}$ is selected from the group consisting of A, C, D, E, F, G, H, I, K, L, M, N, P, Q, R, S, T, V, W, and Y; $X_{56}$ is G; $X_{57}$ is selected from the group consisting of A, C, G, H, I, K, L, M, N, Q, R, S, V, W, and Y; $X_{58}$ is selected from the group consisting of A, G, L, M, and S; and $X_{59}$ is selected from the group consisting of C, H, N, Q, S, and Y; the DE loop comprises an amino acid sequence according to the formula G-R-G-$X_{60}$, wherein $X_{60}$ is selected from the group consisting of C, E, I, L, M, Q, T, and V; and the FG loop comprises an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is selected from the group consisting of A, C, I, L, M, and V; $X_{62}$ is C, F, H, I, L, M, Q, R, S, T, V, W, and Y; $X_{63}$ is selected from the group consisting of A, C, D, E, F, G, H, I, L, M, N, P, Q, S, T, V, W, and Y; $X_{64}$ is selected from the group consisting of A, C, D, E, F, G, H, I, K, L, M, N, Q, R, S, T, V, W, and Y; $X_{65}$ is selected from the group consisting of A, D, E, F, G, H, I, L, M, N, Q, S, T, V, W, and Y; $X_{66}$ is selected from the group consisting of C, F, I, L, M, P, T, V, W, and Y; $X_{67}$ is selected from the group consisting of C, F, H, I, K, L, M, N, Q, R, T, V, W, and Y; $X_{68}$ is selected from the group consisting of A, C, E, F, G, I, K, L, M, N, P, Q, R, S, T, V, W, and Y; $X_{69}$ is selected from the group consisting of W and Y; and $X_{70}$ is selected from the group consisting of A, C, D, E, F, G, H, I, K, L, M, N, P, Q, R, S, T, V, W, and Y.

In a more preferred embodiment, the anti-myostatin Adnectin of the invention comprises BC, DE, and FG loops, wherein the BC loop comprises an amino acid sequence according to the formula $X_{51}$-$X_{52}$-$X_{53}$-$X_{54}$-$X_{55}$-$X_{56}$-$X_{57}$-$X_{58}$-$X_{59}$, wherein, $X_{51}$ is selected from the group consisting of F, S, and W; $X_{52}$ is L; $X_{53}$ is P; $X_{54}$ is selected from the group consisting of C, F, G, I, K, M, N, R, S, T, V, W, and Y; $X_{55}$ is selected from the group consisting of A, C, E, F, H, I, K, L, M, P, Q, R, S, T, V, and Y; $X_{56}$ is G; $X_{57}$ is selected from the group consisting of A, C, H, K, L, M, N, R, V, W, and Y; $X_{58}$ is selected from the group consisting of A, G, and L; and $X_{59}$ is selected from the group consisting of H, N, and Q; the DE loop comprises an amino acid sequence according to the formula G-R-G-$X_{60}$, wherein $X_{60}$ is selected from the group consisting of C, E, I, L, M, and V; and the FG loop comprises an amino acid sequence according to the formula $X_{61}$-$X_{62}$-$X_{63}$-$X_{64}$-$X_{65}$-$X_{66}$-$X_{67}$-$X_{68}$-$X_{69}$-$X_{70}$, wherein $X_{61}$ is selected from the group consisting of I and V; $X_{62}$ is C, F, I, L, M, T, V, W, and Y; $X_{63}$ is selected from the group consisting of A, C, D, E, F, G, H, I, L, M, N, Q, S, T, and V; $X_{64}$ is selected from the group consisting of A, C, D, F, G, I, L, M, N, Q, S, T, V, W, and Y; $X_{65}$ is selected from the group consisting of A, G, S, T, and W; $X_{66}$ is selected from the group consisting of F, I, V, W, and Y; $X_{67}$ is selected from the group consisting of F, H, I, L, M, V, W, and Y; $X_{68}$ is selected from the group consisting of A, C, F, G, I, K, L, M, T, V, and W; $X_{69}$ is selected from the group consisting of W and Y; and $X_{70}$ is selected from the group consisting of A, G, K, L, M, P, Q, and R.

In some embodiments, the anti-myostatin Adnectin is encoded by a nucleic acid sequence as set forth in any one of SEQ ID NOs: 124-167, 240-251, and 284-305 (full length sequences from Tables 2, 5, and 6). In some embodiments, the anti-myostatin Adnectin is encoded by a nucleic acid sequence that is at least 70%, 75%, 80%, 85%, 90%, 95%, 98%, 99% or 100% identical to any one of SEQ ID NOS: 124-167, 240-251, and 284-305.

Fibronectin naturally binds certain types of integrins through its integrin-binding motif, "arginine-glycine-aspartic acid" (RGD). In some embodiments, the polypeptide comprises a $^{10}$Fn3 domain that lacks the (RGD) integrin binding motif. The integrin binding domain may be removed by altering the RGD sequence by amino acid substitution, deletion or insertion.

In some embodiments, BC, DE and/or FG loop amino acid sequences identical to the underlined portion of any one of SEQ ID NOS: 7-38, 39-45, and 46-79, respectively, as shown in Table 1, are grafted into non-$^{10}$Fn3 domain protein scaffolds. For instance, one or more loop amino acid sequences is exchanged for or inserted into one or more CDR loops of an antibody heavy or light chain or fragment thereof. In other embodiments, the protein domain into which one or more amino acid loop sequences are exchanged or inserted includes, but is not limited to, consensus Fn3 domains (Centocor, US), ankyrin repeat proteins (Molecular Partners AG, Zurich Switzerland), domain antibodies (Domantis, Ltd, Cambridge, Mass.), single domain camelid nanobodies (Ablynx, Belgium), Lipocalins (e.g., anticalins; Pieris Proteolab AG, Freising, Germany), Avimers (Amgen, Calif.), affibodies (Affibody AG, Sweden), ubiquitin (e.g., affilins; Scil Proteins GmbH, Halle, Germany), protein epitope mimetics (Polyphor Ltd, Allschwil, Switzerland), helical bundle scaffolds (e.g. alphabodies, Complix, Belgium), Fyn SH3 domains (Covagen AG, Switzerland), or atrimers (Anaphor, Inc., CA).

The SEQ ID NOs of the BC, DE and FG loops of the exemplary anti-myostatin Adnectins of the invention are presented in Table 1.

TABLE 1

Anti-Myostatin Adnectin BC, DE, and FG Loops

Loop Sequences

| Clone | BC Loop | SEQ ID NO: | DE Loop | SEQ ID NO: | FG Loop | SEQ ID NO: |
|---|---|---|---|---|---|---|
| 1979_B06 | SWSLPHAGHVN | 7 | PGRGVT | 39 | TLTKSQMIHYMP | 46 |
| 2062_G02 | SWVSPRGRAR | 8 | PGRGST | 40 | TIYRDGMSHHDP | 47 |
| 2522_C09 | SWEVPRGLAR | 9 | LGRGST | 41 | TVYRDGPLLLAP | 48 |
| 2523_G06 | SWWAPLGLAR | 10 | PGRGST | 40 | TIFRTGMVQYDP | 49 |
| 2524_C11 | SWTLPHAGLAH | 11 | PGRGVT | 39 | TLTNSEIILYKP | 50 |
| 2524_D09 | SWYLPYPAHMN | 12 | PGRGLT | 42 | TLTKSQILHHRP | 51 |
| 2524_E10 | SWSLPFAGHLN | 13 | PGRGVT | 39 | TLTRSKIIHYMP | 52 |
| 2524_H05 | SWSLPYSGLAN | 14 | PGRGVT | 39 | TLTHSNIIRYVP | 53 |
| 2524_H11 | SWSLPHAGHAH | 15 | PGRGVT | 39 | TVSSTKVIVYLP | 54 |
| 2525_B01 | SWTLPNFGLIN | 16 | PGRGVT | 39 | TITKSTIIIYKP | 55 |
| 2525_D02 | SWTLPHAGRAH | 17 | PGRGVT | 39 | TVTTTSVILYKP | 56 |
| 2525_D05 | SWSLPYAGHLN | 18 | PGRGVT | 39 | TLTKSQLIHYMP | 57 |
| 2525_F07 | SWSLPYAAHMN | 19 | PGRGVT | 39 | TLTRSQVIHYMP | 58 |
| 2987_A06 | SWSLPHAGHAH | 15 | PGRGVT | 39 | TLTKSKIIHYMP | 59 |
| 2987_B04 | SWSLPYPGHLN | 20 | PGRGVT | 39 | TLTKSKIIHYMP | 59 |
| 2987_B09 | SWTLPHAGRAH | 17 | PGRGVT | 39 | TLTRSKIIHYMP | 52 |
| 2987_C02 | SWSLPYAGHAH | 21 | PGRGVT | 39 | TLTKSKIIHYMP | 59 |
| 2987_D05 | SWSLPHAGHAH | 15 | PGRGVT | 39 | TLTRSKIIHYMP | 52 |
| 2987_E03 | SWSLPYPGHLN | 20 | PGRGVT | 39 | TLTRSKIIHYMP | 52 |
| 2987_E08 | SWTLPHAGRAH | 17 | PGRGVT | 39 | TVSSTKVIHYKP | 60 |
| 2987_F01 | SWSLPYAGHAH | 21 | PGRGVT | 39 | TLTRSKIIHYMP | 52 |
| 2987_F06 | SWSLPHAGHAH | 15 | PGRGVT | 39 | TLTKSKVIHYMP | 61 |
| 2987_G04 | SWSLPYPGHLN | 20 | PGRGVT | 39 | TLTKSKVIHYMP | 61 |
| 2987_G09 | SWTLPHAGRAH | 17 | PGRGVT | 39 | TVSSTKVIVYLP | 54 |
| 2987_H02 | SWSLPYAGHAH | 21 | PGRGVT | 39 | TLTKSKVIHYMP | 61 |
| 2987_H07 | SWTLPHAGRAH | 17 | PGRGVT | 39 | TVTTTKVIHYKP | 62 |
| 3006_A10 | SWDAPGGLAR | 22 | IGRGST | 43 | TIDRDGVNHFAP | 63 |
| 3007_B08 | SWSLPTPGLAH | 23 | PGRGVT | 39 | TVTHHGVIGYKP | 64 |
| 3007_C09 | SWSLPHRGVAN | 24 | PGRGVT | 39 | TLTGANVIIYKP | 65 |
| 3007_C10 | SWSLPSSGVAH | 25 | PGRGVT | 39 | TVTNTGVIIYKP | 66 |
| 3008_A03 | SWSLPHHGFGH | 26 | PGRGVT | 39 | TVTATGIIIYKP | 67 |
| 3008_B08 | SWSLPHAGDAH | 27 | PGRGVT | 39 | TVTRAGFYRYKP | 68 |
| 3008_D04 | SWSLPHNGVAH | 28 | PGRGVT | 39 | TVTREEVISYKP | 69 |
| 3008_F01 | SWSLPRQGLAN | 29 | PGRGVT | 39 | TVTAAGVIIYKP | 70 |
| 3008_G01 | SWSLPGPGHFH | 30 | PGRGVT | 39 | TVTANQPIIYKP | 71 |
| 3008_G03 | SWSLPHPGLGH | 31 | PGRGVT | 39 | TITPETIIVYKP | 72 |
| 3115_D04 | SWDAPRGLAR | 32 | FGRGTT | 44 | TIDRDGTRSFDP | 73 |

TABLE 1-continued

Anti-Myostatin Adnectin BC, DE, and FG Loops

Loop Sequences

| Clone | BC Loop | SEQ ID NO: | DE Loop | SEQ ID NO: | FG Loop | SEQ ID NO: |
|---|---|---|---|---|---|---|
| 3115_E06 | SWDAPAGLAR | 33 | VGRGNT | 45 | TIFRDGPVTWDP | 74 |
| 3116_A06 | SWSLPHQGKAN | 34 | PGRGVT | 39 | TVTDTGYLKYKP | 75 |
| 3116_A07 | SWDAPKGLAR | 35 | VGRGNT | 45 | TIFRDGPVTWDP | 74 |
| 3116_C01 | SWSLPNPGIAH | 36 | PGRGVT | 39 | TLTGSDTIFYKP | 76 |
| 3116_C06 | SWSLPRPGNAH | 37 | PGRGVT | 39 | TVTGKDVIKYKP | 77 |
| 3116_H06 | SWDAPAGLAR | 33 | VGRGNT | 45 | TIFRDGVVNYGP | 78 |
| 3146_A08 | SWSLPNPGNAH | 38 | PGRGVT | 39 | TVTDTGFITYKP | 79 |

The SEQ ID NOs of exemplary anti-myostatin monoAdnectins of the invention are presented in Table 2.

TABLE 2

Anti-Myostatin MonoAdnectins

| | Sequence | |
|---|---|---|
| | Amino Acid Sequence | Nucleic Acid Sequence |
| 1979_B06 also referred to herein as ATI-1133 (Adnectin core 1 sequence having AdNT1 (underlined) and AdCT1 (italics) terminal sequence with His6 tag) | MGVSDVPRDLEVVAATPTSLLIS WSLPHAGHVNYYRITYGETGGN SPVQEFTVPGRGVTATISGLKPG VDYTITVYAVTLTKSQMIHYMPI SINYRT*EIDKPSQ*HHHHHH (SEQ ID NO: 80) | ATGGGAGTTTCTGATGTGCCGCGCGACCT GGAAGTGGTTGCTGCCACCCCCACCAGCC TGCTGATCAGCTGGTCTCTGCCGCATGCT GGTCATGTGAACTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTCTGACTAAATCTCAGATGATCCA TTACATGCCAATTTCCATTAATTACCGCAC AGAAATTGACAAACCATCCCAGCACCATC ACCACCACCAC (SEQ ID NO: 124) |
| 2062_G02 also referred to herein as ATI-1134 (Adnectin core 2 sequence having AdNT1 (underlined) and AdCT1 (italics) terminal sequence with His6 tag) | MGVSDVPRDLEVVAATPTSLLIS WVSPRGRARYYRITYGETGGNS PVQEFTVPGRGSTATISGLKPGV DYTITVYAVTIYRDGMSHHDPISI NYRT*EIDKPSQ*HHHHHH (SEQ ID NO: 81) | ATGGGAGTTTCTGATGTGCCGCGCGACCT GGAAGTGGTTGCTGCCACCCCCACCAGCC TGCTGATCAGCTGGGTTTCTCCGCGTGGT CGTGCTCGATATTACCGCATCACTTACGG CGAAACAGGAGGCAATAGCCCTGTCCAG GAGTTCACTGTGCCTGGTCGTGGTTCTAC AGCTACCATCAGCGGCCTTAAACCTGGCG TTGATTATACCATCACTGTGTATGCTGTCA CTATCTACCGTGACGGTATGTCTCATCAT GACCCAATTTCCATTAATTACCGCACAGA AATTGACAAACCATCCCAGCACCATCACC ACCACCAC (SEQ ID NO: 125) |
| 2522_C09 (Adnectin core 3 sequence having AdNT1 (underlined) and AdCT1 (italics) terminal sequence with His6 tag) | MGVSDVPRDLEVVAATPTSLLIS WEVPRGLARYYRITYGETGGNS PVQEFTVLGRGSTATISGLKPGV DYTITVYAVTVYRDGPLLLAPISI NYRT*EIDKPSQ*HHHHHH (SEQ ID NO: 82) | ATGGGAGTTTCTGATGTGCCGCGCGACCT GGAAGTGGTTGCTGCCACCCCCACCAGCC TGCTGATCAGCTGGGAAGTGCCGCGTGGC CTAGCTCGATATTACCGCATCACTTACGG CGAAACAGGAGGCAATAGCCCTGTCCAG GAGTTCACTGTGCCTTGGTCGTGGTTCTAC AGCTACCATCAGCGGCCTTAAACCTGGCG TTGATTATACCATCACTGTGTATGCTGTCA CTGTGTACCGTGACGGGCCGTTGCTTCTT GCCCCAATTTCCATTAATTACCGCACAGA AATTGACAAACCATCCCAGCACCATCACC ACCACCAC (SEQ ID NO: 126) |
| 2523_G06 (Adnectin core 4 sequence having AdNT1 (underlined) and AdCT1 (italics) | MGVSDVPRDLEVVAATPTSLLIS WWAPLGLARYYRITYGETGGNS PVQEFTVPGRGSTATISGLKPGV DYTITVYAVTIFRTGMVQYDPISI NYRT*EIDKPSQ*HHHHHH (SEQ | ATGGGAGTTTCTGATGTGCCGCGCGACCT GGAAGTGGTTGCTGCCACCCCCACCAGCC TGCTGATCAGCTGGTGGGCCCCGCTGGGT CTTGCTCGATATTACCGCATCACTTACGG CGAAACAGGAGGCAATAGCCCTGTCCAG |

TABLE 2-continued

Anti-Myostatin MonoAdnectins

| | Sequence | |
|---|---|---|
| | Amino Acid Sequence | Nucleic Acid Sequence |
| terminal sequence with His6 tag) | ID NO: 83) | GAGTTCACTGTGCCTGGTCGGGGCTCTAC AGCTACCATCAGCGGCCTTAAACCTGGCG TTGATTATACCATCACTGTGTATGCTGTCA CTATCTTCCGTACGGGCATGGTTCAATAT GACCCAATTTCCATTAATTACCGCACAGA AATTGACAAACCATCCCAGCACCATCACC ACCACCAC (SEQ ID NO: 127) |
| 2524_C11 (Adnectin core 5 sequence having AdNT1 (underlined) and AdCT1 (italics) terminal sequence with His6 tag) | MGVSDVPRDLEVVAATPTSLLIS WTLPHAGLAHYYRITYGETGGN SPVQEFTVPGRGVTATISGLKPG VDYTITVYAVTLTNSEIILYKPISI NYRT*EIDKPSQ*HHHHHH (SEQ ID NO: 84) | ATGGGAGTTTCTGATGTGCCGCGCGACCT GGAAGTGGTTGCTGCCACCCCCACCAGCC TGCTGATCAGCTGGACTCTGCCGCATGCT GGTCTTGCGCACTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTCTGACTAATTCTGAGATTATCCTT TACAAGCCAATTTCCATTAATTACCGCAC AGAAATTGACAAACCATCCCAGCACCATC ACCACCACCAC (SEQ ID NO: 128) |
| 2524_D09 (Adnectin core 6 sequence having AdNT1 (underlined) and AdCT1 (italics) terminal sequence with His6 tag) | MGVSDVPRDLEVVAATPTSLLIS WYLPYPAHMNYYRITYGETGGN SPVQEFTVPGRGLTATISGLKPG VDYTITVYAVTLTKSQILHHRPIS INYRT*EIDKPSQ*HHHHHH (SEQ ID NO: 85) | ATGGGAGTTTCTGATGTGCCGCGCGACCT GGAAGTGGTTGCTGCCACCCCCACCAGCC TGCTGATCAGCTGGTACCTCCCGTATCCT GCGCATATGAACTATTACCGCATCACTTA CGGCGAAACAGGAGGCAATAGCCCTGTC CAGGAGTTCACTGTGCCTGGGCGGGGTCT GACAGCTACCATCAGCGGCCTTAAACCTG GCGTTGATTATACCATCACTGTGTATGCT GTCACTCTGACAAAATCTCAGATTCTCCA TCATAGGCCAATTTCCATTAATTACCGCA CAGAAATTGACAAACCATCCCAGCACCAT CACCACCACCAC (SEQ ID NO: 129) |
| 2524_E10 (Adnectin core 7 sequence having AdNT1 (underlined) and AdCT1 (italics) terminal sequence with His6 tag) | MGVSDVPRDLEVVAATPTSLLIS WSLPFAGHLNYYRITYGETGGN SPVQEFTVPGRGVTATISGLKPG VDYTITVYAVTLTRSKIIHYMPIS INYRT*EIDKPSQ*HHHHHH (SEQ ID NO: 86) | ATGGGAGTTTCTGATGTGCCGCGCGACCT GGAAGTGGTTGCTGCCACCCCCACCAGCC TGCTGATCAGCTGGTCATTGCCGTTTGCTG GTCATTTGAACTATTACCGCATCACTTAC GGCGAAACAGGAGGCAATAGCCCTGTCC AGGAGTTCACTGTGCCTGGTCGTGGTGTT ACAGCTACCATCAGCGGCCTTAAACCTGG CGTTGATTATACCATCACTGTGTATGCTGT CACTCTGACTCGCTCTAAGATTATTCATTA TATGCCAATTTCCATTAATTACCGCACAG AAATTGACAAACCATCCCAGCACCATCAC CACCACCAC (SEQ ID NO: 130) |
| 2524_H05 (Adnectin core 8 sequence having AdNT1 (underlined) and AdCT1 (italics) terminal sequence with His6 tag) | MGVSDVPRDLEVVAATPTSLLIS WSLPYSGLANYYRITYGETGGN SPVQEFTVPGRGVTATISGLKPG VDYTITVYAVTLTHSNIIRYVPISI NYRT*EIDKPSQ*HHHHHH (SEQ ID NO: 87) | ATGGGAGTTTCTGATGTGCCGCGCGACCT GGAAGTGGTTGCTGCCACCCCCACCAGCC TGCTGATCAGCTGGTCTCTGCCTTATTCTG GCCTTGCGAACTATTACCGCATCACTTAC GGCGAAACAGGAGGCAATAGCCCTGTCC AGGAGTTCACTGTGCCTGGTCGTGGGGTT ACAGCTACTATCAGCGGCCTTAAACCTGG CGTTGATTATACCATCACTGTGTATGCTGT CACTCTGACTCACTCTAATATAATTCGAT ACGTGCCAATTTCCATTAATTACCGCACA GAAATTGACAAACCATCCCAGCACCATCA CCACCACCAC (SEQ ID NO: 131) |
| 2524_H11 (Adnectin core 9 sequence having AdNT1 (underlined) and AdCT1 (italics) terminal sequence with His6 tag) | MGVSDVPRDLEVVAATPTSLLIS WSLPHAGHAHYYRITYGETGGN SPVQEFTVPGRGVTATISGLKPG VDYTITVYAVTVSSTKVIVYLPIS INYRT*EIDKPSQ*HHHHHH (SEQ ID NO: 88) | ATGGGAGTTTCTGATGTGCCGCGCGACCT GGAAGTGGTTGCTGCCACCCCCACCAGCC TGCTGATCAGCTGGTCCCTACCGCATGCG GGTCATGCGCACTATTACCGCATCACTTA CGGCGAAACAGGAGGCAATAGCCCTGTC CAGGAGTTCACTGTGCCTGGTCGTGGAGT TACAGCTACCATCAGCGGCCTTAAACCTG GCGTTGATTATACCATCACTGTGTATGCT GTCACTGTGTCTAGTACAAAGGTGATAGT TTACCTGCCAATTTCCATTAATTACCGCAC AGAAATTGACAAACCATCCCAGCACCATC ACCACCACCAC (SEQ ID NO: 132) |

TABLE 2-continued

Anti-Myostatin MonoAdnectins

| | Sequence | |
|---|---|---|
| | Amino Acid Sequence | Nucleic Acid Sequence |
| 2525_B01 (Adnectin core 10 sequence having AdNT1 (underlined) and AdCT1 (italics) terminal sequence with His6 tag) | MGVSDVPRDLEVVAATPTSLLIS WTLPNFGLINYYRITYGETGGNS PVQEFTVPGRGVTATISGLKPGV DYTITVYAVTITKSTIIIYKPISINY RT*EIDKPSQ*HHHHHH (SEQ ID NO: 89) | ATGGGAGTTTCTGATGTGCCGCGCGACCT GGAAGTGGTTGCTGCCACCCCCACCAGCC TGCTGATCAGCTGGACTTTGCCGAATTTC GGTCTTATTAATTATTACCGCATCACTTAC GGCGAAACAGGAGGCAATAGCCCTGTCC AGGAGTTCACTGTGCCTGGTCGTGGTGTT ACAGCTACCATCAGCGGCCTTAAACCTGG CGTTGATTATACCATCACTGTGTATGCTGT CACTATCACCAAATCTACTATCATCATTTA CAAGCCAATTTCCATTAATTACCGCACAG AAATTGACAAACCATCCCAGCACCATCAC CACCACCAC (SEQ ID NO: 133) |
| 2525_D02 (Adnectin core 11 sequence having AdNT1 (underlined) and AdCT1 (italics) terminal sequence with His6 tag) | MGVSDVPRDLEVVAATPTSLLIS WTLPHAGRAHYYRITYGETGGN SPVQEFTVPGRGVTATISGLKPG VDYTITVYAVTVTTTSVILYKPIS INYRT*EIDKPSQ*HHHHHH (SEQ ID NO: 90) | ATGGGAGTTTCTGATGTGCCGCGCGACCT GGAAGTGGTTGCTGCCACCCCCACCAGCC TGCTGATCAGCTGGACTTTGCCGCATGCT GGTCGTGCGCACTATTACCGCATCACTTA CGGCGAAACAGGAGGCAATAGCCCTGTC CAGGAGTTCACTGTGCCTGGGCGGGGTGT TACAGCTACCATCAGCGGCCTTAAACCTG GCGTTGATTATACCATCACTGTGTATGCT GTCACTGTGACGACAACTTCGGTGATCCT TTACAAGCCAATTTCCATTAATTACCGCA CAGAAATTGACAAACCATCCCAGCACCAT CACCACCACCAC (SEQ ID NO: 134) |
| 2525_D05 (Adnectin core 12 sequence having AdNT1 (underlined) and AdCT1 (italics) terminal sequence with His6 tag) | MGVSDVPRDLEVVAATPTSLLIS WSLPYAGHLNYYRITYGETGGN SPVQEFTVPGRGVTATISGLKPG VDYTITVYAVTLTKSQLIHYMPI SINYRT*EIDKPSQ*HHHHHH (SEQ ID NO: 91) | ATGGGAGTTTCTGATGTGCCGCGCGACCT GGAAGTGGTTGCTGCCACCCCCACCAGCC TGCTGATCAGCTGGTCTCTTCCTTATGCTG GTCATCTAAACTATTACCGCATCACTTAC GGCGAAACAGGAGGCAATAGCCCTGTCC AGGAGTTCACTGTGCCTGGTCGTGGTGTG ACAGCTACCATCAGCGGCCTTAAACCTGG CGTTGATTATACCATCACTGTGTATGCTGT CACTCTGACTAAGTCTCAGCTGATACATT ACATGCCAATTTCCATTAATTACCGCACA GAAATTGACAAACCATCCCAGCACCATCA CCACCACCAC (SEQ ID NO: 135) |
| 2525_F07 (Adnectin core 13 sequence having AdNT1 (underlined) and AdCT1 (italics) terminal sequence with His6 tag) | MGVSDVPRDLEVVAATPTSLLIS WSLPYAAHMNYYRITYGETGGN SPVQEFTVPGRGVTATISGLKPG VDYTITVYAVTLTRSQVIHYMPI SINYRT*EIDKPSQ*HHHHHH (SEQ ID NO: 92) | ATGGGAGTTTCTGATGTGCCGCGCGACCT GGAAGTGGTTGCTGCCACCCCCACCAGCC TGCTGATCAGCTGGTCTCTGCCGTATGCT GCTCACATGAACTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTTTGACTAGATCACAGGTGATTCA TTACATGCCAATTTCCATTAATTACCGCAC AGAAATTGACAAACCATCCCAGCACCATC ACCACCACCAC (SEQ ID NO: 136) |
| 2987_A06 (Adnectin core 14 sequence having AdNT1 (underlined) and AdCT1 (italics) terminal sequence with His6 tag) | MGVSDVPRDLEVVAATPTSLLIS WSLPHAGHAHYYRITYGETGGN SPVQEFTVPGRGVTATISGLKPG VDYTITVYAVTLTKSKIIHYMPIS INYRT*EIDKPSQ*HHHHHH (SEQ ID NO: 93) | ATGGGTGTTAGTGATGTTCCGCGTGATCT GGAAGTTGTTGCAGCAACCCCGACCAGCC TGCTGATTAGCTGGTCACTGCCGCATGCA GGTCATGCACATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCCTGACCAAAAGCAAAATTATTCATTA TATGCCGATTAGCATTAATTATCGCACCG AAATTGATAAACCGAGCCAGCATCATCAT CACCATCAT (SEQ ID NO: 137) |
| 2987_B04 (Adnectin core 15 sequence having AdNT1 (underlined) and AdCT1 (italics) terminal sequence with His6 tag) | MGVSDVPRDLEVVAATPTSLLIS WSLPYPGHLNYYRITYGETGGN SPVQEFTVPGRGVTATISGLKPG VDYTITVYAVTLTKSKIIHYMPIS INYRT*EIDKPSQ*HHHHHH (SEQ ID NO: 94) | ATGGGTGTTAGTGATGTTCCGCGTGATCT GGAAGTTGTTGCAGCAACCCCGACCAGCC TGCTGATTAGCTGGTCACTGCCGTATCCG GGTCATCTGAATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCCTGACCAAAAGCAAAATTATTCATTA |

TABLE 2-continued

Anti-Myostatin MonoAdnectins

| | Sequence | |
|---|---|---|
| | Amino Acid Sequence | Nucleic Acid Sequence |
| | | TATGCCGATTAGCATTAATTATCGCACCG<br>AAATTGATAAACCGAGCCAGCATCATCAT<br>CACCATCAT (SEQ ID NO: 138) |
| 2987_B09<br>(Adnectin core 16<br>sequence having<br>AdNT1 (underlined)<br>and AdCT1 (italics)<br>terminal sequence<br>with His6 tag) | MGVSDVPRDLEVVAATPTSLLIS<br>WTLPHAGRAHYYRITYGETGGN<br>SPVQEFTVPGRGVTATISGLKPG<br>VDYTITVYAVTLTRSKIIHYMPIS<br>INYRTEIDKPSQHHHHHH (SEQ<br>ID NO: 95) | ATGGGTGTTAGTGATGTTCCGCGTGATCT<br>GGAAGTTGTTGCAGCAACCCCGACCAGCC<br>TGCTGATTAGCTGGACCCTGCCGCATGCA<br>GGTCGTGCACATTATTATCGTATTACCTAT<br>GGTGAAACCGGTGGTAATAGTCCGGTTCA<br>GGAATTCACCGTTCCGGGTCGTGGTGTTA<br>CCGCAACCATTAGCGGTCTGAAACCGGGT<br>GTTGATTACACCATTACCGTTTATGCAGTT<br>ACCCTGACCCGCAGCAAAATTATTCATTA<br>TATGCCGATTAGCATTAATTATCGCACCG<br>AAATTGATAAACCGAGCCAGCATCATCAT<br>CACCATCAT (SEQ ID NO: 139) |
| 2987_C02<br>(Adnectin core 17<br>sequence having<br>AdNT1 (underlined)<br>and AdCT1 (italics)<br>terminal sequence<br>with His6 tag) | MGVSDVPRDLEVVAATPTSLLIS<br>WSLPYAGHAHYYRITYGETGGN<br>SPVQEFTVPGRGVTATISGLKPG<br>VDYTITVYAVTLTKSKIIHYMPIS<br>INYRTEIDKPSQHHHHHH (SEQ<br>ID NO: 96) | ATGGGTGTTAGTGATGTTCCGCGTGATCT<br>GGAAGTTGTTGCAGCAACCCCGACCAGCC<br>TGCTGATTAGCTGGTCACTGCCGTATGCA<br>GGTCATGCACATTATTATCGTATTACCTAT<br>GGTGAAACCGGTGGTAATAGTCCGGTTCA<br>GGAATTCACCGTTCCGGGTCGTGGTGTTA<br>CCGCAACCATTAGCGGTCTGAAACCGGGT<br>GTTGATTACACCATTACCGTTTATGCAGTT<br>ACCCTGACCAAAGCAAAATTATTCATTA<br>TATGCCGATTAGCATTAATTATCGCACCG<br>AAATTGATAAACCGAGCCAGCATCATCAT<br>CACCATCAT (SEQ ID NO: 140) |
| 2987_D05<br>(Adnectin core 18<br>sequence having<br>AdNT1 (underlined)<br>and AdCT1 (italics)<br>terminal sequence<br>with His6 tag) | MGVSDVPRDLEVVAATPTSLLIS<br>WSLPHAGHAHYYRITYGETGGN<br>SPVQEFTVPGRGVTATISGLKPG<br>VDYTITVYAVTLTRSKIIHYMPIS<br>INYRTEIDKPSQHHHHHH (SEQ<br>ID NO: 97) | ATGGGTGTTAGTGATGTTCCGCGTGATCT<br>GGAAGTTGTTGCAGCAACCCCGACCAGCC<br>TGCTGATTAGCTGGTCACTGCCGCATGCA<br>GGTCATGCACATTATTATCGTATTACCTAT<br>GGTGAAACCGGTGGTAATAGTCCGGTTCA<br>GGAATTCACCGTTCCGGGTCGTGGTGTTA<br>CCGCAACCATTAGCGGTCTGAAACCGGGT<br>GTTGATTACACCATTACCGTTTATGCAGTT<br>ACCCTGACCCGCAGCAAAATTATTCATTA<br>TATGCCGATTAGCATTAATTATCGCACCG<br>AAATTGATAAACCGAGCCAGCATCATCAT<br>CACCATCAT (SEQ ID NO: 141) |
| 2987_E03<br>(Adnectin core 19<br>sequence having<br>AdNT1 (underlined)<br>and AdCT1 (italics)<br>terminal sequence<br>with His6 tag) | MGVSDVPRDLEVVAATPTSLLIS<br>WSLPYPGHLNYYRITYGETGGN<br>SPVQEFTVPGRGVTATISGLKPG<br>VDYTITVYAVTLTRSKIIHYMPIS<br>INYRTEIDKPSQHHHHHH (SEQ<br>ID NO: 98) | ATGGGTGTTAGTGATGTTCCGCGTGATCT<br>GGAAGTTGTTGCAGCAACCCCGACCAGCC<br>TGCTGATTAGCTGGTCACTGCCGTATCCG<br>GGTCATCTGAATTATTATCGTATTACCTAT<br>GGTGAAACCGGTGGTAATAGTCCGGTTCA<br>GGAATTCACCGTTCCGGGTCGTGGTGTTA<br>CCGCAACCATTAGCGGTCTGAAACCGGGT<br>GTTGATTACACCATTACCGTTTATGCAGTT<br>ACCCTGACCCGCAGCAAAATTATTCATTA<br>TATGCCGATTAGCATTAATTATCGCACCG<br>AAATTGATAAACCGAGCCAGCATCATCAT<br>CACCATCAT (SEQ ID NO: 142) |
| 2987_E08<br>(Adnectin core 20<br>sequence having<br>AdNT1 (underlined)<br>and AdCT1 (italics)<br>terminal sequence<br>with His6 tag) | MGVSDVPRDLEVVAATPTSLLIS<br>WTLPHAGRAHYYRITYGETGGN<br>SPVQEFTVPGRGVTATISGLKPG<br>VDYTITVYAVTVSSTKVIHYKPIS<br>INYRTEIDKPSQHHHHHH (SEQ<br>ID NO: 99) | ATGGGTGTTAGTGATGTTCCGCGTGATCT<br>GGAAGTTGTTGCAGCAACCCCGACCAGCC<br>TGCTGATTAGCTGGACCCTGCCGCATGCA<br>GGTCGTGCACATTATTATCGTATTACCTAT<br>GGTGAAACCGGTGGTAATAGTCCGGTTCA<br>GGAATTCACCGTTCCGGGTCGTGGTGTTA<br>CCGCAACCATTAGCGGTCTGAAACCGGGT<br>GTTGATTACACCATTACCGTTTATGCAGTT<br>ACCGTTAGCAGCACCAAAGTGATTCATTA<br>TAAACCGATTAGCATTAATTATCGCACCG<br>AAATTGATAAACCGAGCCAGCATCATCAT<br>CACCATCAT (SEQ ID NO: 143) |
| 2987_F01<br>(Adnectin core 21<br>sequence having<br>AdNT1 (underlined)<br>and AdCT1 (italics) | MGVSDVPRDLEVVAATPTSLLIS<br>WSLPYAGHAHYYRITYGETGGN<br>SPVQEFTVPGRGVTATISGLKPG<br>VDYTITVYAVTLTRSKIIHYMPIS<br>INYRTEIDKPSQHHHHHH (SEQ | ATGGGTGTTAGTGATGTTCCGCGTGATCT<br>GGAAGTTGTTGCAGCAACCCCGACCAGCC<br>TGCTGATTAGCTGGTCACTGCCGTATGCA<br>GGTCATGCACATTATTATCGTATTACCTAT<br>GGTGAAACCGGTGGTAATAGTCCGGTTCA |

TABLE 2-continued

Anti-Myostatin MonoAdnectins

| | Sequence | |
|---|---|---|
| | Amino Acid Sequence | Nucleic Acid Sequence |
| terminal sequence with His6 tag) | ID NO: 100) | GGAATTCACCGTTCCGGGTCGTGGTGTTA CCGCAACCATTAGCGGTCTGAAACCGGGT GTTGATTACACCATTACCGTTTATGCAGTT ACCCTGACCCGCAGCAAAATTATTCATTA TATGCCGATTAGCATTAATTATCGCACCG AAATTGATAAACCGAGCCAGCATCATCAT CACCATCAT (SEQ ID NO: 144) |
| 2987_F06 (Adnectin core 22 sequence having AdNT1 (underlined) and AdCT1 (italics) terminal sequence with His6 tag) | MGVSDVPRDLEVVAATPTSLLIS WSLPHAGHAHYYRITYGETGGN SPVQEFTVPGRGVTATISGLKPG VDYTITVYAVTLTKSKVIHYMPI SINYRTEIDKPSQHHHHHH (SEQ ID NO: 101) | ATGGGTGTTAGTGATGTTCCGCGTGATCT GGAAGTTGTTGCAGCAACCCCGACCAGCC TGCTGATTAGCTGGTCACTGCCGCATGCA GGTCATGCACATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCCTGACCAAAAGCAAAGTGATTCATTA TATGCCGATTAGCATTAATTATCGCACCG AAATTGATAAACCGAGCCAGCATCATCAT CACCATCAT (SEQ ID NO: 145) |
| 2987_G04 (Adnectin core 23 sequence having AdNT1 (underlined) and AdCT1 (italics) terminal sequence with His6 tag) | MGVSDVPRDLEVVAATPTSLLIS WSLPYPGHLNYYRITYGETGGN SPVQEFTVPGRGVTATISGLKPG VDYTITVYAVTLTKSKVIHYMPI SINYRTEIDKPSQHHHHHH (SEQ ID NO: 102) | ATGGGTGTTAGTGATGTTCCGCGTGATCT GGAAGTTGTTGCAGCAACCCCGACCAGCC TGCTGATTAGCTGGTCACTGCCGTATCCG GGTCATCTGAATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCCTGACCAAAAGCAAAGTGATTCATTA TATGCCGATTAGCATTAATTATCGCACCG AAATTGATAAACCGAGCCAGCATCATCAT CACCATCAT (SEQ ID NO: 146) |
| 2987_G09 (Adnectin core 24 sequence having AdNT1 (underlined) and AdCT1 (italics) terminal sequence with His6 tag) | MGVSDVPRDLEVVAATPTSLLIS WTLPHAGRAHYYRITYGETGGN SPVQEFTVPGRGVTATISGLKPG VDYTITVYAVTVSSTKVIVYLPIS INYRTEIDKPSQHHHHHH (SEQ ID NO: 103) | ATGGGTGTTAGTGATGTTCCGCGTGATCT GGAAGTTGTTGCAGCAACCCCGACCAGCC TGCTGATTAGCTGGACCCTGCCGCATGCA GGTCGTGCACATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCGTTAGCAGCACCAAAGTTATTGTTTA TCTGCCGATTAGCATTAATTATCGCACCG AAATTGATAAACCGAGCCAGCATCATCAT CACCATCAT (SEQ ID NO: 147) |
| 2987_H02 (Adnectin core 25 sequence having AdNT1 (underlined) and AdCT1 (italics) terminal sequence with His6 tag) | MGVSDVPRDLEVVAATPTSLLIS WSLPYAGHAHYYRITYGETGGN SPVQEFTVPGRGVTATISGLKPG VDYTITVYAVTLTKSKVIHYMPI SINYRTEIDKPSQHHHHHH (SEQ ID NO: 104) | ATGGGTGTTAGTGATGTTCCGCGTGATCT GGAAGTTGTTGCAGCAACCCCGACCAGCC TGCTGATTAGCTGGTCACTGCCGTATGCA GGTCATGCACATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCCTGACCAAAAGCAAAGTGATTCATTA TATGCCGATTAGCATTAATTATCGCACCG AAATTGATAAACCGAGCCAGCATCATCAT CACCATCAT (SEQ ID NO: 148) |
| 2987_H07 (Adnectin core 26 sequence having AdNT1 (underlined) and AdCT1 (italics) terminal sequence with His6 tag) | MGVSDVPRDLEVVAATPTSLLIS WTLPHAGRAHYYRITYGETGGN SPVQEFTVPGRGVTATISGLKPG VDYTITVYAVTVTTTKVIHYKPI SINYRTEIDKPSQHHHHHH (SEQ ID NO: 105) | ATGGGTGTTAGTGATGTTCCGCGTGATCT GGAAGTTGTTGCAGCAACCCCGACCAGCC TGCTGATTAGCTGGACCCTGCCGCATGCA GGTCGTGCACATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCGTTACCACCACCAAAGTGATTCATTA TAAACCGATTAGCATTAATTATCGCACCG AAATTGATAAACCGAGCCAGCATCATCAT CACCATCAT (SEQ ID NO: 149) |

TABLE 2-continued

Anti-Myostatin MonoAdnectins

| | Sequence | |
|---|---|---|
| | Amino Acid Sequence | Nucleic Acid Sequence |
| 3006_A10 (Adnectin core 27 sequence having AdNT1 (underlined) and AdCT1 (italics) terminal sequence with His6 tag) | MGVSDVPRDLEVVAATPTSLLIS WDAPGGLARYYRITYGETGGNS PVQEFTVIGRGSTATISGLKPGVD YTITVYAVTIDRDGVNHFAPISIN YRT*EIDKPSQ*HHHHHH (SEQ ID NO: 106) | ATGGGAGTTTCTGATGTGCCGCGCGACCT GGAAGTGGTTGCTGCCACCCCCACCAGCC TGCTGATCAGCTGGGACGCTCCGGGTGGT CTGGCTCGATATTACCGCATCACTTACGG CGAAACAGGAGGCAATAGCCCTGTCCAG GAGTTCACTGTGATCGGTCGTGGTAGCAC AGCTACCATCAGCGGCCTTAAACCTGGCG TTGATTATACCATCACTGTGTATGCTGTCA CTATCGACCGTGACGGTGTCAACCACTTC GCCCCAATTTCCATTAATTACCGCACAGA AATTGACAAACCATCCCAGCACCATCACC ACCACCAC (SEQ ID NO: 150) |
| 3007_B08 (Adnectin core 28 sequence having AdNT1 (underlined) and AdCT1 (italics) terminal sequence with His6 tag) | MGVSDVPRDLEVVAATPTSLLIS WSLPTPGLAHYYRITYGETGGNS PVQEFTVPGRGVTATISGLKPGV DYTITVYAVTVTHHGVIGYKPISI NYRT*EIDKPSQ*HHHHHH (SEQ ID NO: 107) | ATGGGAGTTTCTGATGTGCCGCGCGACCT GGAAGTGGTTGCTGCCACCCCCACCAGCC TGCTGATCAGCTGGTCTCTGCCGACTCCA GGTCTCGCCCATTATTACCGCATCACTTAC GGCGAAACAGGAGGCAATAGCCCTGTCC AGGAGTTCACTGTGCCTGGTCGTGGTGTT ACAGCTACCATCAGCGGCCTTAAACCTGG CGTTGATTATACCATCACTGTGTATGCTGT CACTGTCACTCATCACGGCGTCATCGGCT ACAAACCAATTTCCATTAATTACCGCACA GAAATTGACAAACCATCCCAGCACCATCA CCACCACCAC (SEQ ID NO: 151) |
| 3007_C09 (Adnectin core 29 sequence having AdNT1 (underlined) and AdCT1 (italics) terminal sequence with His6 tag) | MGVSDVPRDLEVVAATPTSLLIS WSLPHRGVANYYRITYGETGGN SPVQEFTVPGRGVTATISGLKPG VDYTITVYAVTLTGANVIIYKPIS INYRT*EIDKPSQ*HHHHHH (SEQ ID NO: 108) | ATGGGAGTTTCTGATGTGCCGCGCGACCT GGAAGTGGTTGCTGCCACCCCCACCAGCC TGCTGATCAGCTGGTCTCTGCCGCACCGT GGTGTCGCCAATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTCTCACTGGAGCGAACGTCATCAT CTACAAACCAATTTCCATTAATTACCGCA CAGAAATTGACAAACCATCCCAGCACCAT CACCACCACCAC (SEQ ID NO: 152) |
| 3007_C10 (Adnectin core 30 sequence having AdNT1 (underlined) and AdCT1 (italics) terminal sequence with His6 tag) | MGVSDVPRDLEVVAATPTSLLIS WSLPSSGVAHYYRITYGETGGNS PVQEFTVPGRGVTATISGLKPGV DYTITVYAVTVTNTGVIIYKPISI NYRT*EIDKPSQ*HHHHHH (SEQ ID NO: 109) | ATGGGAGTTTCTGATGTGCCGCGCGACCT GGAAGTGGTTGCTGCCACCCCCACCAGCC TGCTGATCAGCTGGTCTCTGCCGAGCAGC GGTGTCGCCCATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTGTCACTAACACTGGTGTCATCAT CTACAAACCAATTTCCATTAATTACCGCA CAGAAATTGACAAACCATCCCAGCACCAT CACCACCACCAC (SEQ ID NO: 153) |
| 3008_A03 (Adnectin core 31 sequence having AdNT1 (underlined) and AdCT1 (italics) terminal sequence with His6 tag) | MGVSDVPRDLEVVAATPTSLLIS WSLPHHGFGHYYRITYGETGGN SPVQEFTVPGRGVTATISGLKPG VDYTITVYAVTVTATGIIIYKPISI NYRT*EIDKPSQ*HHHHHH (SEQ ID NO: 110) | ATGGGAGTTTCTGATGTGCCGCGCGACCT GGAAGTGGTTGCTGCCACCCCCACCAGCC TGCTGATCAGCTGGTCTCTGCCGCATCAC GGTTTCGGCCATTATTACCGCATCACTTAC GGCGAAACAGGAGGCAATAGCCCTGTCC AGGAGTTCACTGTGCCTGGTCGTGGTGTT ACAGCTACCATCAGCGGCCTTAAACCTGG CGTTGATTATACCATCACTGTGTATGCTGT CACTGTCACTGCTACGGGGATCATCATCT ACAAACCAATTTCCATTAATTACCGCACA GAAATTGACAAACCATCCCAGCACCATCA CCACCACCAC (SEQ ID NO: 154) |
| 3008_B08 (Adnectin core 32 sequence having AdNT1 (underlined) and AdCT1 (italics) terminal sequence with His6 tag) | MGVSDVPRDLEVVAATPTSLLIS WSLPHAGDAHYYRITYGETGGN SPVQEFTVPGRGVTATISGLKPG VDYTITVYAVTVTRAGFYRYKPI SINYRT*EIDKPSQ*HHHHHH (SEQ ID NO: 111) | ATGGGAGTTTCTGATGTGCCGCGCGACCT GGAAGTGGTTGCTGCCACCCCCACCAGCC TGCTGATCAGCTGGTCTCTGCCGCACGCC GGTGACGCCCATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTGTTACTAGAGCGGGTTTCTACCG |

TABLE 2-continued

Anti-Myostatin MonoAdnectins

| | Sequence | |
|---|---|---|
| | Amino Acid Sequence | Nucleic Acid Sequence |
| | | CTACAAACCAATTTCCATTAATTACCGCA CAGAAATTGACAAACCATCCCAGCACCAT CACCACCACCAC (SEQ ID NO: 155) |
| 3008_D04 (Adnectin core 33 sequence having AdNT1 (underlined) and AdCT1 (italics) terminal sequence with His6 tag) | MGVSDVPRDLEVVAATPTSLLIS WSLPHNGVAHYYRITYGETGGN SPVQEFTVPGRGVTATISGLKPG VDYTITVYAVTVTREEVISYKPIS INYRT*EIDKPSQ*HHHHHH (SEQ ID NO: 112) | ATGGGAGTTTCTGATGTGCCGCGCGACCT GGAAGTGGTTGCTGCCACCCCCACCAGCC TGCTGATCAGCTGGTCTCTGCCGCATAAT GGTGTCGCCCATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTGTCACTCGGGAGGAAGTCATCAG CTACAAACCAATTTCCATTAATTACCGCA CAGAAATTGACAAACCATCCCAGCACCAT CACCACCACCAC (SEQ ID NO: 156) |
| 3008_F01 (Adnectin core 34 sequence having AdNT1 (underlined) and AdCT1 (italics) terminal sequence with His6 tag) | MGVSDVPRDLEVVAATPTSLLIS WSLPRQGLANYYRITYGETGGN SPVQEFTVPGRGVTATISGLKPG VDYTITVYAVTVTAAGVIIYKPIS INYRT*EIDKPSQ*HHHHHH (SEQ ID NO: 113) | ATGGGAGTTTCTGATGTGCCGCGCGACCT GGAAGTGGTTGCTGCCACCCCCACCAGCC TGCTGATCAGCTGGTCTCTGCCGCGTCAG GGTCTCGCCAATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTGTCACTGCTGCTGGGGTCATCAT CTACAAACCAATTTCCATTAATTACCGCA CAGAAATTGACAAACCATCCCAGCACCAT CACCACCACCAC (SEQ ID NO: 157) |
| 3008_G01 (Adnectin core 35 sequence having AdNT1 (underlined) and AdCT1 (italics) terminal sequence with His6 tag) | MGVSDVPRDLEVVAATPTSLLIS WSLPGPGHFHYYRITYGETGGNS PVQEFTVPGRGVTATISGLKPGV DYTITVYAVTVTANQPIIYKPISI NYRT*EIDKPSQ*HHHHHH (SEQ ID NO: 114) | ATGGGAGTTTCTGATGTGCCGCGCGACCT GGAAGTGGTTGCTGCCACCCCCACCAGCC TGCTGATCAGCTGGTCTCTGCCGGGACCG GGTCACTTCCATTATTACCGCATCACTTAC GGCGAAACAGGAGGCAATAGCCCTGTCC AGGAGTTCACTGTGCCTGGTCGTGGTGTT ACAGCTACCATCAGCGGCCTTAAACCTGG CGTTGATTATACCATCACTGTGTATGCTGT CACTGTCACTGCTAACCAGCCCATCATCT ACAAACCAATTTCCATTAATTACCGCACA GAAATTGACAAACCATCCCAGCACCATCA CCACCACCAC (SEQ ID NO: 158) |
| 3008_G03 (Adnectin core 36 sequence having AdNT1 (underlined) and AdCT1 (italics) terminal sequence with His6 tag) | MGVSDVPRDLEVVAATPTSLLIS WSLPHPGLGHYYRITYGETGGN SPVQEFTVPGRGVTATISGLKPG VDYTITVYAVTITPETIIVYKPISI NYRT*EIDKPSQ*HHHHHH (SEQ ID NO: 115) | ATGGGAGTTTCTGATGTGCCGCGCGACCT GGAAGTGGTTGCTGCCACCCCCACCAGCC TGCTGATCAGCTGGTCTCTGCCGCACCCC GGTCTCGGCCATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTATCACTCCGGAAACGATCATCGT CTACAAACCAATTTCCATTAATTACCGCA CAGAAATTGACAAACCATCCCAGCACCAT CACCACCACCAC (SEQ ID NO: 159) |
| 3115_D04 (Adnectin core 37 sequence having AdNT1 (underlined) and AdCT1 (italics) terminal sequence with His6 tag) | MGVSDVPRDLEVVAATPTSLLIS WDAPRGLARYYRITYGETGGNS PVQEFTVFGRGTTATISGLKPGV DYTITVYAVTIDRDGTRSFDPISI NYRT*EIDKPSQ*HHHHHH (SEQ ID NO: 116) | ATGGGAGTTTCTGATGTGCCGCGCGACCT GGAAGTGGTTGCTGCCACCCCCACCAGCC TGCTGATCAGCTGGGACGCTCCGAGAGGT CTGGCTCGATATTACCGCATCACTTACGG CGAAACAGGAGGCAATAGCCCTGTCCAG GAGTTCACTGTGTTCGGTCGTGGTACCAC AGCTACCATCAGCGGCCTTAAACCTGGCG TTGATTATACCATCACTGTGTATGCTGTCA CTATCGACCGTGACGGTACCCGCAGCTTC GACCCAATTTCCATTAATTACCGCACAGA AATTGACAAACCATCCCAGCACCATCACC ACCACCAC (SEQ ID NO: 160) |
| 3115_E06 (Adnectin core 38 sequence having AdNT1 (underlined) and AdCT1 (italics) | MGVSDVPRDLEVVAATPTSLLIS WDAPAGLARYYRITYGETGGNS PVQEFTVVGRGNTATISGLKPGV DYTITVYAVTIFRDGPVTWDPISI NYRT*EIDKPSQ*HHHHHH (SEQ | ATGGGAGTTTCTGATGTGCCGCGCGACCT GGAAGTGGTTGCTGCCACCCCCACCAGCC TGCTGATCAGCTGGGACGCTCCGGCTGGT CTGGCTCGATATTACCGCATCACTTACGG CGAAACAGGAGGCAATAGCCCTGTCCAG |

TABLE 2-continued

Anti-Myostatin MonoAdnectins

| | Sequence | |
|---|---|---|
| | Amino Acid Sequence | Nucleic Acid Sequence |
| terminal sequence with His6 tag) | ID NO: 117) | GAGTTCACTGTGGTCGGTCGTGGTAACAC AGCTACCATCAGCGGCCTTAAACCTGGCG TTGATTATACCATCACTGTGTATGCTGTCA CTATCTTCCGTGACGGTCCCGTCACCTGG GACCCAATTTCCATTAATTACCGCACAGA AATTGACAAACCATCCCAGCACCATCACC ACCACCAC (SEQ ID NO: 161) |
| 3116_A06 (Adnectin core 39 sequence having AdNT1 (underlined) and AdCT1 (italics) terminal sequence with His6 tag) | MGVSDVPRDLEVVAATPTSLLIS WSLPHQGKANYYRITYGETGGN SPVQEFTVPGRGVTATISGLKPG VDYTITVYAVTVTDTGYLKYKPI SINYRTEIDKPSQHHHHHH (SEQ ID NO: 118) | ATGGGAGTTTCTGATGTGCCGCGCGACCT GGAAGTGGTTGCTGCCACCCCCACCAGCC TGCTGATCAGCTGGTCTCTGCCGCACCAA GGTAAAGCCAATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTGTTACTGATACAGGGTACCTCAA GTACAAACCAATTTCCATTAATTACCGCA CAGAAATTGACAAACCATCCCAGCACCAT CACCACCACCAC (SEQ ID NO: 162) |
| 3116_A07 (Adnectin core 40 sequence having AdNT1 (underlined) and AdCT1 (italics) terminal sequence with His6 tag) | MGVSDVPRDLEVVAATPTSLLIS WDAPKGLARYYRITYGETGGNS PVQEFTVVGRGNTATISGLKPGV DYTITVYAVTIFRDGPVTWDPISI NYRTEIDKPSQHHHHHH (SEQ ID NO: 119) | ATGGGAGTTTCTGATGTGCCGCGCGACCT GGAAGTGGTTGCTGCCACCCCCACCAGCC TGCTGATCAGCTGGGACGCTCCGAAGGGT CTGGCTCGATATTACCGCATCACTTACGG CGAAACAGGAGGCAATAGCCCTGTCCAG GAGTTCACTGTGGTCGGTCGTGGTAACAC AGCTACCATCAGCGGCCTTAAACCTGGCG TTGATTATACCATCACTGTGTATGCTGTCA CTATCTTCCGTGACGGTCCCGTCACCTGG GACCCAATTTCCATTAATTACCGCACAGA AATTGACAAACCATCCCAGCACCATCACC ACCACCAC (SEQ ID NO: 163) |
| 3116_C01 (Adnectin core 41 sequence having AdNT1 (underlined) and AdCT1 (italics) terminal sequence with His6 tag) | MGVSDVPRDLEVVAATPTSLLIS WSLPNPGIAHYYRITYGETGGNS PVQEFTVPGRGVTATISGLKPGV DYTITVYAVTLTGSDTIFYKPISI NYRTEIDKPSQHHHHHH (SEQ ID NO: 120) | ATGGGAGTTTCTGATGTGCCGCGCGACCT GGAAGTGGTTGCTGCCACCCCCACCAGCC TGCTGATCAGCTGGTCTCTGCCGAATCCC GGTATCGCCCATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTCTCACTGGCAGTGACACCATCTT CTACAAACCAATTTCCATTAATTACCGCA CAGAAATTGACAAACCATCCCAGCACCAT CACCACCACCAC (SEQ ID NO: 164) |
| 3116_C06 (Adnectin core 42 sequence having AdNT1 (underlined) and AdCT1 (italics) terminal sequence with His6 tag) | MGVSDVPRDLEVVAATPTSLLIS WSLPRPGNAHYYRITYGETGGN SPVQEFTVPGRGVTATISGLKPG VDYTITVYAVTVTGKDVIKYKPI SINYRTEIDKPSQHHHHHH (SEQ ID NO: 121) | ATGGGAGTTTCTGATGTGCCGCGCGACCT GGAAGTGGTTGCTGCCACCCCCACCAGCC TGCTGATCAGCTGGTCTCTGCCGCGGCCG GGTAACGCCCATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTGTTACTGGCAAAGATGTCATCAA GTACAAACCAATTTCCATTAATTACCGCA CAGAAATTGACAAACCATCCCAGCACCAT CACCACCACCAC (SEQ ID NO: 165) |
| 3116_H06 (Adnectin core 43 sequence having AdNT1 (underlined) and AdCT1 (italics) terminal sequence with His6 tag) | MGVSDVPRDLEVVAATPTSLLIS WDAPAGLARYYRITYGETGGNS PVQEFTVVGRGNTATISGLKPGV DYTITVYAVTIFRDGVVNYGPISI NYRTEIDKPSQHHHHHH (SEQ ID NO: 122) | ATGGGAGTTTCTGATGTGCCGCGCGACCT GGAAGTGGTTGCTGCCACCCCCACCAGCC TGCTGATCAGCTGGGACGCTCCGGCTGGT CTGGCTCGATATTACCGCATCACTTACGG CGAAACAGGAGGCAATAGCCCTGTCCAG GAGTTCACTGTGGTCGGTCGTGGTAACAC AGCTACCATCAGCGGCCTTAAACCTGGCG TTGATTATACCATCACTGTGTATGCTGTCA CTATCTTCCGTGACGGTGTCGTCAACTAC GGCCCAATTTCCATTAATTACCGCACAGA AATTGACAAACCATCCCAGCACCATCACC ACCACCAC (SEQ ID NO: 166) |

TABLE 2-continued

Anti-Myostatin MonoAdnectins

| | Sequence | |
|---|---|---|
| | Amino Acid Sequence | Nucleic Acid Sequence |
| 3146_A08 (Adnectin core 44 sequence having AdNT1 (underlined) and AdCT1 (italics) terminal sequence with His6 tag) | MGVSDVPRDLEVVAATPTSLLIS WSLPNPGNAHYYRITYGETGGN SPVQEFTVPGRGVTATISGLKPG VDYTITVYAVTVTDTGFITYKPIS INYRT*EIDKPSQ*HHHHHH (SEQ ID NO: 123) | ATGGGAGTTTCTGATGTGCCGCGCGACCT GGAAGTGGTTGCTGCCACCCCCACCAGCC TGCTGATCAGCTGGTCTCTGCCGAATCCG GGTAACGCCCATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTGTTACTGACACAGGTTTCATCAC GTACAAACCAATTTCCATTAATTACCGCA CAGAAATTGACAAACCATCCCAGCACCAT CACCACCACCAC (SEQ ID NO: 167) |

Cross-Competing Adnectins and/or Adnectins that Bind to the Same Adnectin Binding Site In one embodiment, Adnectins of the invention compete (e.g., cross-compete) for binding to myostatin with the particular anti-myostatin Adnectins described herein. Such competing Adnectins can be identified based on their ability to competitively inhibit binding to myostatin of Adnectins described herein in standard myostatin binding assays. For example, standard ELISA assays can be used in which a recombinant myostatin protein is immobilized on the plate, one of the Adnectins is fluorescently labeled and the ability of non-labeled Adnectins to compete off the binding of the labeled Adnectin is evaluated.

In one embodiment, a competitive ELISA format can be performed to determine whether two anti-myostatin Adnectins bind overlapping Adnectin binding sites on myostatin. In one format, Adnectin #1 is coated on a plate, which is then blocked and washed. To this plate is added either myostatin alone, or myostatin pre-incubated with a saturating concentration of Adnectin #2. After a suitable incubation period, the plate is washed and probed with a polyclonal anti-myostatin antibody, such as a biotinylated goat anti-myostatin polyclonal antibody (R&D Systems), followed by detection with streptavidin-HRP conjugate and standard tetramethylbenzidine development procedures. If the OD signal is the same with or without preincubation with Adnectin #2, then the two Adnectins bind independently of one another, and their Adnectin binding sites do not overlap. If, however, the OD signal for wells that received myostatin/Adnectin#2 mixtures is lower than for those that received myostatin alone, then binding of Adnectin #2 is confirmed to block binding of Adnectin #1 to myostatin.

Alternatively, a similar experiment is conducted by surface plasmon resonance (SPR, e.g., BIAcore). Adnectin #1 is immobilized on an SPR chip surface, followed by injections of either myostatin alone or myostatin pre-incubated with a saturating concentration of Adnectin #2. If the binding signal for myostatin/Adnectin#2 mixtures is the same or higher than that of myostatin alone, then the two Adnectins bind independently of one another, and their Adnectin binding sites do not overlap. If, however, the binding signal for myostatin/Adnectin#2 mixtures is lower than the binding signal for myostatin alone, then binding of Adnectin #2 is confirmed to block binding of Adnectin #1 to myostatin. A feature of these experiments is the use of saturating concentrations of Adnectin #2. If myostatin is not saturated with Adnectin #2, then the conclusions above do not hold.

Similar experiments can be used to determine if any two myostatin binding proteins bind to overlapping Adnectin binding sites.

Both assays exemplified above may also be performed in the reverse order where Adnectin#2 is immobilized and myostatin—Adnectin#1 are added to the plate. Alternatively, Adnectin #1 and/or #2 can be replaced with a monoclonal antibody and/or soluble receptor-Fc fusion protein.

In another embodiment, competition can be determined using a HTRF sandwich assay, as described in Example 4.

In other embodiments, the competing Adnectin is an Adnectin that binds to the same Adnectin binding site on myostatin as a particular anti-myostatin Adnectin described herein. Standard mapping techniques, such as protease mapping, mutational analysis, x-ray crystallography and 2-dimensional nuclear magnetic resonance, can be used to determine whether an Adnectin binds to the same Adnectin binding site as a reference Adnectin (see, e.g., *Epitope Mapping Protocols in Methods in Molecular Biology*, Vol. 66, G. E. Morris, Ed. (1996)).

Candidate competing anti-myostatin Adnectins can inhibit the binding of anti-myostatin Adnectins of the invention to myostatin by at least 50%, at least 55%, at least 60%, at least 65%, at least 70%, at least 75%, at least 80%, at least 85%, at least 90%, at least 95%, at least 97%, at least 98%, or at least 99%. The % competition can be determined using the methods described above.

In some embodiments, molecules that compete with the anti-myostatin Adnectins of the invention need not be an Adnectin, but can be any type of molecule that binds to myostatin, such as, but not limited to, an antibody, a small molecule, a peptide, and the like.

In some embodiments, Adnectins of the invention bind to a discontinuous Adnectin binding site on myostatin. In some embodiments, the polypeptides bind a region within amino acids 55-66 of myostatin (SEQ ID NO: 3). In some embodiments, the polypeptides bind a region within amino acids 85-101 of myostatin (SEQ ID NO: 3). In yet other embodiments, the polypeptides bind within two regions, amino acids 85-101 and 55-66, of myostatin (SEQ ID NO: 3).

In some embodiments, the polypeptides of the invention do not compete for binding to myostatin with ActRIIB In some embodiments, the polypeptides of the invention compete for binding to myostatin with ALK4 and/or ALK5.

II. Extension Sequences

In certain embodiments, the anti-myostatin Adnectin molecules of the present invention may be modified to comprise an N-terminal extension sequence and/or a C-terminal extension. For example, an MG sequence may be placed at the N-terminus of the $^{10}$Fn3 defined by SEQ ID NO: 4. The M will usually be cleaved off, leaving a G at the N-terminus. Alternatively, the first 10 amino acids of the anti-myostatin Adnectins shown in Table 2 may be replaced with an alternative N-terminal sequence, referred to herein as N-terminal extensions, as shown in Table 7. In addition, an M, G or MG may also be placed N-terminal to any of the N-terminal extensions shown in Table 7. The anti-myostatin Adnectins described herein may also comprise alternative C-terminal tail sequences, referred to herein as C-terminal extension sequences. For example, the anti-myostatin Adnectin sequences shown in Table 2 may be truncated at the threonine corresponding to T94 of SEQ ID NO: 4 (i.e., truncated after INYRT (SEQ ID NO: 168) portion of the sequence). Such truncated version may be used as therapeutic molecules in the truncated form, or alternative C-terminal extensions may be added after the threonine residue. Exemplary C-terminal extension sequences are shown in Table 7. Exemplary anti-myostatin Adnectins comprising C-terminal extension sequences are shown in Table 2 as SEQ ID NOs: 80-123. For example, SEQ ID NO: 80 (clone 1979_B06) comprises the naturally occurring C-terminal extension EIDKPSQ (SEQ ID NO: 211) followed by a His6 tag (SEQ ID NO: 328). However, it should be understood that the His6 tag is completely optional.

In certain embodiments, the C-terminal extension sequences (also called "tails"), comprise E and D residues, and may be between 8 and 50, 10 and 30, 10 and 20, 5 and 10, and 2 and 4 amino acids in length. In some embodiments, tail sequences include ED-based linkers in which the sequence comprises tandem repeats of ED. In exemplary embodiments, the tail sequence comprises 2-10, 2-7, 2-5, 3-10, 3-7, 3-5, 3, 4 or 5 ED repeats. In certain embodiments, the ED-based tail sequences may also include additional amino acid residues, such as, for example: EI, EID, ES, EC, EGS, and EGC. Such sequences are based, in part, on known Adnectin tail sequences, such as EIDKPSQ (SEQ ID NO: 211), in which residues D and K have been removed. In exemplary embodiments, the ED-based tail comprises an E, I or EI residues before the ED repeats.

In other embodiments, the N- or C-terminal sequences may be combined with known linker sequences (e.g., SEQ ID NO: 181-227 in Table 4) as necessary when designing an anti-myostatin Adnectin fusion molecule. In some embodiments, sequences may be placed at the C-terminus of the $^{10}$Fn3 domain to facilitate attachment of a pharmacokinetic moiety. For example, a cysteine containing linker such as GSGC (SEQ ID NO: 189) may be added to the C-terminus to facilitate site directed PEGylation on the cysteine residue. Exemplary anti-myostatin Adnectins comprising a cysteine containing linker are shown in Table 5 as SEQ ID NOs: 228-239.

III. Pharmacokinetic Moieties

In one aspect, the application provides for anti-myostatin Adnectins further comprising a pharmacokinetic (PK) moiety. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The anti-myostatin Adnectin may be attached to a moiety that reduces the clearance rate of the polypeptide in a mammal (e.g., mouse, rat, or human) by greater than two-fold, greater than three-fold, greater than four-fold or greater than five-fold relative to the unmodified anti-myostatin Adnectin. Other measures of improved pharmacokinetics may include serum half-life, which is often divided into an alpha phase and a beta phase. Either or both phases may be improved significantly by addition of an appropriate moiety. For example, the PK moiety may increase the serum half-life of the polypeptide by more than 5, 10, 20, 30, 40, 50, 60, 70, 80, 90, 100, 120, 150, 200, 400, 600, 800, 1000% or more relative to the Fn3 domain alone.

Moieties that slow clearance of a protein from the blood, herein referred to as "PK moieties", include polyoxyalkylene moieties (e.g., polyethylene glycol), sugars (e.g., sialic acid), and well-tolerated protein moieties (e.g., Fc and fragments and variants thereof, transferrin, or serum albumin). The anti-myostatin Adnectin may also be fused to albumin or a fragment (portion) or variant of albumin as described in U.S. Publication No. 2007/0048282, or may be fused to one or more serum albumin binding Adnectin, as described herein.

Other PK moieties that can be used in the invention include those described in Kontermann et al., (*Current Opinion in Biotechnology* 2011; 22:868-76), herein incorporated by reference. Such PK moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

Accordingly, in some embodiments the invention provides an anti-myostatin Adnectin fused to a PK moiety that is a polymeric sugar. In some embodiments, the PK moiety is a polyethylene glycol moiety or an Fc region. In some embodiments the PK moiety is a serum albumin binding protein such as those described in U.S. Publication Nos. 2007/0178082 and 2007/0269422. In some embodiments the PK moiety is human serum albumin. In some embodiments, the PK moiety is transferrin.

Polyethylene Glycol

In some embodiments, the anti-myostatin Adnectin comprises polyethylene glycol (PEG). PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_{n-1}CH_2CH_2OH$, where n is 20 to 2300 and X is H or a terminal modification, e.g., a $C_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEGs are described in, for example, European Published Application No. 473084A and U.S. Pat. No. 5,932,462.

One or more PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

PEGylation may be achieved by site-directed PEGylation, wherein a suitable reactive group is introduced into the protein to create a site where PEGylation preferentially occurs. In some embodiments, the protein is modified to introduce a cysteine residue at a desired position, permitting site-directed PEGylation on the cysteine. Mutations may be introduced into a protein coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework, based on which binding polypeptides are designed and evolved, has been solved (see Himanen et al., *Nature* 2001; 414:933-8) and thus the surface-exposed residues identified. PEGylation of cysteine residues may be carried out using, for example, PEG-maleimide, PEG-vinylsulfone, PEG-iodoacetamide, or PEG-orthopyridyl disulfide.

The PEG is typically activated with a suitable activating group appropriate for coupling to a desired site on the polypeptide. PEGylation methods are well-known in the art and further described in Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky (1995) *Advanced Drug Reviews* 16: 157-182.

PEG may vary widely in molecular weight and may be branched or linear. Typically, the weight-average molecular weight of PEG is from about 100 Daltons to about 150,000 Daltons. Exemplary weight-average molecular weights for PEG include about 20,000 Daltons, about 40,000 Daltons, about 60,000 Daltons and about 80,000 Daltons. In certain embodiments, the molecular weight of PEG is 40,000 Daltons. Branched versions of PEG having a total molecular weight of any of the foregoing can also be used. In some embodiments, the PEG has two branches. In other embodiments, the PEG has four branches. In another embodiment, the PEG is a bis-PEG (NOF Corporation, DE-200MA), in which two Adnectins are conjugated (see, e.g., Example 1 and ATI-1341 of Table 5).

Conventional separation and purification techniques known in the art can be used to purify PEGylated anti-myostatin Adnectins, such as size exclusion (e.g., gel filtration) and ion exchange chromatography. Products may also be separated using SDS-PAGE. Products that may be separated include mono-, di-, tri-, poly- and un-PEGylated Adnectins, as well as free PEG. The percentage of mono-PEG conjugates can be controlled by pooling broader fractions around the elution peak to increase the percentage of mono-PEG in the composition. About 90% mono-PEG conjugates represent a good balance of yield and activity.

In some embodiments, the PEGylated anti-myostatin Adnectins will preferably retain at least about 25%, 50%, 60%, 70%, 80%, 85%, 90%, 95% or 100% of the biological activity associated with the unmodified anti-myostatin Adnectin. In some embodiments, biological activity refers to its ability to bind to myostatin, as assessed by $K_D$, $k_{on}$, or $k_{off}$. In some embodiments, the PEGylated anti-myostatin Adnectin shows an increase in binding to myostatin relative to unPEGylated anti-myostatin Adnectin.

Exemplary PEG-modified anti-myostatin Adnectins are shown in Table 5.

Immunoglobulin Fc Domain (and Fragments)

In some embodiments, the anti-myostatin Adnectin is fused to an immunoglobulin Fc domain, or a fragment or variant thereof. As used herein, a "functional Fc region" is an Fc domain or fragment thereof which retains the ability to bind FcRn. In some embodiments, a functional Fc region binds to FcRn, bud does not possess effector function. The ability of the Fc region or fragment thereof to bind to FcRn can be determined by standard binding assays known in the art. In other embodiments, the Fc region or fragment thereof binds to FcRn and possesses at least one "effector function" of a native Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an anti-myostatin Adnectin) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

In an exemplary embodiment, the Fc domain is derived from an IgG1 subclass, however, other subclasses (e.g., IgG2, IgG3, and IgG4) may also be used. Shown below is the sequence of a human IgG1 immunoglobulin Fc domain:

(SEQ ID NO: 169)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK

The core hinge sequence is underlined, and the CH2 and CH3 regions are in regular text. It should be understood that the C-terminal lysine is optional.

The fusion may be formed by attaching an anti-myostatin Adnectin to either end of the Fc molecule, i.e., Fc-anti-myostatin Adnectin or anti-myostatin Adnectin-Fc arrangements. In certain embodiments, the Fc and anti-myostatin Adnectin are fused via a linker. Exemplary linker sequences include GAGGGGSG (SEQ ID NO: 181), EPKSSD (SEQ ID NO: 182), D, ESPKAQASSVPTAQPQAEGLA (SEQ ID NO: 183), ELQLEESAAEAQDGELD (SEQ ID NO: 184), GQPDEPGGS (SEQ ID NO: 185), GGSGSGSGSGSGS (SEQ ID NO: 186), ELQLEESAAEAQEGELE (SEQ ID NO: 187), GSGSG (SEQ ID NO: 188), GSGC (SEQ ID NO: 189), AGGGGSG (SEQ ID NO: 190), GSGS (SEQ ID NO: 191), QPDEPGGS (SEQ ID NO: 192), GSGSGS (SEQ ID NO: 193), TVAAPS (SEQ ID NO: 194), KAGGGGSG (SEQ ID NO: 195), KGSGSGSGSGSGS (SEQ ID NO: 196), KQPDEPGGS (SEQ ID NO: 197), KELQLEESAAE-AQDGELD (SEQ ID NO: 198), KTVAAPS (SEQ ID NO: 199), KAGGGGSGG (SEQ ID NO: 200), KGSGSGSGSGSGSG (SEQ ID NO: 201), KQPDEPGGSG (SEQ ID NO: 202), KELQLEESAAEAQDGELDG (SEQ ID NO: 203), KTVAAPSG (SEQ ID NO: 204), AGGGGSGG (SEQ ID NO: 205), AGGGGSG (SEQ ID NO: 206), GSGSGSGSGSGSG (SEQ ID NO: 207), QPDEPGGSG (SEQ ID NO: 208), and TVAAPSG (SEQ ID NO: 209).

In some embodiments, the Fc region used in the anti-myostatin Adnectin fusion comprises the hinge region of an Fc molecule. As used herein, the "hinge" region comprises the core hinge residues spanning positions 1-16 of SEQ ID NO: 169 (DKTHTCPPCPAPELLG; SEQ ID NO: 170) of the IgG1 Fc region. In certain embodiments, the anti-myostatin Adnectin-Fc fusion adopts a multimeric structure (e.g., dimer) owing, in part, to the cysteine residues at positions 6 and 9 of SEQ ID NO: 169 within the hinge region. In other embodiments, the hinge region as used herein, may further include residues derived from the CH1 and CH2 regions that flank the core hinge sequence, as shown in SEQ ID NO: 169. In yet other embodiments, the hinge sequence is GSTHTCPPCPAPELLG (i.e., hinge sequence for PRD-932; SEQ ID NO: 180).

In some embodiments, the hinge sequence, may include substitutions that confer desirable pharmacokinetic, biophysical, and/or biological properties. Some exemplary hinge sequences include EPKSS<u>DKTHTCPPCPAPELLG</u>GPS (SEQ ID NO: 171; core hinge region underlined), EPKSS<u>DKTHTCPPCPAPELLG</u>SS (SEQ ID NO 172; core hinge region underlined), EPKSS<u>GSTHTCPPCPAPELLG</u>SS (SEQ ID NO: 173; core hinge region underlined), <u>DKTHTCPPCPAPELLG</u>PS (SEQ ID NO: 174; core hinge region underlined), and <u>DKTHTCPPCPAPELLG</u>SS (SEQ ID NO: 175; core hinge region underlined). In one embodiment, the residue P at position 18 of SEQ ID NO: 169 has been replaced with S to ablate Fc effector function; this replacement is exemplified in hinges having any one of SEQ ID NOs: 172, 173, and 175. In another embodiment, the residues DK at positions 1-2 of SEQ ID NO: 169 have been replaced with GS to remove a potential clip site; this replacement is exemplified in SEQ ID NO: 173. In another embodiment, the C at position 103 of SEQ ID NO: 176, which corresponds to the heavy chain constant region of human IgG1 (i.e., domains CH1-CH3), has been replaced with S to prevent improper cysteine bond formation in the absence of a light chain; this replacement is exemplified in SEQ ID NOs: 171-173.

```
                                    (SEQ ID NO: 176)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In certain embodiments, an anti-myostatin Adnectin-Fc fusion may have the following configurations: 1) anti-myostatin Adnectin-hinge-Fc or 2) hinge-Fc-anti-myostatin Adnectin. Therefore, any anti-myostatin Adnectin of the present invention can be fused to an Fc region comprising a hinge sequence according to these configurations. In some embodiments, a linker may be used to join the anti-myostatin Adnectin to the hinge-Fc moiety, for example, an exemplary fusion protein may have the configuration anti-myostatin Adnectin-linker-hinge-Fc or hinge-Fc-linker-anti-myostatin Adnectin. Additionally, depending on the system in which the fusion polypeptide is produced, a leader sequence may placed at the N-terminus of the fusion polypeptide. For example, if the fusion is produced in a mammalian system, a leader sequence such as METDTLLLWV-LLLWVPGSTG (SEQ ID NO: 177) may be added to the N-terminus of the fusion molecule. If the fusion is produced in *E. coli*, the fusion sequence will be preceded by a methionine.

The following sequence exemplifies an anti-myostatin Adnectin-hinge-Fc construct:

```
                                (PRD-1171; SEQ ID NO: 253)
GVSDVPRDLEVVAATPTSLLISWTLPHAGRAHYYRITYGETGGNSPVQEF

TVPGRGVTATISGLKPGVDYTITVYAVTVTTTKVIHYKPISINYRTEIEP

KSSDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

The leader sequence is in bold, the anti-myostatin Adnectin sequence is in italics, and the hinge region is underlined. It should be understood that the C-terminal lysine is optional.

Here, the Fc domain comprises the human IgG1 CH2 and CH3 regions as follows:

```
                                    (SEQ ID NO: 178)
VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPGK
``` and the hinge sequence DKTHTCPPCPAPELLG (SEQ ID NO: 170)

The following sequence exemplifies an Fc-anti-myostatin Adnectin construct:

(PRD-1474; SEQ ID NO: 273)
<u>DKTHTCPPCPAPELLG</u>GPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPELQLEESAAEAQEGELEGVSDVPRD

L*EVVAATPTSLLISWSLPHQGKANYYRITYGETGGNSPVQEFTVPGRGVT*

*ATISGLKPGVDYTITVYAVTVTDTGYLKYKPISINYRTEI*.

The hinge region is underlined, the leader sequence is in bold, and the anti-myostatin Adnectin sequence is in italics.

Here, the Fc domain comprises the human IgG1 CH2 and CH3 regions as follows:

(SEQ ID NO: 179)
VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSP and the hinge sequence DKTHTCPPCPAPELLG (SEQ ID NO: 170).

Exemplary anti-myostatin Adnectin-Fc fusions and Fc-anti-myostatin Adnectin fusions are shown in Table 6 (SEQ ID NOs: 252-273). All sequences may begin with a methionine or a mammalian leader sequence (e.g., SEQ ID NO: 177).

Adnectins

In some embodiments the PK moiety is another Adnectin specific, for example, to a serum protein (e.g., human serum albumin), as described in US 2012/0094909, herein incorporated by reference in its entirety. Other PK moieties that may be used with the Adnectins of the invention are disclosed in Kontermann et al. (*Current Opinion in Biotechnology* 2011; 22:868-76), as discussed supra. By way of example, such Adnectin based PK moieties may be directly or indirectly linked to an anti-myostatin Adnectin via a polypeptide linker. Suitable linkers for joining Fn3 domains are those which allow the separate domains to fold independently of each other and form a three dimensional structure that permits high affinity binding to a target molecule. Exemplary polypeptide linkers include PSTSTST (SEQ ID NO: 210), EIDKPSQ (SEQ ID NO: 211), and GS linkers, such as GSGSGSGS (SEQ ID NO: 213) and multimers thereof. In some embodiments, the linker is a glycine-serine based linker. These linkers comprise glycine and serine residues and may be between 8 and 50, 10 and 30, and 10 and 20 amino acids in length. Examples include linkers having an amino acid sequence $(GS)_7$ (SEQ ID NO: 215), $G(GS)_6$ (SEQ ID NO: 216), and $G(GS)_7G$ (SEQ ID NO: 217). Other linkers contain glutamic acid, and include, for example, $(GSE)_5$ (SEQ ID NO: 218) and GGSEGGSE (SEQ ID NO: 219). Other exemplary glycine-serine linkers include $(GS)_4$ (SEQ ID NO: 212), $(GGGGS)_7$ (SEQ ID NO: 220), $(GGGGS)_5$ (SEQ ID NO: 221), and $(GGGGS)_3G$ (SEQ ID NO: 222). In some embodiments, the linker is a glycine-proline based linker. These linkers comprise glycine and proline residues and may be between 3 and 30, 10 and 30, and 3 and 20 amino acids in length. Examples include linkers having an amino acid sequence $(GP)_3G$ (SEQ ID NO: 223), $(GP)_5G$ (SEQ ID NO: 224), and GPG. In other embodiments, the linker may be a proline-alanine based linker having between 3 and 30, 10 and 30, and 3 and 20 amino acids in length. Examples of proline alanine based linkers include, for example, $(PA)_3$ (SEQ ID NO: 225), $(PA)_6$ (SEQ ID NO: 226) and $(PA)_9$ (SEQ ID NO: 227). Optimal linker length and amino acid composition may be determined by routine experimentation in view of the teachings provided herein. In some embodiments, an anti-myostatin Adnectin is linked, for example, to an anti-HSA Adnectin via a polypeptide linker having a protease site that is cleavable by a protease in the blood or target tissue. Such embodiments can be used to release an anti-myostatin Adnectin for better delivery or therapeutic properties or more efficient production.

Additional linkers or spacers, may be introduced at the N-terminus or C-terminus of a Fn3 domain between the Fn3 domain and the polypeptide linker.

In some embodiments, an anti-myostatin Adnectin may be directly or indirectly linked for example, to an anti-HSA Adnectin via a polymeric linker. Polymeric linkers can be used to optimally vary the distance between each component of the fusion to create a protein fusion with one or more of the following characteristics: 1) reduced or increased steric hindrance of binding of one or more protein domains when binding to a protein of interest, 2) increased protein stability or solubility, 3) decreased protein aggregation, and 4) increased overall avidity or affinity of the protein.

In some embodiments, an anti-myostatin Adnectin is linked, for example, to an anti-HSA Adnectin, via a biocompatible polymer such as a polymeric sugar. The polymeric sugar can include an enzymatic cleavage site that is cleavable by an enzyme in the blood or target tissue. Such embodiments can be used to release an anti-myostatin Adnectin for better delivery or therapeutic properties or more efficient production.

A summary of monoAdnectins and their corresponding PK moiety modified forms (e.g., PEGylated and Fc fusions) are presented in Table 3.

TABLE 3

| Mono-Adnectin[a] | Cysteine mutant [modification][b] | X-linker-Fc[c] | Fc-linker-X[d] |
|---|---|---|---|
| 1979_B06 (SEQ ID NO: 80) | ATI-1107 (SEQ ID NO: 229) [40k 2-br] | | |
| 2062_G02 (SEQ ID NO: 81) | ATI-1106 (SEQ ID NO: 228) [40k 2-br] | | |

TABLE 3-continued

| Mono-Adnectin[a] | Cysteine mutant [modification][b] | X-linker-Fc[c] | Fc-linker-X[d] |
|---|---|---|---|
| 2522_C09 (SEQ ID NO: 82) | | | |
| 2523_G06 (SEQ ID NO: 83) | | | |
| 2524_C11 (SEQ ID NO: 84) | | | |
| 2524_D09 (SEQ ID NO: 85) | ATI-1275 (SEQ ID NO: 231) [NEM]; ATI-1276 (SEQ ID NO: 231) [40k 2-br] | | |
| 2524_E10 (SEQ ID NO: 86) | | | |
| 2524_H05 (SEQ ID NO: 87) | | | |
| 2524_H11 (SEQ ID NO: 88) | | | |
| 2525_B01 (SEQ ID NO: 89) | | | |
| 2525_D02 (SEQ ID NO: 90) | ATI-1267 (SEQ ID NO: 230) [NEM]; ATI-1266 (SEQ ID NO: 230) [40k 2-br] | | |
| 2525_D05 (SEQ ID NO: 91) | ATI-1277 (SEQ ID NO: 232) [NEM]; ATI-1278 (SEQ ID NO: 232) [40k 2-br] | | PRD-932 [L1] (SEQ ID NO: 252) |
| 2525_F07 (SEQ ID NO: 92) | | | |
| 2987_A06 (SEQ ID NO: 93) | | | |
| 2987_B04 (SEQ ID NO: 94) | | | |
| 2987_B09 (SEQ ID NO: 95) | | | |
| 2987_C02 (SEQ ID NO: 96) | | | |
| 2987_D05 (SEQ ID NO: 97) | | | |
| 2987_E03 (SEQ ID NO: 98) | | | |
| 2987_E08 (SEQ ID NO: 99) | | | |
| 2987_F01 (SEQ ID NO: 100) | | | |
| 2987_F06 (SEQ ID NO: 101) | | | |
| 2987_G04 (SEQ ID NO: 102) | | | |
| 2987_G09 (SEQ ID NO: 103) | | | |
| 2987_H02 (SEQ ID NO: 104) | | | |

TABLE 3-continued

| Mono-Adnectin[a] | Cysteine mutant [modification][b] | X-linker-Fc[c] | Fc-linker-X[d] |
|---|---|---|---|
| 2987_H07 (SEQ ID NO: 105) | ATI-1310 (SEQ ID NO: 233) [none]; ATI-1340 (SEQ ID NO: 233) [NEM]; ATI-1338 (SEQ ID NO: 233) [40k 2-br]; ATI-1359 (SEQ ID NO: 233) [no His, 40k 2-br]; ATI-1339 (SEQ ID NO: 233) [40k 4-br]; ATI-1341 (SEQ ID NO: 233) [20k bis-PEG] | PRD-1171[L2] (SEQ ID NO: 253); PRD-1173[L3] (SEQ ID NO: 254); PRD-1174[L4] (SEQ ID NO: 255) | PRD-1175[L1] (SEQ ID NO: 256); PRD-1177[L5] (SEQ ID NO: 257); PRD-1178[L6] (SEQ ID NO: 258); PRD-1180[L7] (SEQ ID NO: 259); PRD-1471[L8] (SEQ ID NO: 270) |
| 3006_A10 (SEQ ID NO: 106) | | | |
| 3007_B08 (SEQ ID NO: 107) | | | |
| 3007_C09 (SEQ ID NO: 108) | | | |
| 3007_C10 (SEQ ID NO: 109) | | | |
| 3008_A03 (SEQ ID NO: 110) | | | |
| 3008_B08 (SEQ ID NO: 111) | | | |
| 3008_D04 (SEQ ID NO: 112) | | | |
| 3008_F01 (SEQ ID NO: 113) | | | |
| 3008_G01 (SEQ ID NO: 114) | | | |
| 3008_G03 (SEQ ID NO: 115) | | | |
| 3115_D04 (SEQ ID NO: 116) | ATI-1375 (SEQ ID NO: 235) [40k 2-br] | PRD-1301[L2] (SEQ ID NO: 265) | PRD-1284[L5] (SEQ ID NO: 260) |
| 3115_E06 (SEQ ID NO: 117) | ATI-1376 (SEQ ID NO: 236) [40k 2-br] | PRD-1302[L2] (SEQ ID NO: 266) | PRD-1285[L5] (SEQ ID NO: 261); PRD-1472[L8] (SEQ ID NO: 271) |
| 3116_A06 (SEQ ID NO: 118) | ATI-1379 (SEQ ID NO: 239) [40k 2-br]; ATI-1523 (SEQ ID NO: 239) [NEM] | PRD-1305[L2] (SEQ ID NO: 269) | PRD-1288[L5] (SEQ ID NO: 264); PRD-1474[L8] (SEQ ID NO: 273) |
| 3116_A07 (SEQ ID NO: 119) | ATI-1377 (SEQ ID NO: 237) [40k 2-br] | PRD-1303[L2] (SEQ ID NO: 267) | PRD-1286[L5] (SEQ ID NO: 262); PRD-1473[L8] (SEQ ID NO: 272) |
| 3116_C01 (SEQ ID NO: 120) | | | |
| 3116_C06 (SEQ ID NO: 121) | | | |
| 3116_H06 (SEQ ID NO: 122) | | | |

TABLE 3-continued

| Mono-Adnectin[a] | Cysteine mutant [modification][b] | X-linker-Fc[c] | Fc-linker-X[d] |
|---|---|---|---|
| 3146_A08 (SEQ ID NO: 123) | ATI-1378 (SEQ ID NO: 238) [40k 2-br] | PRD-1304[L2] (SEQ ID NO: 268) | PRD-1287[L5] (SEQ ID NO: 263) |

[a]Unmodified monoAdnectins have a core Adnectin sequence preceded by a N-terminal extension sequence (MGVSDVPRDL; SEQ ID NO: 306) and followed by a C-terminal tail (EIDKPSQHHHHHH; SEQ ID NO: 325), as shown in Table 2. The core Adnectin sequence corresponds to the monoAdnectin sequence lacking the N-terminal extension and C-terminal tail sequences.
[b]Adnectins with cysteine mutants have the core Adnectin sequence of the monoAdnectin in the first column, and are preceded by a N-terminal extension sequence (MGVSDVPRDL; SEQ ID NO: 306) and followed by a C-terminal tail (GSGC[Modification]HHHHHH; SEQ ID NO: 326 or EGSGC[Modification]HHHHHH; SEQ ID NO: 327), as shown in Table 5.
[c]Adnectins with an Fc moiety on the C-terminus have the core Adnectin sequence of the monoAdnectin in the first column, which is preceded by a N-terminal extension sequence (GVSDVPRDL; SEQ ID NO: 307) and followed by a C-terminal tail (EI), which is followed by a linker sequence (Table 4) and the Fc region sequence, as described in Table 6.
[d]Adnectins with an Fc moiety on the N-terminus have an Fc region sequence which is preceded by a N-terminal hinge sequence and followed by a linker (Table 4) and the core Adnectin sequence of the monoAdnectin in the first column, which itself is preceded by a N-terminal extension sequence (GVSDVPRDL; SEQ ID NO: 307) and followed by a C-terminal tail (EI), as shown in Table 6.

The SEQ ID NOs of exemplary linkers of the invention are presented in Table 4.

TABLE 4

| SEQ ID NO. | LINKER | SEQUENCE |
|---|---|---|
| 181 | L1 | GAGGGGSG |
| 182 | L2 | EPKSSD |
| — | L3 | D |
| 183 | L4 | ESPKAQASSVPTAQPQAEGLA |
| 184 | L5 | ELQLEESAAEAQDGELD |
| 185 | L6 | GQPDEPGGS |
| 186 | L7 | GGSGSGSGSGSGS |
| 187 | L8 | ELQLEESAAEAQEGELE |
| ADDITIONAL EXEMPLARY LINKERS | | |
| 188 | L9 | GSGSG |
| 189 | L10 | GSGC |
| 190 | L11 | AGGGGSG |
| 191 | L12 | GSGS |
| 192 | L13 | QPDEPGGS |
| 193 | L14 | GSGSGS |
| 194 | L15 | TVAAPS |
| 195 | L16 | KAGGGGSG |
| 196 | L17 | KGSGSGSGSGSGS |
| 197 | L18 | KQPDEPGGS |
| 198 | L19 | KELQLEESAAEAQDGELD |
| 199 | L20 | KTVAAPS |
| 200 | L21 | KAGGGGSGG |
| 201 | L22 | KGSGSGSGSGSG |
| 202 | L23 | KQPDEPGGSG |
| 203 | L24 | KELQLEESAAEAQDGELDG |
| 204 | L25 | KTVAAPSG |
| 205 | L26 | AGGGGSGG |
| 206 | L27 | AGGGGSG |
| 207 | L28 | GSGSGSGSGSGSG |
| 208 | L29 | QPDEPGGSG |
| 209 | L30 | TVAAPSG |
| 210 | L31 | PSTSTST |
| 211 | L32 | EIDKPSQ |
| 212 | L33 | GSGSGSGS |
| 213 | L34 | GSGSGSGSGS |
| 214 | L35 | GSGSGSGSGSGS |
| 215 | L36 | GSGSGSGSGSGSGS |
| 216 | L37 | GGSGSGSGSGSGS |
| 217 | L38 | GGSGSGSGSGSGSG |
| 218 | L39 | GSEGSEGSEGSEGSE |
| 219 | L40 | GGSEGGSE |
| 220 | L41 | GGGGSGGGGSGGGGSGGGGSGGGGSGGGGSGGGGS |
| 221 | L42 | GGGGSGGGGSGGGGSGGGGSGGGGS |
| 222 | L43 | GGGGSGGGGSGGGGSG |
| 223 | L44 | GPGPGPG |
| 224 | L45 | GPGPGPGPGPG |
| — | L46 | GPG |
| 225 | L47 | PAPAPA |
| 226 | L48 | PAPAPAPAPAPA |
| 227 | L49 | PAPAPAPAPAPAPAPA |

The SEQ ID NOs of exemplary PEGylated anti-myostatin Adnectins of the invention are presented in Table 5.

TABLE 5

PEGylated Anti-Myostatin Adnectins

| Clone | Amino Acid Sequence | Nucleic Acid Sequence |
|---|---|---|
| ATI-1106 [40K 2-branch PEG] | MGVSDVPRDLEVVAATPTSLLIS WVSPRGRARYYRITYGETGGNS PVQEFTVPGRGSTATISGLKPGV DYTITVYAVTIYRDGMSHHDPISI NYRTGSGC[Modification]HHHHH H (SEQ ID NO: 228) | ATGGGAGTTTCTGATGTGCCGCGCGACCT GGAAGTGGTTGCTGCCACCCCCACCAGCC TGCTGATCAGCTGGGTTTCTCCGCGTGGT CGTGCTCGATATTACCGCATCACTTACGG CGAAACAGGAGGCAATAGCCCTGTCCAG GAGTTCACTGTGCCTGGTCGTGGTTCTAC AGCTACCATCAGCGGCCTTAAACCTGGCG TTGATTATACCATCACTGTGTATGCTGTCA CTATCTACCGTGACGGTATGTCTCATCAT GACCCAATTTCCATTAATTACCGCACAGG TAGCGGTTGCCACCATCACCACCATCAC (SEQ ID NO: 240) |
| ATI-1107 [40K 2-branch PEG] | MGVSDVPRDLEVVAATPTSLLIS WSLPHAGHVNYYRITYGETGGN SPVQEFTVPGRGVTATISGLKPG VDYTITVYAVTLTKSQMIHYMPI SINYRTGSGC[Modification]HHHH HH (SEQ ID NO: 229) | ATGGGAGTTTCTGATGTGCCGCGCGACCT GGAAGTGGTTGCTGATCAGCTGGTCTCTGCCGCATGCT GGTCATGTGAACTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTCTGACTAAATCTCAGATGATCCA TTACATGCCAATTTCCATTAATTACCGCAC AGGTAGCGGTTGCCACCATCACCACCATC AC (SEQ ID NO: 241) |
| ATI-1266 [40K 2-branch PEG] ATI-1267 [N-ethylmaleimide] | MGVSDVPRDLEVVAATPTSLLIS WTLPHAGRAHYYRITYGETGGN SPVQEFTVPGRGVTATISGLKPG VDYTITVYAVTVTTTSVILYKPIS INYRTEGSGC[Modification]HHHH HH (SEQ ID NO: 230) | ATGGGAGTTTCTGATGTGCCGCGCGACCT GGAAGTGGTTGCTGCCACCCCCACCAGCC TGCTGATCAGCTGGACTTTGCCGCATGCT GGTCGTGCGCACTATTACCGCATCACTTA CGGCGAAACAGGAGGCAATAGCCCTGTC CAGGAGTTCACTGTGCCTGGGCGGGGTGT TACAGCTACCATCAGCGGCCTTAAACCTG GCGTTGATTATACCATCACTGTGTATGCT GTCACTGTGACGACAACTTCGGTGATCCT TTACAAGCCAATTTCCATTAATTACCGCA CAGAAGGTAGCGGTTGCCACCATCACCAC CATCAC (SEQ ID NO: 242) |
| ATI-1275 [N-ethylmaleimide] ATI-1276 [40K 2-branch PEG] | MGVSDVPRDLEVVAATPTSLLIS WYLPYPAHMNYYRITYGETGGN SPVQEFTVPGRGLTATISGLKPG VDYTITVYAVTLTKSQILHHRPIS INYRTEGSGC[Modification]HHHH HH (SEQ ID NO: 231) | ATGGGAGTTTCTGATGTGCCGCGCGACCT GGAAGTGGTTGCTGCCACCCCCACCAGCC TGCTGATCAGCTGGTACCTCCCGTATCCT GCGCATATGAACTATTACCGCATCACTTA CGGCGAAACAGGAGGCAATAGCCCTGTC CAGGAGTTCACTGTGCCTGGGCGGGGTCT GACAGCTACCATCAGCGGCCTTAAACCTG GCGTTGATTATACCATCACTGTGTATGCT GTCACTCTGACAAAATCTCAGATTCTCCA TCATAGGCCAATTTCCATTAATTACCGCA CAGAAGGTAGCGGTTGCCACCATCACCAC CATCAC (SEQ ID NO: 243) |
| ATI-1277 [N-ethylmaleimide] ATI-1278 [40K 2-branch PEG] | MGVSDVPRDLEVVAATPTSLLIS WSLPYAGHLNYYRITYGETGGN SPVQEFTVPGRGVTATISGLKPG VDYTITVYAVTLTKSQLIHYMPI SINYRTEGSGC[Modification]HHH HHH (SEQ ID NO: 232) | ATGGGAGTTTCTGATGTGCCGCGCGACCT GGAAGTGGTTGCTGCCACCCCCACCAGCC TGCTGATCAGCTGGTCTCTTCCTTATGCTG GTCATCTAAACTATTACCGCATCACTTAC GGCGAAACAGGAGGCAATAGCCCTGTCC AGGAGTTCACTGTGCCTGGTCGTGGTGTG ACAGCTACCATCAGCGGCCTTAAACCTGG CGTTGATTATACCATCACTGTGTATGCTGT CACTCTGACTAAGTCTCAGCTGATACATT ACATGCCAATTTCCATTAATTACCGCACA GAAGGTAGCGGTTGCCACCATCACCACCA TCAC (SEQ ID NO: 244) |
| ATI-1310 [free Cys] ATI-1338 [40K 2-branch PEG] ATI-1339 [40K 4-branch PEG] ATI-1340 [N-ethylmaleimide] ATI-1341 [20K Bis-PEG] | MGVSDVPRDLEVVAATPTSLLIS WTLPHAGRAHYYRITYGETGGN SPVQEFTVPGRGVTATISGLKPG VDYTITVYAVTVTTTTKVIHYKPI SINYRTEGSGC[Modification]HHH HHH (SEQ ID NO: 233) | ATGGGTGTTAGTGATGTTCCGCGTGATCT GGAAGTTGTTGCAGCAACCCCCGACCAGCC TGCTGATTAGCTGGACCCTGCCGCATGCA GGTCGTGCACATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCGTTACCACCACCAAAGTGATTCATTA |

TABLE 5-continued

PEGylated Anti-Myostatin Adnectins

| Clone | Amino Acid Sequence | Nucleic Acid Sequence |
|---|---|---|
| | | TAAACCGATTTCCATTAATTACCGCACAG AAGGTAGCGGTTGCCACCATCACCACCAT CAC (SEQ ID NO: 245) |
| ATI-1359 [40K 2-branch PEG] | MGVSDVPRDLEVVAATPTSLLIS WTLPHAGRAHYYRITYGETGGN SPVQEFTVPGRGVTATISGLKPG VDYTITVYAVTVTTTKVIHYKPI SINYRTEGSGC[Modification]HHH HHH (SEQ ID NO: 234) | ATGGGTGTTAGTGATGTTCCGCGTGATCT GGAAGTTGTTGCAGCAACCCCGACCAGCC TGCTGATTAGCTGGACCCTGCCGCATGCA GGTCGTGCACATTATTATCGTATTACCTAT GGTGAAACCGGTGGTAATAGTCCGGTTCA GGAATTCACCGTTCCGGGTCGTGGTGTTA CCGCAACCATTAGCGGTCTGAAACCGGGT GTTGATTACACCATTACCGTTTATGCAGTT ACCGTTACCACCACCAAAGTGATTCATTA TAAACCGATTTCCATTAATTACCGAACAG AAGGTAGCGGTTGC (SEQ ID NO: 246) |
| ATI-1375 [40K 2-branch PEG] | MGVSDVPRDLEVVAATPTSLLIS WDAPRGLARYYRITYGETGGNS PVQEFTVFGRGTTATISGLKPGV DYTITVYAVTIDRDGTRSFDPISI NYRTEGSGC[Modification]HHHH HH (SEQ ID NO: 235) | ATGGGAGTTTCTGATGTGCCGCGCGACCT GGAAGTGGTTGCTGCCACCCCCACCAGCC TGCTGATCAGCTGGGACGCTCCGAGAGGT CTGGCTCGATATTACCGCATCACTTACGG CGAAACAGGAGGCAATAGCCCTGTCCAG GAGTTCACTGTGTTCGGTCGTGGTACCAC AGCTACCATCAGCGGCCTTAAACCTGGCG TTGATTATACCATCACTGTGTATGCTGTCA CTATCGACCGTGACGGTACCCGCAGCTTC GACCCAATTTCCATTAATTACCGCACAGA AGGTAGCGGTTGCCACCATCACCACCATC AC (SEQ ID NO: 247) |
| ATI-1376 [40K 2-branch PEG] | MGVSDVPRDLEVVAATPTSLLIS WDAPAGLARYYRITYGETGGNS PVQEFTVVGRGNTATISGLKPGV DYTITVYAVTIFRDGPVTWDPISI NYRTEGSGC[Modification]HHHH HH (SEQ ID NO: 236) | ATGGGAGTTTCTGATGTGCCGCGCGACCT GGAAGTGGTTGCTGCCACCCCCACCAGCC TGCTGATCAGCTGGGACGCTCCGGCTGGT CTGGCTCGATATTACCGCATCACTTACGG CGAAACAGGAGGCAATAGCCCTGTCCAG GAGTTCACTGTGGTCGGTCGTGGTAACAC AGCTACCATCAGCGGCCTTAAACCTGGCG TTGATTATACCATCACTGTGTATGCTGTCA CTATCTTCCGTGACGGTCCCGTCACCTGG GACCCAATTTCCATTAATTACCGCACAGA AGGTAGCGGTTGCCACCATCACCACCATC AC (SEQ ID NO: 248) |
| ATI-1377 [40K 2-branch PEG] | MGVSDVPRDLEVVAATPTSLLIS WDAPKGLARYYRITYGETGGNS PVQEFTVVGRGNTATISGLKPGV DYTITVYAVTIFRDGPVTWDPISI NYRTEGSGC[Modification]HHHH HH (SEQ ID NO: 237) | ATGGGAGTTTCTGATGTGCCGCGCGACCT GGAAGTGGTTGCTGCCACCCCCACCAGCC TGCTGATCAGCTGGGACGCTCCGAAGGGT CTGGCTCGATATTACCGCATCACTTACGG CGAAACAGGAGGCAATAGCCCTGTCCAG GAGTTCACTGTGGTCGGTCGTGGTAACAC AGCTACCATCAGCGGCCTTAAACCTGGCG TTGATTATACCATCACTGTGTATGCTGTCA CTATCTTCCGTGACGGTCCCGTCACCTGG GACCCAATTTCCATTAATTACCGCACAGA AGGTAGCGGTTGCCACCATCACCACCATC AC (SEQ ID NO: 249) |
| ATI-1378 [40K 2-branch PEG] | MGVSDVPRDLEVVAATPTSLLIS WSLPNPGNAHYYRITYGETGGN SPVQEFTVPGRGVTATISGLKPG VDYTITVYAVTVTDTGFITYKPIS INYRTEGSGC[Modification]HHHH HH (SEQ ID NO: 238) | ATGGGAGTTTCTGATGTGCCGCGCGACCT GGAAGTGGTTGCTGCCACCCCCACCAGCC TGCTGATCAGCTGGTCTCTGCCGAATCCG GGTAACGCCCATTATTACCGCATCACTTA CGGCGAAACAGGAGGCAATAGCCCTGTC CAGGAGTTCACTGTGCCTGGTCGTGGTGT TACAGCTACCATCAGCGGCCTTAAACCTG GCGTTGATTATACCATCACTGTGTATGCT GTCACTGTTACTGACACAGGTTTCATCAC GTACAAACCAATTTCCATTAATTACCGCA CAGAAGGTAGCGGTTGCCACCATCACCAC CATCAC (SEQ ID NO: 250) |
| ATI-1379 [40K 2-branch PEG] ATI-1523 [N-ethylmaleimide] | MGVSDVPRDLEVVAATPTSLLIS WSLPHQGKANYYRITYGETGGN SPVQEFTVPGRGVTATISGLKPG VDYTITVYAVTVTDTGYLYKPI SINYRTEGSGC[Modification]HHH HHH (SEQ ID NO: 239) | ATGGGAGTTTCTGATGTGCCGCGCGACCT GGAAGTGGTTGCTGCCACCCCCACCAGCC TGCTGATCAGCTGGTCTCTGCCGCACCAA GGTAAAGCCAATTATTACCGCATCACTTA CGGCGAAACAGGAGGCAATAGCCCTGTC CAGGAGTTCACTGTGCCTGGTCGTGGTGT |

TABLE 5-continued

PEGylated Anti-Myostatin Adnectins

| Clone | Amino Acid Sequence | Nucleic Acid Sequence |
|---|---|---|
| | | TACAGCTACCATCAGCGGCCTTAAACCTG GCGTTGATTATACCATCACTGTGTATGCT GTCACTGTTACTGATACAGGGTACCTCAA GTACAAACCAATTTCCATTAATTACCGCA CAGAAGGTAGCGGTTGCCACCATCACCAC CATCAC (SEQ ID NO: 251) |

The SEQ ID NOs of exemplary Fc-fused anti-myostatin Adnectins of the invention are presented in Table 6.

TABLE 6

Fc-fused Anti-Myostatin Adnectins

| Clone | Amino Acid Sequence | N-terminal domain | Linker | C-terminal domain | Nucleic Acid Sequence |
|---|---|---|---|---|---|
| PRD-932 | EPKSSGSTHTC PPCPAPELLGG SSVFLFPPKPK DTLMISRTPEV TCVVVDVSHED PEVKFNWYVDG VEVHNAKTKPR EEQYNSTYRVV SVLTVLHQDWL NGKEYKCKVSN KALPAPIEKTI SKAKGQPREPQ VYTLPPSRDEL VYTLPPSRDEL TKNQVSLTCLV KGFYPSDIAVE WESNGQPENNY KTTPPVLDSDG SFFLYSKLTVD KSRWQQGNVFS CSVMHEALHNH YTQKSLSLSPG AGGGGSGGVSD VPRDLEVVAAT PTSLLISWSLP YAGHLNYYRIT YGETGGNSPVQ EFTVPGRGVTA TISGLKPGVDY TITVYAVTLTK SQLIHYMPISI NYRTEI (SEQ ID NO: 252) | EPKSSGSTHTCP PCPAPELLGGSS VFLFPPKPKDTL MISRTPEVTCVV VDVSHEDPEVKF NWYVDGVEVHNA KTKPREEQYNST YRVVSVLTVLHQ DWLNGKEYKCKV SNKALPAPIEKT ISKAKGQPREPQ VYTLPPSRDELT KNQVSLTCLVKG FYPSDIAVEWES NGQPENNYKTTP PVLDSDGSFFLY SKLTVDKSRWQQ GNVFSCSVMHEA LHNHYTQKSLSL SP (SEQ ID NO: 274) | GAGGGGSG (SEQ ID NO: 181) | GVSDVPRDLEVVA ATPTSLLISWSLP YAGHLNYYRITYG ETGGNSPVQEFTV PGRGVTATISGLK PGVDYTITVYAVT LTKSQLIHYMPIS INYRTEI (SEQ ID NO: 282) | GAGCCCAAATCTAGCGGGTC GACTCACACATGCCCACCGT GCCCAGCACCTGAACTCCTG GGGGGAAGCTCAGTCTTCCT CTTCCCCCCAAAACCCAAGG ACACCCTCATGATCTCCCGG ACCCCTGAGGTCACATGCGT GGTGGTGGACGTGAGCCACG AAGACCCTGAGGTCAAGTTC AACTGGTACGTGGACGGCGT GGAGGTGCATAATGCCAAGA CAAAGCCGCGGGAGGAGCAG TACAACAGCACGTACCGTGT GGTCAGCGTCCTCACCGTCC TGCACCAGGACTGGCTGAAT GGCAAGGAGTACAAGTGCAA GGTCTCCAACAAAGCCCTCC CAGCCCCCATCGAGAAACC ATCTCCAAAGCCAAGGGCA GCCCCGAGAACCACAGGTGT ACACCCTGCCCCCATCCCGG GATGAGCTGACCAAGAACCA GGTCAGCCTGACCTGCCTGG TCAAAGGCTTCTATCCCAGC GACATCGCCGTGGAGTGGGA GAGCAATGGGCAGCCGGAGA ACAACTACAAGACCACGCCT CCCGTGCTGGACTCCGACGG CTCCTTCTTCCTCTACAGCA AGCTCACCGTGGACAAGAGC AGGTGGCAGCAGGGGAACGT CTTCTCATGCTCCGTGATGC ATGAGGCTCTGCACAACCAC TACACGCAGAAGAGCCTCTC CCTGTCTCCCGGCGCCGGAG GCGGCGGATCCGGTGGAGTT TCTGATGTGCCGCGCGACCT GGAAGTGGTTGCTGCCACCC CCACCAGCCTGCTGATCAGC TGGTCTCTTCCTTATGCTGG TCATCTAAACTATTACCGCA TCACTTACGGCGAAACAGGA GGCAATAGCCCTGTCCAGGA GTTCACTGTGCCTGGTCGTG GTGTGACAGCTACCATCAGC GGCCTTAAACCTGGCGTTGA TTATACCATCACTGTGTATG CTGTCACTCTGACTAAGTCT CAGCTGATACATTACATGCC AATTTCCATTAATTACCGGA CCGAAATC (SEQ ID NO: 284) |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| PRD-1171 | GVSDVPRDLEV VAATPTSLLIS WTLPHAGRAHY YRITYGETGGN SPVQEFTVPGR GVTATISGLKP GVDYTITVYAV TVTTTKVIHYK PISINYRTEIE PKSSDKTHTCP PCPAPELLGGP SVFLFPPKPKD TLMISRTPEVT CVVVDVSHEDP EVKFNWYVDGV EVHNAKTKPRE EQYNSTYRVVS VLTVLHQDWLN GKEYKCKVSNK ALPAPIEKTIS KAKGQPREPQV YTLPPSRDELT KNQVSLTCLVK GFYPSDIAVEW ESNGQPENNYK TTPPVLDSDGS FFLYSKLTVDK SRWQQGNVFSC SVMHEALHNHY TQKSLSLSPGK (SEQ ID NO: 253) | GVSDVPRDLEVV AATPTSLLISWT LPHAGRAHYYRI TYGETGGNSPVQ EFTVPGRGVTAT ISGLKPGVDYTI GVDYTITVYAV TVYAVTVTTTKV IHYKPISINYRT PISINYRTEIE EI (SEQ ID NO: 275) | EPKSSD (SEQ ID NO: 182) | KTHTCPPCPAPEL LGGPSVFLFPPKP KDTLMISRTPEVT CVVVDVSHEDPEV KFNWYVDGVEVHN AKTKPREEQYNST YRVVSVLTVLHQD WLNGKEYKCKVSN KALPAPIEKTISK AKGQPREPQVYTL PPSRDELTKNQVS LTCLVKGFYPSDI AVEWESNGQPENN YKTTPPVLDSDGS FFLYSKLTVDKSR WQQGNVFSCSVMH EALHNHYTQKSLS LSPGK (SEQ ID NO: 283) | GGCGTGAGCGACGTGCCCCG GGATCTAGAAGTGGTGGCTG CTACCCCCACAAGCTTGCTG ATCTCCTGGACACTGCCTCA CGCTGGCCGGGCTCATTACT ATAGAATTACCTACGGGGAG ACAGGCGGGAACTCTCCCGT GCAGGAATTCACCGTGCCTG GAAGGGGCGTGACTGCCACC ATCAGTGGGCTGAAGCCAGG AGTGGACTACACAATTACCG TGTACGCTGTGACTGTGACC ACAACTAAAGTGATCCACTA CAAACCCATCTCTATTAATT ATCGGACCGAAATTGAGCCT AAGAGCTCCGACAAAACCCA CACATGCCCACCTTGTCCAG CCCCCGAACTGCTGGGCGGC CCTTCAGTCTTCCTCTTCCC CCCAAAACCCAAGGACACCC TCATGATCTCCCGGACCCCT GAGGTCACATGCGTGGTGGT GGACGTGAGCCACGAAGACC CTGAGGTCAAGTTCAACTGG TACGTGGACGGCGTGGAGGT GCATAATGCCAAGACAAAGC CGCGGGAGGAGCAGTACAAC AGCACGTACCGTGTGGTCAG CGTCCTCACCGTCCTGCACC AGGACTGGCTGAATGGCAAG GAGTACAAGTGCAAGGTCTC CAACAAAGCCCTCCCAGCCC CCATCGAGAAAACCATCTCC AAAGCCAAAGGGCAGCCCCG AGAACCACAGGTGTACACCC TGCCCCCATCCCGGGATGAG CTGACCAAGAACCAGGTCAG CCTGACCTGCCTGGTCAAAG GCTTCTATCCCAGCGACATC GCCGTGGAGTGGGAGAGCAA TGGGCAGCCGGAGAACAACT ACAAGACCACGCCTCCCGTG TTGGACTCCGACGGCTCCTT CTTCCTCTACAGCAAGCTCA CCGTGGACAAGAGCAGGTGG CAGCAGGGGAACGTCTTCTC ATGCTCCGTGATGCATGAGG CTCTGCACAACCACTACACG CAGAAGAGCCTCTCCCTGTC TCCCGGGAAA (SEQ ID NO: 285) |
| PRD-1173 | GVSDVPRDLEV VAATPTSLLIS WTLPHAGRAHY YRITYGETGGN SPVQEFTVPGR GVTATISGLKP GVDYTITVYAV TVTTTKVIHYK PISINYRTEID EI KTHTCPPCPAP ELLGGPSVFLF PPKPKDTLMIS RTPEVTCVVVD VSHEDPEVKFN WYVDGVEVHNA KTKPREEQYNS TYRVVSVLTVL HQDWLNGKEYK CKVSNKALPAP IEKTISKAKGQ | GVSDVPRDLEVV AATPTSLLISWT LPHAGRAHYYRI TYGETGGNSPVQ EFTVPGRGVTAT ISGLKPGVDYTI GVDYTITVYAV TVYAVTVTTTKV IHYKPISINYRT PISINYRTEID EI (SEQ ID NO: 275) | D | KTHTCPPCPAPEL LGGPSVFLFPPKP KDTLMISRTPEVT CVVVDVSHEDPEV KFNWYVDGVEVHN AKTKPREEQYNST YRVVSVLTVLHQD WLNGKEYKCKVSN KALPAPIEKTISK AKGQPREPQVYTL PPSRDELTKNQVS LTCLVKGFYPSDI AVEWESNGQPENN YKTTPPVLDSDGS FFLYSKLTVDKSR WQQGNVFSCSVMH EALHNHYTQKSLS LSPGK (SEQ ID NO: 283) | GGCGTGAGCGACGTGCCCCG GGATCTAGAAGTGGTGGCTG CTACCCCCACAAGCTTGCTG ATCTCCTGGACACTGCCTCA CGCTGGCCGGGCTCATTACT ATAGAATTACCTACGGGGAG ACAGGCGGGAACTCTCCCGT GCAGGAATTCACCGTGCCTG GAAGGGGCGTGACTGCCACC ATCAGTGGGCTGAAGCCAGG AGTGGACTACACAATTACCG TGTACGCTGTGACTGTGACC ACAACTAAAGTGATCCACTA CAAACCCATCTCTATTAATT ATCGGACCGAAATTGACAAG ACCCACACATGCCCACCTTG TCCAGCCCCCGAGCTGCTGG GCGGCCCTTCAGTCTTCCTC TTCCCCCCAAAACCCAAGGA CACCCTCATGATCTCCCGGA |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | PREPQVYTLPP SRDELTKNQVS LTCLVKGFYPS DIAVEWESNGQ PENNYKTTPPV LDSDGSFFLYS KLTVDKSRWQQ GNVFSCSVMHE ALHNHYTQKSL SLSPGK (SEQ ID NO: 254) | | | | CCCCTGAGGTCACATGCGTG GTGGTGGACGTGAGCCACGA AGACCCTGAGGTCAAGTTCA ACTGGTACGTGGACGGCGTG GAGGTGCATAATGCCAAGAC AAAGCCGCGGGAGGAGCAGT ACAACAGCACGTACCGTGTG GTCAGCGTCCTCACCGTCCT GCACCAGGACTGGCTGAATG GCAAGGAGTACAAGTGCAAG GTCTCCAACAAAGCCCTCCC AGCCCCCATCGAGAAAACCA TCTCCAAAGCCAAAGGGCAG CCCCGAGAACCACAGGTGTA CACCCTGCCCCCATCCCGGG ATGAGCTGACCAAGAACCAG GTCAGCCTGACCTGCCTGGT CAAAGGCTTCTATCCCAGCG ACATCGCCGTGGAGTGGGAG AGCAATGGGCAGCCGGAGAA CAACTACAAGACCACGCCTC CCGTGTTGGACTCCGACGGC TCCTTCTTCCTCTACAGCAA GCTCACCGTGGACAAGAGCA GGTGGCAGCAGGGGAACGTC TTCTCATGCTCCGTGATGCA TGAGGCTCTGCACAACCACT ACACGCAGAAGAGCCTCTCC CTGTCTCCCGGGAAA (SEQ ID NO: 286) |
| PRD-1174 | GVSDVPRDLEV VAATPTSLLIS WTLPHAGRAHY YRITYGETGGN SPVQEFTVPGR GVTATISGLKP GVDYTITVYAV TVTTTKVIHYK PISINYRTEIE SPKAQASSVPT AQPQAEGLAKT HTCPPCPAPEL LGGPSVFLFPP KPKDTLMISRT PEVTCVVVDVS HEDPEVKFNWY VDGVEVHNAKT KPREEQYNSTY RVVSVLTVLHQ DWLNGKEYKCK VSNKALPAPIE KTISKAKGQPR EPQVYTLPPSR DELTKNQVSLT CLVKGFYPSDI AVEWESNGQPE NNYKTTPPVLD SDGSFFLYSKL TVDKSRWQQGN VFSCSVMHEAL HNHYTQKSLSL SPGK (SEQ ID NO: 255) | GVSDVPRDLEVV AATPTSLLISWT LPHAGRAHYYRI TYGETGGNSPVQ EFTVPGRGVTAT ISGLKPGVDYTI TVYAVTVTTTKV IHYKPISINYRT EIE (SEQ ID NO: 275) | ESPKAQASS VPTAQPQAE GLA (SEQ ID NO: 183) | KTHTCPPCPAPEL LGGPSVFLFPPKP KDTLMISRTPEVT CVVVDVSHEDPEV KFNWYVDGVEVHN AKTKPREEQYNST YRVVSVLTVLHQD WLNGKEYKCKVSN KALPAPIEKTISK AKGQPREPQVYTL PPSRDELTKNQVS LTCLVKGFYPSDI AVEWESNGQPENN YKTTPPVLDSDGS FFLYSKLTVDKSR WQQGNVFSCSVMH EALHNHYTQKSLS LSPGK (SEQ ID NO: 283) | GGCGTGAGCGACGTGCCCCG GGATCTAGAAGTGGTGGCTG CTACCCCCACAAGCTTGCTG ATCTCCTGGACACTGCCTCA CGCTGGCCGGGCTCATTACT ATAGAATTACCTACGGGGAG ACAGGCGGGAACTCTCCCGT GCAGGAATTCACCGTGCCTG GAAGGGGCGTGACTGCCACC ATCAGTGGGCTGAAGCCAGG AGTGGACTACACAATTACCG TGTACGCTGTGACTGTGACC ACAACTAAAGTGATCCACTA CAAACCCATCTCTATTAATT ATCGGACCGAAATTGAGTCT CCAAAGGCTCAGGCCAGCTC CGTGCCTACCGCTCAGCCAC AGGCTGAGGGCCTGGCTAAG ACCCACACATGCCCCCCTTG TCCAGCTCCCGAACTGCTGG GCGGGCCTTCAGTCTTCCTC TTCCCCCCAAAACCCAAGGA CACCCTCATGATCTCCCGGA CCCCTGAGGTCACATGCGTG GTGGTGGACGTGAGCCACGA AGACCCTGAGGTCAAGTTCA ACTGGTACGTGGACGGCGTG GAGGTGCATAATGCCAAGAC AAAGCCGCGGGAGGAGCAGT ACAACAGCACGTACCGTGTG GTCAGCGTCCTCACCGTCCT GCACCAGGACTGGCTGAATG GCAAGGAGTACAAGTGCAAG GTCTCCAACAAAGCCCTCCC AGCCCCCATCGAGAAAACCA TCTCCAAAGCCAAAGGGCAG CCCCGAGAACCACAGGTGTA CACCCTGCCCCCATCCCGGG ATGAGCTGACCAAGAACCAG GTCAGCCTGACCTGCCTGGT CAAAGGCTTCTATCCCAGCG ACATCGCCGTGGAGTGGGAG |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | | | | | AGCAATGGGCAGCCGGAGAA CAACTACAAGACCACGCCTC CCGTGCTGGACTCCGACGGC TCCTTCTTCCTCTACAGCAA GCTCACCGTGGACAAGAGCA GGTGGCAGCAGGGGAACGTC TTCTCATGCTCCGTGATGCA TGAGGCTCTGCACAACCACT ACACGCAGAAGAGCCTCTCC CTGTCTCCCGGGAAA (SEQ ID NO: 287) |
| PRD-1175 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV LTCLVKGFYP SDLTCLVKGFYPSD IAVEWESNGQPE NNYKTTPPVLDS QPENNYKTTPP DGSFFLYSKLTV VLDSDGSFFLY SKLTVDKSRWQ QGNVFSCSVMH EALHNHYTQKS LSLSPGAGGGG SGGVSDVPRDL EVVAATPTSLL ISWTLPHAGRA HYYRITYGETG GNSPVQEFTVP GRGVTATISGL KPGVDYTITVY AVTVTTTKVIH YKPISINYRTE I (SEQ ID NO: 256) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP | GAGGGGSG (SEQ ID NO: 181) | GVSDVPRDLEVVA ATPTSLLISWTLP HAGRAHYYRITYG ETGGNSPVQEFTV PGRGVTATISGLK PGVDYTITVYAVT VTTTKVIHYKPIS INYRTEI (SEQ ID NO: 275) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGTTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGGCGC CGGAGGCGGCGGATCCGGTG GCGTGTCCGACGTGCCCCGG GATCTAGAAGTGGTGGCTGC TACCCCCACAAGCTTGCTGA TCTCCTGGACACTGCCTCAC GCTGGCCGGGCTCATTACTA TAGAATTACCTACGGGGAGA CAGGCGGGAACTCTCCCGTG CAGGAATTCACCGTGCCTGG AAGGGGCGTGACTGCCACCA TCAGTGGGCTGAAGCCAGGA GTGGACTACACAATTACCGT GTACGCTGTGACTGTGACCA CAACTAAAGTGATCCACTAC AAACCCATCTCTATTAATTA TCGGACCGAAATC (SEQ ID NO: 288) |
| PRD-1177 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKAL | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL | ELQLEESAA EAQDGELD (SEQ ID NO: 184) | GVSDVPRDLEVVA ATPTSLLISWTLP HAGRAHYYRITYG ETGGNSPVQEFTV PGRGVTATISGLK PGVDYTITVYAVT VTTTKVIHYKPIS INYRTEI (SEQ ID NO: 275) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH EALHNHYTQKS LSLSPELQLEE SAAEAQDGELD GVSDVPRDLEV VAATPTSLLIS WTLPHAGRAHY YRITYGETGGN SPVQEFTVPGR GVTATISGLKP GVDYTITVYAV TVTTTKVIHYK PISINYRTEI (SEQ ID NO: 257) | PAPIEKTISKAK GQPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP EALHNHYTQKS (SEQ ID NO: 276) | | | GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGAGCT GCAGCTGGAGGAAAAGCGCC CTGAGGCTCAGGACGGAGAA CTGGATGGCGTGAGCGACGT GCCACGGGATCTAGAAGTGG TGGCTGCTACCCCCACAAGC TTGCTGATCTCCTGGACACT GCCTCACGCTGGCCGGGCTC ATTACTATAGAATTACCTAC GGGGAGACAGGCGGGAACTC TCCCGTGCAGGAATTCACCG TGCCTGGAAGGGGCGTGACT GCCACCATCAGTGGGCTGAA GCCAGGAGTGGACTACACAA TTACCGTGTACGCTGTGACT GTGACCACAACTAAAGTGAT CCACTACAAACCCATCTCTA TTAATTATCGGACCGAAATT (SEQ ID NO: 289) |
| PRD-1178 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH EALHNHYTQKS LSLSPGQPDEP GGSGVSDVPRD LEVVAATPTSL LISWTLPHAGR AHYYRITYGET GGNSPVQEFTV PGRGVTATISG LKPGVDYTITV YAVTVTTTKVI | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL KCKVSNKALPA PAPIEKTISKAK PIEKTISKAKG GQPREPQVYTLP QPREPQVYTLP PSRDELTKNQVS PSRDELTKNQV LTCLVKGFYPSD SLTCLVKGFYP IAVEWESNGQPE SDIAVEWESNG NNYKTTPPVLDS QPENNYKTTPP DGSFFLYSKLTV VLDSDGSFFLY DKSRWQQGNVFS SKLTVDKSRWQ CSVMHEALHNHY QGNVFSCSVMH TQKSLSLSP EALHNHYTQKS (SEQ ID NO: 276) | GQPDEPGGS (SEQ ID NO: 185) | GVSDVPRDLEVVA ATPTSLLISWTLP HAGRAHYYRITYG ETGGNSPVQEFTV PGRGVTATISGLK PGVDYTITVYAVT VTTTKVIHYKPIS INYRTEI (SEQ ID NO: 275) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | HYKPISINYRT EI (SEQ ID NO: 258) | | | | AGAGCAGGTGGCAGCAGGGG AACGTCTTCTCATGCTCCGT GATGCATGAGGCTCTGCACA ACCACTACACGCAGAAGAGC CTCTCCCTGTCTCCCGGCCA GCCCGACGAGCCTGGCGGGA GCGGCGTGAGCGACGTGCCA CGGGATCTAGAAGTGGTGGC TGCTACCCCCACAAGCTTGC TGATCTCCTGGACACTGCCT CACGCTGGCCGGGCTCATTA CTATAGAATTACCTACGGGG AGACAGGCGGGAACTCTCCC GTGCAGGAATTCACCGTGCC TGGAAGGGGCGTGACTGCCA CCATCAGTGGGCTGAAGCCA GGAGTGGACTACACAATTAC CGTGTACGCTGTGACTGTGA CCACAACTAAAGTGATCCAC TACAAACCCATCTCTATTAA TTATCGGACCGAAATT (SEQ ID NO: 290) |
| PRD-1180 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH EALHNHYTQKS LSLSPGGSGSG SGSGSGSVSD VPRDLEVVAAT PTSLLISWTLP HAGRAHYYRIT YGETGGNSPVQ EFTVPGRGVTA TISGLKPGVDY TITVYAVTVTT TKVIHYKPISI NYRTEI (SEQ ID NO: 259) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP (SEQ ID NO: 276) | GGSGSGSGS GSGS (SEQ ID NO: 186) | GVSDVPRDLEVVA ATPTSLLISWTLP HAGRAHYYRITYG ETGGNSPVQEFTV PGRGVTATISGLK PGVDYTITVYAVT VTTTKVIHYKPIS INYRTEI (SEQ ID NO: 275) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCAGG GTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGGCGG CAGCGGGTCTGGATCTGGCA GTGGGAGCGGCTCTGGCGTG AGCGACGTGCCACGGGATCT AGAAGTGGTGGCTGCTACCC CCACAAGCTTGCTGATCTCC TGGACACTGCCTCACGCTGG CCGGGCTCATTACTATAGAA TTACCTACGGGGAGACAGGC GGGAACTCTCCCGTGCAGGA ATTCACCGTGCCTGGAAGGG GCGTGACTGCCACCATCAGT GGGCTGAAGCCAGGAGTGGA |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | | | | | CTACACAATTACCGTGTACG CTGTGACTGTGACCACAACT AAAGTGATCCACTACAAACC CATCTCTATTAATTATCGGA CCGAAATT (SEQ ID NO: 291) |
| PRD-1284 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH EALHNHYTQKS LSLSPELQLEE SAAEAQDGELD GVSDVPRDLEV VAATPTSLLIS WDAPRGLARYY RITYGETGGNS PVQEFTVFGRG TTATISGLKPG VDYTITVYAVT IDRDGTRSFDP ISINYRTEI (SEQ ID NO: 260) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAKG QPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP (SEQ ID NO: 276) | ELQLEESAA EAQDGELD (SEQ ID NO: 184) | GVSDVPRDLEVVA ATPTSLLISWDAP RGLARYYRITYGE TGGNSPVQEFTVF GRGTTATISGLKP GVDYTITVYAVTI DRDGTRSFDPISI NYRTEI (SEQ ID NO: 277) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCCGGACCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGAGCT GCAGCTGGAGGAAAGCGCCG CTGAGGCTCAGGACGGAGAA CTGGATGGCGTGAGCGACGT GCCACGGGATCTAGAAGTGG TGGCTGCTACCCCCACAAGC TTGCTGATCAGCTGGGACGC TCCGAGAGGTCTGGCTCGAT ATTACCGCATCACTTACGGC GAAACAGGAGGCAATAGCCC TGTCCAGGAGTTCACTGTGT TCGGTCGTGGTACCACAGCT ACCATCAGCGGCCTTAAACC TGGCGTTGATTATACCATCA CTGTGTATGCTGTCACTATC GACCGTGACGGTACCCGCAG CTTCGACCCAATTTCCATTA ATTACCGGACCGAAATT (SEQ ID NO: 292) |
| PRD-1285 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAKG QPREPQVYTLP PSRDELTKNQVS LTCLVKGFYPSD | ELQLEESAA EAQDGELD (SEQ ID NO: 184) | GVSDVPRDLEVVA ATPTSLLISWDAP AGLARYYRITYGE TGGNSPVQEFTVV GRGNTATISGLKP GVDYTITVYAVTI FRDGPVTWDPISI NYRTEI (SEQ ID NO: 278) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCCGGACCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | SLTCLVKGFYP SDIAVEWESNG QPENNYKTTPP VLDSDGSFFLY SKLTVDKSRWQ QGNVFSCSVMH EALHNHYTQKS LSLSPELQLEE SAAEAQDGELD GVSDVPRDLEV VAATPTSLLIS WDAPAGLARYY RITYGETGGNS PVQEFTVVGRG NTATISGLKPG VDYTITVYAVT IFRDGPVTWDP ISINYRTEI (SEQ ID NO: 261) | IAVEWESNGQPE NNYKTTPPVLDS DGSFFLYSKLTV DKSRWQQGNVFS CSVMHEALHNHY TQKSLSLSP (SEQ ID NO: 276) | | | CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGAGCT GCAGCTGGAGGAAAGCGCCG CTGAGGCTCAGGACGGAGAA CTGGATGGCGTGAGCGACGT GCCCACGGGATCTAGAAGTGG TGGCTGCTACCCCCACAAGC TTGCTGATCAGCTGGGACGC TCCGGCTGGTCTGGCTCGAT ATTACCGCATCACTTACGGC GAAACAGGAGGCAATAGCCC TGTCCAGGAGTTCACTGTGG TCGGTCGTGGTAACACAGCT ACCATCAGCGGCCTTAAACC TGGCGTTGATTATACCATCA CTGTGTATGCTGTCACTATC TTCCGTGACGGTCCCGTCAC CTGGGACCCAATTTCCATTA ATTACCGGACCGAAATT (SEQ ID NO: 293) |
| PRD-1286 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQVS LTCLVKGFYPSD SLTCLVKGFYP SDIAVEWESNG QPENNYKTTPP VLDSDGSFFLY SKLTVDKSRWQ QGNVFSCSVMH EALHNHYTQKS LSLSPELQLEE SAAEAQDGELD GVSDVPRDLEV VAATPTSLLIS WDAPKGLARYY RITYGETGGNS PVQEFTVVGRG NTATISGLKPG VDYTITVYAVT IFRDGPVTWDP ISINYRTEI (SEQ ID NO: 262) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP (SEQ ID NO: 276) | ELQLEESAA EAQDGELD (SEQ ID NO: 184) | GVSDVPRDLEVVA ATPTSLLISWDAP KGLARYYRITYGE TGGNSPVQEFTVV GRGNTATISGLKP GVDYTITVYAVTI FRDGPVTWDPISI NYRTEI (SEQ ID NO: 279) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | | | | | CTCTCCCTGTCTCCCGAGCT GCAGCTGGAGGAAAGCGCCG CTGAGGCTCAGGACGGAGAA CTGGATGGCGTGAGCGACGT GCCACGGGATCTAGAAGTGG TGGCTGCTACCCCCACAAGC TTGCTGATCAGCTGGGACGC TCCGAAGGGTCTGGCTCGAT ATTACCGCATCACTTACGGC GAAACAGGAGGCAATAGCCC TGTCCAGGAGTTCACTGTGG TCGGTCGTGGTAACACAGCT ACCATCAGCGGCCTTAAACC TGGCGTTGATTATACCATCA CTGTGTATGCTGTCACTATC TTCCGTGACGGTCCCGTCAC CTGGGACCCAATTTCCATTA ATTACCGGACCGAAATT (SEQ ID NO: 294) |
| PRD-1287 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQVS LTCLVKGFYP SDLTCLVKGFYP SDIAVEWESNGQPE NNYKTTPPVLDS DGSFFLYSKLTV VLDSDGSFFLY SKLTVDKSRWQ QGNVFSCSVMH EALHNHYTQKS LSLSPELQLEE SAAEAQDGELD GVSDVPRDLEV VAATPTSLLIS WSLPNPGNAHY YRITYGETGGN SPVQEFTVPGR GVTATISGLKP GVDYTITVYAV TVTDTGFITYK PISINYRTEI (SEQ ID NO: 263) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQV LTCLVKGFYPSD IAVEWESNGQPE NNYKTTPPVLDS DGSFFLYSKLTV DKSRWQQGNVFS CSVMHEALHNHY TQKSLSLSP (SEQ ID NO: 276) | ELQLEESAA EAQDGELD (SEQ ID NO: 184) | GVSDVPRDLEVVA ATPTSLLISWSLP NPGNAHYYRITYG ETGGNSPVQEFTV PGRGVTATISGLK PGVDYTITVYAVT VTDTGFITYKPIS INYRTEI (SEQ ID NO: 280) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGAGCT GCAGCTGGAGGAAAGCGCCG CTGAGGCTCAGGACGGAGAA CTGGATGGCGTGAGCGACGT GCCACGGGATCTAGAAGTGG TGGCTGCTACCCCCACAAGC TTGCTGATCAGCTGGTCTCT GCCGAATCCGGGTAACGCCC ATTATTACCGCATCACTTAC GGCGAAACAGGAGGCAATAG CCCTGTCCAGGAGTTCACTG TGCCTGGTCGTGGTGTTACA GCTACCATCAGCGGCCTTAA ACCTGGCGTTGATTATACCA TCACTGTGTATGCTGTCACT GTTACTGACACAGGTTTCAT CACGTACAAACCAATTTCCA TTAATTACCGGACCGAAATT (SEQ ID NO: 295) |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| PRD-1288 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH EALHNHYTQKS LSLSPELQLEE SAAEAQDGELD GVSDVPRDLEV VAATPTSLLIS WSLPHQGKANY YRITYGETGGN SPVQEFTVPGR GVTATISGLKP GVDYTITVYAV TVTDTGYLKYK PISINYRTEI (SEQ ID NO: 264) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP EALHNHYTQKS (SEQ ID NO: 276) | ELQLEESAA EAQDGELD (SEQ ID NO: 184) | GVSDVPRDLEVVA ATPTSLLISWSLP HQGKANYYRITYG ETGGNSPVQEFTV PGRGVTATISGLK PGVDYTITVYAVT VTDTGYLKYKPIS INYRTEI (SEQ ID NO: 281) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCGAGCT GCAGCTGGAGGAAAGCGCCG CTGAGGCTCAGGACGGAGAA CTGGATGGCGTGAGCGACGT GCCACGGGATCTAGAAGTGG TGGCTGCTACCCCCACAAGC TTGCTGATCAGCTGGTCTCT GCCGCACCAAGGTAAAGCCA ATTATTACCGCATCACTTAC GGCGAAACAGGAGGCAATAG CCCTGTCCAGGAGTTCACTG TGCCTGGTCGTGGTGTTACA GCTACCATCAGCGGCCTTAA ACCTGGCGTTGATTATACCA TCACTGTGTATGCTGTCACT GTTACTGATACAGGGTACCT CAAGTACAAACCAATTTCCA TTAATTACCGGACCGAAATT (SEQ ID NO: 296) |
| PRD-1301 | GVSDVPRDLEV VAATPTSLLIS WDAPRGLARYY RITYGETGGNS PVQEFTVFGRG TTATISGLKPG VDYTITVYAVT IDRDGTRSFDP ISINYRTEIEP IKSSDKTHTCPP CPAPELLGGPS VFLFPPKPKDT LMISRTPEVTC VVVDVSHEDPE VKFNWYVDGVE VHNAKTKPREE QYNSTYRVVSV LTVLHQDWLNG KEYKCKVSNKA LPAPIEKTISK | GVSDVPRDLEVV AATPTSLLISWD APRGLARYYRIT YGETGGNSPVQE FTVFGRGTTATI SGLKPGVDYTIT VYAVTIDRDGTR SFDPISINYRTE IEP I (SEQ ID NO: 277) | EPKSSD (SEQ ID NO: 182) | KTHTCPPCPAPEL LGGPSVFLFPPKP KDTLMISRTPEVT CVVVDVSHEDPEV KFNWYVDGVEVHN AKTKPREEQYNST YRVVSVLTVLHQD WLNGKEYKCKVSN KALPAPIEKTISK AKGQPREPQVYTL PPSRDELTKNQVS LTCLVKGFYPSDI AVEWESNGQPENN YKTTPPVLDSDGS FFLYSKLTVDKSR WQQGNVFSCSVMH EALHNHYTQKSLS LSPGK (SEQ ID NO: 283) | GGCGTGAGCGACGTGCCCCG GGATCTAGAAGTGGTGGCTG CTACCCCCACAAGCTTGCTG ATCAGCTGGGACGCTCCGAG AGGTCTGGCTCGATATTACC GCATCACTTACGGCGAAACA GGAGGCAATAGCCCTGTCCA GGAGTTCACTGTGTTCGGTC GTGGTACCACAGCTACCATC AGCGGCCTTAAACCTGGCGT TGATTATACCATCACTGTGT ATGCTGTCACTATCGACCGT GACGGTACCCGCAGCTTCGA CCCAATTTCCATTAATTACC GGACCGAAATTGAGCCTAAG AGC TCCGACAAAACCCACAC ATGCCCACCTTGTCCAGCCC CGAACTGCTGGGCGGCCCT TCAGTCTTCCTCTTCCCCCC AAAACCCAAGGACACCCTCA |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | AKGQPREPQVY TLPPSRDELTK NQVSLTCLVKG FYPSDIAVEWE SNGQPENNYKT TPPVLDSDGSF FLYSKLTVDKS RWQQGNVFSCS VMHEALHNHYT QKSLSLSPGK (SEQ ID NO: 265) | | | | TGATCTCCCGGACCCCTGAG GTCACATGCGTGGTGGTGGA CGTGAGCCACGAAGACCCTG AGGTCAAGTTCAACTGGTAC GTGGACGGCGTGGAGGTGCA TAATGCCAAGACAAAGCCGC GGGAGGAGCAGTACAACAGC ACGTACCGTGTGGTCAGCGT CCTCACCGTCCTGCACCAGG ACTGGCTGAATGGCAAGGAG TACAAGTGCAAGGTCTCCAA CAAAGCCCTCCCAGCCCCCA TCGAGAAAACCATCTCCAAA GCCAAGGGCAGCCCCGAGA ACCACAGGTGTACACCCTGC CCCCATCCCGGGATGAGCTG ACCAAGAACCAGGTCAGCCT GACCTGCCTGGTCAAAGGCT TCTATCCCAGCGACATCGCC GTGGAGTGGGAGAGCAATGG GCAGCCGGAGAACAACTACA AGACCACGCCTCCCGTGTTG GACTCCGACGGCTCCTTCTT CCTCTACAGCAAGCTCACCG TGGACAAGAGCAGGTGGCAG CAGGGGAACGTCTTCTCATG CTCCGTGATGCATGAGGCTC TGCACAACCACTACACGCAG AAGAGCCTCTCCCTGTCTCC CGGGAAA (SEQ ID NO: 297) |
| PRD-1302 | GVSDVPRDLEV VAATPTSLLIS WDAPAGLARYY RITYGETGGNS PVQEFTVVGRG NTATISGLKPG VDYTITVYAVT IFRDGPVTWDP ISINYRTEIEP I KSSDKTHTCPP CPAPELLGGPS VFLFPPKPKDT LMISRTPEVTC VVVDVSHEDPE VKFNWYVDGVE VHNAKTKPREE QYNSTYRVVSV LTVLHQDWLNG KEYKCKVSNKA LPAPIEKTISK AKGQPREPQVY TLPPSRDELTK NQVSLTCLVKG FYPSDIAVEWE SNGQPENNYKT TPPVLDSDGSF FLYSKLTVDKS RWQQGNVFSCS VMHEALHNHYT QKSLSLSPGK (SEQ ID NO: 266) | GVSDVPRDLEVV AATPTSLLISWD APAGLARYY APAGLARYYRIT YGETGGNSPVQE FTVVGRGNTATI SGLKPGVDYTIT VYAVTIFRDGPV TWDPISINYRTE I (SEQ ID NO: 278) | EPKSSD (SEQ ID NO: 182) | KTHTCPPCPAPEL LGGPSVFLFPPKP KDTLMISRTPEVT CVVVDVSHEDPEV KFNWYVDGVEVHN AKTKPREEQYNST YRVVSVLTVLHQD WLNGKEYKCKVSN KALPAPIEKTISK AKGQPREPQVYTL PPSRDELTKNQVS LTCLVKGFYPSDI AVEWESNGQPENN YKTTPPVLDSDGS FFLYSKLTVDKSR WQQGNVFSCSVMH EALHNHYTQKSLS LSPGK (SEQ ID NO: 283) | GGCGTGAGCGACGTGCCCCG GGATCTAGAAGTGGTGGCTG CTACCCCCACAAGCTTGCTG ATCAGCTGGGACGCTCCGGC TGGTCTGGCTCGATATTACC GCATCACTTACGGCGAAACA GGAGGCAATAGCCCCTGTCA GGAGTTCACTGTGGTCGGTC GTGGTAACACAGCTACCATC AGCGGCCTTAAACCTGGCGT TGATTATACCATCACTGTGT ATGCTGTCACTATCTTCCGT GACGGTCCCGTCACCTGGGA CCCCAATTTCCATTAATTACC GGACCGAAATTGAGCCTAAG AGCTCCGACAAAACCCACAC ATGCCCACCTTGTCCAGCCC CCGAACTGCTGGGCGGCCCT TCAGTCTTCCTCTTCCCCCC AAAACCCAAGGACACCCTCA TGATCTCCCGGACCCCTGAG GTCACATGCGTGGTGGTGGA CGTGAGCCACGAAGACCCTG AGGTCAAGTTCAACTGGTAC GTGGACGGCGTGGAGGTGCA TAATGCCAAGACAAAGCCGC GGGAGGAGCAGTACAACAGC ACGTACCGTGTGGTCAGCGT CCTCACCGTCCTGCACCAGG ACTGGCTGAATGGCAAGGAG TACAAGTGCAAGGTCTCCAA CAAAGCCCTCCCAGCCCCCA TCGAGAAAACCATCTCCAAA GCCAAGGGCAGCCCCGAGA ACCACAGGTGTACACCCTGC CCCCATCCCGGGATGAGCTG ACCAAGAACCAGGTCAGCCT GACCTGCCTGGTCAAAGGCT TCTATCCCAGCGACATCGCC GTGGAGTGGGAGAGCAATGG GCAGCCGGAGAACAACTACA |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | | | | | AGACCACGCCTCCCGTGTTG GACTCCGACGGCTCCTTCTT CCTCTACAGCAAGCTCACCG TGGACAAGAGCAGGTGGCAG CAGGGGAACGTCTTCTCATG CTCCGTGATGCATGAGGCTC TGCACAACCACTACACGCAG AAGAGCCTCTCCCTGTCTCC CGGGAAA (SEQ ID NO: 298) |
| PRD-1303 | GVSDVPRDLEV VAATPTSLLIS WDAPKGLARYY RITYGETGGNS PVQEFTVVGRG NTATISGLKPG VDYTITVYAVT IFRDGPVTWDP ISINYRTEIEP KSSDKTHTCPP CPAPELLGGPS VFLFPPKPKDT LMISRTPEVTC VVVDVSHEDPE VKFNWYVDGVE VHNAKTKPREE QYNSTYRVVSV LTVLHQDWLNG KEYKCKVSNKA LPAPIEKTISK AKGQPREPQVY TLPPSRDELTK NQVSLTCLVKG FYPSDIAVEWE SNGQPENNYKT TPPVLDSDGSF FLYSKLTVDKS RWQQGNVFSCS VMHEALHNHYT QKSLSLSPGK (SEQ ID NO: 267) | GVSDVPRDLEVV AATPTSLLISWD APKGLARYYRIT YGETGGNSPVQE FTVVGRGNTATI SGLKPGVDYTIT VYAVTIFRDGPV TWDPISINYRTE I (SEQ ID NO: 279) | EPKSSD (SEQ ID NO: 182) | KTHTCPPCPAPEL LGGPSVFLFPPKP KDTLMISRTPEVT CVVVDVSHEDPEV KFNWYVDGVEVHN AKTKPREEQYNST YRVVSVLTVLHQD WLNGKEYKCKVSN KALPAPIEKTISK AKGQPREPQVYTL PPSRDELTKNQVS LTCLVKGFYPSDI AVEWESNGQPENN YKTTPPVLDSDGS FFLYSKLTVDKSR WQQGNVFSCSVMH EALHNHYTQKSLS LSPGK (SEQ ID NO: 283) | GGCGTGAGCGACGTGCCCCG GGATCTAGAAGTGGTGGCTG CTACCCCCACAAGCTTGCTG ATCAGCTGGGACGCTCCGAA GGGTCTGGCTCGATATTACC GCATCACTTACGGCGAAACA GGAGGCAATAGCCCCTGTCCA GGAGTTCACTGTGGTCGGTC GTGGTAACACAGCTACCATC AGCGGCTTAAACCTGGCGT TGATTATACCATCACTGTGT ATGCTGTCACTATCTTCCGT GACGGTCCCGTCACCTGGGA CCCAATTTCCATTAATTACC GGACCGAAATTGAGCCTAAG AGCTCCGACAAAACCCACAC ATGCCCACCTTGTCCAGCCC CCGAACTGCTGGGCGGCCCT TCAGTCTTCCTCTTCCCCCC AAAACCCAAGGACACCCTCA TGATCTCCCGGACCCCTGAG GTCACATGCGTGGTGGTGGA CGTGAGCCACGAAGACCCTG AGGTCAAGTTCAACTGGTAC GTGGACGGCGTGGAGGTGCA TAATGCCAAGACAAAGCCGC GGGAGGAGCAGTACAACAGC ACGTACCGTGTGGTCAGCGT CCTCACCGTCCTGCACCAGG ACTGGCTGAATGGCAAGGAG TACAAGTGCAAGGTCTCCAA CAAAGCCCTCCCAGCCCCCA TCGAGAAAACCATCTCCAAA GCCAAGGGCAGCCCCGAGA ACCACAGGTGTACACCCTGC CCCCATCCCGGGATGAGCTG ACCAAGAACCAGGTCAGCCT GACCTGCCTGGTCAAAGGCT TCTATCCCAGCGACATCGCC GTGGAGTGGGAGAGCAATGG GCAGCCGGAGAACAACTACA AGACCACGCCTCCCGTGTTG GACTCCGACGGCTCCTTCTT CCTCTACAGCAAGCTCACCG TGGACAAGAGCAGGTGGCAG CAGGGGAACGTCTTCTCATG CTCCGTGATGCATGAGGCTC TGCACAACCACTACACGCAG AAGAGCCTCTCCCTGTCTCC CGGGAAA (SEQ ID NO: 299) |
| PRD-1304 | GVSDVPRDLEV VAATPTSLLIS WSLPNPGNAHY YRITYGETGGN SPVQEFTVPGR GVTATISGLKP GVDYTITVYAV TVTDTGFITYK PISINYRTEIE PKSSDKTHTCP | GVSDVPRDLEVV AATPTSLLISWS LPNPGNAHYYRI TYGETGGNSPVQ EFTVPGRGVTAT ISGLKPGVDYTI TVYAVTVTDTGF ITYKPISINYRT EI (SEQ ID NO: 280) | EPKSSD (SEQ ID NO: 182) | KTHTCPPCPAPEL LGGPSVFLFPPKP KDTLMISRTPEVT CVVVDVSHEDPEV KFNWYVDGVEVHN AKTKPREEQYNST YRVVSVLTVLHQD WLNGKEYKCKVSN KALPAPIEKTISK AKGQPREPQVYTL | GGCGTGAGCGACGTGCCCCG GGATCTAGAAGTGGTGGCTG CTACCCCCACAAGCTTGCTG ATCAGCTGGTCTCTGCCGAA TCCGGGTAACGCCCATTATT ACCGCATCACTTACGGCGAA ACAGGAGGCAATAGCCCTGT CCAGGAGTTCACTGTGCCTG GTCGTGGTGTTACAGCTACC ATCAGCGGCCTTAAACCTGG |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | PCPAPELLGGP SVFLFPPKPKD TLMISRTPEVT CVVVDVSHEDP EVKFNWYVDGV EVHNAKTKPRE EQYNSTYRVVS VLTVLHQDWLN GKEYKCKVSNK ALPAPIEKTIS KAKGQPREPQV YTLPPSRDELT KNQVSLTCLVK GFYPSDIAVEW ESNGQPENNYK TTPPVLDSDGS FFLYSKLTVDK SRWQQGNVFSC SVMHEALHNHY TQKSLSLSPGK (SEQ ID NO: 268) | | | PPSRDELTKNQVS LTCLVKGFYPSDI AVEWESNGQPENN YKTTPPVLDSDGS FFLYSKLTVDKSR WQQGNVFSCSVMH EALHNHYTQKSLS LSPGK (SEQ ID NO: 283) | CGTTGATTATACCATCACTG TGTATGCTGTCACTGTTACT GACACAGGTTTCATCACGTA CAAACCAATTTCCATTAATT ACCGGACCGAAATTGAGCCT AAGAGCTCCGACAAAACCCA CACATGCCCACCTTGTCCAG CCCCCGAACTGCTGGGCGGC CCTTCAGTCTTCCTCTTCCC CCCAAAACCCAAGGACACCC TCATGATCTCCCGGACCCCT GAGGTCACATGCGTGGTGGT GGACGTGAGCCACGAAGACC CTGAGGTCAAGTTCAACTGG TACGTGGACGGCGTGGAGGT GCATAATGCCAAGACAAAGC CGCGGGAGGAGCAGTACAAC AGCACGTACCGTGTGGTCAG CGTCCTCACCGTCCTGCACC AGGACTGGCTGAATGGCAAG GAGTACAAGTGCAAGGTCTC CAACAAAGCCCTCCCAGCCC CCATCGAGAAAACCATCTCC AAAGCCAAAGGGCAGCCCCG AGAACCACAGGTGTACACCC TGCCCCCATCCCGGGATGAG CTGACCAAGAACCAGGTCAG CCTGACCTGCCTGGTCAAAG GCTTCTATCCCAGCGACATC GCCGTGGAGTGGGAGAGCAA TGGGCAGCCGGAGAACAACT ACAAGACCACGCCTCCCGTG TTGGACTCCGACGGCTCCTT CTTCCTCTACAGCAAGCTCA CCGTGGACAAGAGCAGGTGG CAGCAGGGGAACGTCTTCTC ATGCTCCGTGATGCATGAGG CTCTGCACAACCACTACACG CAGAAGAGCCTCTCCCTGTC TCCCGGGAAA (SEQ ID NO: 300) |
| PRD-1305 | GVSDVPRDLEV VAATPTSLLIS WSLPHQGKANY YRITYGETGGN SPVQEFTVPGR GVTATISGLKP GVDYTITVYAV TVTDTGYLKYK PISINYRTEIE PKSSDKTHTCP PCPAPELLGGP SVFLFPPKPKD TLMISRTPEVT CVVVDVSHEDP EVKFNWYVDGV EVHNAKTKPRE EQYNSTYRVVS VLTVLHQDWLN GKEYKCKVSNK ALPAPIEKTIS KAKGQPREPQV YTLPPSRDELT KNQVSLTCLVK GFYPSDIAVEW ESNGQPENNYK TTPPVLDSDGS FFLYSKLTVDK SRWQQGNVFSC SVMHEALHNHY TQKSLSLSPGK (SEQ ID NO: | GVSDVPRDLEVV AATPTSLLISWS LPHQGKANYYRI TYGETGGNSPVQ EFTVPGRGVTAT ISGLKPGVDYTI TVYAVTVTDTGY LKYKPISINYRT EI (SEQ ID NO: 281) | EPKSSD (SEQ ID NO: 182) | KTHTCPPCPAPEL LGGPSVFLFPPKP KDTLMISRTPEVT CVVVDVSHEDPEV KFNWYVDGVEVHN AKTKPREEQYNST YRVVSVLTVLHQD WLNGKEYKCKVSN KALPAPIEKTISK AKGQPREPQVYTL PPSRDELTKNQVS LTCLVKGFYPSDI AVEWESNGQPENN YKTTPPVLDSDGS FFLYSKLTVDKSR WQQGNVFSCSVMH EALHNHYTQKSLS LSPGK (SEQ ID NO: 283) | GGCGTGAGCGACGTGCCCCG GGATCTAGAAGTGGTGGCTG CTACCCCCACAAGCTTGCTG ATCAGCTGGTCTCTGCCGCA CCAAGGTAAAGCCAATTATT ACCGCATCACTTACGGCGAA ACAGGAGGCAATAGCCCTGT CCAGGAGTTCACTGTGCCTG GTCGTGGTGTTACAGCTACC ATCAGCGGCCTTAAACCTGG CGTTGATTATACCATCACTG TGTATGCTGTCACTGTTACT GATACAGGGTACCTCAAGTA CAAACCAATTTCCATTAATT ACCGGACCGAAATTGAGCCT AAGAGCTCCGACAAAACCCA CACATGCCCACCTTGTCCAG CCCCCGAACTGCTGGGCGGC CCTTCAGTCTTCCTCTTCCC CCCAAAACCCAAGGACACCC TCATGATCTCCCGGACCCCT GAGGTCACATGCGTGGTGGT GGACGTGAGCCACGAAGACC CTGAGGTCAAGTTCAACTGG TACGTGGACGGCGTGGAGGT GCATAATGCCAAGACAAAGC CGCGGGAGGAGCAGTACAAC AGCACGTACCGTGTGGTCAG CGTCCTCACCGTCCTGCACC AGGACTGGCTGAATGGCAAG GAGTACAAGTGCAAGGTCTC |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | 269) | | | | CAACAAAGCCCTCCCAGCCC CCATCGAGAAAACCATCTCC AAAGCCAAAGGGCAGCCCCG AGAACCACAGGTGTACACCC TGCCCCCATCCCGGGATGAG CTGACCAAGAACCAGGTCAG CCTGACCTGCCTGGTCAAAG GCTTCTATCCCAGCGACATC GCCGTGGAGTGGGAGAGCAA TGGGCAGCCGGAGAACAACT ACAAGACCACGCCTCCCGTG TTGGACTCCGACGGCTCCTT CTTCCTCTACAGCAAGCTCA CCGTGGACAAGAGCAGGTGG CAGCAGGGGAACGTCTTCTC ATGCTCCGTGATGCATGAGG CTCTGCACAACCACTACACG CAGAAGAGCCTCTCCCTGTC TCCCGGGAAA (SEQ ID NO: 301) |
| PRD-1471 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH EALHNHYTQKS LSLSPELQLEE SAAEAQEGELE GVSDVPRDLEV VAATPTSLLIS WTLPHAGRAHY YRITYGETGGN SPVQEFTVPGR GVTATISGLKP GVDYTITVYAV TVTTTKVIHYK PISINYRTEI (SEQ ID NO: 270) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP EALHNHYTQKS (SEQ ID NO: 276) | ELQLEESAA EAQEGELE (SEQ ID NO: 187) | GVSDVPRDLEVVA ATPTSLLISWTLP HAGRAHYYRITYG ETGGNSPVQEFTV PGRGVTATISGLK PGVDYTITVYAVT VTTTKVIHYKPIS INYRTEI (SEQ ID NO: 275) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGAGCT GCAGCTGGAGGAAAGCGCCG CTGAGGCTCAGGAAGGAGAA CTGGAAGGCGTGAGCGACGT GCCACGGGATCTAGAAGTGG TGGCTGCTACCCCCACAAGC TTGCTGATCTCCTGGACACT GCCTCACGCTGGCCGGGCTC ATTACTATAGAATTACCTAC GGGGAGACAGGCGGGAACTC TCCCGTGCAGGAATTCACCG TGCCTGGAAGGGGCGTGACT GCCACCATCAGTGGGCTGAA GCCAGGAGTGGACTACACAA TTACCGTGTACGCTGTGACT GTGACCACAACTAAAGTGAT CCACTACAAACCCATCTCTA TTAATTATCGGACCGAAATT (SEQ ID NO: 302) |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| PRD-1472 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH EALHNHYTQKS LSLSPELQLEE SAAEAQEGELE GVSDVPRDLEV VAATPTSLLIS WDAPAGLARYY RITYGETGGNS PVQEFTVVGRG NTATISGLKPG VDYTITVYAVT IFRDGPVTWDP ISINYRTEI (SEQ ID NO: 271) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP (SEQ ID NO: 276) | ELQLEESAA EAQEGELE (SEQ ID NO: 187) | GVSDVPRDLEVVA ATPTSLLISWDAP AGLARYYRITYGE TGGNSPVQEFTVV GRGNTATISGLKP GVDYTITVYAVTI FRDGPVTWDPISI NYRTEI (SEQ ID NO: 278) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCGAGCT GCAGCTGGAGGAAAGCGCCG CTGAGGCTCAGGAAGGAGAA CTGGAAGGCGTGAGCGACGT GCCACGGGATCTAGAAGTGG TGGCTGCTACCCCCACAAGC TTGCTGATCAGCTGGGACGC TCCGGCTGGTCTGGCTCGAT ATTACCGCATCACTTACGGC GAAACAGGAGGCAATAGCCC TGTCCAGGAGTTCACTGTGG TCGGTCGTGGTAACACAGCT ACCATCAGCGGCCTTAAACC TGGCGTTGATTATACCATCA CTGTGTATGCTGTCACTATC TTCCGTGACGGTCCCGTCAC CTGGGACCCAATTTCCATTA ATTACCGGACCGAAATT (SEQ ID NO: 303) |
| PRD-1473 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH TQKSLSLSP | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQVS LTCLVKGFYPSD IAVEWESNGQPE NNYKTTPPVLDS DGSFFLYSKLTV DKSRWQQGNVFS CSVMHEALHNHY TQKSLSLSP | ELQLEESAA EAQEGELE (SEQ ID NO: 187) | GVSDVPRDLEVVA ATPTSLLISWDAP KGLARYYRITYGE TGGNSPVQEFTVV GRGNTATISGLKP GVDYTITVYAVTI FRDGPVTWDPISI NYRTEI (SEQ ID NO: 279) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | EALHNHYTQKS LSLSPELQLEE SAAEAQEGELE GVSDVPRDLEV VAATPTSLLIS WDAPKGLARYY RITYGETGGNS PVQEFTVVGRG NTATISGLKPG VDYTITVYAVT IFRDGPVTWDP ISINYRTEI (SEQ ID NO: 272) | | | | GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGAGCT GCAGCTGGAGGAAAGCGCCG CTGAGGCTCAGGAAGGAGAA CTGGAAGGCGTGAGCGACGT GCCACGGGATCTAGAAGTGG TGGCTGCTACCCCCACAAGC TTGCTGATCAGCTGGGACGC TCCGAAGGGTCTGGCTCGAT ATTACCGCATCACTTACGGC GAAACAGGAGGCAATAGCCC TGTCCAGGAGTTCACTGTGG TCGGTCGTGGTAACACAGCT ACCATCAGCGGCCTTAAACC TGGCGTTGATTATACCATCA CTGTGTATGCTGTCACTATC TTCCGTGACGGTCCCGTCAC CTGGGACCCAATTTCCATTA ATTACCGGACCGAAATT (SEQ ID NO: 304) |
| PRD-1474 | DKTHTCPPCPA PELLGGPSVFL FPPKPKDTLMI SRTPEVTCVVV DVSHEDPEVKF NWYVDGVEVHN AKTKPREEQYN STYRVVSVLTV LHQDWLNGKEY KCKVSNKALPA PIEKTISKAKG QPREPQVYTLP PSRDELTKNQV SLTCLVKGFYP SDIAVEWESNG QPENNYKTTPP VLDSDGSFFLY SKLTVDKSRWQ QGNVFSCSVMH EALHNHYTQKS LSLSPELQLEE SAAEAQEGELE GVSDVPRDLEV VAATPTSLLIS WSLPHQKANY YRITYGETGGN SPVQEFTVPGR GVTATISGLKP GVDYTITVYAV TVTDTGYLKYK PISINYRTEI (SEQ ID NO: 273) | DKTHTCPPCPAP ELLGGPSVFLFP PKPKDTLMISRT PEVTCVVVDVSH EDPEVKFNWYVD GVEVHNAKTKPR EEQYNSTYRVVS VLTVLHQDWLNG KEYKCKVSNKAL PAPIEKTISKAK GQPREPQVYTLP PSRDELTKNQV LTCLVKGFYPSD IAVEWESNGQPE NNYKTTPPVLDS DGSFFLYSKLTV DKSRWQQGNVFS CSVMHEALHNHY TQKSLSLSP | ELQLEESAA EAQEGELE (SEQ ID NO: 187) | GVSDVPRDLEVVA ATPTSLLISWSLP HQGKANYYRITYG ETGGNSPVQEFTV PGRGVTATISGLK PGVDYTITVYAVT VTDTGYLKYKPIS INYRTEI (SEQ ID NO: 281) | GACAAAACTCACACATGCCC ACCGTGCCCAGCACCTGAAC TCCTGGGGGGACCGTCAGTC TTCCTCTTCCCCCCAAAACC CAAGGACACCCTCATGATCT CCCGGACCCCTGAGGTCACA TGCGTGGTGGTGGACGTGAG CCACGAAGACCCTGAGGTCA AGTTCAACTGGTACGTGGAC GGCGTGGAGGTGCATAATGC CAAGACAAAGCCGCGGGAGG AGCAGTACAACAGCACGTAC CGTGTGGTCAGCGTCCTCAC CGTCCTGCACCAGGACTGGC TGAATGGCAAGGAGTACAAG TGCAAGGTCTCCAACAAAGC CCTCCCAGCCCCCATCGAGA AAACCATCTCCAAAGCCAAA GGGCAGCCCCGAGAACCACA GGTGTACACCCTGCCCCCAT CCCGGGATGAGCTGACCAAG AACCAGGTCAGCCTGACCTG CCTGGTCAAAGGCTTCTATC CCAGCGACATCGCCGTGGAG TGGGAGAGCAATGGGCAGCC GGAGAACAACTACAAGACCA CGCCTCCCGTGCTGGACTCC GACGGCTCCTTCTTCCTCTA CAGCAAGCTCACCGTGGACA AGAGCAGGTGGCAGCAGGGG AACGTCTTCTCATGCTCCGT GATGCATGAGGCTCTGCACA ACCACTACACGCAGAAGAGC CTCTCCCTGTCTCCCGAGCT GCAGCTGGAGGAAAGCGCCG CTGAGGCTCAGGAAGGAGAA CTGGAAGGCGTGAGCGACGT GCCACGGGATCTAGAAGTGG TGGCTGCTACCCCCACAAGC |

TABLE 6-continued

Fc-fused Anti-Myostatin Adnectins

| Clone | Amino Acid Sequence | N-terminal domain | Linker | C-terminal domain | Nucleic Acid Sequence |
|---|---|---|---|---|---|
| | | | | | TTGCTGATCAGCTGGTCTCT GCCGCACCAAGGTAAAGCCA ATTATTACCGCATCACTTAC GGCGAAACAGGAGGCAATAG CCCTGTCCAGGAGTTCACTG TGCCTGGTCGTGGTGTTACA GCTACCATCAGCGGCCTTAA ACCTGGCGTTGATTATACCA TCACTGTGTATGCTGTCACT GTTACTGATACAGGGTACCT CAAGTACAAACCAATTTCCA TTAATTACCGGACCGAAATT (SEQ ID NO: 305) |

The SEQ ID NOs of exemplary leader (N-terminal extension) and C-terminal tail sequences of the invention are presented in Table 7.

TABLE 7

Summary of Exemplary Sequences

| SEQ ID NO | Description | Name | Sequence |
|---|---|---|---|
| 306 | Exemplary leader | AdNT1 | MGVSDVPRDL |
| 307 | Exemplary leader | AdNT2 | GVSDVPRDL |
| 308 | Exemplary leader | AdNT3 | VSDVPRDL |
| 309 | Exemplary leader | AdNT4 | SDVPRDL |
| 310 | Exemplary leader | AdNT5 | DVPRDL |
| 311 | Exemplary leader | AdNT6 | VPRDL |
| 312 | Exemplary leader | AdNT7 | PRDL |
| — | Exemplary leader | AdNT8 | RDL |
| — | Exemplary leader | AdNT9 | DL |
| 211 | Exemplary tail | AdCT1 | EIDKPSQ |
| — | Exemplary tail | AdCT2 | EI |
| 313 | Exemplary tail | AdCT3 | EIEPKSS |
| 314 | Exemplary tail | AdCT4 | EIDKPC |
| 315 | Exemplary tail | AdCT5 | EIDKP |
| 316 | Exemplary tail | AdCT6 | EIDK |
| 317 | Exemplary tail | AdCT7 | EIDKPS |
| 318 | Exemplary tail | AdCT8 | EIEKPSQ |
| 319 | Exemplary tail | AdCT9 | EIDKPSQLE |
| 320 | Exemplary tail | AdCT10 | EIEDEDEDED |
| 321 | Exemplary tail | AdCT11 | EGSGS |
| 322 | Exemplary tail | AdCT12 | EIDKPCQ |
| 189 | Exemplary tail | AdCT13 | GSGC |
| 323 | Exemplary tail | AdCT14 | EGSGC |
| 324 | Exemplary tail | AdCT15 | EIDKPCQLE |
| 325 | Exemplary tail | AdCT16 | EIDKPSQHHHHHH |
| 326 | Exemplary tail | AdCT17 | GSGCHHHHHH |
| 327 | Exemplary tail | AdCT18 | EGSGCHHHHHH |
| 328 | Tag | T1 | HHHHHH |

IV. Nucleic Acid-Protein Fusion Technology

In one aspect, the invention provides an Adnectin comprising fibronectin type III domains that binds myostatin. One way to rapidly make and test Fn3 domains with specific binding properties is the nucleic acid-protein fusion technology of Adnexus, a Bristol-Myers Squibb R&D Company. This disclosure utilizes the in vitro expression and tagging technology, termed TROfusion' which exploits nucleic acid-protein fusions (RNA- and DNA-protein fusions) to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558, 6,261,804, 6,214,553, 6,281,344, 6,207,446, 6,518,018 and 6,818,418; Roberts et al., Proc. Natl. Acad. Sci., 1997; 94:12297-12302; and Kurz et al., Molecules, 2000; 5:1259-64, all of which are herein incorporated by reference.

V. Vectors and Polynucleotides

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*, 100(2):438-442 (Jan. 21, 2003); Sinclair et al., *Protein Expr. Purif.*, 26(I):96-105 (October 2002); Connell, N. D., *Curr. Opin. Biotechnol.*, 12(5):446-449 (October 2001); Makrides et al., *Microbiol. Rev.*, 60(3):512-538 (September 1996); and Sharp et al., *Yeast*, 7(7):657-678 (October 1991).

General techniques for nucleic acid manipulation are described in, for example, Sambrook et al., Molecular Cloning: A Laboratory Manual, 2nd Edition, Vols. 1-3, Cold Spring Harbor Laboratory Press (1989), or Ausubel, F. et al., Current Protocols in Molecular Biology, Green Publishing and Wiley-Interscience, New York (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding site, and sequences that control the termination of transcription and translation. The ability to replicate in a host, usually conferred by an origin of replication, and a selection gene to facilitate recognition of transformants is additionally incorporated.

The proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. An exemplary N-terminal leader sequence for production of polypeptides in a mammalian system is: METDTLLLWVLLLWVPG-STG (SEQ ID NO: 177), which is removed by the host cell following expression.

For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders.

For yeast secretion the native signal sequence may be substituted by, e.g., a yeast invertase leader, a factor leader (including *Saccharomyces* and *Kluyveromyces* alpha-factor leaders), or acid phosphatase leader, the *C. albicans* glucoamylase leader, or the signal sequence described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein of the invention, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein of the invention. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding protein of the invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature*, 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein of the invention. One useful transcription termination component is the bovine growth hormone polyadenylation region. See WO 94/11026 and the expression vector disclosed therein.

The recombinant DNA can also include any type of protein tag sequence that may be useful for purifying the protein. Examples of protein tags include, but are not limited to, a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York (1985)), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (Bio/Technology, 6:47 (1988)). Examples of suitable mammalian host cell lines include endothelial cells, COS-7 monkey kidney cells, CV-1, L cells, C127, 3T3, Chinese hamster ovary (CHO), human embryonic kidney ceils, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

VI. Protein Production

The present invention is also directed to cell lines that express an anti-myostatin Adnectin or fusion polypeptide thereof. Creation and isolation of cell lines producing an anti-myostatin Adnectin can be accomplished using standard techniques known in the art, such as those described herein.

Host cells are transformed with the herein-described expression or cloning vectors for protein production and cultured in conventional nutrient media modified as appropriate for inducing promoters, selecting transformants, or amplifying the genes encoding the desired sequences. In the examples shown here, the host cells used for high-throughput protein production (HTPP) and mid-scale production were those from the HMS 174-bacterial strain.

Adnectins of the present invention can also be obtained in aglycosylated form by producing the Adnectins in, e.g., prokaryotic cells (e.g., *E. coli*). Notably, aglycosylated forms of the Adnectins of the invention exhibit the same affinity, potency, and mechanism of action as glycosylated Adnectins when tested in vitro.

The host cells used to produce the proteins of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma)) are suitable for culturing the host cells. In addition, many of the media described in Ham et al., Meth. Enzymol., 58:44 (1979), Barites et al., Anal. Biochem., 102:255 (1980), U.S. Pat. Nos. 4,767,704, 4,657,866, 4,927,762, 4,560,655, 5,122,469, 6,048,728, 5,672,502, or U.S. Pat. No. RE 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Proteins of the invention can also be produced by chemical synthesis (e.g., by the methods described in Solid Phase Peptide Synthesis, 2nd Edition, The Pierce Chemical Co., Rockford, Ill. (1984)). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, or preferably at least 95% pure, and most preferably at least 98% pure. Regardless of the exact numerical value of the purity, the polypeptide is sufficiently pure for use as a pharmaceutical product.

VII. Biophysical and Biochemical Characterization

Binding of an anti-myostatin Adnectin of the invention to a target molecule (e.g., myostatin) may be assessed in terms of equilibrium constants (e.g., dissociation, $K_D$) and in terms of kinetic constants (e.g., on-rate constant, $k_{on}$ and off-rate constant, $k_{off}$). An Adnectin will generally bind to a target molecule with a $K_D$ of less than 500 nM, 100 nM, 10 nM, 1 nM, 500 pM, 200 pM, or 100 pM, although higher $K_D$ values may be tolerated where the $k_{off}$ is sufficiently low or the $k_{on}$, is sufficiently high.

In Vitro Assays for Binding Affinity

Anti-myostatin Adnectins that bind to and antagonize myostatin can be identified using various in vitro assays. Preferably, the assays are high-throughput assays that allow for screening multiple candidate Adnectins simultaneously. In some embodiments, BMP-11, which shares 90% amino acid identity with myostatin, can be used as a surrogate for myostatin in in vitro assays when the assay is performed under saturating conditions. Notably, anti-myostatin Adnectins fused to Fc domains can bind both myostatin and BMP-11, whereas monoAdnectins bind preferentially to myostatin. Without being bound by theory, this may reflect the increased avidity of bivalent Fc-fused Adnectins compared to monovalent Adnectins. Similar enhanced binding to BMP11 is observed with bivalent PEGylated Adnectins, such as ATI-1341, which comprise Adnectins fused to two ends of a 20 kDa PEG moiety.

Exemplary assays for determining the binding affinity of anti-myostatin Adnectins are described in the Examples infra, and include, but are not limited to, solution phase methods such as the kinetic exclusion assay (KinExA) (Blake et al., *JBC* 1996; 271:27677-85; Drake et al., *Anal Biochem* 2004; 328:35-43), surface plasmon resonance (SPR) with the Biacore system (Uppsala, Sweden) (Welford et al., *Opt. Quant. Elect* 1991; 23:1; Morton and Myszka, *Methods in Enzymology* 1998; 295:268) and homogeneous time resolved fluorescence (HTRF) assays (Newton et al., *J Biomol Screen* 2008; 13:674-82; Patel et al., *Assay Drug Dev Technol* 2008; 6:55-68).

In some embodiments, biomolecular interactions can be monitored in real time with the Biacore system, which uses SPR to detect changes in the resonance angle of light at the surface of a thin gold film on a glass support due to changes in the refractive index of the surface up to 300 nm away. Biacore analysis generates association rate constants, dissociation rate constants, equilibrium dissociation constants, and affinity constants. Binding affinity is obtained by assessing the association and dissociation rate constants using a Biacore surface plasmon resonance system (Biacore, Inc.). A biosensor chip is activated for covalent coupling of the target. The target is then diluted and injected over the chip to obtain a signal in response units of immobilized material. Since the signal in resonance units (RU) is proportional to the mass of immobilized material, this represents a range of immobilized target densities on the matrix. Association and dissociation data are fit simultaneously in a global analysis to solve the net rate expression for a 1:1 bimolecular interaction, yielding best fit values for $k_{on}$, $k_{off}$ and $R_{max}$ (maximal response at saturation). Equilibrium dissociation constants for binding, $K_D$'s are calculated from SPR measurements as $k_{off}/k_{on}$.

In some embodiments, the anti-myostatin Adnectins of the invention exhibit a $K_D$ in the SPR affinity assay described in Example 6 of 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, 10 nM or less, 5 nM or less, or 1 nM or less. Preferably, the $K_D$ is 15 nM or less. More preferably, the $K_D$ is 2.0 nM or less.

In some embodiments, the anti-myostatin Adnectins of the invention exhibit an IC50 in the HTRF assay described in Example 4 of 5 nM or less, 4 nM or less, 3 nM or less, 2.5 nM or less, 2 nM or less, 1.5 nM or less, 1 nM or less, 0.5 nM or less, 0.2 nM or less, or 0.1 nM or less. Preferably, the IC50 is 1.5 nM or less. More preferably, the IC50 is 0.5 nM or less.

In some embodiments, the anti-myostatin Adnectins of the invention exhibit $K_D$ in the kinetic exclusion assay described in Example 7 of 2 nM or less, 1.5 nM or less, 1 nM or less, 900 pM or less, 850 pM or less, 800 pM or less, 750 pM or less, 700 pM or less, 650 pM or less, 600 pM or less, 550 pM or less, 500 pM or less, 450 pM or less, 400 pM or less, 350 pM or less, 340 pM or less, 330 pM or less, 300 pM or less, 250 pM or less, 200 pM or less, 150 pM or less, or 100 pM or less. Preferably, the $K_D$ is 850 pM or less.

It should be understood that the assays described herein above are exemplary, and that any method known in the art for determining the binding affinity between proteins (e.g., fluorescence based-transfer (FRET), enzyme-linked immunosorbent assay, and competitive binding assays (e.g., radioimmunoassays)) can be used to assess the binding affinities of the anti-myostatin Adnectins of the invention.

In Vitro Assays for Antagonist Activity

The ability of anti-myostatin Adnectins to antagonize myostatin activity can be readily determined using various in vitro assays. Preferably, the assays are high-throughput assays that allow for screening multiple candidate Adnectins simultaneously. In some embodiments, the antagonist effects of anti-myostatin Adnectins on myostatin activity can be determined in cell-based activin responsive element (ARE)-luciferase reporter assays, as described in Example 3. In certain embodiments, the anti-myostatin Adnectins of the invention decrease myostatin-induced ARE-luciferase activity by at least 10%, at least 20%, at least 30%, at least 40%, at least 50%, at least 60%, at least 70%, at least 80%, at least 90% or more relative to a control upon co-incubating myostatin with an anti-myostatin Adnectin prior to stimulating cells with the mixture. An exemplary control reaction involves treating cells with myostatin alone or myostatin preincubated with an excess of a benchmark myostatin inhibitor such as Human Activin RIIB Fc Chimera (R&D Systems) or ActRIIb-Fc as described in Morrison et al. (*Experimental Neurology* 2009; 217:258-68). In other embodiments, the anti-myostatin Adnectins of the invention inhibit ARE-luciferase reporter activity with an IC50 of 500 nM or less, 400 nM or less, 300 nM or less, 200 nM or less, 100 nM or less, 50 nM or less, 10 nM or less, 5 nM or less, 1 nM, 0.5 nM or less, 0.4 nM or less, 0.3 nM or less, 0.2 nM or less, or 0.10 nM or less, as described in Example 3.

In other embodiments, the antagonistic effects of anti-myostatin Adnectins on myostatin activity can be determined by measuring the extent of SMAD phosphorylation in myostatin-treated cells, as described in Example 5. In certain embodiments, the anti-myostatin Adnectins of the invention decrease myostatin-induced SMAD phosphorylation by at least 10%, at least 20%, at least 30%, at least 40%, at least 50%, at least 60%, at least 70%, at least 80%, at least 90%, at least 95%, or at least 97% or more relative to a control upon co-incubating myostatin with an anti-myostatin Adnectin prior to stimulating the cells with the mixture. An exemplary control reaction involves treating cells with myostatin alone or myostatin preincubated with an excess of a benchmark myostatin inhibitor such as Human Activin RIIB Fc Chimera (R&D Systems) or ActRIIb-Fc as described in Morrison et al. (*Experimental Neurology* 2009; 217:258-68). In some embodiments, the anti-myostatin Adnectins of the invention inhibit SMAD phosphorylation with an IC50 of 1 nM or less, 0.8 nM or less, 0.6 nM or less, 0.4 nM or less, 0.3 nM or less, 0.2 nM or less, or 0.1 nM or less in a 12-point or 4-point inhibition response, as described in Example 5. In other embodiments, the anti-myostatin Adnectins of the invention at 10 nM inhibit SMAD phosphorylation by myostatin by at least 50%, at least 60%, at least 70%, at least 80%, at least 90%, at least 91%, at least 92%, at least 93%, at least 94%, at least 95%, at least 96%, at least 97%, or at least 98% or more, as described in Example 5.

Additionally, several in vitro model systems are known which use cells, tissue culture and histological methods for studying motor neuron disease. For example, a rat spinal cord organotypic slice subjected to glutamate excitotoxicity is useful as a model system to test the effectiveness of anti-myostatin Adnectins in preventing motor neuron degeneration. Corse et al., Neurobiol. Dis. (1999) 6:335 346. For a discussion of in vitro systems for use in studying ALS, see, e.g., Bar, P. R., Eur. J. Pharmacol. (2000) 405:285 295; Silani et al., J. Neurol. (2000) 247 Suppl 1:128 36; Martin et al., Int. J. Mol. Med. (2000) 5:3 13.

It should be understood that the assays described herein are exemplary, and that any method known in the art that can serve as a readout for myostatin activity are suitable for use for testing the myostatin antagonizing effects of the anti-myostatin Adnectins of the invention (e.g., real-time RT-PCR of mRNAs of SMAD target genes (e.g., Smad 7; Ciarmela et al., *Journal of Clinical Endocrinology & Metabolism* 2011; 96; 755-65) or mRNAs of ARE-containing genes).

In Vivo Models

Various art-recognized animal models exist that recapitulate the symptoms of diseases, disorders, and conditions associated with muscle wasting associated, for example with muscular, neuromuscular, neurological and metabolic disorders. These models can be used to test the efficacy of the anti-myostatin Adnectins of the invention.

For example, non-limiting examples of such animal models include, e.g., the X-linked muscular dystrophy mouse (mdx) model (US2011/0008375, Gehrig et al., *Nature* 2012; 484:394-8), including 4 additional strains of mdx mouse—mdx2cv, mdx3cv, mdx4cv, or mdx5cv mouse (Phelps et al., *Human Molecular Genetics*. 1996; 5(8):1149-1153), the mdx mouse with additional ablation of the dystrophin homologue utrophin (mdx/utr$^{-/-}$) (Deconinck et al., *Cell.* 1997; 90(4):717-727), the alpha-SG-null C57BL/6 mouse (Duclos et al.(1998) J. Cell Biol. 142, 1461-1471), and those recently reviewed in Nakamura et al., (*J Biomed Biotechnol.* 2011; Article ID No: 184393), e.g., the mdx52 mouse, in which exon 52 of the murine DMD gene is deleted, the Golden Retriever muscular dystrophy (GRMD) model, the Canine X-Linked Muscular Dystrophy (CXMD$_j$) model, and the Hypertrophy Feline Muscular Dystrophy (HFMD) model (e.g., Shelton et al., *Neuromuscular Disorders*. 2005; 15(2):127-138).

Animal models for the study of motoneuron disorders such as ALS are transgenic mice with an ALS-linked mutant Cu/Zn superoxide dismutase (SOD1) gene (mSOD1G93A and/or mSOD1G37R). These mice develop a dominantly inherited adult-onset paralytic disorder with many of the clinical and pathological features of familial ALS. (e.g., Gurney et al., Science (1994) 264:1772 1775; Nagano et al., Life Sci (2002) 72:541 548). Other animal models include two naturally occurring murine models for progressive motor neuronopathy (pmn) and wobbler (Haegggeli and Kato, Neurosci. Lett. (2002) 335:39 43). For a review of various animal models for use in studying motoneuron diseases such as ALS, see, e.g., Jankowsky et al., Curr Neurol Neurosci. Rep. (2002) 2:457 464; Elliott, J. L., Neurobiol. Dis. (1999) 6:310 20; and Borchelt et al., Brain Pathol. (1998) 8:735 757.

Animal models of other neurodegenerative or neuropathological diseases in addition to ALS include a transgenic mouse model for evaluating spinal and bulbar muscular atrophy (SBMA) (Katsuno et al., Neuron (2002) 35:843 854), animal models for human paralytic poliomyelitis (Ford et al., Microb. Pathog. (2002) 33:97 107), animal models of spinal muscular atrophy (Schmid et al., J. Child Neurol. 22, 1004-1012, 2007), animal models for distal myopathy and hereditary inclusion body myopathy (Malicdan et al., Acta Myol. 2007 December; 26(3): 171-175), the murine model of genetic demyelinating disease (Suzuki et al., Microsc. Res. Tech. 1995; 32:204-214), and those described by Meyer ZuHorste et al. (Curr. Opin. Neurol. 2006; 19:464-473).

Animal models for testing the efficacy of the anti-myostatin Adnectins of the invention against muscle volume loss due to atrophy and/or inactivity include, but are not limited to, mouse models of unilateral immobilization (Madaro et al., *Basic Applied Myology* 2008; 18:149-153), Achilles tendon laceration (tenotomy) (Bialek et al., *Physiol Genomics* 2011; 43:1075-86), and those disclosed in Powers et al. (*Am J Physiol Regul Integr Comp Physiol* 2005; 288:R337-44), such as, hindlimb suspension of animals, limb immobilization, and controlled mechanical ventilation.

Relevant animal models for testing the efficacy of the anti-myostatin Adnectins of the invention in the treatment of metabolic disorders include, but are not limited to, those disclosed in Ramaro et al. (Indian *J Med Res* 2007; 125: 451-472) and Kennedy et al. (*Disease Models & Mechanisms* 2010; 3:156-166), both of which are herein incorporated by reference in its entirety). Non-limiting examples of such animal models include Lep$^{ob/ob}$ mice, Lepr$^{db}$ mice, Kuo Kondo mice, KK/$^{Ay}$ mice, New Zealand Obese (NZO) mice, NONcNZO10 mice, Tsumara Suzuki Obese Diabetes (TSOD) and Tsumara Suzuki Non Obese (TSNO)mice, M16 mice, Zucker fatty rats, Zucker diabetic fatty rats, SHR/N-cp rat, JCR/LA—cp rats, Otsuka Long Evans Tokushima Fatty rats, Obese rhesus monkeys, Cohen diabetic rats, Goto-Kakizaki rats, and non-obese mutant C57 BL/6 (Akita) mice. Type 2 diabetes can also be induced by diet by, e.g., feeding high fat feed to non-obese, non-diabetic C57BL6 mice (Surwit et al., *Diabetes* 1988; 37:1163-7). Type 2 diabetes can also be chemically induced with, e.g., goldthioglucose (Le Marchand Brustel et al., *Am J Physiol* 1978; 234:E348-58) or streptozotocin, or induced surgically (e.g., partial pancreatomized diabetic animals) (McNeil J H., Experimental models of diabetes. Florida, US: CRC Press LLc; 1999; Sasaki et al., *In Vivo* 2000; 14:535-41). Many genetic animal models are also known to recapitulate the symptoms and phenotypes of metabolic disorders, such as those reviewed in Kennedy et al., 2010 (supra).

In some embodiments, the efficacy of the anti-myostatin Adnectins of the invention for increasing muscle mass or volume can be tested by subcutaneous injection of mice, as described in Example 9. Given that the inhibition of myostatin increases muscle mass, the anti-myostatin Adnectins of the invention are expected to increase body weight and muscle mass, the extent to which can be used to determine the potency of the Adnectins.

In some embodiments, particularly when anti-myostatin Adnectins are immunogenic in mice (e.g., due to the use of human fibronectin type III domain) and chronic treatments are desired, the anti-myostatin Adnectins of the invention can be administered to SCID mice, which are unable to mount cellular or humoral immune responses. In some embodiments, SCID mice can be crossed with other genetic models, such as those described herein (e.g., diabetic mice), to develop an immunocompromised mouse model amenable to chronic treatment with the anti-myostatin Adnectins of the invention.

VIII. Therapeutic Applications

In one aspect, the present invention provides anti-myostatin Adnectins useful for the treatment of myostatin-related disease or disorders, e.g., muscle wasting disorders, muscle atrophy, metabolic disorders, and bone degenerative disorders. Accordingly, in certain embodiments the invention provides methods for attenuating or inhibiting a myostatin-related disease or disorder in a subject comprising administering an effective amount of myostatin-binding polypeptide, i.e., an anti-myostatin Adnectin, to a subject. In some embodiments, the subject is a human. In some embodiments, the anti-myostatin Adnectins are pharmaceutically acceptable to a mammal, in particular a human. A "pharmaceutically acceptable" polypeptide refers to a polypeptide that is administered to an animal without significant adverse medical consequences, such as essentially endotoxin free, or very low endotoxin levels.

In some embodiments, the anti-myostatin Adnectins of the present invention will be administered to a subject in combination (concurrently or separately) with an agent known in the art to be useful for the particular disorder or disease being treated.

In some embodiments, the target patient population for anti-myostatin Adnectin therapy is one that is not amenable to standard therapy for the disease, disorder, or condition being treated due to, e.g., age, pre-existing conditions, genetic makeup, and/or co-morbidities. The anti-myostatin Adnectins of the invention can serve as alternatives to existing therapies that are associated with substantial side effects (e.g., reproductive performance) or safety concerns.

Exemplary diseases, disorders, and conditions for which the anti-myostatin Adnectins of the present invention will be useful are described in more detail below.

Muscular, Neurological, and Metabolic Diseases and Disorders

The anti-myostatin Adnectins of the present invention can be used to treat muscular, neurological and metabolic disorders associated with muscle wasting and/or muscle atrophy. For example, myostatin overexpression in vivo induces signs and symptoms characteristic of cachexia, and myostatin binding agents can partially resolve the muscle wasting effect of myostatin (Zimmers et al., *Science* 2002; 296:1486-8). Patients with AIDS also exhibit increased serum levels of myostatin immunoreactive material compared to patients without AIDS or to AIDS patients who do not exhibit weight loss (Gonzalez-Cadavid et al., *PNAS* 1998; 95:14938-43). It has also been observed that heart-specific elimination of myostatin reduces skeletal muscle atrophy in mice with heart failure, and conversely, specifically overexpressing myostatin in the heart is sufficient to induce muscle wasting (Breitbart et al., *AJP-Heart;* 2011; 300:H1973-82). In contrast, myostatin knockout mice show increased muscle mass, and an age-dependent decrease in fat accumulation compared to their wild type counterparts (McPherron et al., *J. Clin. Invest.* 2002; 109:595-601).

Exemplary disorders that can be treated according to the methods of the invention include myopathies and neuropathies, including, for example, motor neuron disease, neuromuscular and neurological disorders.

For example, anti-myostatin Adnectins can be used to treat inherited myopathies and neuromuscular disorders (e.g., muscular dystrophy (Gonzalez-Kadavid et al., *PNAS*, 1998; 95:14938-43), motor neuron disorders, congenital myopathies, inflammatory myopathies and metabolic myopathies), as well as acquired myopathies (e.g., drug induced myopathy, toxin induced myopathy, infection induced myopathy, paraneoplastic myopathy and other myopathies associated with critical illnesses).

Such disorders include, but are not limited to, Duchenne's muscular dystrophy, progressive muscular dystrophy, Becker's type muscular dystrophy, Dejerine-Landouzy muscular dystrophy, Erb's muscular dystrophy, Emery Dreifuss muscular dystrophy, limb girdle muscular dystrophy, oculopharyngeal muscular dystrophy (OPMD), facioscapulohumeral muscular dystrophy, congenital muscular dystrophy, infantile neuroaxonal muscular dystrophy, myotonic dystrophy (Steinert's disease), distal muscular dystrophy, nemaline myopathy, familial periodic paralysis, nondystrophic myotonia, periodic paralyses, spinal muscular atrophy, spinal muscular atrophy (SMA), amyotrophic lateral sclerosis (ALS), primary lateral sclerosis (PLS), progressive muscular atrophy (PMA), distal myopathy, myotubular/centronuclear myopathy, nemaline myopathy, mini core disease, central core disease, desminopathy, inclusion body myositis, dermatomyositis, polymyositis, mitochondrial myopathy, congenital myasthenic syndrome, myasthenia gravis, post-polio muscle dysfunction, steroid myopathy, alcoholic myopathy, perioperative muscular atrophy and ICU neuromyopathy.

Inherited and acquired neuropathies and radiculopathies which can be treated with anti-myostatin Adnectins include, but are not limited to, rigid spine syndrome, muscle-eye-brain disease, heredity motor and sensory neuropathy, Carcot-Marie-Tooth disease, chronic inflammatory neuropathy, progressive hypertrophic neuropathy, tomaculous neuropathy, lupus, Guillain-Barre syndrome, chronic inflammatory demyelinating polyneuropathy, multiple sclerosis, sarcoidosis, diabetic neuropathy, alcoholic neuropathy, disease related neuropathies (e.g., HIV/AIDS, Lyme disease), toxin related neuropathies (e.g., heavy metal, chemotherapy), compression neuropathies (e.g., tumors, entrapment neuropathy), and neuropathies associated with injury or trauma (e.g., cauda equine syndrome, paraplegia, quadriplegia).

In some embodiments, the anti-myostatin Adnectins of the invention can be used to treat muscular dystrophies (e.g., Duchenne's muscular dystrophy, Becker's type muscular dystrophy), ALS, and sarcopenia.

Additional disorders associated with muscle wasting that can be treated with the anti-myostatin Adnectins of the invention include cachexia, wasting syndrome, sarcopenia, congestive obstructive pulmonary disease, cystic fibrosis (pulmonary cachexia), cardiac disease or failure (cardiac cachexia), cancer, wasting due to AIDS, wasting due to renal failure, renal disease, claudication, cachexia associated with dialysis, uremia, rheumatoid arthritis, muscle injury, surgery, repair of damaged muscle, frailty, disuse atrophy, osteoporosis, osteoarthritis, ligament growth and repair.

The methods of the invention can also be used to increase muscle volume in subjects who suffer from muscle atrophy due to disuse. Disuse atrophy may result from numerous causes including any disorder or state which leads to prolonged immobility or disuse, including, but not limited to prolonged bedrest, being wheelchair bound, limb immobilization, unloading of the diaphragm via mechanical ventilation, solid organ transplant, joint replacement, stroke, CNS damage related weakness, spinal cord injury, recovery from severe burn, sedentary chronic hemodialysis, post-trauma recovery, post-sepsis recovery and exposure to microgravity (Powers et al., *Am J Physiol Regul Integr Comp Physiol* 2005; 288:R337-44).

In addition, age-related increases in fat to muscle ratios, and age-related muscular atrophy appear to be related to myostatin. For example, the average serum myostatin-immunoreactive protein increased with age in groups of young (19-35 yr old), middle-aged (36-75 yr old), and elderly (76-92 yr old) men and women, while the average muscle mass and fat-free mass declined with age in these groups (Yarasheski et al. *J Nutr Aging* 6(5):343-8 (2002)). Accordingly, Subjects with muscle atrophy due to aging, and/or subjects who are frail due to, for example, sarcopenia, would also benefit from treatment with the anti-myostatin Adnectins of the invention.

Also contemplated are methods for increasing muscle mass in food animals by administering an effective dosage of the anti-myostatin Adnectins to these animals. Since the mature C-terminal myostatin polypeptide is identical in all species, anti-myostatin Adnectins would be expected to effectively increase muscle mass and reducing fat in any agriculturally important species, for example, but not limited to, cattle, chicken, turkeys, and pigs.

The efficacy of the anti-myostatin Adnectin in the treatment of muscle wasting disorders or muscle atrophy can be determined, for example, by one or more methods for measuring an increase in muscle mass or volume, an increase in the number of muscle cells (hyperplasia), an increase in muscle cell size (hypertrophy) and/or an increase in muscle strength. For example, the muscle volume increasing effects of the anti-myostatin Adnectins of the present invention are demonstrated in the Examples described infra. Methods for determining "increased muscle mass" are well known in the art. For example, muscle content can be measured before and after administration of an anti-myostatin Adnectin of the invention using standard techniques, such as underwater weighing (see, e.g., Bhasin et al. New Eng. J. Med. (1996) 335:1-7) and dual-energy x-ray absorptiometry (see, e.g., Bhasin et al. Mol. Endocrinol. (1998) 83:3155-3162). An increase in muscle size may be evidenced by weight gain of at least about 5-10%, preferably at least about 10-20% or more.

Metabolic Disorders

The anti-myostatin Adnectins of the present invention, which reduce myostatin activity and/or signaling, are useful for treating metabolic disorders, such as obesity, type II diabetes mellitus, diabetes associated disorders, metabolic syndrome, and hyperglycemia.

Myostatin is involved in the pathogenesis of type II diabetes mellitus. Myostatin is expressed in adipose tissue and myostatin deficient mice exhibit reduced fat accumulation as they age. Moreover, glucose load, fat accumulation, and total body weight are reduced in myostatin lacking agouti lethal yellow and obese ($Lep^{ob/ob}$) mice (Yen et al., *FASEB J.* 8:479, 1994; McPherron et al., 2002). As disclosed in US2011/0008375, myostatin antagonists can decrease the fat to muscle ratio in an aged mouse model, preserve skeletal muscle mass and lean body mass, and attenuate kidney hypertrophy in STZ-induced diabetic mice.

As used herein, "obesity" is a condition in which excess body fat has accumulated to such an extent that health may be negatively affected. It is commonly defined as a body mass index (BMI) of 30 kg/m2 or higher which distinguishes it from being overweight as defined by a BMI of 25 kg/m2 or higher (see, e.g., World Health Organization (2000) (PDF). Technical report series 894: Obesity: Preventing and managing the global epidemic. Geneva: World Health Organization). Excessive body weight is associated with various diseases, particularly cardiovascular diseases, diabetes mellitus type II, obstructive sleep apnea, certain types of cancer, and osteoarthritis.

A subject with obesity may be identified, for example, by determining BMI (BMI is calculated by dividing the subject's mass by the square of his or her height), waist circumference and waist-hip ratio (the absolute waist circumference (>102 cm in men and >88 cm in women) and the waist-hip ratio (the circumference of the waist divided by that of the hips of >0.9 for men and >0.85 for women) (see, e.g., Yusuf S, et al., (2004). Lancet 364: 937-52), and/or body fat percentage (total body fat expressed as a percentage of total body weight: men with more than 25% body fat and women with more than 33% body fat are obese; body fat percentage can be estimated from a person's BMI by the following formula: Bodyfat %=(1.2*BMI)+(0.23*age)−5.4−(10.8*gender), where gender is 0 if female and 1 if male). Body fat percentage measurement techniques include, for example, computed tomography (CT scan), magnetic resonance imaging (MRI), and dual energy X-ray absorptiometry (DEXA).

The term "type II diabetes" refers to a chronic, life-long disease that results when the body's insulin does not work effectively. A main component of type II diabetes is "insulin resistance," wherein the insulin produced by the pancreas cannot connect with fat and muscle cells to allow glucose inside to produce energy, causing hyperglycemia (high blood glucose). To compensate, the pancreas produces more insulin, and cells, sensing this flood of insulin, become even more resistant, resulting in a vicious cycle of high glucose levels and often high insulin levels.

The phrase "disorders associated with diabetes" or "diabetes associated disorders" or "diabetes related disorders," as used herein, refers to conditions and other diseases which are commonly associated with or related to diabetes. Example of disorders associated with diabetes include, for example, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, and osteoporosis.

The efficacy of the anti-myostatin Adnectins in the treatment of metabolic disorders can be determined, for example, by one or more methods of measuring an increase in insulin sensitivity, an increase in glucose uptake by cells from the subject, a decrease in blood glucose levels, and a decrease in body fat.

For example, in subjects having type II diabetes or who are at risk of developing diabetes HbA1c levels can be monitored. The term "hemoglobin 1AC" or "HbA1c" as used herein refers to the product of a non-enzymatic glycation of the hemoglobin B chain. The desired target range of HbA1c levels for people with diabetes can be determined from American Diabetes Association (ADA) guidelines, i.e., the Standards of Medical Care in Diabetes (*Diabetes Care* 2012; 35(Suppl 1):S511-563). Current HbA1c target levels are generally <7.0% for people with diabetes, and people who do not have diabetes typically have HbA1c values of less than 6%. Accordingly, the efficacy of the anti-myostatin Adnectins of the present invention can be determined by an observed decrease in the HBA1c level in a subject.

The methods of the invention further include administration of an anti-myostatin Adnectin alone, or in combination with other agents that are known in the art for glycemic control (e.g., insulin, GLP1) or for treating art-recognized diabetes-related complications.

Other Disorders

Myostatin knockout mice exhibit increased muscle mass, as well as increased mineral content and density of the mouse humerus, and increased mineral content of both trabecular and cortical bone at regions where muscles attach (Hamrick et al. *Calcif Tissue Intl* 2002; 71:63-8). This suggests that increasing muscle mass may help improve bone strength and reduce osteoporosis and other degenerative bone diseases.

Additional diseases or disorders for which the anti-myostatin Adnectins of the present invention are useful include wound healing, anti-fibrotic disease, Lambert-Eaton Syndrome, and Parkinson's Disease.

Combination Therapies

The anti-myostatin Adnectins provided herein may be employed in combination with antidiabetic agents, anti-hyperglycemic agents, anti-hyperinsulinemic agents, anti-retinopathic agents, anti-neuropathic agents, anti-neurodegenerative agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, neuro- or musculo-restorative treatments, treatments for heart failure, treatments for peripheral arterial disease and anti-inflammatory agents.

The antidiabetic agents used in combination with the anti-myostatin Adnectins include, but are not limited to, insulin secretagogues or insulin sensitizers, GPR40 receptor modulators, or other antidiabetic agents. These agents include, but are not limited to, dipeptidyl peptidase IV (DP4) inhibitors (for example, sitagliptin, saxagliptin, alogliptin, vildagliptin and the like), biguanides (for example, metformin, phenformin and the like), sulfonyl ureas (for example, gliburide, glimepiride, glipizide and the like), glucosidase inhibitors (for example, acarbose, miglitol, and the like), PPARγ agonists such as thiazolidinediones (for example, rosiglitazone, pioglitazone, and the like), PPAR α/γ dual agonists (for example, muraglitazar, tesaglitazar, aleglitazar, and the like), glucokinase activators (as described in Fyfe et al., *Drugs of the Future*, 34(8):641-653 (2009) and incorporated herein by reference), GPR119 receptor modulators (MBX-2952, PSN821, APD597 and the like), SGLT2 inhibitors (dapagliflozin, canagliflozin, remagliflozin and the like), amylin analogs such as pramlintide, and/or insulin. Reviews of current and emerging therapies for the treatment of diabetes can be found in: Mohler et al., *Medicinal Research Reviews*, 29(1):125-195 (2009), and Mizuno et al., *Current Medicinal Chemistry*, 15:61-74 (2008).

The anti-myostatin Adnectins of the present invention may also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The anti-myostatin Adnectins of the present invention may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasally, or by transdermal or buccal devices. Reviews of current and emerging therapies for the treatment of obesity can be found in: Melnikova et al., *Nature Reviews Drug Discovery*, 5:369-370 (2006); Jones, *Nature Reviews: Drug Discovery*, 8:833-834 (2009); Obici, *Endocrinology*, 150(6): 2512-2517 (2009); and Elangbam, *Vet. Pathol.*, 46(1):10-24 (2009).

The anti-myostatin Adnectins of the present invention can also be administered with one or more additional therapeutic agents, as appropriate for the particular disease or disorder being treated. Non-limiting examples of additional agents include those that are useful for treating metabolic disorders such as type II diabetes and sarcopenia and include, but are not limited to, GLP-1, GLP-1-like, amylin, and FGF21; those that are useful for treating anti-fibrotic disease, neuromuscular disease, motor neuron disease, and sarcopenia and include, but are not limited to, ghrelin, SARM, Riluzole, testosterone, androgens, growth hormone, hormone replacement therapy, COX-2 inhibitors, troponin activators, β2 agonists, CTLA4-Ig (e.g., abetacept, belatacept) and anti-TGFβ antibodies; those that are useful for treating cachexia and other wasting syndromes and include, but are not limited to, TGFβ receptor kinase inhibitors, anti-IL-6, and ubiquitin-proteasome inhibitors; those that are useful to treat muscle cramps associated with myotonia and PLS include, but are not limited to phytoin, quinine, Baclofen and tizanidine; those that are useful for neuropathies include antidepressants (e.g., tricyclics and selective serotonin-norepinephrine re-uptake inhibitors (SNRI's)), anticonvulsants, cannbinoids, botulinum toxin Type A, NMDA antagonists (e.g., ketamine), dietary supplements (e.g., alpha lipoic acid and benfotiamine); those that are useful for treating chronic inflammatory neuropathies include, but are not limited to, corticosteroids, intravenous immunoglobulin, and immunosuppressive drugs (e.g., cyclophosphamide, ciclosporin, azathiprine, mycophenolate mofetil, anti-thymocyte globulin, rituximab); and those that are useful for treating Guillain Barré syndrome, sarcopenia, fracture, and bone loss and include, but are not limited to, Boniva (ibandronate) and PTH.

The anti-myostatin Adnectins of the present invention can be administered with one or more additional agents used in symptomatic therapy. Non-limiting examples of such agents for treating the symptoms of ALS include mitochondrial permeability transition (MPT) pore activators, fast skeletal troponin activators, macrophage regulators (e.g., NP001), lysosomal storage disease-treating agents (e.g., NP003), and nicotinic acetylcholine receptor (nAchR) antagonists. A non-limiting example of an additional agent for use in treating the symptoms of DMD/BMD is an agent that increases ATP levels.

The anti-myostatin Adnectins of the present invention can also be administered with one or more additional agents used in disease modification therapy. Non-limiting examples of such agents for treating ALS include free radical scavengers (e.g., edaravone (norphenazone), CV-3611), VEGF agonists (e.g., sNN0029), Nogo-A protein I (e.g., GSK122324), SOD1 inhibitors (e.g., ISIS-SOD1Rx), and PGE synthase 1 inhibitors (e.g., AAD-2004). Non-limiting examples of such agents for treating DMD/BMD include those that promote exon skipping (e.g., antisense molecules such as drisapersen (PRO051/GSK2402968), PRO044, Eteplirsen, AVI-4658, AVI-5038, Ataluren (PTC124)), gene therapy agents, anti-inflammatory agents (e.g., CRD007), and anti-fibrotic agents (e.g., HT-100).

As discussed above, agents that promote exon-skipping can be used in combination with the anti-myostatin Adnectins of the present invention for treating Duchenne's muscular dystrophy and Becker's type muscular dystrophy. Examples of specific exons that can be targeted to restore functional dystrophin include exons 7, 8, 17, 43, 44, 45, 46, 50, 51, 52, 53, and 55 (see, e.g., Lu et al., *Molecular Therapy* 2011; 19:9-15). In some embodiments, more than one agent, e.g., antisense oligonucleotides, can be used to induce multi-exon skipping.

IX. Pharmaceutical Compositions

The present invention further provides pharmaceutical compositions comprising an anti-myostatin Adnectin or fusion proteins thereof described herein, wherein the composition is essentially endotoxin free, or at least contain no more than acceptable levels of endotoxins as determined by the appropriate regulatory agency (e.g., FDA).

Compositions of the present invention can be in the form of a pill, tablet, capsule, liquid, or sustained release tablet for oral administration; a liquid for intravenous, subcutaneous or parenteral administration; or a gel, lotion, ointment, cream, or a polymer or other sustained release vehicle for local administration.

Methods well known in the art for making compositions are found, for example, in "Remington: The Science and Practice of Pharmacy" (20th ed., ed. A. R. Gennaro AR., 2000, Lippincott Williams & Wilkins, Philadelphia, Pa.). Compositions for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate compositions (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the composition varies depending upon a number of factors, including the dosage of the drug to be administered, and the route of administration.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, PLURONIC™ or polyethylene glycol (PEG).

The polypeptides of the present invention may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

The active ingredients may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the proteins of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins of the invention may remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Compositions of the present invention for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Compositions for oral use may also be provided as chewable tablets, or as hard gelatin capsules wherein the active ingredient is mixed with an inert solid diluent, or as soft gelatin capsules wherein the active ingredient is mixed with water or an oil medium.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

The compositions herein may also contain more than one active compound as necessary for the particular indication being treated, preferably those with complementary activities that do not adversely affect each other. Such molecules are suitably present in combination in amounts that are effective for the purpose intended.

X. Administration

A pharmaceutical composition comprising an anti-myostatin Adnectin of the present invention can be administered to a subject at risk for or exhibiting pathologies as described herein using standard administration techniques including oral, parenteral, pulmonary, transdermal, intramuscular, intranasal, buccal, sublingual, or suppository administration. Preferably, administration of the anti-myostatin Adnectins the invention is parenteral. The term parenteral as used herein includes intravenous, intramuscular, subcutaneous, rectal, vaginal, or intraperitoneal administration. Peripheral systemic delivery by intravenous or intraperitoneal or subcutaneous injection is preferred.

A therapeutically effective dose refers to a dose that produces the therapeutic effects for which it is administered. An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient.

For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment, and may be ascertained using standard techniques. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. In general, the anti-myostatin Adnectins of the present invention are administered at about 0.01 mg/kg to about 50 mg/kg per day, preferably 0.01 mg/kg to about 30 mg/kg per day, most preferably 0.01 mg/kg to about 20 mg/kg per day. In some embodiments, the anti-myostatin Adnectins of the present invention are administered at weekly dosages of about 1 to 50 mg, more preferably about 10-50 mg. In other embodiments, the anti-myostatin Adnectins of the present invention are administered at monthly doses of 30-200 mg, preferably 50-150 mg, and more preferably 60-120 mg.

The frequency of dosing will depend upon the pharmacokinetic parameters of the binding agent molecule in the formulation used. Typically, a composition is administered until a dosage is reached that achieves the desired effect. The composition may therefore be administered as a single dose or as multiple doses (at the same or different concentrations/dosages) over time, or as a continuous infusion. Further refinement of the appropriate dosage is routinely made. Appropriate dosages may be ascertained through use of appropriate dose-response data. For example, the anti-myostatin Adnectin may be given daily (e.g., once, twice, three times, or four times daily) or less frequently (e.g., once every other day, once or twice weekly, or monthly). In addition, as is known in the art, adjustments for age as well as the body weight, general health, sex, diet, time of administration, drug interaction, and the severity of the disease may be necessary, and will be ascertainable with routine experimentation by those skilled in the art. The anti-myostatin Adnectin is suitably administered to the patient at one time or over a series of treatments.

Administration of an anti-myostatin Adnectin or a fusion thereof, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being administered.

XI. Methods of Detection and Diagnostics

The anti-myostatin Adnectins of the invention are also useful in a variety of diagnostic applications. For example, an anti-myostatin Adnectin of the invention may be used to diagnose a disorder or disease associated with increased levels of myostatin. In a similar manner, an anti-myostatin Adnectin can be used in an assay to monitor myostatin levels in a subject being treated for a myostatin-associated condition. The anti-myostatin Adnectins may be used with or without modification, and are labeled by covalent or non-covalent attachment of a detectable moiety. The detectable moiety can be any one which is capable of producing, either directly or indirectly, a detectable signal. For example, the detectable moiety may be a radioisotope, such as H3, C14 or 13, P32, S35, or 1131; a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for conjugating a protein to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982). In vitro methods include conjugation chemistry well known in the art, including chemistry compatible with proteins, such as chemistry for specific amino acids, such as Cys and Lys. In order to link a moiety (such as PEG) to a protein of the invention, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups depending on the application. For polypeptides without a Cys amino acid, a Cys can be engineered in a location to allow for activity of the protein to exist while creating a location for conjugation.

Anti-myostatin Adnectins linked with a detectable moiety also are useful for in vivo imaging. The polypeptide may be linked to a radio-opaque agent or radioisotope, administered to a subject, preferably into the bloodstream, and the presence and location of the labeled protein in the subject is assayed. This imaging technique is useful in the staging and treatment of malignancies. The protein may be labeled with any moiety that is detectable in a subject, whether by nuclear magnetic resonance, radiology, or other detection means known in the art.

Anti-myostatin Adnectins also are useful as affinity purification agents. In this process, the polypeptides are immobilized on a suitable support, such a Sephadex resin or filter paper, using methods well known in the art.

Anti-myostatin Adnectins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

In certain aspects, the disclosure provides methods for detecting a target molecule in a sample. A method may comprise contacting the sample with an anti-myostatin Adnectins described herein, wherein said contacting is carried out under conditions that allow anti-myostatin Adnectin-target complex formation; and detecting said complex, thereby detecting said target in said sample. Detection may be carried out using any art-recognized technique, such as, e.g., radiography, immunological assay, fluorescence detection, mass spectroscopy, or surface plasmon resonance. The sample may be from a human or other mammal. The anti-myostatin Adnectins may be labeled with a labeling moiety, such as a radioactive moiety, a fluorescent moiety, a chromogenic moiety, a chemiluminescent moiety, or a hapten moiety. The anti-myostatin Adnectins may be immobilized on a solid support.

XII. Kits and Articles of Manufacture

The anti-myostatin Adnectin of the invention can be provided in a kit, a packaged combination of reagents in predetermined amounts with instructions for use in the therapeutic or diagnostic methods of the invention.

For example, in one embodiment of the invention, an article of manufacture containing materials useful for the treatment or prevention of the disorders or conditions described above is provided. The article of manufacture comprises a container and a label. Suitable containers include, for example, bottles, vials, syringes, and test tubes. The containers may be formed from a variety of materials such as glass or plastic. The container holds a composition of the invention which is effective for preventing or treating the disorder or condition and may have a sterile access port (for example the container may be an intravenous solution bag or a vial having a stopper pierceable by a hypodermic injection needle). The active agent in the composition is an anti-myostatin Adnectin of the invention. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

INCORPORATION BY REFERENCE

All documents and references, including patent documents and websites, described herein are individually incorporated by reference to into this document to the same extent as if there were written in this document in full or in part.

EXAMPLES

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

Example 1

Protein Production

High Throughput Protein Production (HTPP)

Selected binders cloned into the PET9d vector upstream of a $HIS_6$tag and transformed into *E. coli* BL21 DE3 plysS cells were inoculated in 5 ml LB medium containing 50 µg/mL kanamycin in a 24-well format and grown at 37° C. overnight. Fresh 5 ml LB medium (50 µg/mL kanamycin) cultures were prepared for inducible expression by aspiration of 200 µl from the overnight culture and dispensing it into the appropriate well. The cultures were grown at 37° C. until $A_{600}$ 0.6-0.9. After induction with 1 mM isopropyl-β-thiogalactoside (IPTG), the culture was expressed for 6 hours at 30° C. and harvested by centrifugation for 10 minutes at 2750 g at 4° C.

Cell pellets (in 24-well format) were lysed by resuspension in 450W of Lysis buffer (50 mM $NaH_2PO_4$, 0.5 M NaCl, 1×Complete™ Protease Inhibitor Cocktail-EDTA free (Roche), 1 mM PMSF, 10 mM CHAPS, 40 mM imidazole, 1 mg/ml lysozyme, 30 µg/ml DNAse, 2 µg/ml aprotinin, pH 8.0) and shaken at room temperature for 1-3 hours. Lysates were cleared and re-racked into a 96-well format by transfer into a 96-well Whatman GF/D Unifilter fitted with a 96-well, 1.2 ml catch plate and filtered by positive pressure. The cleared lysates were transferred to a 96-well Nickel or Cobalt-Chelating Plate that had been equilibrated with equilibration buffer (50 mM $NaH_2PO_4$, 0.5 M NaCl, 40 mM imidazole, pH 8.0) and were incubated for 5 min. Unbound material was removed by positive pressure. The resin was washed twice with 0.3 ml/well with Wash buffer #1 (50 mM $NaH_2PO_4$, 0.5 M NaCl, 5 mM CHAPS, 40 mM imidazole, pH 8.0). Each wash was removed by positive pressure. Prior to elution, each well was washed with 50 µl Elution buffer (PBS+20 mM EDTA), incubated for 5 min, and this wash was discarded by positive pressure. Protein was eluted by applying an additional 100 µl of Elution buffer to each well. After a 30 minute incubation at room temperature, the plate(s) were centrifuged for 5 minutes at 200 g and eluted protein collected in 96-well catch plates containing 5 µl of 0.5 M $MgCl_2$ added to the bottom of elution catch plate prior to elution. Eluted protein was quantified using a total protein assay with wild-type $^{10}Fn3$ domain as the protein standard.

Expression and Purification of Insoluble Fibronectin-Based Scaffold Protein Binders For expression, selected clone(s), followed by the $HIS_6$tag, were cloned into a pET9d vector and were expressed in *E. coli* BL21 DE3 plysS cells. Twenty ml of an inoculum culture (generated from a single plated colony) was used to inoculate 1 liter of LB medium or TB-Overnight Expression Media (auto induction) containing 50 µg/ml Kanamycin and 34 µg/ml chloramphenicol. Cultures in LB medium were incubated at 37° C. until $A_{600}$ 0.6-1.0 at which time they were induced with 1 mM isopropyl-β-thiogalactoside (IPTG) and grown for 4 hours at 30° C. Cultures grown in TB-Overnight Expression Media were incubated at 37° C. for 5 hours, at which time the temperature was lowered to 18° C. and grown for 19 hours. Cultures were harvested by centrifugation for 30 minutes at 10,000 g at 4° C. Cell pellets were frozen at −80° C. After thawing, the cell pellet was resuspended in 25 ml of lysis buffer (20 mM $NaH_2PO_4$, 0.5 M NaCl, 1×Complete™ Protease Inhibitor Cocktail-EDTA free (Roche), pH 7.4) using an Ultra-turrax homogenizer (IKA works) on ice. Cell lysis was achieved by high pressure homogenization (≥18,000 psi) using a Model M-110S Microfluidizer (Microfluidics). The insoluble fraction was separated by centrifugation for 30 minutes at ≥23,300 g at 4° C. The insoluble pellet recovered from centrifugation of the lysate was washed with 20 mM sodium phosphate/500 mM NaCl, pH7.4. The pellet was resolubilized in 6 M guanidine hydrochloride in 20 mM sodium phosphate/500 mM NaCl pH 7.4 with sonication, followed by incubation at 37 degrees for 1-2 hours. The resolubilized pellet was filtered with a 0.45 µm filter and loaded onto a Histrap column equilibrated with the 20 mM sodium phosphate/500 mM NaCl/6 M guanidine pH7.4 buffer. After loading, the column was washed for an additional 25 column volumes with the same buffer. Bound protein was eluted with 50 mM imidazole in 20 mM sodium phosphate/500 mM NaCl/6 M guanidine-HCl, pH 7.4. The purified protein was refolded by dialysis against 50 mM sodium acetate/150 mM NaCl, pH 4.5 or PBS, pH 7.2.

Expression and Purification of Soluble Fibronectin-Based Scaffold Protein Binders As an alternative to purification of insoluble binders, the purification of soluble binders may also be used. For expression, selected clone(s), followed by the $HIS_6$tag, were cloned into a pET9d vector and expressed in *E. coli* BL21 DE3 plysS cells. Twenty ml of an inoculum culture (generated from a single plated colony) were used to inoculate 1 liter of LB medium or TB-Overnight Expression Media (auto induction) containing 50 µg/ml Kanamycin and 34 µg/ml chloramphenicol. Cultures in LB medium were incubated at 37° C. until $A_{600}$ 0.6-1.0, followed by induction with 1 mM isopropyl-β-thiogalactoside (IPTG) and grown for 4 hours at 30° C. Cultures grown in TB-Overnight Expression Media were incubated at 37° C. for 5 hours, after which the temperature was lowered to 18° C. and they were grown for 19 hours. Cultures were harvested by centrifugation for 30 minutes at 10,000 g at 4° C. Cell pellets were frozen at −80° C. The thawed cell pellet was resuspended in 25 ml of lysis buffer (20 mM $NaH_2PO_4$, 0.5 M NaCl, 1×Complete™ Protease Inhibitor Cocktail-EDTA free (Roche), pH 7.4) using an Ultra-turrax homogenizer (IKA works) on ice. Cell lysis was achieved by high pressure homogenization (≥18,000 psi) using a Model M-110S Microfluidizer (Microfluidics). The soluble fraction was separated by centrifugation for 30 minutes at ≥23,300 g at 4° C. The supernatant was clarified using a 0.45 µm filter. The clarified lysate is loaded onto a Histrap column (GE) pre-equilibrated with 20 mM sodium phosphate/500 mM NaCl, pH 7.4. The column was then washed with 25 column volumes of the same buffer, followed by 20 column volumes of 20 mM sodium phosphate/500 mM NaCl/25 mM imidazole, pH 7.4 and then 35 column volumes of 20 mM sodium phosphate/500 mM NaCl/40 mM imidazole, pH 7.4. Protein was eluted with 15 column volumes of 20 mM sodium phosphate/500 mM NaCl/500 mM imidazole, pH 7.4, fractions were pooled based on absorbance at $A_{280}$, and dialyzed against 1×PBS or 50 mM Tris, 150 mM NaCl, pH 8.5 or 50 mM NaOAc, 150 mM NaCl, pH4.5. Precipitates were removed by filtering with a 0.22 µm filter.

Site-Specific PEGylation of Adnectins with Polyethylene Glycol (PEG)

Adnectins containing an engineered cysteine residue were conjugated with PEG or cysteine-blocking reagent via Michael-addition chemistry between the thiol group on the cysteine and the maleimide functional group of the PEG or n-ethylmaleimide (NEM). For PEGylation with 2-branched 40 kDa PEG (NOF Corporation, P/N GL2-400MA), PEG was added in molar excess to the protein solution under slightly acidic to neutral conditions. The reaction was allowed to proceed at room temperature for 2 hours to overnight. The reaction was then applied to an ion exchange column to separate the PEGylated Adnectin from the unreacted PEG-maleimide and non-PEGylated Adnectin. For PEGylation with 4-branched 40 kDa PEG (NOF, P/N GL4-400MA) or 20 kDa bis-PEG (NOF corporation, P/N DE-200MA), the Adnectin was purified from SP FF in citrate buffer, pH 6.5. Following reduction with DTT, the sample was desalted on a G25 column into the same buffer to remove DTT and reacted with 20 kDa bis-PEG or 4-branched 40K PEG at a 2:1 (PEG:adnectin) ratio for 2 hours at room temperature, and the reaction stopped with the addition of excess BME. The sample was purified by a Resource 15S column (GE #17-0944-10) to selectively remove un-PEGylated species (and mono-PEGylated species in the case of 20 kDa bis-PEG reaction). A final preparative SEC column (GE #17-1071-01, Superdex200, 26/60) was used (if needed) to remove high molecular species and unreactive Adnectin. To prepare a CYS-blocked Adnectin, a 10-fold molar excess of NEM (Pierce Chemical) was added immediately after the above mentioned G25 desalting step in citrate (pH 6.5) buffer. This was incubated for 1 hour at room temperature and the reaction stopped by the addition of excess BME. The sample was then extensively dialysed against PBS. The purified conjugated adnectins were analyzed by SDS-PAGE and size exclusion chromatography.

Purification and PEGylation of Un-Tagged Fibronectin-Based Scaffold Protein Binders Selected binders were cloned into a pET9d vector with no $HIS_6$tag and expressed in *E. coli* BL21 DE3 plysS cells. 25 ml of an inoculums culture previously isolated from a single plated colony were grown in a 125 ml flask until OD 600 nm reached 1-2, using pH 6.85 media+50 ug/ml kanamycin (Ammonium Chloride, Citric Acid, Ferric Ammonium Citrate, Magnesium Sulfate, Sodium Phosphate Monobasic Monohydrate, Dextrose Anhydrous, Glycerol, Phytone Peptone, Yeast Extract Granulated, Kanamycin Sulfate, Ammonium Sulfate for pH adjustment). A 10 L fermentor (7.5 L starting volume of batch media) was inoculated at a final OD 600 nm of 0.003. The culture was grown overnight at 25° C. with constant mixing at 650 rpm and dissolved $O_2$ levels of >30%, while maintaining pH. The next day, the temperature was shifted to 37° C. and the culture was grown until OD 600 nm reached 20-25. Once the target OD was achieved, the temperature was shifted to 30° C. and the culture induced with IPTG (final concentration: 1 mM). A feed media (Glycerol, Phytone Peptone, Yeast Extract Granulated, Kanamycin Sulfate, and Phosphoric Acid for pH adjustment) was added at a rate of 40 ml media/L formation volume/hr. Cells were harvested by centrifugation at 10,000 g for 30 min at 4° C. Cell pellets were frozen at −80° C.

Cell paste was thawed in 1×PBS at a ratio of 10 ml buffer/g cell paste. Once thawed, the sample was disrupted with an UltraTurrax homogenizer (IKA works) until homogenous. The solution was then passed twice through a microfluidizer at 18,000 psi. The soluble fraction was separated by centrifugation for 30 minutes at ≥10,000 g at 4° C. The supernatant was diluted 1:1 with sodium acetate (pH 4.5), and clarified with a 0.2 µm filter. The clarified lysate was loaded onto a SP FF column (SP1; GE) pre-equilibrated with 50 mM sodium acetate (pH 4.5). The column was then washed with 2 column volumes of the same buffer, followed by 8 column volumes of 50 mM sodium acetate/350 mM NaCl, pH 4.5. Protein was eluted with 50 mM sodium acetate/700 mM NaCl, pH 4.5. Elutions were pooled based on absorbance at $A_{280}$.

The SP1 elution was diluted 1:5 with 20 mM sodium phosphate (pH 6.7) and loaded onto a SP FF column (SP2) pre-equilibrated with 20 mM sodium phosphate/100 mM NaCl, pH 6.7. The column was then washed with 2 column volumes of the same buffer. Protein was eluted from the column with 20 mM sodium phosphate/0.5 M NaCl, pH 6.7. Elutions were pooled based on absorbance at $A_{280}$.

The SP2 elution was diluted to 100 mM NaCl with 20 mM sodium phosphate (pH 6.7) and loaded onto a Q FF column (GE) pre-equilibrated with 20 mM sodium phosphate/100 mM NaCl, pH 6.7. The FT peak (containing product) was collected. The column was washed with equilibration buffer until the FT peak returned to baseline.

Adnectins containing an engineered cysteine residue were conjugated with PEG via Michael-addition chemistry between the thiol group on the cysteine and the maleimide functional group of the PEG reagent. The Q FT fraction was PEGylated with 40 kDa branched PEG at a molar ratio of 2:1 PEG to protein. The sample was incubated overnight at room temperature. The PEGylation reaction was diluted with 2 parts 50 mM sodium acetate (pH 4.5) and loaded onto a SP FF column (GE) pre-equilibrated with 50 mM sodium acetate (pH 4.5). The column was washed with 2 column volumes of the same buffer. PEGylated protein was eluted from the column with 50 mM sodium acetate/200 mM NaCl, pH 4.5). Elutions were pooled based on absorbance at $A_{280}$. PEGylated protein was concentrated using a 30 kDa Millipore Biomax membrane. The sample was filtered over a 0.22 µm filter and stored at, for example, 4° C., −20° C., or −80° C.

Transient Expression and Purification of Fc Formatted Fibronectin-Based Scaffold Protein Binders For DNA generation, selected candidates were cloned into a pDV-16 plasmid from which E. coli Top10 cells were transformed. pDV-16 is a modified version of pTT5 (Yves Durocher, NRC Canada), wherein the human IgG1-Fc coding sequence has been introduced, preceded by signal sequence, and restriction sites were included to allow insertion of Adnectin coding sequences at either terminus of the Fc. Transformed cells were expanded by inoculating 1 L of Luria broth containing 100 m/ml Ampicillin and incubating in a rotating incubator at 225 rpm for 18 hours at 37° C. Bacterial pellets were harvested by centrifugation at >10000 g for 30 minutes at 4° C. Purified plasmid DNA was isolated using a QIAGEN Plasmid Plus Mega Kit (QIAGEN) as described in the manufacturer's protocol. Purified DNA was quantified using absorbance at 260 nm and frozen at −80° C. prior to use.

HEK 293-EBNA1 (clone 6E) (Yves Durocher, NRC Canada) cells were expanded to $2 \times 10^6$ cells/ml in 2 L of F17 media in a 10 L GE Healthcare Wave bag at 37° C., 5% $CO_2$, and mixed by rocking at an 8 degree angle at 18 rpm.

DNA was prepared for transfection as follows: F17 media was warmed to 37° C. DNA and a PEI transfection reagent were thawed in a sterile biosafety hood. DNA (2.25 mg) was added to 100 ml of warmed F17 media in a sterile polypropylene culture flask and gently mixed by swirling. In a separate flask, 6.75 mg of PEI (1 mg/ml) was combined with 100 ml of pre-warmed F17 media and gently mixed by swirling. The flasks were allowed to rest for 5 minutes prior to combining the contents by adding the PEI solution to the flask containing the DNA and gently mixing by swirling.

The contents of the flask containing the DNA:PEI mixture were added to the wave bag containing the HEK 293-6E cells after incubating at room temperature for 15 minutes in the biosafety hood. The bag containing the transfected HEK 293-6E cells was incubated for twenty four hours at 37° C., 5% $CO_2$, and mixed by rocking at an 8 degree angle at 18 RPM. After 24 hours, 100 ml of sterile filtered 20% Tryptone N1 (Organotechnie, Canada) dissolved in F17 media was aseptically added to the culture. The cells and media were harvested after an additional 72 hours of incubation as described above. Alternatively, transient HEK expression in shake flasks (0.5 L media in a 2 L flask) can be performed with a DNA:PEI ratio of 1:2. Cells were separated from the conditioned media by centrifugation at 6000 g for 30 minutes at 4° C. The conditioned media was retained, filtered through a 0.2 µM filter, and stored at 4° C.

The conditioned media was applied to a 10 ml chromatography column containing GE MabSelect Sure resin pre-equilibrated in PBS at a rate of 5 ml/minute. After loading the filtered conditioned media, the column was washed with at least 100 ml of PBS at room temperature. The purified product was eluted from the column with the application of 100 mM Glycine/100 mM NaCl, pH 3.0. Fractions were neutralized in pH either by collecting into tubes containing 1/6 volume of 1M Tris pH 8, or by pooling according to A280 absorbance followed by addition of 1M Tris pH 8 to 100 mM. If the content of high molecular weight species is greater than 5% after Protein A elution, then the sample is further purified by a Superdex 200 (26/60) column (GE Healthcare) in PBS. The SEC fractions containing monomers are pooled and concentrated. The resulting protein A or SEC pool was exhaustively dialyzed against PBS at 4° C., and sterile filtered using a 0.22 µm cutoff filter prior to freezing at −80° C.

Bulk Manufacturing: Mammalian Expression and Primary Recovery: UCOE CHO System

A mammalian Research Cell Bank (RCB) was created by transfecting anti-myostatin Adnectin-Fc fusions cloned into the pUCOE vector containing the Ubiquitous Chromatin Opening Element (UCOE) [Modified UCOE vector from Millipore] in CHO-S cells. An RCB was established by expanding cells in selection media (0.04% (v/v) L-Glutamine (Invitrogen) and 0.01% (v/v) HT Supplement (Invitrogen) in CD CHO medium (Invitrogen)) containing 12.5 µg/mL puromycin. Low passage number cells were aseptically isolated via centrifugation, resuspended in banking media (0.04% (v/v) L-Glutamine (Invitrogen), 0.01% (v/v) HT Supplement (Invitrogen) and 7.5% (v/v) DMSO in CD CHO medium (Invitrogen)) to a final concentration of $1 \times 10^7$ cells/mL. These cells were initially frozen in a 70% isopropyl alcohol bath at −80° C. overnight and then transferred to liquid nitrogen for long term storage the following day.

Cell culture was initiated by thawing a single RCB vial into 25 mL of selection media containing 12.5 µg/mL puromycin and expanding the culture in the same media. Cells were allowed to reach a concentration between 1-2× $10^6$ cells/mL before being split back to $0.2 \times 10^6$ cells/mL. Cells were generally maintained between 2-4 weeks prior to seeding a bioreactor. The expansion culture was passaged a final time and allowed to grow to the point where a 15 L bioreactor containing 8 L of production media (Invitrogen CD CHO media containing 0.01% (v/v) HT Supplement (Invitrogen), 0.04% (v/v) Glutamax (Gibco), and 0.005% (v/v) Pluronic F-68 (Gibco)) could be seeded at a final density of $0.2 \times 10^6$ cells/mL. The bioreactor culture was monitored daily for VCD (Viable Cell Density), percent Viability, pH, and glucose concentration. The bioreactor culture was fed on days 3 and 6 with a 10% total volume bolus addition of Feed Media. The culture was harvested between Day 7 and Day 9 with a percent viability >70%. During culture, the bioreactor culture was controlled at a pH of 7.1, temperature of 37° C., % DO2 of 40%, and a constant RPM of 100.

On the day of harvest, the bioreactor cultures were directly passed through a 6.0/3.0 µm depth filter followed by a sterile 0.8/0.2 µm filtration into a sterile bag. Clarified sterile culture was stored overnight at 2-8° C. The clarified culture was then concentrated via flatsheet TFF using a 30,000 kDa membrane. The approximate concentration was 6×, depending on harvest titer. Concentrated supernatant was then sterile filtered into PETG bottles and either processed directly or stored at −80° C.

Anti-Myostatin-Adnectin-Fc Fusion Purification

Harvested culture supernatant (neat or concentrated) is loaded onto a MabSelect Protein A column previously equilibrated with PBS. Column is washed with 5CV of 50 mM Tris pH8.0, 1M Urea, 10% PG. Adnectin-Fc fusion is eluted with 100 mM Glycine pH 3.3, collecting the peak into a container which is previously charged with 1CV of 200 mM Sodium Acetate pH 4.5. Peak elution is based on absorbance at A280.

The Protein A elution is diluted to pH 3.0 with the addition of 2 M Citric Acid and left at room temperature for 1 hour, for viral inactivation. Sample is then diluted with 200 mM Sodium Phosphate Tribasic until pH 4.5 is reached. If necessary, the solution is further diluted with water to lower conductivity below 10 ms/cm.

The diluted Protein A elution is passed over a Tosoh Q 600C AR (Tosoh Bioscience), previously conditioned with 50 mM Sodium Acetate pH 4.5, in a negative capture mode. The flowthrough peak is collected, based on absorbance at A280. The column is washed with 50 mM Sodium Acetate and stripped with 0.2N NaOH.

The Q 600C AR flowthrough is formulated using tangential flow filtration utilizing a 30K NMWCO hollow fiber membrane (GE), with very gentle mixing of the retentate. The adnectin-Fc fusion is diafiltered into 25 mM Sodium Phosphate 150 mM Trehalose pH 7.0 for 6 diavolumes, and then concentrated to a target protein concentration.

Example 2

Biophysical Assessment of Anti-Myostatin Proteins

Size Exclusion Chromatography: Standard size exclusion chromatography (SEC) was performed on candidate Adnectins resulting from the midscale process. SEC of midscaled material was performed using a Superdex 200 10/30 or on a Superdex 75 10/30 column (GE Healthcare) on an Agilent 1100 or 1200 HPLC system with UV detection at A214 nm and A280 nm and with fluorescence detection (excitation 280 nm, emission 350 nm). A buffer of 100 mM sodium sulfate/100 mM sodium phosphate/150 mM sodium chloride, pH 6.8 was used at the appropriate flow rate for the SEC column employed. Gel filtration standards (Bio-Rad Laboratories, Hercules, Calif.) were used for molecular weight calibration. The results of the SEC on midscaled purified Adnectins showed predominantly monomeric adnectin and elution in the approximate range of 10 kDa vs. globular Gel Filtration standards (BioRad) as shown in Tables 9 and 10.

Thermostability: Thermal Scanning Fluorescence (TSF) analysis of HTPP Adnectins was performed to screen them by relative thermal stability. Samples were normalized to 0.2 mg/ml in PBS. 1 µl of Sypro orange dye diluted 1:40 with PBS was added to 25 µl of each sample and the plate was sealed with a clear 96 well microplate adhesive seal. Samples were scanned using a BioRad RT-PCR machine by ramping the temperature from 25° C.-95° C., at a rate of 2 degrees per minute. The data was analyzed using BioRad CFX manager 2.0 software. Th values obtained by TSF have been shown to correlate well with Tm values obtained by DSC over a melting range of 40° C. to 70° C. This is considered the acceptable working range for this technique. A result of ND ("No data") is obtained when the slope of the transition curve is too small to allow its derivative peak (the rate of change in fluorescence with time) to be distinguished from noise. An "ND" result cannot be interpreted as an indication of thermostability. Differential Scanning calorimetry (DSC) analyses of dialyzed HTPP'd and midscaled Adnectins were performed to determine their respective $T_m$'s. A 0.5 mg/ml solution was scanned in a VP-Capillary Differential Scanning calorimeter (GE Microcal) by ramping the temperature from 15° C. to 110° C., at a rate of 1 degree per minute under 70 p.s.i pressure. The data was analyzed vs. a control run of the appropriate buffer using a best fit using Origin Software (OriginLab Corp). The results of the TSF and DSC analyses are summarized in Tables 8-10. As shown in Tables 8-10, many of the clones exhibited unfolding temperatures of over 60° C., indicating a highly biophysically stable structure suitable for medicinal formulation. Adnectins were generally tolerant of PEGylation or Fc-formatting with no apparent loss in stability. In some cases, these formats afforded improved stability. For example, 3116_A07 as an unmodified Adnectin has a Tm by TSF of 60° C., but when PEGylated (ATI-1377) the Tm by DSC was 68° C., and in an Fc-X format (PRD-1286) the Tm by DSC was 66° C.

Example 3

Cell-Based Luciferase Assay

A luciferase reporter plasmid, Activin-Responsive Element (ARE)-luc, was generated by ligating nine repeats of the ARE in tandem to the firefly luciferase reporter. The plasmid was transiently transfected into HepG2 cells. Plasmid pGL4.74[hRluc/TK] was co-transfected to normalize for transfection efficiency. 10,000 cells were plated per well in a 96-well plate. When a protein such as myostatin, activin, or BMP-11, is added to cells and binds to its cognate receptor, downstream SMAD signaling is triggered, leading to binding of a phosphorylated SMAD complex to the ARE. The amount of, e.g., myostatin, exposed to the cells is directly proportional to the amount of luciferase protein produced and, consequently, luciferase activity measured. When a myostatin antagonist (e.g., an anti-myostatin Adnectin) is added concurrently with myostatin to the cells, activation of the ARE decreases, leading to a decreased luciferase production and activity.

In this experiment, (1) Anti-myostatin Adnectin and myostatin, (2) anti-myostatin Adnectin and activin A, or (3) anti-myostatin Adnectin and BMP-11 were preincubated prior to addition to cells. Myostatin (R&D Systems) was used at 10-500 pM, activin A (R&D Systems) at 10-500 pM, and BMP-11 (R&D Systems) at 10-500 pM. After overnight incubation with these various combinations, cells were lysed and luciferase activity (luminescence) measured using the Dual-Glo Luciferase Assay System® (EnVision). The IC50 is defined as the concentration of Adnectin required to reach 50% inhibition of myostatin-induced ARE-luciferase activity.

As shown in Tables 8-10, anti-myostatin Adnectins inhibited myostatin-mediated increases in ARE-luc reporter activity.

Example 4

HTRF Binding Assay

An HTRF assay was used to measure the binding affinities of anti-myostatin Adnectins to myostatin. The assay was a competitive HTRF assay using Eu-W1024 label as a donor fluorophore and Alexa Fluor® 647 as an acceptor fluorophore. The biotinylated Adnectin 1889E01 and Alexa Fluor® 647 labeled rhActRIIb-Fc can bind myostatin simultaneously at two distinct binding sites. The Eu-W 1024 labeled Streptavidin is used to bind biotinylated 1889E01. The two fluorophores, Eu-W1024 and Alexa Fluor® 647, are brought together by the formation of a 1889E01/myostatin/ActRIIb-Fc complex, and the HTRF signal can be read on an EnVision platereader (Perkin Elmer) using an HTRF protocol. In the presence of a competitive Adnectin, the HTRF signal decreases. IC50s are presented in Tables 8-10.

TABLE 8

Biophysical characterization, ARE-luciferase reporter assay, and HTRF binding assay results for anti-myostatin mono-Adnectins.

| ID | Tm-TSF | Tm-DSC | Myo IC50 (nM) | BMP-11 IC50 (nM) | Activin A IC50 (nM) | HTRF Myo IC50 (nM) |
|---|---|---|---|---|---|---|
| 1979_B06 | | 48 | 0.11 | 3.3 | 194 | ND |
| 2062_G02 | | 48 | 205 | 1500 | >1500 | ND |
| 2522_C09 | 40 | | 0.06 | 1.6 | 1000 | ND |
| 2523_G06 | 49 | 49 | 4.2 | 46 | >2000 | ND |
| 2524_C11 | ND | 55 | 0.1 | 0.89 | 765 | ND |
| 2524_D09 | 54 | 49 | 0.06 | 0.55 | 84 | ND |
| 2524_E10 | ND | | 0.09 | 5.6 | >1000 | ND |
| 2524_H05 | 40 | | 0.09 | 7.3 | >1000 | ND |
| 2524_H11 | 49 | | 0.03 | 6.2 | >1000 | ND |
| 2525_B01 | ND | | 0.11 | 3.2 | 73 | ND |
| 2525_D02 | 58 | 55 | 0.05 | 1.1 | 345 | ND |
| 2525_D05 | ND | 69 | 0.11 | 3.9 | >1000 | ND |
| 2525_F07 | 46 | | 0.13 | 3.4 | >1000 | ND |
| 2987_A06 | | 50 | 0.10 | 23 | 283 | ND |
| 2987_B04 | | 48 | 0.12 | 3.3 | 239 | ND |
| 2987_B09 | | 52 | 0.01 | 0.92 | 172 | ND |
| 2987_C02 | | 50 | 0.06 | 7.1 | 464 | ND |
| 2987_D05 | | 49 | 0.11 | 2.4 | 2000 | ND |
| 2987_E03 | | 51 | 0.10 | 2.3 | 224 | ND |
| 2987_E08 | | 52 | 0.05 | 2.8 | 352 | ND |
| 2987_F01 | | 49 | 0.05 | 6.5 | 594 | ND |
| 2987_F06 | | 52 | 0.08 | 20 | 538 | ND |
| 2987_G04 | | 49 | 0.09 | 3.3 | 171 | ND |
| 2987_G09 | | 54 | 0.05 | 0.91 | >2000 | ND |
| 2987_H02 | | 51 | 0.05 | 11 | 794 | ND |
| 2987_H07 | | 57 | 0.02 | 5.5 | >400 | ND |
| 3006_A10 | 62 | | 0.08 | 2.0 | >2000 | 0.15 |
| 3007_B08 | 57 | | 0.06 | 0.23 | 423 | 0.14 |
| 3007_C09 | 63 | | 0.04 | 0.89 | 417 | 0.14 |
| 3007_C10 | 66 | | 0.03 | 1.0 | >2000 | 0.14 |
| 3008_A03 | 59 | | 0.11 | 22.6 | >2000 | 0.22 |
| 3008_B08 | 57 | | 0.35 | 9.3 | 254 | 0.37 |
| 3008_D04 | 56 | | 0.09 | 1.2 | 720 | 0.14 |
| 3008_F01 | 63 | | 0.08 | 0.12 | >2000 | 0.21 |
| 3008_G01 | 57 | | 0.03 | 0.31 | >2000 | 0.11 |
| 3008_G03 | 58 | | 0.09 | 1.3 | >2000 | 0.13 |
| 3115_D04 | 64 | | 0.16 | 3.6 | >1000 | 0.20 |
| 3115_E06 | 62 | | 0.07 | 2.0 | >1000 | 0.14 |
| 3116_A06 | 64 | | 0.14 | 13 | >1000 | 0.15 |
| 3116_A07 | 60 | | 0.04 | 0.5 | >1000 | 0.11 |
| 3116_C01 | 60 | | 0.10 | 6.7 | 1000 | 0.35 |
| 3116_C06 | 61 | | 0.14 | 8.9 | >1000 | 0.18 |
| 3116_H06 | 60 | | 0.10 | 1.6 | >1000 | 0.13 |
| 3146_A08 | 69 | | 0.70 | 48 | >1000 | 0.26 |
| ATI-1267 | | 60 | 0.06 | 0.50 | 644 | 0.12 |
| ATI-1275 | | 53 | 0.03 | 0.14 | 19 | 0.19 |
| ATI-1277 | | no transition | 0.14 | 1.18 | 2000 | 0.38 |
| ATI-1340 | | 54 | 0.05 | 4.87 | 324 | 0.16 |

TABLE 9

Biophysical characterization, ARE-luciferase reporter assay, and HTRF binding assay results for PEGylated anti-myostatin Adnectins.

| ID | Tm-TSF | Tm-DSC | % Monomer (SEC) | ARE-luciferase assay Myo IC50 (nM) | BMP-11 IC50 (nm) | Activin A IC50 (nM) | HTRF Myo IC50 (nM) |
|---|---|---|---|---|---|---|---|
| ATI-1106 | | | | 177 | 1414 | >2000 | |
| ATI-1107 | 63 | 98 | | 19 | 888 | >2000 | ND |
| ATI-1266 | 60 | 97.8 | | 0.12 | 0.89 | 2000 | 0.21 |
| ATI-1276 | 56 | 94.6 | | 0.08 | 0.15 | 110 | 0.28 |
| ATI-1278 | 46 | 93.7 | | 0.27 | 1.1 | >2000 | 0.54 |
| ATI-1338 | 59 | | | 0.28 | 5.8 | >1000 | 0.24 |
| ATI-1339 | 61 | | | 0.28 | 6.0 | >1000 | 0.28 |
| ATI-1341 | 53 | | | 0.03 | 0.14 | 14 | 0.13 |
| ATI-1359 | 57 | 96.5 | | 0.26 | 3.1 | >1000 | 0.36 |
| ATI-1375 | 67 | >99 | | 0.17 | 1.6 | >1000 | 0.76 |
| ATI-1376 | 70 | >99 | | 0.03 | 0.83 | >1000 | 0.32 |
| ATI-1377 | 68 | >99 | | 0.05 | 0.78 | >1000 | 0.15 |
| ATI-1378 | 74 | >99 | | 0.29 | 5.4 | >1000 | 1.29 |
| ATI-1379 | 69 | >99 | | 0.10 | 4.3 | >1000 | 0.28 |

TABLE 10

Biophysical characterization, ARE-luciferase reporter assay, and HTRF binding assay results for Fc-fused anti-myostatin Adnectins.

| ID | Tm-TSF | Tm-DSC | % Monomer (SEC) | ARE-luciferase assay Myo IC50 (nM) | BMP-11 IC50 (nm) | Activin A IC50 (nM) | HTRF Myo IC50 (nM) |
|---|---|---|---|---|---|---|---|
| PRD-932 | | | | 0.24 | ND | ND | ND |
| PRD-1171 | | | | 0.08 | 0.20 | 19 | 0.14 |
| PRD-1173 | | | | 0.02 | 0.10 | 6 | 0.12 |
| PRD-1174 | | Tm1 61 Tm2 67 Tm3 83 | | 0.04 | 0.10 | 4 | 0.09 |
| PRD-1175 | | | | 0.10 | 0.28 | 19 | 0.15 |
| PRD-1177 | | | | 0.16 | 0.28 | 21 | 0.64 |
| PRD-1178 | | Tm1 60 Tm2 69 Tm3 84 | | 0.08 | 0.25 | 16 | 0.27 |
| PRD-1180 | | Tm1 68 Tm2 83 | | 0.07 | 0.11 | 14 | 0.13 |
| PRD-1284 | | | | 0.02 | 0.04 | 44 | 0.62 |
| PRD-1285 | | Tm1 67 Tm2 68 Tm3 80 | 97 | 0.05 | 0.03 | 216 | 0.49 |
| PRD-1286 | | Tm1 66 Tm2 68 Tm3 81 | 99 | 0.10 | 0.11 | 94 | 0.73 |
| PRD-1287 | | | | 0.30 | 0.80 | >1000 | 2.70 |
| PRD-1288 | | Tm1 65 Tm2 69 Tm3 81 | 93 | 0.08 | 0.10 | >1000 | 0.47 |
| PRD-1301 | | | | 0.06 | 0.06 | 15 | 0.07 |
| PRD-1302 | | | | 0.03 | 0.02 | 14 | 0.12 |
| PRD-1303 | | | | 0.02 | 0.03 | 314 | 0.11 |
| PRD-1304 | | | | 0.05 | 0.07 | 45 | 0.24 |
| PRD-1305 | | | | 0.06 | 0.07 | 113 | 0.10 |
| PRD-1471 | | Tm1 62 Tm2 68 Tm3 81 | 99 | 0.16 | 0.16 | 60 | 0.47 |
| PRD-1472 | | Tm1 62 Tm2 69 Tm3 80 | 100 | 0.07 | 0.05 | 1000 | 0.41 |
| PRD-1473 | | Tm1 63 Tm2 69 Tm3 81 | 100 | 0.07 | 0.06 | 125 | 0.73 |
| PRD-1474 | | Tm1 63 Tm2 69 Tm3 81 | 100 | 0.08 | 0.09 | >1000 | 0.45 |

Example 5

Anti-Myostatin Adnectin-Mediated Inhibition of Myostatin-Induced SMAD2 Phosphorylation Human rhabdomyosarcoma RH41 cells (DSMZ, Braunschweig, Germany) were used for the 12-, 2-, and 4-point inhibition response analysis described below. Cells were removed from culture medium and washed to remove serum and quiesced in assay media containing BSA for 4 hours. Cells were lifted off the flask using versene and transferred to 96-well, V-bottom polypropylene plates at $5 \times 10^5$ cells/well. For the 12-point inhibition response, 100 pM recombinant myostatin (R&D Systems), preincubated for 1 hour with a 5-fold dilution concentration range of Adnectins starting at 1000 nM (i.e., 1000 nM, 200 nM, 40 nM, 8 nM, 1.6 nM, 0.32 nM, 0.064 nM, 0.0128 nM, 0.00256 nM, 0.000512 nM, 0.000102 nM, 0.0000204 nM), was added to the cells. For the 4-point inhibition response, 100 pM of myostatin, preincubated for 1 hour with a concentration range of Adnectins (30 nM, 3 nM, 0.1 nM or 0.001 nM), was added to the cells. For the 2-point inhibition response, 100 pM of myostatin, preincubated for 1 hour with a concentration range of Adnectins (10 nM or 0.5 nM), was added to the cells. Cells were treated with the myostatin-Adnectin mixture for 1 hour at 37° C. to induce SMAD2 phosphorylation (pSmad2). Stimulation was stopped by placing the cells on ice and adding ice-cold PBS. Cells were pelleted and lysed following standard protocols and SMAD2 phosphorylation detected using an ELISA assay (Cell Signaling Technologies). The inhibition achieved by the concentration range of Adnectins was plotted using GraphPad Prism Software and normalizing data points to controls which gave 100% and 0% inhibition. The IC50 is defined as the concentration of Adnectin required to reach 50% inhibition of myostatin-induced SMAD2 phosphorylation. The data presented in Table 11 indicate that Adnectins derived from affinity optimization of parental clones 1979_B06 and 2062_G02 both potently and completely inhibited myostatin-induced pSMAD phosphorylation and demonstrated IC50 values ranging from 0.78 nM to 0.06 nM. This represents a greater than 16-75 fold improvement in IC50 values over the parental clones 1979_B06 (IC50=12.8 nM) and 2062_G02 (IC50=59.1 nM).

TABLE 11

Inhibition of SMAD2 phosphorylation (pSMAD2) by anti-myostatin Adnectins pSmad2 Assay

| ID | Myo IC50 (nM) 12-point | Myo IC50 (nM) 4-point | Myo % inhibition at 10 nM |
|---|---|---|---|
| 1979_B06 (aka ATI-1133) | 12.8 ± 2.4 | | |
| 2062_G02 (aka ATI-1134) | 59.1 ± 16.2 | | |
| 2522_C09 | | 0.13 | |
| 2523_G06 | | 0.78 | |
| 2524_C11 | | 0.14 | |
| 2524_D09 | | 0.11 | |
| 2524_E10 | | 0.13 | |
| 2524_H05 | | 0.13 | |
| 2524_H11 | | 0.11 | |
| 2525_B01 | | 0.14 | |
| 2525_D02 | | 0.36 | |
| 2525_D05 | | 0.20 | |
| 2525_F07 | | 0.27 | |
| 3006_A10 | | | 51 |
| 3007_B08 | | | 97 |
| 3007_C09 | | | 80 |
| 3007_C10 | | | 76 |
| 3008_A03 | | | 87 |
| 3008_B08 | | | 90 |
| 3008_D04 | | | 92 |
| 3008_F01 | | | 86 |
| 3008_G01 | | | 98 |
| 3008_G03 | | | 91 |
| 3115_D04 | | 0.06 | |
| 3115_E06 | | 0.06 | |
| 3116_A06 | | 0.27 | |
| 3116_A07 | | 0.06 | |
| 3116_C01 | | 0.26 | |
| 3116_C06 | | 0.73 | |
| 3116_H06 | | 0.06 | |
| 3146_A08 | | 0.78 | |

Example 6

SPR Affinity Measurements for Anti-Myostatin Adnectins Adnectin Binding Kinetics Using SPR Format A Anti-human Fc antibody (Biacore/GE) was immobilized on a Biacore CM5 chip via NHS/EDC coupling according to the manufacturer's instructions. ActRIIb-Fc (R&D Systems) was captured on both reference and active flow cells, followed by capture of human myostatin (R&D Systems), human BMP-11 (GDF-11; R&D Systems), or human Activin A (R&D Systems) on active flow cells only (each solubilized according to manufacturer's suggested protocol and diluted in HBSP running buffer). A concentration range of anti-myostatin Adnectin was applied across all flow cells in HBSP running buffer. Regeneration of the chip surface between cycles was accomplished with two 30 second pulses of 3M $MgCl_2$. Kinetic traces of reference-subtracted sensorgrams were fit to a 1:1 binding model using Biaevaluation software. A summary of Biacore kinetic data is shown in Table 12.

The data shown in Table 12 indicate that optimized progeny Adnectins bind myostatin tightly, with $K_D$s in the range of 0.06-1.47 nM, compared to parental Adnectins 1979_B06 and 2062 G02, which displayed $K_D$s of 29 and 49 nM, respectively.

Upon PEGylation, there is some loss in myostatin affinity, with $K_D$s ranging from 0.76 to 14.4 nM, although there is no effect of PEGylation on potency in the ARE-luciferase assay (see Tables 8 and 9).

Adnectin selectivity over BMP-11 ranges from entirely non-selective to up to 17-fold, whereas binding to activin is either extremely weak or non-existent, suggesting high selectivity over activin.

Adnectin Binding Kinetics Using SPR Format B (Useful for Fc-Formatted Adnectins)

Human myostatin (R&D Systems), human BMP-11 (GDF-11; R&D Systems), or human Activin A (R&D Systems) was solubilized according to manufacturer-suggested protocol and immobilized on a Biacore CM5 chip at 1-10 µg/mL in acetate (pH 4.0 or 4.5) buffer using standard NHS/EDC coupling. A concentration range of anti-myostatin Adnectins was applied in HBSP running buffer. Regeneration of the chip surface between cycles was accomplished with 60 seconds of 10-50 mM NaOH. Kinetic traces of reference-subtracted sensorgrams were fit to a 1:1 binding model using Biaevaluation software. For Fc-formatted Adnectins, interaction kinetics are driven by avidity of bivalent Fc and dimeric myostatin even at low immobilization density. A summary of Biacore kinetic data is shown in Table 12. The data shown in Table 12 indicate that some of the Adnectins run in this SPR format bind myostatin and BMP-11 and also activin with similar affinities. The substantial selectivity over activin in the ARE-luciferase assay, however, suggests the affinity for activin may be artificially accentuated in this SPR assay format.

TABLE 12

Summary of SPR kinetic data for anti-myostatin adnectins. Formats A and B are described in Example 6.

| ID | Myo KD (nM) | BMP-11 KD (nM) | Activin A KD (nM) | Format |
|---|---|---|---|---|
| 1979_B06 (aka ATI-1133) | 29 | 489 | no binding | A, 25C |
| 2062_G02 (aka ATI-1134) | 48.8 | 697 | no binding | A, 25C |
| 2522_C09 | 0.51 | 0.45 | no/weak binding | A, 25C |
| 2523_G06 | 1.465 | 10.65 | no binding | A, 25C |
| 2524_C11 | 0.62 | 0.67 | no binding | A, 25C |
| 2524_D09 | 0.64 | 0.81 | weak binding | A, 25C |
| 2524_E10 | 1.34 | 1.42 | no binding | A, 25C |
| 2524_H05 | 0.88 | 0.87 | weak binding | A, 25C |
| 2524_H11 | 1.12 | 1.22 | no binding | A, 25C |
| 2525_B01 | 1.29 | 1.58 | weak binding | A, 25C |
| 2525_D02 | 0.24 | 0.30 | no/weak binding | A, 25C |
| 2525_D05 | 1.28 | 1.99 | no binding | A, 25C |
| 2525_F07 | 0.79 | 0.97 | no/weak binding | A, 25C |
| 2987_H07 | 0.99 | 2.25 | weak binding | A, 25C |
| ATI-1267 | 0.057 | 0.065 | weak binding | A, 25C |
| ATI-1275 | 0.15 | 0.15 | weak binding | A, 25C |
| ATI-1277 | 0.16 | 0.14 | weak binding | A, 25C |
| ATI-1107 | 128 | ~300 | no binding | A, 25C |
| ATI-1266 | 0.76 | 2.57 | weak binding | A, 25C |
| ATI-1276 | 4.18 | 8.8 | no binding | A, 25C |
| ATI-1278 | 6.04 | 3.3 | no binding | A, 25C |
| ATI-1338 | 1.9 | 3.8 | 4.6 | B, 37C |
| ATI-1339 | 3.6 | 6.9 | 6.5 | B, 37C |
| ATI-1359 | 7.9 | 35.45 | weak binding | A, 25C |
| ATI-1375 | 12.6 | 33.2 | weak binding | A, 25C |
| ATI-1376 | 8.21 | 13.4 | weak binding | A, 25C |
| ATI-1377 | 8.21 | 14.2 | weak binding | A, 25C |
| ATI-1378 | 14.4 | 59.6 | weak binding | A, 25C |
| ATI-1379 | 9.5 | 21.6 | weak binding | A, 25C |
| PRD-932 | 1.43 | ND | ND | B, 25C |
| PRD-1474 (aka ATI-1465) | 0.59 | ND | ND | B, 37C |

Example 7

Solution Phase Affinity for Anti-Myostatin Adnectins

The solution affinity of PRD-1474, an Fc-fused anti-myostatin Adnectin, for myostatin was measured using a Kinetic Exclusion Assay (KinExA). Quadruplicate titrations of PRD-1474 were performed with myostatin at a monomer concentration of 2 nM (n=2), 1 nM (n=1), and 0.7 nM (n=1). The relative unbound myostatin concentration was measured by capture on an ATI-1310 solid matrix (coupled to polyacrylamide beads via an engineered free cysteine) followed by detection with a fluorescent-labeled construct of the myostatin co-receptor, ActRIIB-Ig which can bind myostatin simultaneously with the Adnectin. ATI-1310 is a related Adnectin which competes with PRD-1474 for binding to myostatin and allows for capture of unbound myostatin. The global Kd analysis shown in Table 13 gives a Kd of 170 pM with a 95% confidence interval of 330-60 pM. The affinities of PRD-1177 and ATI-1338 were also measured using the same assay format. Triplicate titrations of PRD-1177 were performed with myostatin at a monomer concentration of 1 nM (n=2) and 0.8 nM (n=1). Triplicate titrations of ATI-1338 were performed with myostatin at a monomer concentration of 5 nM (n=1), 1.6 nM (n=1), and 1.4 nM (n=1). These analyses indicate that PRD-1177 binds myostatin with a global Kd value of 250 pM and a 95% confidence interval of 340-130 pM (Table 13). ATI-1338 binds myostatin with a global Kd value of 850 pM and a 95% confidence interval of 1400-330 pM.

TABLE 13

KinExA solution phase affinity measurements for binding myostatin.

| | | 95% confidence interval: | |
|---|---|---|---|
| Adnectin | Kd | Kd high | Kd low |
| PRD-1474 | 170 pM | 330 pM | 60 pM |
| PRD-1177 | 250 pM | 340 pM | 130 pM |
| ATI-1338 | 850 pM | 1400 pM | 330 pM |

Example 8

Mutational Analysis of 3116_A06

In order to understand the relative tolerance of loop positions to mutation, two similar but separate studies were conducted. The first was a traditional alanine scan, where the binding and efficacy of discrete alanine mutations in the loops of Adnectin 3116_A06 (SEQ ID NO: 118) were assessed in biochemical and cell-based assays. The second study consisted of deep mutational scanning in which we created a library of single-site mutations in the same positions of 3116_A06 (SEQ ID 118), but substituted each position with 20 of the possible amino acids. These library components were then expressed as protein-mRNA fusions and subjected to a single round of mRNA display (as described in Section IV), separating the library components associated with biotinylated myostatin from those remaining unbound using streptavidin magnetic beads. In this approach, next-generation sequencing of input and bound populations allowed for the determination of the relative enrichment/depletion of each sequence, reflecting its intrinsic affinity for myostatin.

Alanine Scanning: PCR site-directed mutagenesis was used to create single site alanine mutations in 3116_A06 (SEQ ID NO: 118) in the BC loop (residues 25-33), DE loop (residues 55-58), and FG loop (residues 80-89). Clones were expressed in *E. coli* and purified by HTPP as described in Example 1. Size exclusion chromatography (SEC, as described in Example 2) confirmed that all alanine-substituted proteins were predominantly monomeric (Table 14). Both ARE-luciferase (Example 3) and HTRF assays (Example 4) were conducted. In the HTRF competition binding assay, potencies ranged from IC50=1.5 nM to >100 nM (Table 14). Most positions tolerated alanine substitution in the HTRF assay to some degree, with the exception of Gly55, Arg56, and Gly57 of the DE loop, for which binding was drastically reduced (IC50s >100 nM). A lesser effect occurred in positions Gly30 of the BC loop, and Val80, Thr81, and Tyr88 of the FG loop, which still showed binding but with a >10-fold increase in IC50 relative to the parental sequence ("WT"). In the ARE-luciferase cell-based assay, potency of mutants ranged from IC50=0.6 nM to >100 nM (Table 14). The impact of alanine mutations was generally larger in the cell-based assay relative to the HTRF assay. Gly55, Arg56, and Gly57 of the DE loop and Val80 and Tyr88 of the FG loop all displayed drastically reduced potency in this assay, with IC50s >100 nM. A more moderate effect was observed for BC positions Leu26, Pro27, His28, Gly30, and Asn33, and FG positions Thr81, Tyr85, and Leu86, which all had IC50s >10-fold that of the parent sequence.

TABLE 14

Biochemical characterization and cell-based potencies for alanine mutants of 3116_A06

| | Mutation | SEC* | Myostatin HTRF IC50 (nM) | Myostatin ARE-luc IC50 (nM) |
|---|---|---|---|---|
| | WT parent | 1 | 0.3 | 0.6 |
| BC | S25A | 1 | 0.8 | 2.9 |
| | L26A | 1 | 2.3 | 16 |
| | P27A | 1 | 1.0 | 10 |
| | H28A | 1 | 0.8 | 6.2 |
| | Q29A | 1 | 0.7 | 1.5 |
| | G30A | 2 | 5.1 | 40 |
| | K31A | 1 | 0.6 | 2.2 |
| | N33A | 1 | 2.0 | 9.8 |
| DE | G55A | 2 | >100 | >100 |
| | R56A | 1 | 55 | >100 |
| | G57A | 1 | >100 | >100 |
| | V58A | 2 | 1.6 | 3.3 |
| FG | V80A | 1 | 4.0 | >100 |
| | T81A | 1 | 4.9 | 32 |
| | D82A | 1 | 0.8 | 1.8 |
| | T83A | 1 | 1.3 | 1.8 |
| | G84A | 1 | 2.0 | 3.6 |
| | Y85A | 1 | 2.0 | 5.5 |
| | L86A | 2 | 1.4 | 12 |
| | K87A | 1 | 0.8 | 2.0 |
| | Y88A | 1 | 11 | >100 |
| | K89A | 1 | 0.7 | 1.6 |

*SEC 1: Highly monomeric; SEC 2: Mostly monomeric

Deep Mutational Scanning: High throughput sequencing was combined with protein display to allow simultaneous measurement of the relative fitness of every possible single-site loop mutant, on a scale that would be onerous for a traditional approach like that described above (for review of "Deep Mutational Scanning" approaches, see Araya et al., *Trends in Biotechnology* 29: 435-442, 2011; a similar approach is further exemplified in Forsyth et al., mAbs 5: 523-532, 2013).

Library Construction and Selection: Three separate libraries were created that contained every possible single-site mutation in each of the three loops of 3116_A06 (SEQ ID NO: 118): BC loop (positions 25-33), DE loop (positions 55-58), and FG loop (positions 80-89). For each loop, multiple oligonucleotides were designed that individually incorporated an NNK codon at each position, where N=A, C, G, T and K=G, T. The use of these degenerate codons allow for the encoding of all 20 amino acids (plus a stop codon) at the position where the NNK is incorporated. The oligonucleotides were assembled via overlap extension PCR to generate the full-length Adnectin libraries, where Lib-BC contained every single amino acid BC loop mutation of 3116_A06, Lib-DE contained contained every single amino acid DE loop mutation of 3116_A06, and Lib-FG contained every single amino acid FG loop mutation of 3116_A06. The three libraries were expressed as mRNA-protein fusion molecules using PROfusion according to Xu et al., *Chemistry & Biology* 9: 933-942, 2002. Lib-BC, Lib-DE, and Lib-FG PROfusion molecules were separately selected against 3 nM biotinylated myostatin, and binding molecules were subsequently captured on streptavidin magnetic beads. The binders were eluted from the beads using 100 mM KOH. The molecules eluted from the beads represent variants of 3116_A06 that can still bind to myostatin, while those present in the initial library but not found in the elution represent variants of 3116_A06 that do not bind as well to myostatin.

NGS Barcoding and Mixing: Two populations, input (prior to myostatin binding) and binders (eluted from beads post-selection), derived from each of the three libraries (Lib-BC, Lib-DE, and Lib-FG) were collected and amplified separately. Each population was appended with a 5'-TruSeq Universal Adaptor, 3'-Truseq Adaptor II, and a unique 6-nucleotide barcode by PCR. A total of six barcoded populations were then individually quantified and mixed (Lib-BC: Lib-DE: Lib-FG=9:4:10) based on the number of randomized residues in each loop, in order to obtain similar numbers of sequences per randomized position statistically. The pooled sample was sequenced by Miseq 150 bp paired-end (Illumina) next-generation sequencing.

NGS Data Analysis: Forward-read sequences from next-generation sequencing were binned according to population, mutation position, and identity of the mutated amino acid. All sequences of poor quality and those containing multiple mutation sites were eliminated from the analysis. Next, the frequency of each sequence in the post-selection population was divided by its frequency in the input population to derive an enrichment ratio (ER). Comparison of ERs of the parental sequences (WT, which functions as a positive control) and sequences containing a stop codon (which function as a negative control, representing the background noise of survival by chance) showed that the ratio of signal to background (S/B) varied between the three loops, presumably because each loop library was put through selections individually. For this reason, every sequence was normalized to the average stop and average wt ERs for its own specific loop, to derive $ER^{norm}$.

$$ER^{norm} = \frac{ER - ER_{stop}}{ER_{wt} - ER_{stop}}$$

The deep mutational scan was validated by comparing the relative fitness of the single site alanine mutants to the biochemical data from the traditional alanine scan. Overall, the correlation was quite strong (FIG. 8). NGS ERs define a profile of enrichment and depletion of alanine mutants across the loops that correlates well with the impact observed in HTRF and ARE-luciferase assays.

The biochemical HTRF 1050 was also plotted directly versus the NGS ER' for each alanine mutant, as shown in FIG. 9.

Based on the alanine correlations, three categories were established into which all single site amino acid mutations could be binned via their NGS enrichment ratios: Most preferable mutations ($ER^{norm}$>0.8), more preferable mutations ($ER^{norm}$>0.5), and preferable mutations ($ER^{norm}$>3 standard deviations from the loop average $ER_{stop}$). The lower limits of $ER^{norm}$ defining the latter category differed for the three loops: BC=0.25; DE=0.15; FG=0.35. All single site mutants in the loops of 3116_A06 were binned according to their normalized enrichment ratios to determine the relative tolerance of each position to mutation (Table 15).

TABLE 15

Single site mutations in the loop sequences of 3116_A06 that maintain binding to myostatin

| Position | Preferable Mutations | More Preferable Mutations | Most Preferable Mutations |
|---|---|---|---|
| 25 | $X_{51}$ ACDFHIKLNQRSTVWY | CFISVWY | FSW |
| 26 | $X_{52}$ LMV | L | L |
| 27 | $X_{53}$ ACDEIKLMNPQRSTVY | P | P |
| 28 | $X_{54}$ ACDEFGHIKLMNQRSTVWY | CDEFGHIKLMNQRSTVWY | CFGIKLMNRSTVWY |
| 29 | $X_{55}$ ACDEFGHIKLMNPQRSTVWY | ACDEFGHIKLMNPQRSTVWY | ACEFHIKLMPQRSTVYWY |
| 30 | $X_{56}$ GS | G | G |
| 31 | $X_{57}$ ACDEFGHIKLMNQRSTVWY | ACGHIKLMNQRSVWY | ACHKLMNRVWY |
| 32 | $X_{58}$ ACGLMST | AGLMS | AGL |
| 33 | $X_{59}$ ACFHNPQRSY | CHNQSY | HNQ |
| 55 | G | G | G |
| 56 | R | R | R |
| 57 | G | G | G |
| 58 | $X_{60}$ ACDEFIKLMNQSTV | CEILMQTV | CEILMV |
| 80 | $X_{61}$ ACFILMQTVWY | ACILMV | IV |
| 81 | $X_{62}$ ACFGHIKLMNQRSTVWY | CFHILMQRSTVWY | CFILMTVWY |
| 82 | $X_{63}$ ACDEFGHIKLMNPQRSTVWY | ACDEFGHILMNPQSTVWY | ACDEFGHILMNQSTV |
| 83 | $X_{64}$ ACDEFGHIKLMNPQRSTVWY | ACDEFGHIKLMNQRSTVWY | ACDFGILMNQSTVWY |
| 84 | $X_{65}$ ACDEFGHIKLMNQRSTVWY | ADEFGHILMNQSTVWY | AGSTW |
| 85 | $X_{66}$ ACFHILMNPSTVWY | CFILMPTVWY | FIVWY |
| 86 | $X_{67}$ ACEFHIKLMNQRSTVWY | CFHIKLMNQRTVWY | FHILMVWY |
| 87 | $X_{68}$ ACDEFGHIKLMNPQRSTVWY | ACEFGIKLMNPQRSTVWY | ACFGIKLMTVW |
| 88 | $X_{69}$ FWY | WY | WY |
| 89 | $X_{70}$ ACDEFGHIKLMNPQRSTVWY | ACDEGHKLMNPQRSTV | AGKLMPQR |

Using the full deep mutational scanning data, BC loop positions 25, 26, 27, 30, 32, and 33, DE loop positions 55, 56, and 57, and FG loop positions 80 and 88 appear to be the most conserved, where only a single or a few amino acid types at these positions maintain binding to myostatin. On the other hand, other positions are highly tolerant to mutation, including BC loop positions 28, 29, and 31, and FG loop positions 82, 83, and 87.

Example 9

Evaluation of Anti-Myostatin Adnectin Pharmacokinetics

To investigate the pharmacokinetic profile of Adnectins with different PEGylated formats, anti-myostatin Adnectin 2987_H07 was formatted with 2-branched 40 KD PEG (ATI-1338), 4-branched 40 KD PEG (ATI-1339), and Bis 20 KD PEG (ATI-1341). Single dose studies of subcutaneous administration with these three PEGylated Adnectins were conducted in C57BL6 mice. Total drug concentrations were determined by ELISA assay. Bioanalytical PK immunoassay for the quantitation of ATI-1338 used a standard sandwich format ELISA assay, where the 1338 was captured with a monoclonal antibody to HIS-TAG protein, then detected with a polyclonal anti-PEG antibody. As shown in Table 16, the two 40 KD PEGylated formats, ATI-1338 and ATI-1339, provided more prominent pharmacokinetic enhancement (i.e., longer half life ($t_{1/2}$) and higher dose-normalized exposure) than the Bis-20 KD PEGylated format, ATI-1341.

TABLE 16

Pharmacokinetic Comparison of Three PEGylated Formats for Adnectin 2987_H07

| PK Parameters | ATI-1338 | ATI-1339 | ATI-1341 |
|---|---|---|---|
| Dose (mg/kg) | 5 | 3.9 | 4 |
| Cmax/Dose (nM/(mg/kg)) | 547 | 370 | 113 |

TABLE 16-continued

Pharmacokinetic Comparison of Three
PEGylated Formats for Adnectin 2987_H07

| PK Parameters | ATI-1338 | ATI-1339 | ATI-1341 |
|---|---|---|---|
| Tmax (h) | 24 | 24 | 4 |
| AUC/Dose (nM * hr/(mg/kg)) | 32 | 23 | 2.1 |
| $t_{1/2}$ (h) | 25 | 31 | 16 |

Single dose studies following intravenous and subcutaneous administration of Fc-fused anti-myostatin Adnectins (PRD-1177, PRD-1286, and PRD-1474) were conducted in C57BL6 mice to evaluate the effects of Fc-fusion on pharmacokinetic parameters. Total drug concentrations were determined by ELISA assays. Bioanalytical PK immunoassay for the quantitation of the Fc conjugates for PRD1177, 1474, and 1286 all used a standard sandwich format ELISA assay using ECL technology, where the 1177 was captured with a polyclonal antibody to the scaffold Adnectin, then detected with an anti-human IgG antibody. As shown in Table 17, all three Fc-fused Adnectins had a longer half life (58-172 h) than the PEGylated Adnectin ATI-1338 (25 h). A lower SC bioavailability likely reflects proteolysis during interstitial and lymphatic transit of the biologic molecule. The SC bioavailability of the Fc-fused Adnectins are within a reasonable range based on published literature (e.g., Richter et al., *AAPS J.* 2012; 14:559-70).

TABLE 17

Pharmacokinetic Comparison of Three Fc-fused anti-myostatin Adnectins

| PK Parameters | PRD-1177 | PRD-1286 | PRD-1474 |
|---|---|---|---|
| Dose (mg/kg) | 2 | 2 | 2 |
| Clearance (mL/min/kg) | 0.017 | 0.016 | 0.014 |
| Vdss (L/kg) | 0.093 | 0.190 | 0.054 |
| $t_{1/2}$ (h) | 68 | 172 | 58 |
| SC Bioavailability | 60% | 100% | 94% |

Example 10

Mechanism of Anti-Myostatin Adnectin Inhibition

Figure 10:
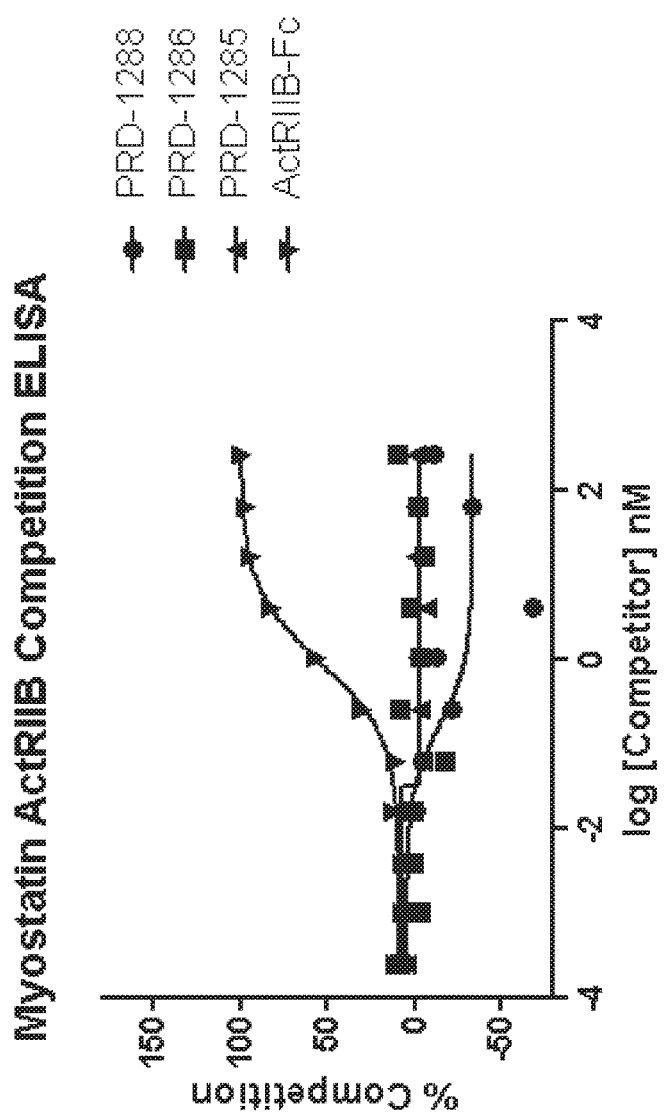
FIG. 10 depicts a graph of a competitive binding assay (competitive ELISA) showing that Adnectins PRD-1285, PRD-1286, and PRD-1288 do not block myostatin binding to ActRIIb-Fc. Indicated is the % competition of ActRIIb-Fc binding to myostatin. As expected, the positive control ActRIIb-Fc construct competed with ActRIIb-Fc binding to myostatin.

Competitive ELISA: Competitive binding assays to evaluate the ability of anti-myostatin Adnectins to compete with the ActRIIB receptor binding to myostatin were carried out using competitive ELISA. Nunc Maxisorp plates were coated with 2 µg/mL ActRIIb-Fc (R&D Systems) in 0.2M sodium carbonate pH 9.6 buffer overnight at 4° C. After washing with PBS-T (PBS containing 0.05% Tween-20), wells were blocked with OptEIA buffer (BD Biosciences) for 1 h at 25° C. with shaking. Myostatin (10 nM; R&D Systems) was preincubated with a concentration range of Adnectin or ActRIIb-Fc competitor (0.2 pM to 1 µM) in OptEIA buffer for 1 h at 25° C. with shaking. The blocked and coated assay plate was washed with PBS-T, and then myostatin/competitor mixtures were added and incubated for 30 min at 25° C. with shaking. The assay plate was washed with PBS-T, after which bound myostatin was detected with 1:1000 biotinylated goat anti-myostatin polyclonal (R&D Systems) diluted in OptEIA, for 1 h at 25° C. with shaking. After washing with PBS-T, 1:5000 Streptavidin-HRP (Thermo/Pierce) diluted in OptEIA was added, followed by incubation for 30 min at 25° C. with shaking. The assay plate was developed with TMB (BD Biosciences), quenched with 2N sulfuric acid, and absorbance read at A450. As shown in FIG. 10, ActRIIb-Fc in solution fully blocks myostatin binding to ActRIIb-Fc coated on the plate, as expected. In contrast, however, PRD-1288 (differs from PRD-1474 only in the linker sequence), PRD-1285, and PRD-1286 at concentrations up to 1 µM do not block myostatin from binding ActRIIb.

Competition SPR: Competitive binding assays to evaluate the ability of anti-myostatin Adnectins to compete with Type I and Type II receptors for binding to myostatin or BMP11, as a surrogate for myostatin, were also conducted using SPR on a Biacore T100 instrument, in two different experimental formats. In "SPR Format A", sensor chip surfaces were prepared by immobilizing 100 ug/ml protein A (Pierce) in 10 mM acetate pH 4.5 to 4500 RU on a CM5 sensor chip (Biacore/GE Healthcare) using standard ethyl(dimethylaminopropyl) carbodiimide (EDC)/N-hydroxysuccinimide (NHS) chemistry, with ethanolamine blocking. ALK4-Fc (R&D Systems), ALK5-Fc (R&D Systems), ActRIIB-Fc (produced in house), an anti-myostatin/BMP11 monoclonal antibody (mAb-A) which competes for binding to myostatin with ActRIIB but does not compete with 3116A06 for binding to mysotatin (produced in house), or Adnectin-Fc PRD-1474 at concentrations of 7-13 µg/ml were captured via the Fc tail to surface densities of 1600-4300 RU using 60 s injections at 10 µl/min. Competition experiments were performed by flowing 100 nM myostatin (R&D Systems) or BMP11 (R&D Systems) over these surfaces in the absence or presence of 200 nM Adnectin ATI-1523 at a flow rate of 30 µl/min with 180 s association and dissociation times. The running buffer for immobilization and competition experiments was 10 mM HEPES, 150 mM NaCl, 3 mM EDTA, and 0.05% v/v Surfactant P20, pH 7.4, and surfaces were regenerated between cycles using two injections of 10 mM glycine pH 1.5 for 30 s at 30 µl/min.

In SPR Format A, BMP11 bound specifically to ALK4-Fc, ALK5-Fc, ActRIIB-Fc, mAb-A, and PRD-1474 surfaces, whereas myostatin bound specifically to ActRIIB-Fc, mAb-A, and PRD-1474, but not ALK4-Fc or ALK5-Fc. To evaluate the effect of ATI-1523 on myostatin or BMP11 binding, the binding responses for each protein at the end of the 180 s association phase were each normalized to 100%, and compared to the binding responses for myostatin or BMP11 in the presence of ATI-1523 (Table 18). ATI-1523 completely blocked the binding of myostatin or BMP11 to the control PRD-1474 surface, as expected. In the assays to assess the ability of ATI-1523 to block the interaction of myostatin with ALK4-Fc or ALK5-Fc, BMP-11, which also binds to ALK4-Fc and ALK5-Fc, was used as a surrogate for myostatin, since myostatin alone does not bind significantly to ALK4-Fc and ALK5-Fc under this experimental format. ATI-1523 significantly reduced the binding signal for BMP11 toward ALK4-Fc (98% reduction) and ALK5-Fc (69% reduction), suggesting that the Adnectin competes for binding to myostatin with the Type I receptors. In contrast, an increased binding response was observed for myostatin/ATI-1523 or BMP11/ATI-1523 complexes on ActRIIB-Fc or mAb-A surfaces, suggesting that myostatin/ATI-1523 or BMP11/ATI-1523 complexes are able to bind to these surfaces, i.e., the Adnectin is non-competitive with ActRIIB-Fc or mAb-A. The large increase in binding response (>1000% increase) for the myostatin/ATI-1523 complex on ActRIIB-Fc and mAb-A surfaces is consistent with the Adnectin having a solubilizing effect on myostatin.

TABLE 18

SPR binding response for 100 nM myostatin or 100 nM BMP11 in the absence or presence of 200 nM ATI-1523 on ALK4-Fc, ALK5-Fc, ActRIIB-Fc, mAb-A, or PRD-1474 surfaces.

| Analyte | ALK4-Fc | ALK5-Fc | ActRIIB-Fc | mAb-A | PRD-1474 |
|---|---|---|---|---|---|
| Myostatin | | | 100% | 100% | 100% |
| Myostatin + ATI-1523 | | | 1313% | 1544% | −2% |
| BMP11 | 100% | 100% | 100% | 100% | 100% |
| BMP11 + ATI-1523 | 2% | 31% | 189% | 258% | −1% |

Adnectin competition using "SPR format B": The mechanism of action for anti-myostatin Adnectins was further evaluated in "SPR Format B", where myostatin or BMP11 (10 μg/ml in 10 mM acetate pH 4.5) were directly immobilized on a CM5 sensor chip surface using EDC/NHS coupling chemistry to a density of 985 RU (myostatin) or 530 RU (BMP11). Here, the binding response for receptors ALK4-Fc (R&D Systems), ALK5-Fc (R&D Systems), or ActRIIB-monomer (produced in house) injected alone (2 μM for 180 s at 30 μl/min), were compared to the binding responses for these receptors following pre-binding of Adnectin-Fc fusion PRD-1474 to the surface (1 μM for 480 s at 30 μl/min). The running buffer for immobilization and competition experiments was 10 mM HEPES, 150 mM NaCl, 3 mM EDTA, and 0.05% v/v Surfactant P20, pH 7.4, and surfaces were regenerated between cycles using 4 injections of 50 mM NaOH for 15 s at 30 μl/min.

Figure 11:
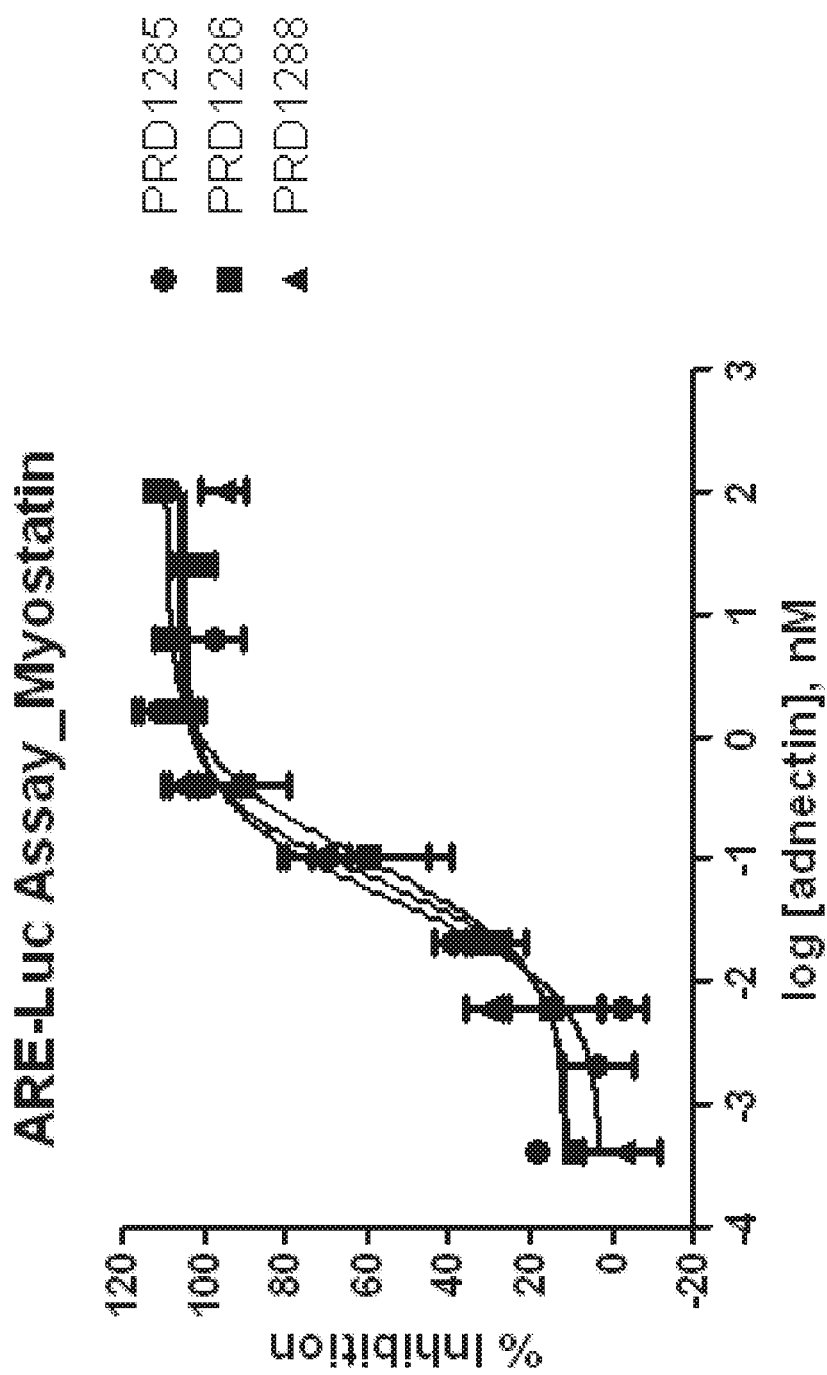
FIG. 11 depicts a graph showing the effects of various concentrations of Adnectins PRD-1285, PRD-1286, and PRD-1288 on myostatin activity in an ARE-luciferase assay. Experimental conditions are as described in Example 3. Each of PRD-1285, PRD-1286, and PRD-1288 inhibited 100% of the myostatin-induced ARE-luciferase activity.
Figure 12A:
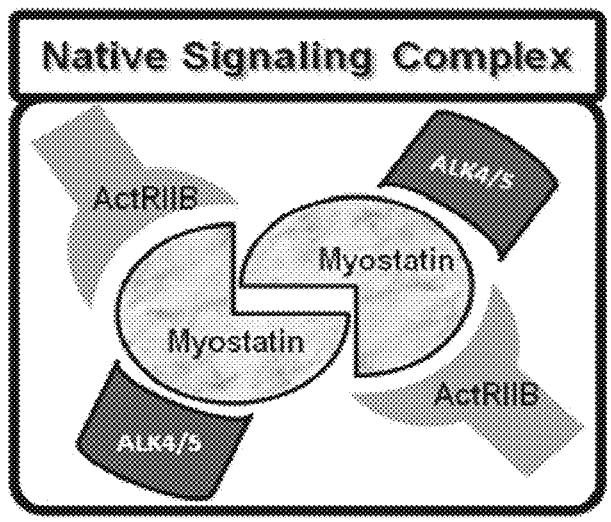
FIGS. 12A and 12B are a schematic depicting the mechanism of action by which the Adnectins of the present invention inhibit myostatin activity. The native signaling complex is shown in FIG. 12A. Specifically, binding of myostatin to ActRIIb is followed by recruitment of activin receptor-like kinase 4 (ALK4) or ALK5, and ActRIIb and ALK4/5 bind to distinct regions of myostatin. The Adnectins of the present invention prevent the binding of ALK4/5, but not ActRIIb, to myostatin (FIG. 12B).
Figure 12B:
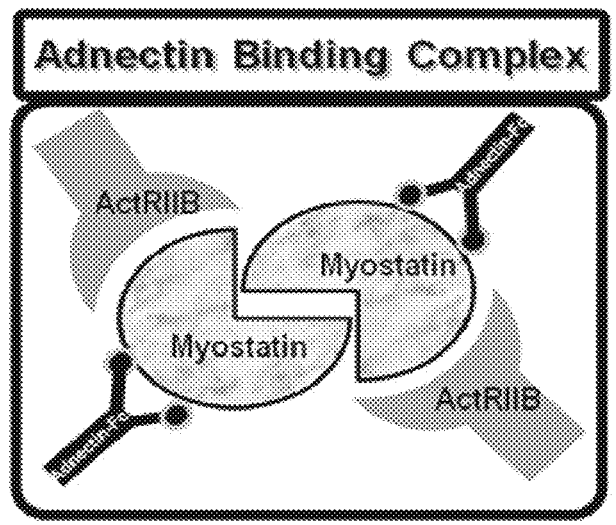

In the absence of PRD-1474, each receptor bound specifically to immobilized BMP11, whereas only ALK5-Fc and ActRIIB-monomer, but not ALK4-Fc, bound to immobilized myostatin. Pre-binding of PRD-1474 significantly reduced the binding signal for ALK4-Fc towards BMP11 (70% reduction) and also reduced the binding of ALK5-Fc towards myostatin or BMP11 (35-41% reduction), but had a minimal impact on ActRIIB-monomer binding to either myostatin or BMP11 surfaces, Table 19. These data, taken together with the SPR competition data from "SPR Format A" (Table 18), the competitive ELISA data (FIG. 10), and the complete inhibition of myostatin signaling observed in the ARE-luciferase assay (FIG. 11), demonstrate that the Adnectin mechanism of action is blockade of recruitment of Type I signalling receptors (ALK4/5), and that the Adnectins do not compete with Type II receptor (ActRIIB) binding.

TABLE 19

SPR binding response for 1 μM ALK4-Fc, ALK5-Fc, or ActRIIB-monomer on immobilized myostatin or BMP11 surfaces with or without pre-bound PRD-1474.

| Surface | Pre-binding PRD-1474 | ALK4-Fc | ALK5-Fc | ActRIIB-monomer |
|---|---|---|---|---|
| Myostatin | no | | 100% | 100% |
| | yes | | 55% | 111% |
| BMP11 | no | 100% | 100% | 100% |
| | yes | 30% | 65% | 92% |

Since these Adnectins represent the sequence families exemplified in the current invention, and individual clones within a well-defined sequence family maintain the same binding site, the sequences covered by the current invention act by blocking ALK4/5 recruitment to the myostatin-ActRIIb complex.

The pharmacokinetic data further indicate that myostatin-Adnectin complex levels accumulate with time and that these complexes bind to ActRIIb, thus acting as a dominant negative inhibitor of signaling independent of free drug. This unique mechanism distinguishes the anti-myostatin Adnectins of the present invention from anti-myostatin antibodies described in the literature (e.g., U.S. Pat. No. 7,632,499), and indicate that the anti-myostatin Adnectins of the invention have increased activity.

Example 11

Mapping of Adnectin Binding Site on Myostatin Using HDX-MS

The Adnectin binding site on myostatin was further evaluated using hydrogen-deuterium exchange mass spectrometry (HDX-MS).

The hydrogen/deuterium exchange mass spectrometry (HDX-MS) method probes protein conformation and conformational dynamics in solution by monitoring the deuterium exchange rate and extent in the backbone amide hydrogens. The level of HDX depends on the solvent accessibility of backbone amide hydrogens and the conformation of the protein. The mass increase of the protein upon HDX can be precisely measured by MS. When this technique is paired with enzymatic digestion, structural features at the peptide level can be obtained, enabling differentiation of surface exposed peptides from those folded inside, or from those sequestered at the interface of a protein-protein complex. Typically, the deuterium labeling and subsequent quenching experiments are performed, followed by online pepsin digestion, peptide separation, and MS analysis.

Because myostatin alone was found to have unsuitably low solubility for HDX-MS under conditions of physiologically relevant pH (<10 μg/ml), we used an alternative strategy of increasing myostatin solubility by complexing the protein with the Fab fragment from mAb-A (Fab-A), which was shown to be non-competitive with the Adnectin using the SPR experiments described in Example 10. The oligomeric state of the HDX-MS samples were characterized by size-exclusion chromatography coupled to a multi-angle laser light scattering detector (SEC-MALS), where the MALS-determined mass of the myostatin/Fab-A complex (~120 kDa) was consistent with the expected stoichiometry of one myostatin homodimer bound to two Fab-A molecules, and the MALS-determined mass of the myostatin/Fab-A/3116_A06 complex (142 kDa) was consistent with the expected stoichiometry of one myostatin homodimer bound to two Fab-A molecules plus two 3116_A06 molecules.

Prior to mapping the Adnectin binding site on myostatin recognized by Adnectin 3116_A06 by HDX-MS, non-deuterated experiments were performed to generate a list of common peptic peptides for myostatin from myostatin/Fab-A (1:1 molar ratio at 30 μM each) and myostatin/Fab-A/3116_A06 (1:1:1 molar ratio at 30 μM each) samples, achieving a sequence coverage of 83.5% for myostatin. In this experiment, 10 mM phosphate buffer (pH 7.0) was used during the labeling step, followed by adding quenching buffer (200 mM phosphate buffer with 4M GdnCl and 0.5M TCEP, pH 2.5, 1:1, v/v). For Adnectin binding site mapping experiments, 5 μL of each sample (myostatin/Fab-A or myostatin/Fab-A/3116_A06) was mixed with 65 μL HDX labeling buffer (10 mM phosphate buffer in D20, pD 7.0) to start the labeling reactions at room temperature (~25° C.). The reactions were carried out for different periods of time: 20 sec, 1 min, 10 min, 60 min, and 240 min. By the end of each labeling reaction period, the reaction was quenched by adding quenching buffer (1:1, v/v) and the quenched sample was injected into Waters HDX-MS system for analysis. The observed common peptic peptides were monitored for their deuterium uptake levels in the absence/presence of 3116_A06.

Experimental data obtained from HDX-MS measurements indicate that Adnectin 3116_A06 recognizes a discontinuous Adnectin binding site comprised of two peptide regions in myostatin:

```
                                             SEQ ID NO: 329
    Region 1: LYFNGKEQIIYGKIPAM (85-101);

SEQ ID NO: 330
    Region 2: PHTHLVHQANP (56-66);
```

Based on relative deuterium uptake levels, the two peptide regions can be ranked as region 1 >2, with region 1 having the most significant changes in deuterium uptake.

Example 12

In Silico Docking of Adnectin 3116_A06 onto Myostatin

Figure 13A:
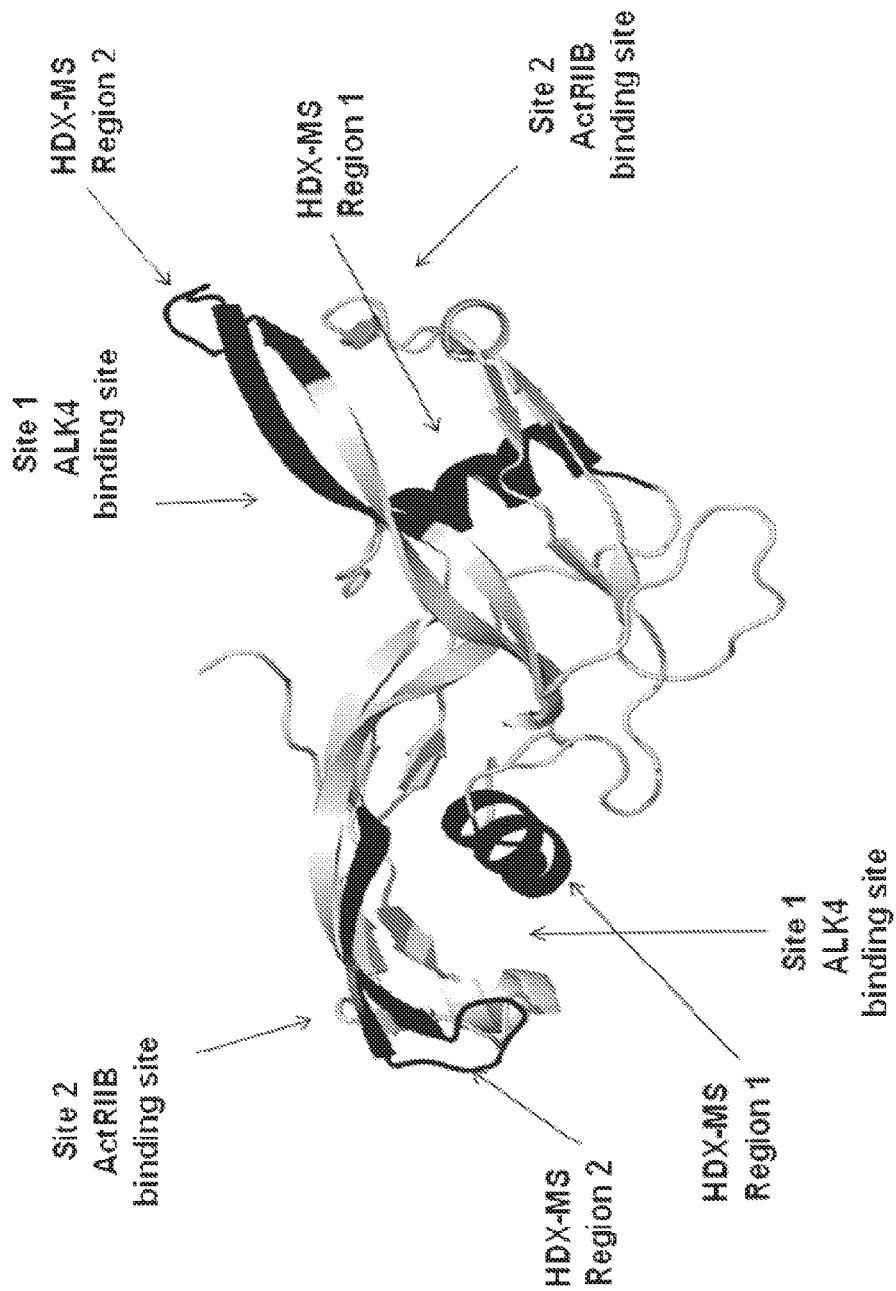
FIGS. 13A and 13B show a computational model depicting the complex of 3116_A06 and myostatin.
Figure 13B:
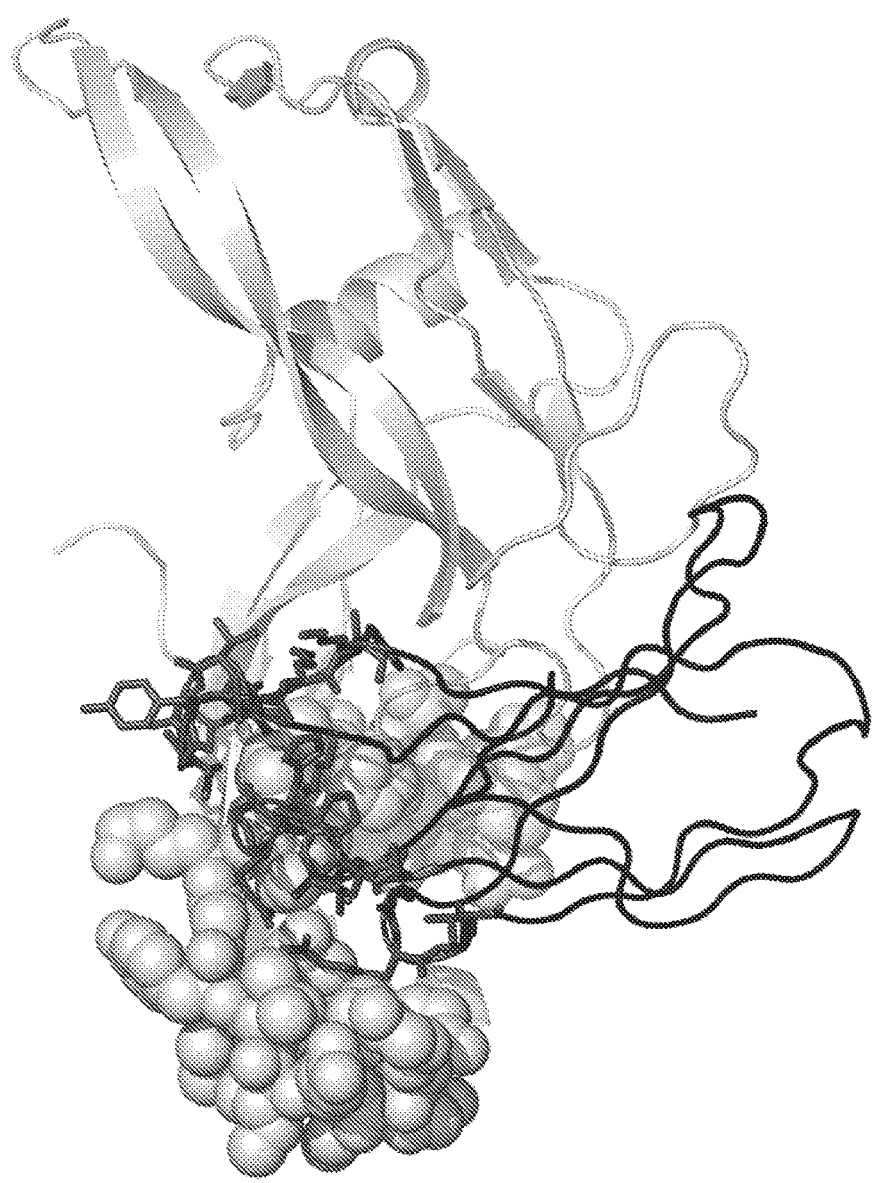

A computational approach was used to generate a structural model of the 3116_A06-myostatin complex that was consistent with the HDX-MS data (FIG. 13). Protein docking of 3116_A06 into the structure of human myostatin (PDB 3HH2 taken from the Protein Data Bank, www.rcsb.org; Cash et al., *EMBO J.* 28:2662-2676, 2009) was performed using ZDOCK (Chen and Wang, *Proteins* 47:281-294, 2002) as implemented in Accelrys software Discovery Studio v3.5 (Accelrys). The ZDOCK protocol utilizes rigid body docking of two protein structures (ligand=3116_A06 and receptor=myostatin). The docked poses were filtered for complexes which contained conformations of 3116_A06 FG (residues Thr79 to Tyr88) and BC (residues Ser25 to N33) loops. A preferred complex was selected based upon complementarity of the interface residues coupled with correlation of the loop favorable substitutions identified by Adnectin mutagenesis. FIG. 13A shows the ALK4 binding site and the ActRIIB binding site mapped onto the myostatin structure (grey). Region 1 and Region 2, which were identified by the HDX-MS experiments as described in Example 11, are indicated in black. FIG. 13B shows a preferred complex from docking, with the BC, DE and FG loop of 3116_A06 (black) rendered in stick, and Regions 1 and 2 of myostatin (grey) represented in space-fill. Several residues that were identified as loop favorable mutations show key contributions. For example, in the BC loop of 3116_A06, residues Ser25, Leu26, and Pro27 are important as structural constraints for maintaining the overall loop conformation. In contrast Ala32 fits into a small hydrophobic cleft formed at the complex interface and the backbone of the residue forms hydrogen bonds with myostatin. The most preferable substitutions at position 32 are Gly or Leu, and they are predicted to fit well in place of the alanine. Similarly, Asn33 is involved with hydrogen bonds to nearby tryptophan residues of myostatin. The most preferable substitutions at position 33 are His and Gln, which also contain sidechains that can contribute as hydrogen bond donors. Residues in the DE loop are critical: the most favorable substitutions are limited to Gly55, Arg56, and Gly 57, and only conservative substitutions are preferable for Val58. In the model structure, Arg56 is a critical residue contributing pi cation interactions with Y86 of myostatin in Region 1 as well as additional hydrogen bonds with the backbone and side chain of other Region 1 residues. For many FG loop residues, the most preferable substitutions were conservative replacements. One critical position identified was Tyr88, which has pi cation interactions and pi-pi interactions with Y55 and other residues from Region 2 of myostatin. The FG loop is also involved with several hydrophobic interactions with both Regions 1 and 2 identified from the mutagenesis experiments. These calculations show good agreement with the HDX-MS and SPR experiment data.

Example 13

In Vivo Mouse Model of Musculoskeletal Efficacy

Figure 14:
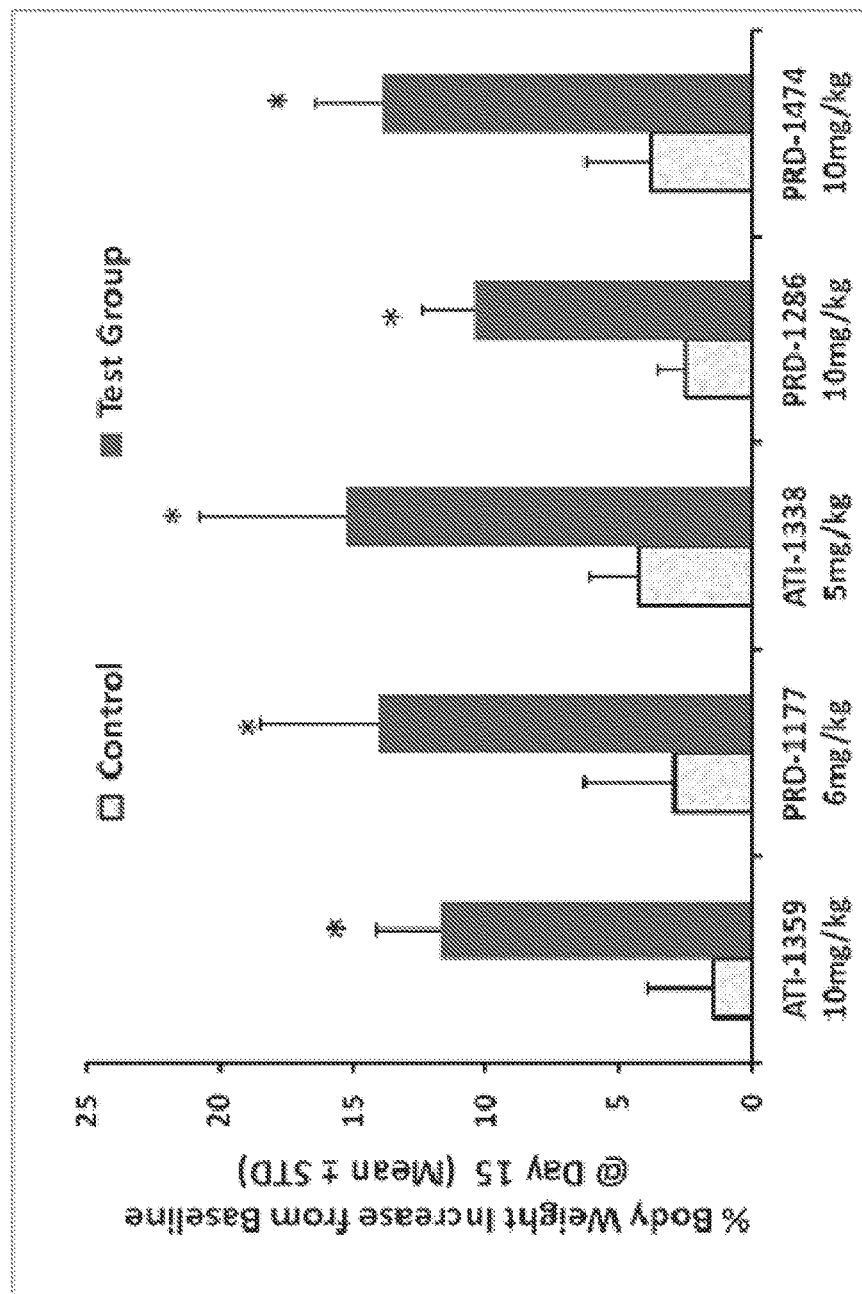
FIG. 14 depicts a bar graph showing percent increases in body weight at day 15 in mice treated with the indicated anti-myostatin Adnectins compared to control mice. B6 SCID mice were treated either biweekly or weekly with subcutaneous injections of anti-myostatin Adnectins for 14 days, as described in Example 13. Body weights were measured throughout the treatment period; calculated percentage change values for day 15 are depicted. (*=indicates statistical differences from respective control group; $p \leq 0.01$ t-test).

Male B6.SCID mice (9-13 weeks old, Jackson Laboratories, Bar Harbor, Me.) were housed in a temperature-controlled room with a reversed 12 hour light/dark cycle. Water and standard chow food were available ad libitum. Mice were randomized and distributed between treatment groups to receive either control or test compounds of the present invention based on body weight (about 20-22 g). In order to demonstrate in vivo efficacy of the compounds of the present invention, the compounds were administered either weekly (Fc-fusion anti-myostatin adnectins) or twice a week (PE-Gylated anti-myostatin adnectins) by subcutaneous injection. Test compounds were administered to the animals in Phosphate-Buffered Saline (PBS). Controls were treated with only reconstitution buffer. Test animals (n=8-10 mice/group) were dosed over a 14 day-time frame subcutaneously, with e.g., 5, 6 or 10 mg/kg/week of a compound of the invention. Body weight measurements were recorded pre-randomization, on randomization day, and two to three times a week during the treatment periods and at the end of the study. Lower leg muscle mass was recorded from body carcasses at the end of the study by quantitative magnetic resonance imaging (MRI, Echo Medical Systems, Tex) analysis. Test groups were compared to the control group. The results show that anti-myostatin Adnectins of the invention increased percent body weight from baseline (FIG. 14) and had significant anabolic effects on skeletal muscle volume (FIG. 15), compared to control mice (e.g., approximately a 7-10% increase in muscle volume compared to control.

Magnetic Resonance Imaging (MRI)

Figure 15:
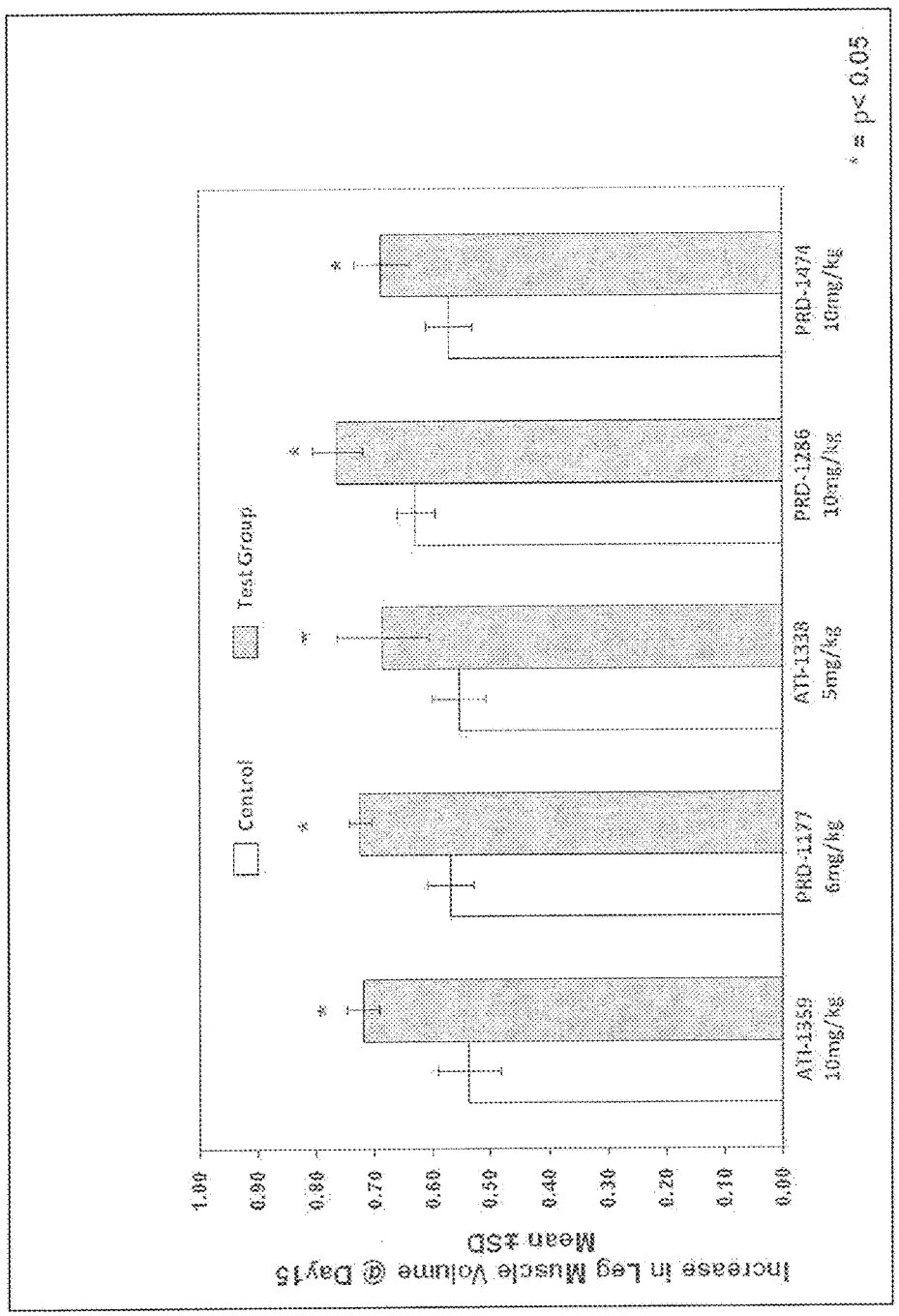
FIG. 15 depicts a bar graph showing increases in leg muscle volume (in $cm^3$) at day 15 in mice treated with the indicated anti-myostatin Adnectins compared to control mice. B6 SCID mice were treated either biweekly or weekly with subcutaneous injections of anti-myostatin Adnectins for 14 days as described in Example 13. (*=indicates statistical differences from respective control group; $p \leq 0.05$ t-test).

MRI for leg muscle volume measurements were performed on a Bruker PharmaScan 4.7 Tesla with a 16 cm bore (Bruker Biospin, Billerica, Ma. USA). A 62 mm volume coil was used for the transmitter and receiver. After collection of localizer images of the lower leg, T2 weighted images were obtained using an axial slice plan. The fast spin-echo (RARE) sequence consisted of a 90° Hermite pulse followed by a 180° Hermite pulse with a TR/TE=2000/23 ms. Eleven axial slices were collected from the top of the knee to the ankle with a matrix dimension of 256×128 data points. The field of view was 5 cm by 2.5 cm, with a 1.25 mm slice thickness and a RARE factor of 4 and 8 signal averages. Leg muscle volumes were calculated by summation of all axial slice areas multiplied by the 1.25 mm slice thickness for total muscle volume in each leg. Images were analyzed as an area average of the region-of-interests (ROI) by Image Sequence Analysis (ISA, Bruker Biospin, Billerica, Ma.). Manual ROIs were drawn around the leg muscle excluding the skin and subcutaneous fat area. The total average muscle volume for both legs is shown in FIG. 15.

MRI for heart volumes as a safety end point was also performed with the same MRI scanner. After obtaining initial localizer images of the thoracic area, 9 axial images were collected from the great vessels to the apex of the heart. Similar to the analysis of leg muscles, the axial areas were added and multiplied by the slice thickness of 1.25 mm to obtain the total heart volume for each animal. No significant change in heart volume was observed by MRI.

Statistics

Differences between groups were assessed using student's t-test 2 tailed paired analysis.

Example 14

Efficacy of PRD-1474 on Muscle Growth In Vivo

Figure 16:
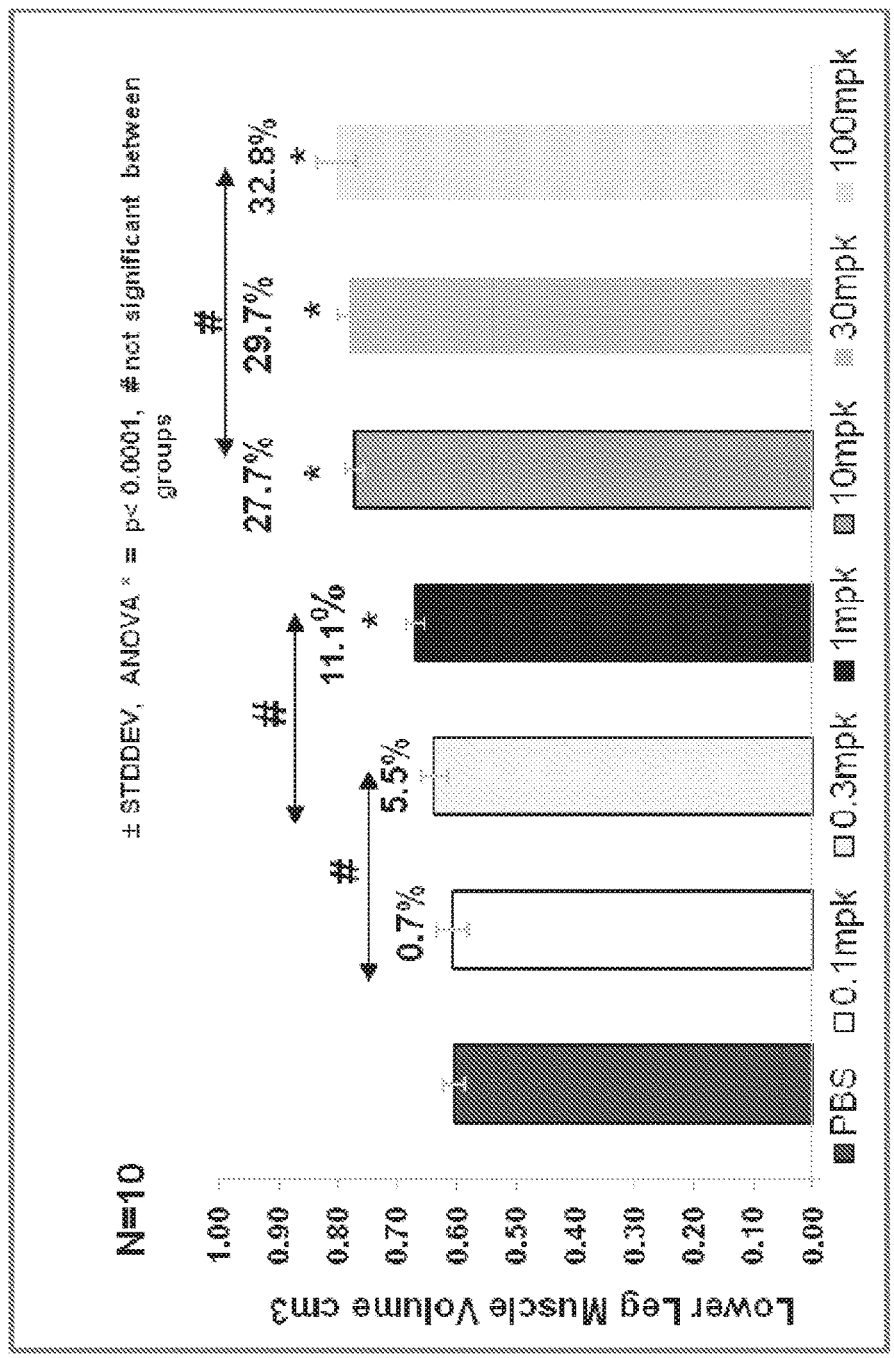
FIG. 16 depicts a bar graph showing increases in leg muscle volume (in $cm^3$) at day 28 in mice treated with the various indicated doses of PRD-1474. B6 SCID mice were treated either biweekly or weekly with subcutaneous injections of PRD-1474 for 28 days as described in Example 14. (*$p<0.0001$; # not significant between groups).

Male B6.SCID mice (n=10/group) were maintained and treated as described in Example 10, with the exception that PRD-1474 was administered at the various doses as indicated in FIG. 16, and the duration of treatment was 28 days. PRD-1474 at 1 mg/kg showed a significant 11.1% increase in lower leg muscle volume compared to the PBS control group (p<0.0001). Significant increases in lower leg muscle volume of 27.7%, 29.7%, and 32.8% were also observed with PRD-1474 at 10 mg/kg, 30 mg/kg, and 100 mg/kg, respectively. No change in heart volume was observed in all treatment dose groups relative to control. Data are presented as mean±standard deviation. The various dosage groups were compared using ANOVA. (*p<0.0001; #not significant between groups).

The data demonstrate that the anti-myostatin Adnectins of the invention are effective at significantly lower dosages than myostatin inhibitors previously described (e.g., U.S. Pat. No. 7,632,499, *J. Clin. Onclo.* 30(Suppl):Abstr. 2516, 2012). Thus, the anti-myostatin Adnectins of the invention provide increased efficacy at lower dosages combined with decreased undesired side effects, when administered alone or in combination with other myostatin inhibitors or other drugs, for treating muscle wasting and metabolic diseases described herein.

We claim:

1. A nucleic acid encoding a polypeptide comprising a fibronectin type III tenth ($^{10}$Fn3) domain which binds to myostatin and (i) comprises AB, BC, CD, DE, EF, and FG loops, wherein at least one loop of the BC, DE, and FG loops of the $^{10}$Fn3 domain has 0, 1, 2, or 3 amino acid substitutions relative to the respective BC, DE, and FG loops of SEQ ID NOs: 34, 39, and 75.

2. The nucleic acid of claim 1, wherein at least one loop of the BC, DE, and FG loops of the $^{10}$Fn3 domain has 1 amino acid substitution relative to the respective BC, DE, and FG loops of SEQ ID NOs: 34, 39, and 75.

3. The nucleic acid of claim 1, wherein:

(i) the serine at position 3 of the BC loop (SEQ ID NO: 34) is substituted with an amino acid selected from the group consisting of A, C, D, F, H, I, K, L, N, Q, R, T, V, W, or Y;

(ii) the leucine at position 4 of the BC loop (SEQ ID NO: 34) is substituted with an amino acid selected from M or V;

(iii) the proline at position 5 of the BC loop (SEQ ID NO: 34) is substituted with an amino acid selected from the group consisting of A, C, D, E, I, K, L, M, N, Q, R, S, T, V, or Y;
(iv) the histidine at position 6 of the BC loop (SEQ ID NO: 34) is substituted with an amino acid selected from the group consisting of A, C, D, E, F, G, I, K, L, M, N, Q, R, S, T, V, W, or Y;
(v) the glutamine at position 7 of the BC loop (SEQ ID NO: 34) is substituted with an amino acid selected from the group consisting of A, C, D, E, F, G, H, I, K, L, M, N, P, R, S, T, V, W, or Y;
(vi) the glycine at position 8 of the BC loop (SEQ ID NO: 34) is substituted with the amino acid S;
(vii) the lysine at position 9 of the BC loop (SEQ ID NO: 34) is substituted with an amino acid selected from the group consisting of A, C, D, E, F, G, H, I, L, M, N, Q, R, S, T, V, W, or Y;
(viii) the alanine at position 10 of the BC loop (SEQ ID NO: 34) is substituted with an amino acid selected from the group consisting of C, G, L, M, S, or T; or
(ix) the asparagine at position 11 of the BC loop (SEQ ID NO: 34) is substituted with an amino acid selected from the group consisting of A, C, F, H, P, Q, R, S, or Y.

4. The nucleic acid of claim 3, wherein:
(i) the serine at position 3 of the BC loop (SEQ ID NO: 34) is substituted with an amino acid selected from the group consisting of C, F, I, V, W, or Y;
(ii) the histidine at position 6 of the BC loop (SEQ ID NO: 34) is substituted with an amino acid selected from the group consisting of C, D, E, F, G, I, K, L, M, N, Q, R, S, T, V, W, or Y;
(iii) the lysine at position 9 of the BC loop (SEQ ID NO: 34) is substituted with an amino acid selected from the group consisting of A, C, G, H, I, L, M, N, Q, R, S, V, W, or Y;
(iv) the alanine at position 10 of the BC loop (SEQ ID NO: 34) is substituted with an amino acid selected from the group consisting of G, L, M, or S; or
(v) the asparagine at position 11 of the BC loop (SEQ ID NO: 34) is substituted with an amino acid selected from the group consisting of C, H, Q, S, or Y.

5. The nucleic acid of claim 3, wherein:
(i) the serine at position 3 of the BC loop (SEQ ID NO: 34) is substituted with the amino acid F or W;
(ii) the histidine at position 6 of the BC loop (SEQ ID NO: 34) is substituted with an amino acid selected from the group consisting of C, F, G, I, K, L, M, N, R, S, T, V, W, or Y;
(iii) the glutamine at position 7 of the BC loop (SEQ ID NO: 34) is substituted with an amino acid selected from the group consisting of A, C, E, F, H, I, K, L, M, P, R, S, T, V, or Y;
(iv) the lysine at position 9 of the BC loop (SEQ ID NO: 34) is substituted with an amino acid selected from the group consisting of A, C, H, L, M, N, R, V, W, or Y;
(v) the alanine at position 10 of the BC loop (SEQ ID NO: 34) is substituted with the amino acid G or L; or
(vi) the asparagine at position 11 of the BC loop (SEQ ID NO: 34) is substituted with the amino acid H or Q.

6. The nucleic acid of claim 1, wherein the valine at position 5 of the DE loop (SEQ ID NO: 39) is substituted with an amino acid selected from the group consisting of A, C, D, E, F, I, K, L, M, N, Q, S, or T.

7. The nucleic acid of claim 6, wherein the valine at position 5 of the DE loop (SEQ ID NO: 39) is substituted with an amino acid selected from the group consisting of C, E, I, L, M, Q, or T.

8. The nucleic acid of claim 6, wherein the valine at position 5 of the DE loop (SEQ ID NO: 39) is substituted with an amino acid selected from the group consisting of C, E, I, L, or M.

9. The nucleic acid of claim 1, wherein:
(i) the valine at position 2 of the FG loop (SEQ ID NO: 75) is substituted with an amino acid selected from the group consisting of A, C, F, I, L, M, Q, T, W, or Y;
(ii) the threonine at position 3 of the FG loop (SEQ ID NO: 75) is substituted with an amino acid selected from the group consisting of A, C, F, G, H, I, K, L, M, N, Q, R, S, V, W, or Y;
(iii) the aspartic acid at position 4 of the FG loop (SEQ ID NO: 75) is substituted with an amino acid selected from the group consisting of A, C, E, F, G, H, I, K, L, M, N, P, Q, R, S, T, V, W, or Y;
(iv) the threonine at position 5 of the FG loop (SEQ ID NO: 75) is substituted to with an amino acid selected from the group consisting of A, C, D, E, F, G, H, I, K, L, M, N, P, Q, R, S, V, W, or Y;
(v) the glycine at position 6 of the FG loop (SEQ ID NO: 75) is substituted to with an amino acid selected from the group consisting of A, C, D, E, F, H, I, K, L, M, N, Q, R, S, T, V, W, or Y;
(vi) the tyrosine at position 7 of the FG loop (SEQ ID NO: 75) is substituted with an amino acid selected from the group consisting of A, C, F, H, I, L, M, N, P, S, T, V, or W;
(vii) the leucine at position 8 of the FG loop (SEQ ID NO: 75) is substituted with an amino acid selected from the group consisting of A, C, E, F, H, I, K, M, N, Q, R, S, T, V, W, or Y;
(viii) the lysine at position 9 of the FG loop (SEQ ID NO: 75) is substituted with an amino acid selected from the group consisting of A, C, D, E, F, G, H, I, L, M, N, P, Q, R, S, T, V, W, or Y;
(ix) the tyrosine at position 10 of the FG loop (SEQ ID NO: 75) is substituted with the amino acid F or W; or
(x) the lysine at position 11 of the FG loop (SEQ ID NO: 75) is substituted with an amino acid selected from the group consisting of A, C, D, E, F, G, H, I, L, M, N, P, Q, R, S, T, V, W, or Y.

10. The nucleic acid of claim 9, wherein:
(i) the valine at position 2 of the FG loop (SEQ ID NO: 75) is substituted with an amino acid selected from the group consisting of A, C, I, L, or M;
(ii) the threonine at position 3 of the FG loop (SEQ ID NO: 75) is substituted with an amino acid selected from the group consisting of C, F, H, I, L, M, Q, R, S, V, W, or Y;
(iii) the aspartic acid at position 4 of the FG loop (SEQ ID NO: 75) is substituted with an amino acid selected from the group consisting of A, C, E, F, G, H, I, L, M, N, P, Q, S, T, V, W, or Y;
(iv) the threonine at position 5 of the FG loop (SEQ ID NO: 75) is substituted with an amino acid selected from the group consisting of A, C, D, E, F, G, H, I, K, L, M, N, Q, R, S, V, W, or Y;
(v) the glycine at position 6 of the FG loop (SEQ ID NO: 75) is substituted with an amino acid selected from the group consisting of A, D, E, F, H, I, L, M, N, Q, S, T, V, W, or Y;

(vi) the tyrosine at position 7 of the FG loop (SEQ ID NO: 75) is substituted with an amino acid selected from the group consisting of C, F, I, L, M, P, T, V, or W;

(vii) the leucine at position 8 of the FG loop (SEQ ID NO: 75) is substituted with an amino acid selected from the group consisting of C, F, H, I, K, M, N, Q, R, T, V, W, or Y;

(viii) the lysine at position 9 of the FG loop (SEQ ID NO: 75) is substituted with an amino acid selected from the group consisting of A, C, E, F, G, I, L, M, N, P, Q, R, S, T, V, W, or Y;

(ix) the tyrosine at position 10 of the FG loop (SEQ ID NO: 75) is substituted with the amino acid W; or (x) the lysine at position 11 of the FG loop (SEQ ID NO: 75) is substituted with an amino acid selected from the group consisting of A, C, D, E, G, H, L, M, N, P, Q, R, S, T, or V.

11. The nucleic acid of claim 9, wherein:

(i) the valine at position 2 of the FG loop (SEQ ID NO: 75) is substituted with the amino acid I;

(ii) the threonine at position 3 of the FG loop (SEQ ID NO: 75) is substituted with an amino acid selected from the group consisting of C, F, I, L, M, V, W, or Y;

(iii) the aspartic acid at position 4 of the FG loop (SEQ ID NO: 75) is substituted with an amino acid selected from the group consisting of A, C, E, F, G, H, I, L, M, N, Q, S, T, or V;

(iv) the threonine at position 5 of the FG loop (SEQ ID NO: 75) is substituted with an amino acid selected from the group consisting of A, C, D, F, G, I, L, M, N, Q, S, V, W, or Y;

(v) the glycine at position 6 of the FG loop (SEQ ID NO: 75) is substituted with an amino acid selected from the group consisting of A, S, T, or W;

(vi) the tyrosine at position 7 of the FG loop (SEQ ID NO: 75) is substituted with an amino acid selected from the group consisting of F, I, V, or W;

(vii) the leucine at position 8 of the FG loop (SEQ ID NO: 75) is substituted with an amino acid selected from the group consisting of F, H, I, M, V, W, or Y;

(viii) the lysine at position 9 of the FG loop (SEQ ID NO: 75) is substituted with an amino acid selected from the group consisting of A, C, F, G, I, L, M, T, V, or W; or (ix) the lysine at position 11 of the FG loop (SEQ ID NO: 75) is substituted with an amino acid selected from the group consisting of A, G, L, M, P, Q, or R.

12. The nucleic acid of claim 1, wherein the $^{10}$Fn3 domain comprises the amino acid sequence of SEQ ID NO: 118.

13. The nucleic acid of claim 1, wherein the polypeptide comprises the amino acid sequence of SEQ ID NO: 281.

14. The nucleic acid of claim 1, wherein the polypeptide comprises the amino acid sequence of SEQ ID NO: 331.

15. The nucleic acid of claim 1, wherein the polypeptide further comprises one or more pharmacokinetic (PK) moieties selected from the group consisting of Fc, Fc fragment, transferrin, serum albumin, a serum albumin binding protein, and a serum immunoglobulin binding protein.

16. The nucleic acid of claim 15, wherein the one or more PK moieties is an Fc.

17. The nucleic acid of claim 1, wherein the polypeptide comprises the amino acid sequence of SEQ ID NO: 273.

* * * * *

SEQUENCE LISTING

<160> NUMBER OF SEQ ID NOS: 331

<210> SEQ ID NO 1
<211> LENGTH: 375
<212> TYPE: PRT
<213> ORGANISM: Homo sapiens

<400> SEQUENCE: 1

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
```

```
                225                 230                 235                 240
            Phe Pro Gly Pro Gly Glu Asp Gly Leu Asn Pro Phe Leu Val Lys
                            245                 250                 255

Val Thr Asp Thr Pro Lys Arg Ser Arg Arg Asp Phe Gly Leu Asp Cys
                            260                 265                 270

Asp Glu His Ser Thr Glu Ser Arg Cys Cys Arg Tyr Pro Leu Thr Val
                            275                 280                 285

Asp Phe Glu Ala Phe Gly Trp Asp Trp Ile Ile Ala Pro Lys Arg Tyr
                290                 295                 300

Lys Ala Asn Tyr Cys Ser Gly Glu Cys Glu Phe Val Phe Leu Gln Lys
            305                 310                 315                 320

Tyr Pro His Thr His Leu Val His Gln Ala Asn Pro Arg Gly Ser Ala
                            325                 330                 335

Gly Pro Cys Cys Thr Pro Thr Lys Met Ser Pro Ile Asn Met Leu Tyr
                            340                 345                 350

Phe Asn Gly Lys Glu Gln Ile Ile Tyr Gly Lys Ile Pro Ala Met Val
                            355                 360                 365

Val Asp Arg Cys Gly Cys Ser
                            370                 375

<210> SEQ ID NO 2
<211> LENGTH: 352
<212> TYPE: PRT
<213> ORGANISM: Homo sapiens

<400> SEQUENCE: 2

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
                20                  25                  30

Ile Lys Ile Gln Ile Leu Ser Lys Leu Arg Leu Glu Thr Ala Pro Asn
            35                  40                  45

Ile Ser Lys Asp Val Ile Arg Gln Leu Leu Pro Lys Ala Pro Pro Leu
        50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                        85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
    210                 215                 220
```

```
Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
            245                 250                 255

Arg Cys Cys Arg Tyr Pro Leu Thr Val Asp Phe Glu Ala Phe Gly Trp
        260                 265                 270

Asp Trp Ile Ile Ala Pro Lys Arg Tyr Lys Ala Asn Tyr Cys Ser Gly
            275                 280                 285

Glu Cys Glu Phe Val Phe Leu Gln Lys Tyr Pro His Thr His Leu Val
    290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
            325                 330                 335

Ile Tyr Gly Lys Ile Pro Ala Met Val Val Asp Arg Cys Gly Cys Ser
        340                 345                 350

<210> SEQ ID NO 3
<211> LENGTH: 109
<212> TYPE: PRT
<213> ORGANISM: Homo sapiens

<400> SEQUENCE: 3

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 4
<211> LENGTH: 94
<212> TYPE: PRT
<213> ORGANISM: Homo sapiens

<400> SEQUENCE: 4

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90
```

```
<210> SEQ ID NO 5
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(21)
<223> OTHER INFORMATION: Xaa, if present, can be any naturally occurring
      amino acid
<220> FEATURE:
<221> NAME/KEY: misc_feature
<222> LOCATION: (26)..(45)
<223> OTHER INFORMATION: Xaa, if present, can be any naturally occurring
      amino acid
<220> FEATURE:
<221> NAME/KEY: misc_feature
<222> LOCATION: (54)..(73)
<223> OTHER INFORMATION: Xaa, if present, can be any naturally occurring
      amino acid
<220> FEATURE:
<221> NAME/KEY: misc_feature
<222> LOCATION: (79)..(98)
<223> OTHER INFORMATION: Xaa, if present, can be any naturally occurring
      amino acid
<220> FEATURE:
<221> NAME/KEY: misc_feature
<222> LOCATION: (102)..(121)
<223> OTHER INFORMATION: Xaa, if present, can be any naturally occurring
      amino acid
<220> FEATURE:
<221> NAME/KEY: misc_feature
<222> LOCATION: (131)..(150)
<223> OTHER INFORMATION: Xaa, if present, can be any naturally occurring
      amino acid

<400> SEQUENCE: 5

Glu Val Val Ala Ala Thr Xaa Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Tyr Tyr Arg
        35                  40                  45

Ile Thr Tyr Gly Glu Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Gln Glu Phe Thr Val Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Ala Thr Ile Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Asp Tyr Thr Ile Thr Val Tyr
        115                 120                 125

Ala Val Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Ile Ser Ile Asn Tyr Arg Thr
145                 150                 155

<210> SEQ ID NO 6
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (13)..(32)
<223> OTHER INFORMATION: Xaa, if present, can be any naturally occurring
      amino acid
<220> FEATURE:
<221> NAME/KEY: misc_feature
<222> LOCATION: (53)..(72)
<223> OTHER INFORMATION: Xaa, if present, can be any naturally occurring
      amino acid
<220> FEATURE:
<221> NAME/KEY: misc_feature
<222> LOCATION: (92)..(111)
<223> OTHER INFORMATION: Xaa, if present, can be any naturally occurring
      amino acid

<400> SEQUENCE: 6

Glu Val Val Ala Ala Thr Pro Thr Ser Leu Leu Ile Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Tyr Tyr Arg Ile Thr Tyr Gly Glu Thr Gly Gly Asn Ser Pro Val Gln
        35                  40                  45

Glu Phe Thr Val Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Ala Thr Ile Ser Gly Leu Lys Pro
65                  70                  75                  80

Gly Val Asp Tyr Thr Ile Thr Val Tyr Ala Val Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Ile
            100                 105                 110

Ser Ile Asn Tyr Arg Thr
        115

<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

Ser Trp Ser Leu Pro His Ala Gly His Val Asn
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Ser Trp Val Ser Pro Arg Gly Arg Ala Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Ser Trp Glu Val Pro Arg Gly Leu Ala Arg
1               5                   10
```

```
<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Ser Trp Trp Ala Pro Leu Gly Leu Ala Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Ser Trp Thr Leu Pro His Ala Gly Leu Ala His
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Ser Trp Tyr Leu Pro Tyr Pro Ala His Met Asn
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Ser Trp Ser Leu Pro Phe Ala Gly His Leu Asn
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Ser Trp Ser Leu Pro Tyr Ser Gly Leu Ala Asn
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Ser Trp Ser Leu Pro His Ala Gly His Ala His
1               5                   10
```

```
<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Ser Trp Thr Leu Pro Asn Phe Gly Leu Ile Asn
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic

<400> SEQUENCE: 17

Ser Trp Thr Leu Pro His Ala Gly Arg Ala His
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic

<400> SEQUENCE: 18

Ser Trp Ser Leu Pro Tyr Ala Gly His Leu Asn
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic

<400> SEQUENCE: 19

Ser Trp Ser Leu Pro Tyr Ala Ala His Met Asn
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Ser Trp Ser Leu Pro Tyr Pro Gly His Leu Asn
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic

<400> SEQUENCE: 21

Ser Trp Ser Leu Pro Tyr Ala Gly His Ala His
1               5                   10

<210> SEQ ID NO 22
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 22

Ser Trp Asp Ala Pro Gly Gly Leu Ala Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic

<400> SEQUENCE: 23

Ser Trp Ser Leu Pro Thr Pro Gly Leu Ala His
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Ser Trp Ser Leu Pro His Arg Gly Val Ala Asn
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Ser Trp Ser Leu Pro Ser Ser Gly Val Ala His
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Ser Trp Ser Leu Pro His His Gly Phe Gly His
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic

<400> SEQUENCE: 27

Ser Trp Ser Leu Pro His Ala Gly Asp Ala His
1               5                   10

<210> SEQ ID NO 28
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 28

Ser Trp Ser Leu Pro His Asn Gly Val Ala His
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic

<400> SEQUENCE: 29

Ser Trp Ser Leu Pro Arg Gln Gly Leu Ala Asn
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic

<400> SEQUENCE: 30

Ser Trp Ser Leu Pro Gly Pro Gly His Phe His
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic

<400> SEQUENCE: 31

Ser Trp Ser Leu Pro His Pro Gly Leu Gly His
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Ser Trp Asp Ala Pro Arg Gly Leu Ala Arg
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic

<400> SEQUENCE: 33

Ser Trp Asp Ala Pro Ala Gly Leu Ala Arg
1               5                   10

<210> SEQ ID NO 34
<211> LENGTH: 11
<212> TYPE: PRT
```

```
<213> ORGANISM: Artificial Sequence
<220> FEATURE:
<223> OTHER INFORMATION: Synthetic

<400> SEQUENCE: 34

Ser Trp Ser Leu Pro His Gln Gly Lys Ala Asn
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Ser Trp Asp Ala Pro Lys Gly Leu Ala Arg
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic

<400> SEQUENCE: 36

Ser Trp Ser Leu Pro Asn Pro Gly Ile Ala His
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic

<400> SEQUENCE: 37

Ser Trp Ser Leu Pro Arg Pro Gly Asn Ala His
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Ser Trp Ser Leu Pro Asn Pro Gly Asn Ala His
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Synthetic

<400> SEQUENCE: 39

Pro Gly Arg Gly Val Thr
1               5

<210> SEQ ID NO 40
<211> LENGTH: 6
<212> TYPE: PRT
<213> ORGANISM: Artificial Sequence
```

```
<220> FEATURE:
<223> OTHER INFORMATION: Synthetic

<400> SEQUENCE: 40

Pro Gly Arg Gly Ser Thr
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic

<400> SEQUENCE: 41

Leu Gly Arg Gly Ser Thr
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

Pro Gly Arg Gly Leu Thr
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic

<400> SEQUENCE: 43

Ile Gly Arg Gly Ser Thr
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Phe Gly Arg Gly Thr Thr
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Val Gly Arg Gly Asn Thr
1               5

<210> SEQ ID NO 46
<211> LENGTH: 12
<212> TYPE: PRT
<213> ORGANISM: Artificial Sequence
<220> FEATURE:
```

```
<223> OTHER INFORMATION: Synthetic

<400> SEQUENCE: 46

Thr Leu Thr Lys Ser Gln Met Ile His Tyr Met Pro
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Thr Ile Tyr Arg Asp Gly Met Ser His His Asp Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic

<400> SEQUENCE: 48

Thr Val Tyr Arg Asp Gly Pro Leu Leu Leu Ala Pro
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic

<400> SEQUENCE: 49

Thr Ile Phe Arg Thr Gly Met Val Gln Tyr Asp Pro
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic

<400> SEQUENCE: 50

Thr Leu Thr Asn Ser Glu Ile Ile Leu Tyr Lys Pro
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic

<400> SEQUENCE: 51

Thr Leu Thr Lys Ser Gln Ile Leu His His Arg Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 52

Thr Leu Thr Arg Ser Lys Ile Ile His Tyr Met Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

Thr Leu Thr His Ser Asn Ile Ile Arg Tyr Val Pro
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic

<400> SEQUENCE: 54

Thr Val Ser Ser Thr Lys Val Ile Val Tyr Leu Pro
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic

<400> SEQUENCE: 55

Thr Ile Thr Lys Ser Thr Ile Ile Ile Tyr Lys Pro
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Thr Val Thr Thr Thr Ser Val Ile Leu Tyr Lys Pro
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Thr Leu Thr Lys Ser Gln Leu Ile His Tyr Met Pro
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 58

Thr Leu Thr Arg Ser Gln Val Ile His Tyr Met Pro
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59

Thr Leu Thr Lys Ser Lys Ile Ile His Tyr Met Pro
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic

<400> SEQUENCE: 60

Thr Val Ser Ser Thr Lys Val Ile His Tyr Lys Pro
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic

<400> SEQUENCE: 61

Thr Leu Thr Lys Ser Lys Val Ile His Tyr Met Pro
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic

<400> SEQUENCE: 62

Thr Val Thr Thr Thr Lys Val Ile His Tyr Lys Pro
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic

<400> SEQUENCE: 63

Thr Ile Asp Arg Asp Gly Val Asn His Phe Ala Pro
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic

<400> SEQUENCE: 64
```

```
Thr Val Thr His His Gly Val Ile Gly Tyr Lys Pro
1               5                   10
```

<210> SEQ ID NO 65
<211> LENGTH: 12
<212> TYPE: PRT
<213> ORGANISM: Artificial Sequence
<220> FEATURE:
<223> OTHER INFORMATION: Synthetic

<400> SEQUENCE: 65

```
Thr Leu Thr Gly Ala Asn Val Ile Ile Tyr Lys Pro
1               5                   10
```

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

```
Thr Val Thr Asn Thr Gly Val Ile Ile Tyr Lys Pro
1               5                   10
```

<210> SEQ ID NO 67
<211> LENGTH: 12
<212> TYPE: PRT
<213> ORGANISM: Artificial Sequence
<220> FEATURE:
<223> OTHER INFORMATION: Synthetic

<400> SEQUENCE: 67

```
Thr Val Thr Ala Thr Gly Ile Ile Ile Tyr Lys Pro
1               5                   10
```

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

```
Thr Val Thr Arg Ala Gly Phe Tyr Arg Tyr Lys Pro
1               5                   10
```

<210> SEQ ID NO 69
<211> LENGTH: 12
<212> TYPE: PRT
<213> ORGANISM: Artificial Sequence
<220> FEATURE:
<223> OTHER INFORMATION: Synthetic

<400> SEQUENCE: 69

```
Thr Val Thr Arg Glu Glu Val Ile Ser Tyr Lys Pro
1               5                   10
```

<210> SEQ ID NO 70
<211> LENGTH: 12
<212> TYPE: PRT
<213> ORGANISM: Artificial Sequence
<220> FEATURE:
<223> OTHER INFORMATION: Synthetic

<400> SEQUENCE: 70

Thr Val Thr Ala Ala Gly Val Ile Ile Tyr Lys Pro
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic

<400> SEQUENCE: 71

Thr Val Thr Ala Asn Gln Pro Ile Ile Tyr Lys Pro
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic

<400> SEQUENCE: 72

Thr Ile Thr Pro Glu Thr Ile Ile Val Tyr Lys Pro
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic

<400> SEQUENCE: 73

Thr Ile Asp Arg Asp Gly Thr Arg Ser Phe Asp Pro
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic

<400> SEQUENCE: 74

Thr Ile Phe Arg Asp Gly Pro Val Thr Trp Asp Pro
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic

<400> SEQUENCE: 75

Thr Val Thr Asp Thr Gly Tyr Leu Lys Tyr Lys Pro
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Thr Leu Thr Gly Ser Asp Thr Ile Phe Tyr Lys Pro

```
1               5                   10
```

<210> SEQ ID NO 77
<211> LENGTH: 12
<212> TYPE: PRT
<213> ORGANISM: Artificial Sequence
<220> FEATURE:
<223> OTHER INFORMATION: Synthetic

<400> SEQUENCE: 77

```
Thr Val Thr Gly Lys Asp Val Ile Lys Tyr Lys Pro
1               5                   10
```

<210> SEQ ID NO 78
<211> LENGTH: 12
<212> TYPE: PRT
<213> ORGANISM: Artificial Sequence
<220> FEATURE:
<223> OTHER INFORMATION: Synthetic

<400> SEQUENCE: 78

```
Thr Ile Phe Arg Asp Gly Val Val Asn Tyr Gly Pro
1               5                   10
```

<210> SEQ ID NO 79
<211> LENGTH: 12
<212> TYPE: PRT
<213> ORGANISM: Artificial Sequence
<220> FEATURE:
<223> OTHER INFORMATION: Synthetic

<400> SEQUENCE: 79

```
Thr Val Thr Asp Thr Gly Phe Ile Thr Tyr Lys Pro
1               5                   10
```

<210> SEQ ID NO 80
<211> LENGTH: 110
<212> TYPE: PRT
<213> ORGANISM: Artificial Sequence
<220> FEATURE:
<223> OTHER INFORMATION: Synthetic

<400> SEQUENCE: 80

```
Met Gly Val Ser Asp Val Pro Arg Asp Leu Glu Val Val Ala Ala Thr
1               5                   10                  15

Pro Thr Ser Leu Leu Ile Ser Trp Ser Leu Pro His Ala Gly His Val
                20                  25                  30

Asn Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
        50                  55                  60

Leu Lys Pro Gly Val Asp Tyr Thr Ile Thr Val Tyr Ala Val Thr Leu
65                  70                  75                  80

Thr Lys Ser Gln Met Ile His Tyr Met Pro Ile Ser Ile Asn Tyr Arg
                85                  90                  95

Thr Glu Ile Asp Lys Pro Ser Gln His His His His His His
            100                 105                 110
```

<210> SEQ ID NO 81
<211> LENGTH: 109
<212> TYPE: PRT
<213> ORGANISM: Artificial Sequence
<220> FEATURE:
<223> OTHER INFORMATION: Synthetic -continued

<400> SEQUENCE: 81

Met Gly Val Ser Asp Val Pro Arg Asp Leu Glu Val Val Ala Ala Thr
1               5                   10                  15

Pro Thr Ser Leu Leu Ile Ser Trp Val Ser Pro Arg Gly Arg Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Arg Gly Ser Thr Ala Thr Ile Ser Gly Leu
50                  55                  60

Lys Pro Gly Val Asp Tyr Thr Ile Thr Val Tyr Ala Val Thr Ile Tyr
65                  70                  75                  80

Arg Asp Gly Met Ser His His Asp Pro Ile Ser Ile Asn Tyr Arg Thr
                85                  90                  95

Glu Ile Asp Lys Pro Ser Gln His His His His His
            100                 105

<210> SEQ ID NO 82
<211> LENGTH: 109
<212> TYPE: PRT
<213> ORGANISM: Artificial Sequence
<220> FEATURE:
<223> OTHER INFORMATION: Synthetic

<400> SEQUENCE: 82

Met Gly Val Ser Asp Val Pro Arg Asp Leu Glu Val Val Ala Ala Thr
1               5                   10                  15

Pro Thr Ser Leu Leu Ile Ser Trp Glu Val Pro Arg Gly Leu Ala Arg
            20                  25                  30

Tyr Tyr Arg Ile Thr Tyr Gly Glu Thr Gly Gly Asn Ser Pro Val Gln
        35                  40                  45

Glu Phe Thr Val Leu Gly Arg Gly Ser Thr Ala Thr Ile Ser Gly Leu
50                  55                  60

Lys Pro Gly Val Asp Tyr Thr Ile Thr Val Tyr Ala Val Thr Val Tyr
65                  70                  75                  80

Arg Asp Gly Pro Leu Leu Leu Ala Pro Ile Ser Ile Asn Tyr Arg Thr
                85                  90                  95

Glu Ile Asp Lys Pro Ser Gln His His His His His
            100                 105

<210> SEQ ID NO 83
<211> LENGTH: 109
<212> TYPE: PRT
<213> ORGANISM: Artificial Sequence
<220> FEATURE:
<223> OTHER INFORMATION: Synthetic

<400> SEQUENCE: 83

Met Gly Val Ser Asp Val Pro Arg Asp Leu Glu Val Val Ala Ala Thr
1               5                   10                  15

Pro Thr Ser Leu Leu Ile Ser Trp Trp Ala Pro Leu Gly Leu Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Arg Gly Ser Thr Ala Thr Ile Ser Gly Leu
50                  55                  60

Lys Pro Gly Val Asp Tyr Thr Ile Thr Val Tyr Ala Val Thr Ile Phe
65                  70                  75                  80

```
Arg Thr Gly Met Val Gln Tyr Asp Pro Ile Ser Ile Asn Tyr Arg Thr
                85                  90                  95

Glu Ile Asp Lys Pro Ser Gln His His His His His
            100                 105
```

<210> SEQ ID NO 84
<211> LENGTH: 110
<212> TYPE: PRT
<213> ORGANISM: Artificial Sequence
<220> FEATURE:
<223> OTHER INFORMATION: Synthetic

<400> SEQUENCE: 84

```
Met Gly Val Ser Asp Val Pro Arg Asp Leu Glu Val Val Ala Ala Thr
1               5                   10                  15

Pro Thr Ser Leu Leu Ile Ser Trp Thr Leu Pro His Ala Gly Leu Ala
                20                  25                  30

His Tyr Tyr Arg Ile Thr Tyr Gly Glu Thr Gly Gly Asn Ser Pro Val
                35                  40                  45

Gln Glu Phe Thr Val Pro Gly Arg Gly Val Thr Ala Thr Ile Ser Gly
            50                  55                  60

Leu Lys Pro Gly Val Asp Tyr Thr Ile Thr Val Tyr Ala Val Thr Leu
65                  70                  75                  80

Thr Asn Ser Glu Ile Ile Leu Tyr Lys Pro Ile Ser Ile Asn Tyr Arg
                85                  90                  95

Thr Glu Ile Asp Lys Pro Ser Gln His His His His His His
            100                 105                 110
```

<210> SEQ ID NO 85
<211> LENGTH: 110
<212> TYPE: PRT
<213> ORGANISM: Artificial Sequence
<220> FEATURE:
<223> OTHER INFORMATION: Synthetic

<400> SEQUENCE: 85

```
Met Gly Val Ser Asp Val Pro Arg Asp Leu Glu Val Val Ala Ala Thr
1               5                   10                  15

Pro Thr Ser Leu Leu Ile Ser Trp Tyr Leu Pro Tyr Pro Ala His Met
                20                  25                  30

Asn Tyr Tyr Arg Ile Thr Tyr Gly Glu Thr Gly Gly Asn Ser Pro Val
                35                  40                  45

Gln Glu Phe Thr Val Pro Gly Arg Gly Leu Thr Ala Thr Ile Ser Gly
            50                  55                  60

Leu Lys Pro Gly Val Asp Tyr Thr Ile Thr Val Tyr Ala Val Thr Leu
65                  70                  75                  80

Thr Lys Ser Gln Ile Leu His His Arg Pro Ile Ser Ile Asn Tyr Arg
                85                  90                  95

Thr Glu Ile Asp Lys Pro Ser Gln His His His His His His
            100                 105                 110
```

<210> SEQ ID NO 86
<211> LENGTH: 110
<212> TYPE: PRT
<213> ORGANISM: Artificial Sequence
<220> FEATURE:
<223> OTHER INFORMATION: Synthetic

<400> SEQUENCE: 86

```
Met Gly Val Ser Asp Val Pro Arg Asp Leu Glu Val Val Ala Ala Thr
1               5                   10                  15

Pro Thr Ser Leu Leu Ile Ser Trp Ser Leu Pro Phe Ala Gly His Leu
            20                  25                  30

Asn Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Arg Ser Lys Ile Ile His Tyr Met Pro Ile Ser Ile Asn Tyr Arg
                85                  90                  95

Thr Glu Ile Asp Lys Pro Ser Gln His His His His His
            100                 105                 110

<210> SEQ ID NO 87
<211> LENGTH: 110
<212> TYPE: PRT
<213> ORGANISM: Artificial Sequence
<220> FEATURE:
<223> OTHER INFORMATION: Synthetic

<400> SEQUENCE: 87

Met Gly Val Ser Asp Val Pro Arg Asp Leu Glu Val Val Ala Ala Thr
1               5                   10                  15

Pro Thr Ser Leu Leu Ile Ser Trp Ser Leu Pro Tyr Ser Gly Leu Ala
            20                  25                  30

Asn Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr His Ser Asn Ile Ile Arg Tyr Val Pro Ile Ser Ile Asn Tyr Arg
                85                  90                  95

Thr Glu Ile Asp Lys Pro Ser Gln His His His His His
            100                 105                 110

<210> SEQ ID NO 88
<211> LENGTH: 110
<212> TYPE: PRT
<213> ORGANISM: Artificial Sequence
<220> FEATURE:
<223> OTHER INFORMATION: Synthetic

<400> SEQUENCE: 88

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Ala Gly His Ala
            20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Ser Ser Thr Lys Val Ile Val Tyr Leu Pro Ile Ser Ile Asn Tyr Arg
                85                  90                  95
```

-continued

Thr Glu Ile Asp Lys Pro Ser Gln His His His His His
            100             105                 110

<210> SEQ ID NO 89
<211> LENGTH: 110
<212> TYPE: PRT
<213> ORGANISM: Artificial Sequence
<220> FEATURE:
<223> OTHER INFORMATION: Synthetic

<400> SEQUENCE: 89

Met Gly Val Ser Asp Val Pro Arg Asp Leu Glu Val Val Ala Ala Thr
1               5                   10                  15

Pro Thr Ser Leu Leu Ile Ser Trp Thr Leu Pro Asn Phe Gly Leu Ile
            20                  25                  30

Asn Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Ile
65                  70                  75                  80

Thr Lys Ser Thr Ile Ile Ile Tyr Lys Pro Ile Ser Ile Asn Tyr Arg
                85                  90                  95

Thr Glu Ile Asp Lys Pro Ser Gln His His His His His
            100             105                 110

<210> SEQ ID NO 90
<211> LENGTH: 110
<212> TYPE: PRT
<213> ORGANISM: Artificial Sequence
<220> FEATURE:
<223> OTHER INFORMATION: Synthetic

<400> SEQUENCE: 90

Met Gly Val Ser Asp Val Pro Arg Asp Leu Glu Val Val Ala Ala Thr
1               5                   10                  15

Pro Thr Ser Leu Leu Ile Ser Trp Thr Leu Pro His Ala Gly Arg Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Thr Thr Thr Ser Val Ile Leu Tyr Lys Pro Ile Ser Ile Asn Tyr Arg
                85                  90                  95

Thr Glu Ile Asp Lys Pro Ser Gln His His His His His
            100             105                 110

<210> SEQ ID NO 91
<211> LENGTH: 110
<212> TYPE: PRT
<213> ORGANISM: Artificial Sequence
<220> FEATURE:
<223> OTHER INFORMATION: Synthetic

<400> SEQUENCE: 91

Met Gly Val Ser Asp Val Pro Arg Asp Leu Glu Val Val Ala Ala Thr
1               5                   10                  15

Pro Thr Ser Leu Leu Ile Ser Trp Ser Leu Pro Tyr Ala Gly His Leu
            20                  25                  30

Asn Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Lys Ser Gln Leu Ile His Tyr Met Pro Ile Ser Ile Asn Tyr Arg
                85                  90                  95

Thr Glu Ile Asp Lys Pro Ser Gln His His His His His
            100                 105                 110

<210> SEQ ID NO 92
<211> LENGTH: 110
<212> TYPE: PRT
<213> ORGANISM: Artificial Sequence
<220> FEATURE:
<223> OTHER INFORMATION: Synthetic

<400> SEQUENCE: 92

Met Gly Val Ser Asp Val Pro Arg Asp Leu Glu Val Val Ala Ala Thr
1               5                   10                  15

Pro Thr Ser Leu Leu Ile Ser Trp Ser Leu Pro Tyr Ala Ala His Met
            20                  25                  30

Asn Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Arg Ser Gln Val Ile His Tyr Met Pro Ile Ser Ile Asn Tyr Arg
                85                  90                  95

Thr Glu Ile Asp Lys Pro Ser Gln His His His His His
            100                 105                 110

<210> SEQ ID NO 93
<211> LENGTH: 110
<212> TYPE: PRT
<213> ORGANISM: Artificial Sequence
<220> FEATURE:
<223> OTHER INFORMATION: Synthetic

<400> SEQUENCE: 93

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Ala Gly His Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Lys Ser Lys Ile Ile His Tyr Met Pro Ile Ser Ile Asn Tyr Arg
                85                  90                  95

Thr Glu Ile Asp Lys Pro Ser Gln His His His His His
            100                 105                 110

<210> SEQ ID NO 94
<211> LENGTH: 110
<212> TYPE: PRT
<213> ORGANISM: Artificial Sequence
<220> FEATURE:
<223> OTHER INFORMATION: Synthetic

<400> SEQUENCE: 94

```
Met Gly Val Ser Asp Val Pro Arg Asp Leu Glu Val Val Ala Ala Thr
1               5                   10                  15

Pro Thr Ser Leu Leu Ile Ser Trp Ser Leu Pro Tyr Pro Gly His Leu
            20                  25                  30

Asn Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Lys Ser Lys Ile Ile His Tyr Met Pro Ile Ser Ile Asn Tyr Arg
                85                  90                  95

Thr Glu Ile Asp Lys Pro Ser Gln His His His His His
            100                 105                 110
```

<210> SEQ ID NO 95
<211> LENGTH: 110
<212> TYPE: PRT
<213> ORGANISM: Artificial Sequence
<220> FEATURE:
<223> OTHER INFORMATION: Synthetic

<400> SEQUENCE: 95

```
Met Gly Val Ser Asp Val Pro Arg Asp Leu Glu Val Val Ala Ala Thr
1               5                   10                  15

Pro Thr Ser Leu Leu Ile Ser Trp Thr Leu Pro His Ala Gly Arg Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Arg Ser Lys Ile Ile His Tyr Met Pro Ile Ser Ile Asn Tyr Arg
                85                  90                  95

Thr Glu Ile Asp Lys Pro Ser Gln His His His His His
            100                 105                 110
```

<210> SEQ ID NO 96
<211> LENGTH: 110
<212> TYPE: PRT
<213> ORGANISM: Artificial Sequence
<220> FEATURE:
<223> OTHER INFORMATION: Synthetic

<400> SEQUENCE: 96

```
Met Gly Val Ser Asp Val Pro Arg Asp Leu Glu Val Val Ala Ala Thr
1               5                   10                  15

Pro Thr Ser Leu Leu Ile Ser Trp Ser Leu Pro Tyr Ala Gly His Ala
            20                  25                  30
```

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Lys Ser Lys Ile Ile His Tyr Met Pro Ile Ser Ile Asn Tyr Arg
                85                  90                  95

Thr Glu Ile Asp Lys Pro Ser Gln His His His His His His
            100                 105                 110

<210> SEQ ID NO 97
<211> LENGTH: 110
<212> TYPE: PRT
<213> ORGANISM: Artificial Sequence
<220> FEATURE:
<223> OTHER INFORMATION: Synthetic

<400> SEQUENCE: 97

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Ala Gly His Ala
            20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Arg Ser Lys Ile Ile His Tyr Met Pro Ile Ser Ile Asn Tyr Arg
                85                  90                  95

Thr Glu Ile Asp Lys Pro Ser Gln His His His His His His
            100                 105                 110

<210> SEQ ID NO 98
<211> LENGTH: 110
<212> TYPE: PRT
<213> ORGANISM: Artificial Sequence
<220> FEATURE:
<223> OTHER INFORMATION: Synthetic

<400> SEQUENCE: 98

Met Gly Val Ser Asp Val Pro Arg Asp Leu Glu Val Val Ala Ala Thr
1               5                   10                  15

Pro Thr Ser Leu Leu Ile Ser Trp Ser Leu Pro Tyr Pro Gly His Leu
            20                  25                  30

Asn Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Arg Ser Lys Ile Ile His Tyr Met Pro Ile Ser Ile Asn Tyr Arg
                85                  90                  95

Thr Glu Ile Asp Lys Pro Ser Gln His His His His His His
            100                 105                 110

<210> SEQ ID NO 99

<211> LENGTH: 110
<212> TYPE: PRT
<213> ORGANISM: Artificial Sequence
<220> FEATURE:
<223> OTHER INFORMATION: Synthetic

<400> SEQUENCE: 99

Met Gly Val Ser Asp Val Pro Arg Asp Leu Glu Val Val Ala Ala Thr
1               5                   10                  15

Pro Thr Ser Leu Leu Ile Ser Trp Thr Leu Pro His Ala Gly Arg Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Ser Ser Thr Lys Val Ile His Tyr Lys Pro Ile Ser Ile Asn Tyr Arg
                85                  90                  95

Thr Glu Ile Asp Lys Pro Ser Gln His His His His His His
            100                 105                 110

<210> SEQ ID NO 100
<211> LENGTH: 110
<212> TYPE: PRT
<213> ORGANISM: Artificial Sequence
<220> FEATURE:
<223> OTHER INFORMATION: Synthetic

<400> SEQUENCE: 100

Met Gly Val Ser Asp Val Pro Arg Asp Leu Glu Val Val Ala Ala Thr
1               5                   10                  15

Pro Thr Ser Leu Leu Ile Ser Trp Ser Leu Pro Tyr Ala Gly His Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Arg Ser Lys Ile Ile His Tyr Met Pro Ile Ser Ile Asn Tyr Arg
                85                  90                  95

Thr Glu Ile Asp Lys Pro Ser Gln His His His His His
            100                 105                 110

<210> SEQ ID NO 101
<211> LENGTH: 110
<212> TYPE: PRT
<213> ORGANISM: Artificial Sequence
<220> FEATURE:
<223> OTHER INFORMATION: Synthetic

<400> SEQUENCE: 101

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Ala Gly His Ala
            20                  25                  30

His Tyr Tyr Arg Ile Thr Tyr Gly Glu Thr Gly Gly Asn Ser Pro Val
        35                  40                  45

-continued

Gln Glu Phe Thr Val Pro Gly Arg Gly Val Thr Ala Thr Ile Ser Gly
            50                  55                  60

Leu Lys Pro Gly Val Asp Tyr Thr Ile Thr Val Tyr Ala Val Thr Leu
 65                  70                  75                  80

Thr Lys Ser Lys Val Ile His Tyr Met Pro Ile Ser Ile Asn Tyr Arg
                 85                  90                  95

Thr Glu Ile Asp Lys Pro Ser Gln His His His His His His
            100                 105                 110

<210> SEQ ID NO 102
<211> LENGTH: 110
<212> TYPE: PRT
<213> ORGANISM: Artificial Sequence
<220> FEATURE:
<223> OTHER INFORMATION: Synthetic

<400> SEQUENCE: 102

Met Gly Val Ser Asp Val Pro Arg Asp Leu Glu Val Val Ala Ala Thr
  1               5                  10                  15

Pro Thr Ser Leu Leu Ile Ser Trp Ser Leu Pro Tyr Pro Gly His Leu
                 20                  25                  30

Asn Tyr Tyr Arg Ile Thr Tyr Gly Glu Thr Gly Gly Asn Ser Pro Val
                 35                  40                  45

Gln Glu Phe Thr Val Pro Gly Arg Gly Val Thr Ala Thr Ile Ser Gly
            50                  55                  60

Leu Lys Pro Gly Val Asp Tyr Thr Ile Thr Val Tyr Ala Val Thr Leu
 65                  70                  75                  80

Thr Lys Ser Lys Val Ile His Tyr Met Pro Ile Ser Ile Asn Tyr Arg
                 85                  90                  95

Thr Glu Ile Asp Lys Pro Ser Gln His His His His His His
            100                 105                 110

<210> SEQ ID NO 103
<211> LENGTH: 110
<212> TYPE: PRT
<213> ORGANISM: Artificial Sequence
<220> FEATURE:
<223> OTHER INFORMATION: Synthetic

<400> SEQUENCE: 103

Met Gly Val Ser Asp Val Pro Arg Asp Leu Glu Val Val Ala Ala Thr
  1               5                  10                  15

Pro Thr Ser Leu Leu Ile Ser Trp Thr Leu Pro His Ala Gly Arg Ala
                 20                  25                  30

His Tyr Tyr Arg Ile Thr Tyr Gly Glu Thr Gly Gly Asn Ser Pro Val
                 35                  40                  45

Gln Glu Phe Thr Val Pro Gly Arg Gly Val Thr Ala Thr Ile Ser Gly
            50                  55                  60

Leu Lys Pro Gly Val Asp Tyr Thr Ile Thr Val Tyr Ala Val Thr Val
 65                  70                  75                  80

Ser Ser Thr Lys Val Ile Val Tyr Leu Pro Ile Ser Ile Asn Tyr Arg
                 85                  90                  95

Thr Glu Ile Asp Lys Pro Ser Gln His His His His His
            100                 105                 110

<210> SEQ ID NO 104
<211> LENGTH: 110
<212> TYPE: PRT
<213> ORGANISM: Artificial Sequence

```
<220> FEATURE:
<223> OTHER INFORMATION: Synthetic

<400> SEQUENCE: 104

Met Gly Val Ser Asp Val Pro Arg Asp Leu Glu Val Val Ala Ala Thr
1               5                   10                  15

Pro Thr Ser Leu Leu Ile Ser Trp Ser Leu Pro Tyr Ala Gly His Ala
                20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Lys Ser Lys Val Ile His Tyr Met Pro Ile Ser Ile Asn Tyr Arg
                85                  90                  95

Thr Glu Ile Asp Lys Pro Ser Gln His His His His His
            100                 105                 110

<210> SEQ ID NO 105
<211> LENGTH: 110
<212> TYPE: PRT
<213> ORGANISM: Artificial Sequence
<220> FEATURE:
<223> OTHER INFORMATION: Synthetic

<400> SEQUENCE: 105

Met Gly Val Ser Asp Val Pro Arg Asp Leu Glu Val Val Ala Ala Thr
1               5                   10                  15

Pro Thr Ser Leu Leu Ile Ser Trp Thr Leu Pro His Ala Gly Arg Ala
                20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Thr Thr Thr Lys Val Ile His Tyr Lys Pro Ile Ser Ile Asn Tyr Arg
                85                  90                  95

Thr Glu Ile Asp Lys Pro Ser Gln His His His His His
            100                 105                 110

<210> SEQ ID NO 106
<211> LENGTH: 109
<212> TYPE: PRT
<213> ORGANISM: Artificial Sequence
<220> FEATURE:
<223> OTHER INFORMATION: Synthetic

<400> SEQUENCE: 106

Met Gly Val Ser Asp Val Pro Arg Asp Leu Glu Val Val Ala Ala Thr
1               5                   10                  15

Pro Thr Ser Leu Leu Ile Ser Trp Asp Ala Pro Gly Gly Leu Ala Arg
                20                  25                  30

Tyr Tyr Arg Ile Thr Tyr Gly Glu Thr Gly Gly Asn Ser Pro Val Gln
            35                  40                  45

Glu Phe Thr Val Ile Gly Arg Gly Ser Thr Ala Thr Ile Ser Gly Leu
    50                  55                  60
```

Lys Pro Gly Val Asp Tyr Thr Ile Thr Val Tyr Ala Val Thr Ile Asp
65                  70                  75                  80

Arg Asp Gly Val Asn His Phe Ala Pro Ile Ser Ile Asn Tyr Arg Thr
                85                  90                  95

Glu Ile Asp Lys Pro Ser Gln His His His His His
                100                 105

<210> SEQ ID NO 107
<211> LENGTH: 110
<212> TYPE: PRT
<213> ORGANISM: Artificial Sequence
<220> FEATURE:
<223> OTHER INFORMATION: Synthetic

<400> SEQUENCE: 107

Met Gly Val Ser Asp Val Pro Arg Asp Leu Glu Val Val Ala Ala Thr
1               5                   10                  15

Pro Thr Ser Leu Leu Ile Ser Trp Ser Leu Pro Thr Pro Gly Leu Ala
                20                  25                  30

His Tyr Tyr Arg Ile Thr Tyr Gly Glu Thr Gly Gly Asn Ser Pro Val
                35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Thr His His Gly Val Ile Gly Tyr Lys Pro Ile Ser Ile Asn Tyr Arg
                85                  90                  95

Thr Glu Ile Asp Lys Pro Ser Gln His His His His His
                100                 105                 110

<210> SEQ ID NO 108
<211> LENGTH: 110
<212> TYPE: PRT
<213> ORGANISM: Artificial Sequence
<220> FEATURE:
<223> OTHER INFORMATION: Synthetic

<400> SEQUENCE: 108

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Arg Gly Val Ala
                20                  25                  30

Asn Tyr Tyr Arg Ile Thr Tyr Gly Glu Thr Gly Gly Asn Ser Pro Val
                35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Gly Ala Asn Val Ile Ile Tyr Lys Pro Ile Ser Ile Asn Tyr Arg
                85                  90                  95

Thr Glu Ile Asp Lys Pro Ser Gln His His His His His
                100                 105                 110

<210> SEQ ID NO 109
<211> LENGTH: 110
<212> TYPE: PRT
<213> ORGANISM: Artificial Sequence
<220> FEATURE:
<223> OTHER INFORMATION: Synthetic -continued

```
<400> SEQUENCE: 109

Met Gly Val Ser Asp Val Pro Arg Asp Leu Glu Val Val Ala Ala Thr
1               5                   10                  15

Pro Thr Ser Leu Leu Ile Ser Trp Ser Leu Pro Ser Ser Gly Val Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Thr Asn Thr Gly Val Ile Ile Tyr Lys Pro Ile Ser Ile Asn Tyr Arg
                85                  90                  95

Thr Glu Ile Asp Lys Pro Ser Gln His His His His His His
            100                 105                 110

<210> SEQ ID NO 110
<211> LENGTH: 110
<212> TYPE: PRT
<213> ORGANISM: Artificial Sequence
<220> FEATURE:
<223> OTHER INFORMATION: Synthetic

<400> SEQUENCE: 110

Met Gly Val Ser Asp Val Pro Arg Asp Leu Glu Val Val Ala Ala Thr
1               5                   10                  15

Pro Thr Ser Leu Leu Ile Ser Trp Ser Leu Pro His His Gly Phe Gly
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Thr Ala Thr Gly Ile Ile Ile Tyr Lys Pro Ile Ser Ile Asn Tyr Arg
                85                  90                  95

Thr Glu Ile Asp Lys Pro Ser Gln His His His His His His
            100                 105                 110

<210> SEQ ID NO 111
<211> LENGTH: 110
<212> TYPE: PRT
<213> ORGANISM: Artificial Sequence
<220> FEATURE:
<223> OTHER INFORMATION: Synthetic

<400> SEQUENCE: 111

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Ala Gly Asp Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80
```

Thr Arg Ala Gly Phe Tyr Arg Tyr Lys Pro Ile Ser Ile Asn Tyr Arg
            85                  90                  95

Thr Glu Ile Asp Lys Pro Ser Gln His His His His His His
            100                 105                 110

<210> SEQ ID NO 112
<211> LENGTH: 110
<212> TYPE: PRT
<213> ORGANISM: Artificial Sequence
<220> FEATURE:
<223> OTHER INFORMATION: Synthetic

<400> SEQUENCE: 112

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Asn Gly Val Ala
            20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
        50                  55                  60

Leu Lys Pro Gly Val Asp Tyr Thr Ile Thr Val Tyr Ala Val Thr Val
65                  70                  75                  80

Thr Arg Glu Glu Val Ile Ser Tyr Lys Pro Ile Ser Ile Asn Tyr Arg
            85                  90                  95

Thr Glu Ile Asp Lys Pro Ser Gln His His His His His His
            100                 105                 110

<210> SEQ ID NO 113
<211> LENGTH: 110
<212> TYPE: PRT
<213> ORGANISM: Artificial Sequence
<220> FEATURE:
<223> OTHER INFORMATION: Synthetic

<400> SEQUENCE: 113

Met Gly Val Ser Asp Val Pro Arg Asp Leu Glu Val Val Ala Ala Thr
1               5                   10                  15

Pro Thr Ser Leu Leu Ile Ser Trp Ser Leu Pro Arg Gln Gly Leu Ala
            20                  25                  30

Asn Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
        50                  55                  60

Leu Lys Pro Gly Val Asp Tyr Thr Ile Thr Val Tyr Ala Val Thr Val
65                  70                  75                  80

Thr Ala Ala Gly Val Ile Ile Tyr Lys Pro Ile Ser Ile Asn Tyr Arg
            85                  90                  95

Thr Glu Ile Asp Lys Pro Ser Gln His His His His His His
            100                 105                 110

<210> SEQ ID NO 114
<211> LENGTH: 110
<212> TYPE: PRT
<213> ORGANISM: Artificial Sequence
<220> FEATURE:
<223> OTHER INFORMATION: Synthetic

<400> SEQUENCE: 114

Met Gly Val Ser Asp Val Pro Arg Asp Leu Glu Val Val Ala Ala Thr

```
1               5                   10                  15
Pro Thr Ser Leu Leu Ile Ser Trp Ser Leu Pro Gly Pro Gly His Phe
            20                  25                  30

His Tyr Tyr Arg Ile Thr Tyr Gly Glu Thr Gly Gly Asn Ser Pro Val
                35                  40                  45

Gln Glu Phe Thr Val Pro Gly Arg Gly Val Thr Ala Thr Ile Ser Gly
            50                  55                  60

Leu Lys Pro Gly Val Asp Tyr Thr Ile Thr Val Tyr Ala Val Thr Val
65                  70                  75                  80

Thr Ala Asn Gln Pro Ile Ile Tyr Lys Pro Ile Ser Ile Asn Tyr Arg
                85                  90                  95

Thr Glu Ile Asp Lys Pro Ser Gln His His His His His
                100                 105                 110

<210> SEQ ID NO 115
<211> LENGTH: 110
<212> TYPE: PRT
<213> ORGANISM: Artificial Sequence
<220> FEATURE:
<223> OTHER INFORMATION: Synthetic

<400> SEQUENCE: 115

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Pro Gly Leu Gly
            20                  25                  30

His Tyr Tyr Arg Ile Thr Tyr Gly Glu Thr Gly Gly Asn Ser Pro Val
                35                  40                  45

Gln Glu Phe Thr Val Pro Gly Arg Gly Val Thr Ala Thr Ile Ser Gly
            50                  55                  60

Leu Lys Pro Gly Val Asp Tyr Thr Ile Thr Val Tyr Ala Val Thr Ile
65                  70                  75                  80

Thr Pro Glu Thr Ile Ile Val Tyr Lys Pro Ile Ser Ile Asn Tyr Arg
                85                  90                  95

Thr Glu Ile Asp Lys Pro Ser Gln His His His His His His
                100                 105                 110

<210> SEQ ID NO 116
<211> LENGTH: 109
<212> TYPE: PRT
<213> ORGANISM: Artificial Sequence
<220> FEATURE:
<223> OTHER INFORMATION: Synthetic

<400> SEQUENCE: 116

Met Gly Val Ser Asp Val Pro Arg Asp Leu Glu Val Val Ala Ala Thr
1               5                   10                  15

Pro Thr Ser Leu Leu Ile Ser Trp Asp Ala Pro Arg Gly Leu Ala Arg
            20                  25                  30

Tyr Tyr Arg Ile Thr Tyr Gly Glu Thr Gly Gly Asn Ser Pro Val Gln
                35                  40                  45

Glu Phe Thr Val Phe Gly Arg Gly Thr Ala Thr Ile Ser Gly Leu
            50                  55                  60

Lys Pro Gly Val Asp Tyr Thr Ile Thr Val Tyr Ala Val Thr Ile Asp
65                  70                  75                  80

Arg Asp Gly Thr Arg Ser Phe Asp Pro Ile Ser Ile Asn Tyr Arg Thr
                85                  90                  95
```

Glu Ile Asp Lys Pro Ser Gln His His His His His
            100                 105

<210> SEQ ID NO 117
<211> LENGTH: 109
<212> TYPE: PRT
<213> ORGANISM: Artificial Sequence
<220> FEATURE:
<223> OTHER INFORMATION: Synthetic

<400> SEQUENCE: 117

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Gly Leu Ala Arg
            20                  25                  30

Tyr Tyr Arg Ile Thr Tyr Gly Glu Thr Gly Gly Asn Ser Pro Val Gln
        35                  40                  45

Glu Phe Thr Val Val Gly Arg Gly Asn Thr Ala Thr Ile Ser Gly Leu
    50                  55                  60

Lys Pro Gly Val Asp Tyr Thr Ile Thr Val Tyr Ala Val Thr Ile Phe
65                  70                  75                  80

Arg Asp Gly Pro Val Thr Trp Asp Pro Ile Ser Ile Asn Tyr Arg Thr
                85                  90                  95

Glu Ile Asp Lys Pro Ser Gln His His His His His
            100                 105

<210> SEQ ID NO 118
<211> LENGTH: 110
<212> TYPE: PRT
<213> ORGANISM: Artificial Sequence
<220> FEATURE:
<223> OTHER INFORMATION: Synthetic

<400> SEQUENCE: 118

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Gln Gly Lys Ala
            20                  25                  30

Asn Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Thr Asp Thr Gly Tyr Leu Lys Tyr Lys Pro Ile Ser Ile Asn Tyr Arg
                85                  90                  95

Thr Glu Ile Asp Lys Pro Ser Gln His His His His His
            100                 105                 110

<210> SEQ ID NO 119
<211> LENGTH: 109
<212> TYPE: PRT
<213> ORGANISM: Artificial Sequence
<220> FEATURE:
<223> OTHER INFORMATION: Synthetic

<400> SEQUENCE: 119

Met Gly Val Ser Asp Val Pro Arg Asp Leu Glu Val Val Ala Ala Thr
1               5                   10                  15

Pro Thr Ser Leu Leu Ile Ser Trp Asp Ala Pro Lys Gly Leu Ala Arg

```
                20                  25                  30
Tyr Tyr Arg Ile Thr Tyr Gly Glu Thr Gly Gly Asn Ser Pro Val Gln
            35                  40                  45

Glu Phe Thr Val Val Gly Arg Gly Asn Thr Ala Thr Ile Ser Gly Leu
         50                  55                  60

Lys Pro Gly Val Asp Tyr Thr Ile Thr Val Tyr Ala Val Thr Ile Phe
 65                  70                  75                  80

Arg Asp Gly Pro Val Thr Trp Asp Pro Ile Ser Ile Asn Tyr Arg Thr
                 85                  90                  95

Glu Ile Asp Lys Pro Ser Gln His His His His His His
                100                 105

<210> SEQ ID NO 120
<211> LENGTH: 110
<212> TYPE: PRT
<213> ORGANISM: Artificial Sequence
<220> FEATURE:
<223> OTHER INFORMATION: Synthetic

<400> SEQUENCE: 120

Met Gly Val Ser Asp Val Pro Arg Asp Leu Glu Val Val Ala Ala Thr
 1               5                  10                  15

Pro Thr Ser Leu Leu Ile Ser Trp Ser Leu Pro Asn Pro Gly Ile Ala
                20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
         50                  55                  60

Leu Lys Pro Gly Val Asp Tyr Thr Ile Thr Val Tyr Ala Val Thr Leu
 65                  70                  75                  80

Thr Gly Ser Asp Thr Ile Phe Tyr Lys Pro Ile Ser Ile Asn Tyr Arg
                 85                  90                  95

Thr Glu Ile Asp Lys Pro Ser Gln His His His His His
                100                 105                 110

<210> SEQ ID NO 121
<211> LENGTH: 110
<212> TYPE: PRT
<213> ORGANISM: Artificial Sequence
<220> FEATURE:
<223> OTHER INFORMATION: Synthetic

<400> SEQUENCE: 121

Met Gly Val Ser Asp Val Pro Arg Asp Leu Glu Val Val Ala Ala Thr
 1               5                  10                  15

Pro Thr Ser Leu Leu Ile Ser Trp Ser Leu Pro Arg Pro Gly Asn Ala
                20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
         50                  55                  60

Leu Lys Pro Gly Val Asp Tyr Thr Ile Thr Val Tyr Ala Val Thr Val
 65                  70                  75                  80

Thr Gly Lys Asp Val Ile Lys Tyr Lys Pro Ile Ser Ile Asn Tyr Arg
                 85                  90                  95

Thr Glu Ile Asp Lys Pro Ser Gln His His His His His
                100                 105                 110
```

<210> SEQ ID NO 122
<211> LENGTH: 109
<212> TYPE: PRT
<213> ORGANISM: Artificial Sequence
<220> FEATURE:
<223> OTHER INFORMATION: Synthetic

<400> SEQUENCE: 122

Met Gly Val Ser Asp Val Pro Arg Asp Leu Glu Val Val Ala Ala Thr
1               5                   10                  15
Pro Thr Ser Leu Leu Ile Ser Trp Asp Ala Pro Ala Gly Leu Ala Arg
            20                  25                  30
Tyr Tyr Arg Ile Thr Tyr Gly Glu Thr Gly Gly Asn Ser Pro Val Gln
        35                  40                  45
Glu Phe Thr Val Val Gly Arg Gly Asn Thr Ala Thr Ile Ser Gly Leu
    50                  55                  60
Lys Pro Gly Val Asp Tyr Thr Ile Thr Val Tyr Ala Val Thr Ile Phe
65                  70                  75                  80
Arg Asp Gly Val Val Asn Tyr Gly Pro Ile Ser Ile Asn Tyr Arg Thr
                85                  90                  95
Glu Ile Asp Lys Pro Ser Gln His His His His His
            100                 105

<210> SEQ ID NO 123
<211> LENGTH: 110
<212> TYPE: PRT
<213> ORGANISM: Artificial Sequence
<220> FEATURE:
<223> OTHER INFORMATION: Synthetic

<400> SEQUENCE: 123

Met Gly Val Ser Asp Val Pro Arg Asp Leu Glu Val Val Ala Ala Thr
1               5                   10                  15
Pro Thr Ser Leu Leu Ile Ser Trp Ser Leu Pro Asn Pro Gly Asn Ala
            20                  25                  30
His Tyr Tyr Arg Ile Thr Tyr Gly Glu Thr Gly Gly Asn Ser Pro Val
        35                  40                  45
Gln Glu Phe Thr Val Pro Gly Arg Gly Val Thr Ala Thr Ile Ser Gly
    50                  55                  60
Leu Lys Pro Gly Val Asp Tyr Thr Ile Thr Val Tyr Ala Val Thr Val
65                  70                  75                  80
Thr Asp Thr Gly Phe Ile Thr Tyr Lys Pro Ile Ser Ile Asn Tyr Arg
                85                  90                  95
Thr Glu Ile Asp Lys Pro Ser Gln His His His His His
            100                 105                 110

<210> SEQ ID NO 124
<211> LENGTH: 330
<212> TYPE: DNA
<213> ORGANISM: Artificial Sequence
<220> FEATURE:
<223> OTHER INFORMATION: Synthetic

<400> SEQUENCE: 124
atgggagttt ctgatgtgcc gcgcgacctg gaagtggttg ctgccacccc caccagcctg     60
ctgatcagct ggtctctgcc gcatgctggt catgtgaact attaccgcat cacttacggc    120
gaaacaggag gcaatagccc tgtccaggag ttcactgtgc ctggtcgtgg tgttacagct    180
accatcagcg gccttaaacc tggcgttgat tataccatca ctgtgtatgc tgtcactctg    240

```
actaaatctc agatgatcca ttacatgcca atttccatta attaccgcac agaaattgac    300
aaaccatccc agcaccatca ccaccaccac                                     330
```

<210> SEQ ID NO 125
<211> LENGTH: 327
<212> TYPE: DNA
<213> ORGANISM: Artificial Sequence
<220> FEATURE:
<223> OTHER INFORMATION: Synthetic

<400> SEQUENCE: 125

```
atgggagttt ctgatgtgcc gcgcgacctg gaagtggttg ctgccacccc caccagcctg     60
ctgatcagct gggtttctcc gcgtggtcgt gctcgatatt accgcatcac ttacggcgaa    120
acaggaggca atagccctgt ccaggagttc actgtgcctg gtcgtggttc tacagctacc    180
atcagcggcc ttaaacctgg cgttgattat accatcactg tgtatgctgt cactatctac    240
cgtgacggta tgtctcatca tgacccaatt tccattaatt accgcacaga aattgacaaa    300
ccatcccagc accatcacca ccaccac                                        327
```

<210> SEQ ID NO 126
<211> LENGTH: 327
<212> TYPE: DNA
<213> ORGANISM: Artificial Sequence
<220> FEATURE:
<223> OTHER INFORMATION: Synthetic

<400> SEQUENCE: 126

```
atgggagttt ctgatgtgcc gcgcgacctg gaagtggttg ctgccacccc caccagcctg     60
ctgatcagct gggaagtgcc gcgtggccta gctcgatatt accgcatcac ttacggcgaa    120
acaggaggca atagccctgt ccaggagttc actgtgcttg gtcgtggttc tacagctacc    180
atcagcggcc ttaaacctgg cgttgattat accatcactg tgtatgctgt cactgtgtac    240
cgtgacgggc cgttgcttct tgccccaatt tccattaatt accgcacaga aattgacaaa    300
ccatcccagc accatcacca ccaccac                                        327
```

<210> SEQ ID NO 127
<211> LENGTH: 327
<212> TYPE: DNA
<213> ORGANISM: Artificial Sequence
<220> FEATURE:
<223> OTHER INFORMATION: Synthetic

<400> SEQUENCE: 127

```
atgggagttt ctgatgtgcc gcgcgacctg gaagtggttg ctgccacccc caccagcctg     60
ctgatcagct ggtgggcccc gctgggtctt gctcgatatt accgcatcac ttacggcgaa    120
acaggaggca atagccctgt ccaggagttc actgtgcctg gtcggggctc tacagctacc    180
atcagcggcc ttaaacctgg cgttgattat accatcactg tgtatgctgt cactatcttc    240
cgtacgggca tggttcaata tgacccaatt tccattaatt accgcacaga aattgacaaa    300
ccatcccagc accatcacca ccaccac                                        327
```

<210> SEQ ID NO 128
<211> LENGTH: 330
<212> TYPE: DNA
<213> ORGANISM: Artificial Sequence
<220> FEATURE:
<223> OTHER INFORMATION: Synthetic

<400> SEQUENCE: 128

```
atgggagttt ctgatgtgcc gcgcgacctg gaagtggttg ctgccacccc caccagcctg      60
ctgatcagct ggactctgcc gcatgctggt cttgcgcact attaccgcat cacttacggc     120
gaaacaggag gcaatagccc tgtccaggag ttcactgtgc ctggtcgtgg tgttacagct     180
accatcagcg gccttaaacc tggcgttgat tataccatca ctgtgtatgc tgtcactctg     240
actaattctg agattatcct ttacaagcca atttccatta attaccgcac agaaattgac     300
aaaccatccc agcaccatca ccaccaccac                                      330
```

<210> SEQ ID NO 129
<211> LENGTH: 330
<212> TYPE: DNA
<213> ORGANISM: Artificial Sequence
<220> FEATURE:
<223> OTHER INFORMATION: Synthetic

<400> SEQUENCE: 129

```
atgggagttt ctgatgtgcc gcgcgacctg gaagtggttg ctgccacccc caccagcctg      60
ctgatcagct ggtacctccc gtatcctgcg catatgaact attaccgcat cacttacggc     120
gaaacaggag gcaatagccc tgtccaggag ttcactgtgc ctgggcgggg tctgacagct     180
accatcagcg gccttaaacc tggcgttgat tataccatca ctgtgtatgc tgtcactctg     240
acaaaatctc agattctcca tcataggcca atttccatta attaccgcac agaaattgac     300
aaaccatccc agcaccatca ccaccaccac                                      330
```

<210> SEQ ID NO 130
<211> LENGTH: 330
<212> TYPE: DNA
<213> ORGANISM: Artificial Sequence
<220> FEATURE:
<223> OTHER INFORMATION: Synthetic

<400> SEQUENCE: 130

```
atgggagttt ctgatgtgcc gcgcgacctg gaagtggttg ctgccacccc caccagcctg      60
ctgatcagct ggtcattgcc gtttgctggt catttgaact attaccgcat cacttacggc     120
gaaacaggag gcaatagccc tgtccaggag ttcactgtgc ctggtcgtgg tgttacagct     180
accatcagcg gccttaaacc tggcgttgat tataccatca ctgtgtatgc tgtcactctg     240
actcgctcta agattattca ttatatgcca atttccatta attaccgcac agaaattgac     300
aaaccatccc agcaccatca ccaccaccac                                      330
```

<210> SEQ ID NO 131
<211> LENGTH: 330
<212> TYPE: DNA
<213> ORGANISM: Artificial Sequence
<220> FEATURE:
<223> OTHER INFORMATION: Synthetic

<400> SEQUENCE: 131

```
atgggagttt ctgatgtgcc gcgcgacctg gaagtggttg ctgccacccc caccagcctg      60
ctgatcagct ggtctctgcc ttattctggc cttgcgaact attaccgcat cacttacggc     120
gaaacaggag gcaatagccc tgtccaggag ttcactgtgc ctggtcgtgg ggttacagct     180
actatcagcg gccttaaacc tggcgttgat tataccatca ctgtgtatgc tgtcactctg     240
actcactcta atataattcg atacgtgcca atttccatta attaccgcac agaaattgac     300
aaaccatccc agcaccatca ccaccaccac                                      330
```

<210> SEQ ID NO 132
<211> LENGTH: 330
<212> TYPE: DNA
<213> ORGANISM: Artificial Sequence
<220> FEATURE:
<223> OTHER INFORMATION: Synthetic

<400> SEQUENCE: 132

```
atgggagttt ctgatgtgcc gcgcgacctg gaagtggttg ctgccacccc caccagcctg      60
ctgatcagct ggtccctacc gcatgcgggt catgcgcact attaccgcat cacttacggc     120
gaaacaggag gcaatagccc tgtccaggag ttcactgtgc ctggtcgtgg agttacagct     180
accatcagcg gccttaaacc tggcgttgat tataccatca ctgtgtatgc tgtcactgtg     240
tctagtacaa aggtgatagt ttacctgcca atttccatta attaccgcac agaaattgac     300
aaaccatccc agcaccatca ccaccaccac                                      330
```

<210> SEQ ID NO 133
<211> LENGTH: 330
<212> TYPE: DNA
<213> ORGANISM: Artificial Sequence
<220> FEATURE:
<223> OTHER INFORMATION: Synthetic

<400> SEQUENCE: 133

```
atgggagttt ctgatgtgcc gcgcgacctg gaagtggttg ctgccacccc caccagcctg      60
ctgatcagct ggactttgcc gaatttcggt cttattaatt attaccgcat cacttacggc     120
gaaacaggag gcaatagccc tgtccaggag ttcactgtgc ctggtcgtgg tgttacagct     180
accatcagcg gccttaaacc tggcgttgat tataccatca ctgtgtatgc tgtcactatc     240
accaaatcta ctatcatcat ttacaagcca atttccatta attaccgcac agaaattgac     300
aaaccatccc agcaccatca ccaccaccac                                      330
```

<210> SEQ ID NO 134
<211> LENGTH: 330
<212> TYPE: DNA
<213> ORGANISM: Artificial Sequence
<220> FEATURE:
<223> OTHER INFORMATION: Synthetic

<400> SEQUENCE: 134

```
atgggagttt ctgatgtgcc gcgcgacctg gaagtggttg ctgccacccc caccagcctg      60
ctgatcagct ggactttgcc gcatgctggt cgtgcgcact attaccgcat cacttacggc     120
gaaacaggag gcaatagccc tgtccaggag ttcactgtgc ctgggcgggg tgttacagct     180
accatcagcg gccttaaacc tggcgttgat tataccatca ctgtgtatgc tgtcactgtg     240
acgacaactt cggtgatcct ttacaagcca atttccatta attaccgcac agaaattgac     300
aaaccatccc agcaccatca ccaccaccac                                      330
```

<210> SEQ ID NO 135
<211> LENGTH: 330
<212> TYPE: DNA
<213> ORGANISM: Artificial Sequence
<220> FEATURE:
<223> OTHER INFORMATION: Synthetic

<400> SEQUENCE: 135

```
atgggagttt ctgatgtgcc gcgcgacctg gaagtggttg ctgccacccc caccagcctg      60
```

```
ctgatcagct ggtctcttcc ttatgctggt catctaaact attaccgcat cacttacggc    120
gaaacaggag gcaatagccc tgtccaggag ttcactgtgc ctggtcgtgg tgtgacagct    180
accatcagcg gccttaaacc tggcgttgat tataccatca ctgtgtatgc tgtcactctg    240
actaagtctc agctgataca ttacatgcca atttccatta attaccgcac agaaattgac    300
aaaccatccc agcaccatca ccaccaccac                                    330
```

<210> SEQ ID NO 136
<211> LENGTH: 330
<212> TYPE: DNA
<213> ORGANISM: Artificial Sequence
<220> FEATURE:
<223> OTHER INFORMATION: Synthetic

<400> SEQUENCE: 136

```
atgggagttt ctgatgtgcc gcgcgacctg gaagtggttg ctgccacccc caccagcctg     60
ctgatcagct ggtctctgcc gtatgctgct cacatgaact attaccgcat cacttacggc    120
gaaacaggag gcaatagccc tgtccaggag ttcactgtgc ctggtcgtgg tgttacagct    180
accatcagcg gccttaaacc tggcgttgat tataccatca ctgtgtatgc tgtcactttg    240
actagatcac aggtgattca ttacatgcca atttccatta attaccgcac agaaattgac    300
aaaccatccc agcaccatca ccaccaccac                                    330
```

<210> SEQ ID NO 137
<211> LENGTH: 330
<212> TYPE: DNA
<213> ORGANISM: Artificial Sequence
<220> FEATURE:
<223> OTHER INFORMATION: Synthetic

<400> SEQUENCE: 137

```
atgggtgtta gtgatgttcc gcgtgatctg gaagttgttg cagcaacccc gaccagcctg     60
ctgattagct ggtcactgcc gcatgcaggt catgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
accaaaagca aaattattca ttatatgccg attagcatta attatcgcac cgaaattgat    300
aaaccgagcc agcatcatca tcaccatcat                                    330
```

<210> SEQ ID NO 138
<211> LENGTH: 330
<212> TYPE: DNA
<213> ORGANISM: Artificial Sequence
<220> FEATURE:
<223> OTHER INFORMATION: Synthetic

<400> SEQUENCE: 138

```
atgggtgtta gtgatgttcc gcgtgatctg gaagttgttg cagcaacccc gaccagcctg     60
ctgattagct ggtcactgcc gtatccgggt catctgaatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
accaaaagca aaattattca ttatatgccg attagcatta attatcgcac cgaaattgat    300
aaaccgagcc agcatcatca tcaccatcat                                    330
```

<210> SEQ ID NO 139
<211> LENGTH: 330

```
<212> TYPE: DNA
<213> ORGANISM: Artificial Sequence
<220> FEATURE:
<223> OTHER INFORMATION: Synthetic

<400> SEQUENCE: 139
atgggtgtta gtgatgttcc gcgtgatctg aagttgttg cagcaacccc gaccagcctg      60
ctgattagct ggaccctgcc gcatgcaggt cgtgcacatt attatcgtat tacctatggt     120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
acccgcagca aaattattca ttatatgccg attagcatta attatcgcac cgaaattgat   300
aaaccgagcc agcatcatca tcaccatcat                                     330

<210> SEQ ID NO 140
<211> LENGTH: 330
<212> TYPE: DNA
<213> ORGANISM: Artificial Sequence
<220> FEATURE:
<223> OTHER INFORMATION: Synthetic

<400> SEQUENCE: 140
atgggtgtta gtgatgttcc gcgtgatctg aagttgttg cagcaacccc gaccagcctg      60
ctgattagct ggtcactgcc gtatgcaggt catgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
accaaaagca aaattattca ttatatgccg attagcatta attatcgcac cgaaattgat   300
aaaccgagcc agcatcatca tcaccatcat                                     330

<210> SEQ ID NO 141
<211> LENGTH: 330
<212> TYPE: DNA
<213> ORGANISM: Artificial Sequence
<220> FEATURE:
<223> OTHER INFORMATION: Synthetic

<400> SEQUENCE: 141
atgggtgtta gtgatgttcc gcgtgatctg aagttgttg cagcaacccc gaccagcctg      60
ctgattagct ggtcactgcc gcatgcaggt catgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
acccgcagca aaattattca ttatatgccg attagcatta attatcgcac cgaaattgat   300
aaaccgagcc agcatcatca tcaccatcat                                     330

<210> SEQ ID NO 142
<211> LENGTH: 330
<212> TYPE: DNA
<213> ORGANISM: Artificial Sequence
<220> FEATURE:
<223> OTHER INFORMATION: Synthetic

<400> SEQUENCE: 142
atgggtgtta gtgatgttcc gcgtgatctg aagttgttg cagcaacccc gaccagcctg      60
ctgattagct ggtcactgcc gtatccgggt catctgaatt attatcgtat tacctatggt    120
gaaaccggtg gtaatagtcc ggttcaggaa ttcaccgttc cgggtcgtgg tgttaccgca    180
```
accattagcg gtctgaaacc gggtgttgat tacaccatta ccgtttatgc agttaccctg    240
acccgcagca aaattattca ttatatgccg attagcatta attatcgcac cgaaattgat    300
aaaccgagcc agcatcatca tcaccatcat                                     330

<210> SEQ ID NO 143
<211> LENGTH: 330
<212> TYPE: DNA
<213> ORGANISM: Artificial Sequence
<220> FEATURE:
<223> OTHER INFORMATION: Synthetic

<400> SEQUENCE: 143
atgggtgtta gtgatgttcc gcgtgatctg gaagttgttg cagcaacccc gaccagcctg    60
ctgattagct ggaccctgcc gcatgcaggt cgtgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccgtt    240
agcagcacca aagtgattca ttataaaccg attagcatta attatcgcac cgaaattgat    300
aaaccgagcc agcatcatca tcaccatcat                                     330

<210> SEQ ID NO 144
<211> LENGTH: 330
<212> TYPE: DNA
<213> ORGANISM: Artificial Sequence
<220> FEATURE:
<223> OTHER INFORMATION: Synthetic

<400> SEQUENCE: 144
atgggtgtta gtgatgttcc gcgtgatctg gaagttgttg cagcaacccc gaccagcctg    60
ctgattagct ggtcactgcc gtatgcaggt catgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
acccgcagca aaattattca ttatatgccg attagcatta attatcgcac cgaaattgat    300
aaaccgagcc agcatcatca tcaccatcat                                     330

<210> SEQ ID NO 145
<211> LENGTH: 330
<212> TYPE: DNA
<213> ORGANISM: Artificial Sequence
<220> FEATURE:
<223> OTHER INFORMATION: Synthetic

<400> SEQUENCE: 145
atgggtgtta gtgatgttcc gcgtgatctg gaagttgttg cagcaacccc gaccagcctg    60
ctgattagct ggtcactgcc gcatgcaggt catgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
accaaaagca aagtgattca ttatatgccg attagcatta attatcgcac cgaaattgat    300
aaaccgagcc agcatcatca tcaccatcat                                     330

<210> SEQ ID NO 146
<211> LENGTH: 330
<212> TYPE: DNA
<213> ORGANISM: Artificial Sequence
<220> FEATURE:
<223> OTHER INFORMATION: Synthetic

<400> SEQUENCE: 146

```
atgggtgtta gtgatgttcc gcgtgatctg aagttgttg cagcaacccc gaccagcctg      60
ctgattagct ggtcactgcc gtatccgggt catctgaatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
accaaaagca aagtgattca ttatatgccg attagcatta attatcgcac cgaaattgat    300
aaaccgagcc agcatcatca tcaccatcat                                     330
```

<210> SEQ ID NO 147
<211> LENGTH: 330
<212> TYPE: DNA
<213> ORGANISM: Artificial Sequence
<220> FEATURE:
<223> OTHER INFORMATION: Synthetic

<400> SEQUENCE: 147

```
atgggtgtta gtgatgttcc gcgtgatctg aagttgttg cagcaacccc gaccagcctg      60
ctgattagct ggaccctgcc gcatgcaggt cgtgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccgtt    240
agcagcacca aagttattgt ttatctgccg attagcatta attatcgcac cgaaattgat    300
aaaccgagcc agcatcatca tcaccatcat                                     330
```

<210> SEQ ID NO 148
<211> LENGTH: 330
<212> TYPE: DNA
<213> ORGANISM: Artificial Sequence
<220> FEATURE:
<223> OTHER INFORMATION: Synthetic

<400> SEQUENCE: 148

```
atgggtgtta gtgatgttcc gcgtgatctg aagttgttg cagcaacccc gaccagcctg      60
ctgattagct ggtcactgcc gtatgcaggt catgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccctg    240
accaaaagca aagtgattca ttatatgccg attagcatta attatcgcac cgaaattgat    300
aaaccgagcc agcatcatca tcaccatcat                                     330
```

<210> SEQ ID NO 149
<211> LENGTH: 330
<212> TYPE: DNA
<213> ORGANISM: Artificial Sequence
<220> FEATURE:
<223> OTHER INFORMATION: Synthetic

<400> SEQUENCE: 149

```
atgggtgtta gtgatgttcc gcgtgatctg aagttgttg cagcaacccc gaccagcctg      60
ctgattagct ggaccctgcc gcatgcaggt cgtgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccgtt    240
accaccacca aagtgattca ttataaaccg attagcatta attatcgcac cgaaattgat    300
```

```
aaaccgagcc agcatcatca tcaccatcat                                     330

<210> SEQ ID NO 150
<211> LENGTH: 327
<212> TYPE: DNA
<213> ORGANISM: Artificial Sequence
<220> FEATURE:
<223> OTHER INFORMATION: Synthetic

<400> SEQUENCE: 150
atgggagttt ctgatgtgcc gcgcgacctg gaagtggttg ctgccacccc caccagcctg    60
ctgatcagct gggacgctcc gggtggtctg gctcgatatt accgcatcac ttacggcgaa   120
acaggaggca atagccctgt ccaggagttc actgtgatcg gtcgtggtag cacagctacc   180
atcagcggcc ttaaacctgg cgttgattat accatcactg tgtatgctgt cactatcgac   240
cgtgacggtg tcaaccactt cgccccaatt tccattaatt accgcacaga aattgacaaa   300
ccatcccagc accatcacca ccaccac                                      327

<210> SEQ ID NO 151
<211> LENGTH: 330
<212> TYPE: DNA
<213> ORGANISM: Artificial Sequence
<220> FEATURE:
<223> OTHER INFORMATION: Synthetic

<400> SEQUENCE: 151
atgggagttt ctgatgtgcc gcgcgacctg gaagtggttg ctgccacccc caccagcctg    60
ctgatcagct ggtctctgcc gactccaggt ctcgcccatt attaccgcat cacttacggc   120
gaaacaggag gcaatagccc tgtccaggag ttcactgtgc ctggtcgtgg tgttacagct   180
accatcagcg gccttaaacc tggcgttgat tataccatca ctgtgtatgc tgtcactgtc   240
actcatcacg gcgtcatcgg ctacaaacca atttccatta attaccgcac agaaattgac   300
aaaccatccc agcaccatca ccaccaccac                                   330

<210> SEQ ID NO 152
<211> LENGTH: 330
<212> TYPE: DNA
<213> ORGANISM: Artificial Sequence
<220> FEATURE:
<223> OTHER INFORMATION: Synthetic

<400> SEQUENCE: 152
atgggagttt ctgatgtgcc gcgcgacctg gaagtggttg ctgccacccc caccagcctg    60
ctgatcagct ggtctctgcc gcaccgtggt gtcgccaatt attaccgcat cacttacggc   120
gaaacaggag gcaatagccc tgtccaggag ttcactgtgc ctggtcgtgg tgttacagct   180
accatcagcg gccttaaacc tggcgttgat tataccatca ctgtgtatgc tgtcactctc   240
actggagcga acgtcatcat ctacaaacca atttccatta attaccgcac agaaattgac   300
aaaccatccc agcaccatca ccaccaccac                                   330

<210> SEQ ID NO 153
<211> LENGTH: 330
<212> TYPE: DNA
<213> ORGANISM: Artificial Sequence
<220> FEATURE:
<223> OTHER INFORMATION: Synthetic

<400> SEQUENCE: 153
atgggagttt ctgatgtgcc gcgcgacctg gaagtggttg ctgccacccc caccagcctg    60
```

```
ctgatcagct ggtctctgcc gagcagcggt gtcgcccatt attaccgcat cacttacggc    120
gaaacaggag gcaatagccc tgtccaggag ttcactgtgc ctggtcgtgg tgttacagct    180
accatcagcg gccttaaacc tggcgttgat tataccatca ctgtgtatgc tgtcactgtc    240
actaacactg gtgtcatcat ctacaaacca atttccatta attaccgcac agaaattgac    300
aaaccatccc agcaccatca ccaccaccac                                     330
```

<210> SEQ ID NO 154
<211> LENGTH: 330
<212> TYPE: DNA
<213> ORGANISM: Artificial Sequence
<220> FEATURE:
<223> OTHER INFORMATION: Synthetic

<400> SEQUENCE: 154

```
atgggagttt ctgatgtgcc gcgcgacctg gaagtggttg ctgccacccc caccagcctg     60
ctgatcagct ggtctctgcc gcatcacggt ttcggccatt attaccgcat cacttacggc    120
gaaacaggag gcaatagccc tgtccaggag ttcactgtgc ctggtcgtgg tgttacagct    180
accatcagcg gccttaaacc tggcgttgat tataccatca ctgtgtatgc tgtcactgtc    240
actgctacgg ggatcatcat ctacaaacca atttccatta attaccgcac agaaattgac    300
aaaccatccc agcaccatca ccaccaccac                                     330
```

<210> SEQ ID NO 155
<211> LENGTH: 330
<212> TYPE: DNA
<213> ORGANISM: Artificial Sequence
<220> FEATURE:
<223> OTHER INFORMATION: Synthetic

<400> SEQUENCE: 155

```
atgggagttt ctgatgtgcc gcgcgacctg gaagtggttg ctgccacccc caccagcctg     60
ctgatcagct ggtctctgcc gcacgccggt gacgcccatt attaccgcat cacttacggc    120
gaaacaggag gcaatagccc tgtccaggag ttcactgtgc ctggtcgtgg tgttacagct    180
accatcagcg gccttaaacc tggcgttgat tataccatca ctgtgtatgc tgtcactgtt    240
actagagcgg gtttctaccg ctacaaacca atttccatta attaccgcac agaaattgac    300
aaaccatccc agcaccatca ccaccaccac                                     330
```

<210> SEQ ID NO 156
<211> LENGTH: 330
<212> TYPE: DNA
<213> ORGANISM: Artificial Sequence
<220> FEATURE:
<223> OTHER INFORMATION: Synthetic

<400> SEQUENCE: 156

```
atgggagttt ctgatgtgcc gcgcgacctg gaagtggttg ctgccacccc caccagcctg     60
ctgatcagct ggtctctgcc gcataatggt gtcgcccatt attaccgcat cacttacggc    120
gaaacaggag gcaatagccc tgtccaggag ttcactgtgc ctggtcgtgg tgttacagct    180
accatcagcg gccttaaacc tggcgttgat tataccatca ctgtgtatgc tgtcactgtc    240
actcgggagg aagtcatcag ctacaaacca atttccatta attaccgcac agaaattgac    300
aaaccatccc agcaccatca ccaccaccac                                     330
```

<210> SEQ ID NO 157

```
<211> LENGTH: 330
<212> TYPE: DNA
<213> ORGANISM: Artificial Sequence
<220> FEATURE:
<223> OTHER INFORMATION: Synthetic

<400> SEQUENCE: 157
atgggagttt ctgatgtgcc gcgcgacctg gaagtggttg ctgccacccc caccagcctg    60
ctgatcagct ggtctctgcc gcgtcagggt ctcgccaatt attaccgcat cacttacggc   120
gaaacaggag gcaatagccc tgtccaggag ttcactgtgc ctggtcgtgg tgttacagct   180
accatcagcg gccttaaacc tggcgttgat tataccatca ctgtgtatgc tgtcactgtc   240
actgctgctg gggtcatcat ctacaaacca atttccatta attaccgcac agaaattgac   300
aaaccatccc agcaccatca ccaccaccac                                     330

<210> SEQ ID NO 158
<211> LENGTH: 330
<212> TYPE: DNA
<213> ORGANISM: Artificial Sequence
<220> FEATURE:
<223> OTHER INFORMATION: Synthetic

<400> SEQUENCE: 158
atgggagttt ctgatgtgcc gcgcgacctg gaagtggttg ctgccacccc caccagcctg    60
ctgatcagct ggtctctgcc gggacccggt cacttccatt attaccgcat cacttacggc   120
gaaacaggag gcaatagccc tgtccaggag ttcactgtgc ctggtcgtgg tgttacagct   180
accatcagcg gccttaaacc tggcgttgat tataccatca ctgtgtatgc tgtcactgtc   240
actgctaacc agcccatcat ctacaaacca atttccatta attaccgcac agaaattgac   300
aaaccatccc agcaccatca ccaccaccac                                     330

<210> SEQ ID NO 159
<211> LENGTH: 330
<212> TYPE: DNA
<213> ORGANISM: Artificial Sequence
<220> FEATURE:
<223> OTHER INFORMATION: Synthetic

<400> SEQUENCE: 159
atgggagttt ctgatgtgcc gcgcgacctg gaagtggttg ctgccacccc caccagcctg    60
ctgatcagct ggtctctgcc gcaccccggt ctcggccatt attaccgcat cacttacggc   120
gaaacaggag gcaatagccc tgtccaggag ttcactgtgc ctggtcgtgg tgttacagct   180
accatcagcg gccttaaacc tggcgttgat tataccatca ctgtgtatgc tgtcactatc   240
actccggaaa cgatcatcgt ctacaaacca atttccatta attaccgcac agaaattgac   300
aaaccatccc agcaccatca ccaccaccac                                     330

<210> SEQ ID NO 160
<211> LENGTH: 327
<212> TYPE: DNA
<213> ORGANISM: Artificial Sequence
<220> FEATURE:
<223> OTHER INFORMATION: Synthetic

<400> SEQUENCE: 160
atgggagttt ctgatgtgcc gcgcgacctg gaagtggttg ctgccacccc caccagcctg    60
ctgatcagct gggacgctcc gagaggtctg gctcgatatt accgcatcac ttacggcgaa   120
acaggaggca atagccctgt ccaggagttc actgtgttcg gtcgtggtac cacagctacc   180
```

```
atcagcggcc ttaaacctgg cgttgattat accatcactg tgtatgctgt cactatcgac    240
cgtgacggta cccgcagctt cgacccaatt tccattaatt accgcacaga aattgacaaa    300
ccatcccagc accatcacca ccaccac                                        327
```

<210> SEQ ID NO 161
<211> LENGTH: 327
<212> TYPE: DNA
<213> ORGANISM: Artificial Sequence
<220> FEATURE:
<223> OTHER INFORMATION: Synthetic

<400> SEQUENCE: 161

```
atgggagttt ctgatgtgcc gcgcgacctg gaagtggttg ctgccacccc caccagcctg     60
ctgatcagct gggacgctcc ggctggtctg gctcgatatt accgcatcac ttacggcgaa    120
acaggaggca atagccctgt ccaggagttc actgtggtcg gtcgtggtaa cacagctacc    180
atcagcggcc ttaaacctgg cgttgattat accatcactg tgtatgctgt cactatcttc    240
cgtgacggtc ccgtcacctg gacccaatt tccattaatt accgcacaga aattgacaaa     300
ccatcccagc accatcacca ccaccac                                        327
```

<210> SEQ ID NO 162
<211> LENGTH: 330
<212> TYPE: DNA
<213> ORGANISM: Artificial Sequence
<220> FEATURE:
<223> OTHER INFORMATION: Synthetic

<400> SEQUENCE: 162

```
atgggagttt ctgatgtgcc gcgcgacctg gaagtggttg ctgccacccc caccagcctg     60
ctgatcagct ggtctctgcc gcaccaaggt aaagccaatt attaccgcat cacttacggc    120
gaaacaggag gcaatagccc tgtccaggag ttcactgtgc ctggtcgtgg tgttacagct    180
accatcagcg gccttaaacc tggcgttgat tataccatca ctgtgtatgc tgtcactgtt    240
actgatacag ggtacctcaa gtacaaacca atttccatta attaccgcac agaaattgac    300
aaaccatccc agcaccatca ccaccaccac                                     330
```

<210> SEQ ID NO 163
<211> LENGTH: 327
<212> TYPE: DNA
<213> ORGANISM: Artificial Sequence
<220> FEATURE:
<223> OTHER INFORMATION: Synthetic

<400> SEQUENCE: 163

```
atgggagttt ctgatgtgcc gcgcgacctg gaagtggttg ctgccacccc caccagcctg     60
ctgatcagct gggacgctcc gaagggtctg gctcgatatt accgcatcac ttacggcgaa    120
acaggaggca atagccctgt ccaggagttc actgtggtcg gtcgtggtaa cacagctacc    180
atcagcggcc ttaaacctgg cgttgattat accatcactg tgtatgctgt cactatcttc    240
cgtgacggtc ccgtcacctg gacccaatt tccattaatt accgcacaga aattgacaaa     300
ccatcccagc accatcacca ccaccac                                        327
```

<210> SEQ ID NO 164
<211> LENGTH: 330
<212> TYPE: DNA
<213> ORGANISM: Artificial Sequence
<220> FEATURE:

<223> OTHER INFORMATION: Synthetic

<400> SEQUENCE: 164

| | |
|---|---|
| atgggagttt ctgatgtgcc gcgcgacctg aagtggttg ctgccacccc caccagcctg | 60 |
| ctgatcagct ggtctctgcc gaatcccggt atcgcccatt attaccgcat cacttacggc | 120 |
| gaaacaggag gcaatagccc tgtccaggag ttcactgtgc ctggtcgtgg tgttacagct | 180 |
| accatcagcg gccttaaacc tggcgttgat tataccatca ctgtgtatgc tgtcactctc | 240 |
| actggcagtg acaccatctt ctacaaacca atttccatta attaccgcac agaaattgac | 300 |
| aaaccatccc agcaccatca ccaccaccac | 330 |

<210> SEQ ID NO 165
<211> LENGTH: 330
<212> TYPE: DNA
<213> ORGANISM: Artificial Sequence
<220> FEATURE:
<223> OTHER INFORMATION: Synthetic

<400> SEQUENCE: 165

| | |
|---|---|
| atgggagttt ctgatgtgcc gcgcgacctg aagtggttg ctgccacccc caccagcctg | 60 |
| ctgatcagct ggtctctgcc gcggccgggt aacgcccatt attaccgcat cacttacggc | 120 |
| gaaacaggag gcaatagccc tgtccaggag ttcactgtgc ctggtcgtgg tgttacagct | 180 |
| accatcagcg gccttaaacc tggcgttgat tataccatca ctgtgtatgc tgtcactgtt | 240 |
| actggcaaag atgtcatcaa gtacaaacca atttccatta attaccgcac agaaattgac | 300 |
| aaaccatccc agcaccatca ccaccaccac | 330 |

<210> SEQ ID NO 166
<211> LENGTH: 327
<212> TYPE: DNA
<213> ORGANISM: Artificial Sequence
<220> FEATURE:
<223> OTHER INFORMATION: Synthetic

<400> SEQUENCE: 166

| | |
|---|---|
| atgggagttt ctgatgtgcc gcgcgacctg aagtggttg ctgccacccc caccagcctg | 60 |
| ctgatcagct gggacgctcc ggctggtctg gctcgatatt accgcatcac ttacggcgaa | 120 |
| acaggaggca atagccctgt ccaggagttc actgtggtcg tcgtggtaa cacagctacc | 180 |
| atcagcggcc ttaaacctgg cgttgattat accatcactg tgtatgctgt cactatcttc | 240 |
| cgtgacggtg tcgtcaacta cggcccaatt tccattaatt accgcacaga aattgacaaa | 300 |
| ccatcccagc accatcacca ccaccac | 327 |

<210> SEQ ID NO 167
<211> LENGTH: 330
<212> TYPE: DNA
<213> ORGANISM: Artificial Sequence
<220> FEATURE:
<223> OTHER INFORMATION: Synthetic

<400> SEQUENCE: 167

| | |
|---|---|
| atgggagttt ctgatgtgcc gcgcgacctg aagtggttg ctgccacccc caccagcctg | 60 |
| ctgatcagct ggtctctgcc gaatcccggt aacgcccatt attaccgcat cacttacggc | 120 |
| gaaacaggag gcaatagccc tgtccaggag ttcactgtgc ctggtcgtgg tgttacagct | 180 |
| accatcagcg gccttaaacc tggcgttgat tataccatca ctgtgtatgc tgtcactgtt | 240 |
| actgacacag gtttcatcac gtacaaacca atttccatta attaccgcac agaaattgac | 300 |

```
aaaccatccc agcaccatca ccaccaccac                                    330
```

<210> SEQ ID NO 168
<211> LENGTH: 5
<212> TYPE: PRT
<213> ORGANISM: Artificial Sequence
<220> FEATURE:
<223> OTHER INFORMATION: Synthetic

<400> SEQUENCE: 168

```
Ile Asn Tyr Arg Thr
1               5
```

<210> SEQ ID NO 169
<211> LENGTH: 227
<212> TYPE: PRT
<213> ORGANISM: Artificial Sequence
<220> FEATURE:
<223> OTHER INFORMATION: Synthetic

<400> SEQUENCE: 169

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 170
<211> LENGTH: 16
<212> TYPE: PRT
<213> ORGANISM: Artificial Sequence
<220> FEATURE:
<223> OTHER INFORMATION: Synthetic

```
<400> SEQUENCE: 170

Asp Lys Thr His Thr Cys Pro Pro Cys Pro Ala Pro Glu Leu Leu Gly
1               5                   10                  15

<210> SEQ ID NO 171
<211> LENGTH: 24
<212> TYPE: PRT
<213> ORGANISM: Artificial Sequence
<220> FEATURE:
<223> OTHER INFORMATION: Synthetic

<400> SEQUENCE: 171

Glu Pro Lys Ser Ser Asp Lys Thr His Thr Cys Pro Pro Cys Pro Ala
1               5                   10                  15

Pro Glu Leu Leu Gly Gly Pro Ser
            20

<210> SEQ ID NO 172
<211> LENGTH: 24
<212> TYPE: PRT
<213> ORGANISM: Artificial Sequence
<220> FEATURE:
<223> OTHER INFORMATION: Synthetic

<400> SEQUENCE: 172

Glu Pro Lys Ser Ser Asp Lys Thr His Thr Cys Pro Pro Cys Pro Ala
1               5                   10                  15

Pro Glu Leu Leu Gly Gly Ser Ser
            20

<210> SEQ ID NO 173
<211> LENGTH: 24
<212> TYPE: PRT
<213> ORGANISM: Artificial Sequence
<220> FEATURE:
<223> OTHER INFORMATION: Synthetic

<400> SEQUENCE: 173

Glu Pro Lys Ser Ser Gly Ser Thr His Thr Cys Pro Pro Cys Pro Ala
1               5                   10                  15

Pro Glu Leu Leu Gly Gly Ser Ser
            20

<210> SEQ ID NO 174
<211> LENGTH: 19
<212> TYPE: PRT
<213> ORGANISM: Artificial Sequence
<220> FEATURE:
<223> OTHER INFORMATION: Synthetic

<400> SEQUENCE: 174

Asp Lys Thr His Thr Cys Pro Pro Cys Pro Ala Pro Glu Leu Leu Gly
1               5                   10                  15

Gly Pro Ser

<210> SEQ ID NO 175
<211> LENGTH: 19
<212> TYPE: PRT
<213> ORGANISM: Artificial Sequence
<220> FEATURE:
<223> OTHER INFORMATION: Synthetic

<400> SEQUENCE: 175

Asp Lys Thr His Thr Cys Pro Pro Cys Pro Ala Pro Glu Leu Leu Gly
```

```
1               5                   10                  15
Gly Ser Ser

<210> SEQ ID NO 176
<211> LENGTH: 330
<212> TYPE: PRT
<213> ORGANISM: Artificial Sequence
<220> FEATURE:
<223> OTHER INFORMATION: Synthetic

<400> SEQUENCE: 176

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 177
```

<211> LENGTH: 20
<212> TYPE: PRT
<213> ORGANISM: Artificial Sequence
<220> FEATURE:
<223> OTHER INFORMATION: Synthetic

<400> SEQUENCE: 177

Met Glu Thr Asp Thr Leu Leu Leu Trp Val Leu Leu Leu Trp Val Pro
1               5                   10                  15

Gly Ser Thr Gly
            20

<210> SEQ ID NO 178
<211> LENGTH: 208
<212> TYPE: PRT
<213> ORGANISM: Artificial Sequence
<220> FEATURE:
<223> OTHER INFORMATION: Synthetic

<400> SEQUENCE: 178

Val Phe Leu Phe Pro Pro Lys Pro Lys Asp Thr Leu Met Ile Ser Arg
1               5                   10                  15

Thr Pro Glu Val Thr Cys Val Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro Gly Lys
        195                 200                 205

<210> SEQ ID NO 179
<211> LENGTH: 206
<212> TYPE: PRT
<213> ORGANISM: Artificial Sequence
<220> FEATURE:
<223> OTHER INFORMATION: Synthetic

<400> SEQUENCE: 179

Val Phe Leu Phe Pro Pro Lys Pro Lys Asp Thr Leu Met Ile Ser Arg
1               5                   10                  15

Thr Pro Glu Val Thr Cys Val Val Val Asp Val Ser His Glu Asp Pro
            20                  25                  30

```
Glu Val Lys Phe Asn Trp Tyr Val Asp Gly Val Glu Val His Asn Ala
             35                  40                  45

Lys Thr Lys Pro Arg Glu Glu Gln Tyr Asn Ser Thr Tyr Arg Val Val
 50                  55                  60

Ser Val Leu Thr Val Leu His Gln Asp Trp Leu Asn Gly Lys Glu Tyr
 65                  70                  75                  80

Lys Cys Lys Val Ser Asn Lys Ala Leu Pro Ala Pro Ile Glu Lys Thr
                 85                  90                  95

Ile Ser Lys Ala Lys Gly Gln Pro Arg Glu Pro Gln Val Tyr Thr Leu
                100                 105                 110

Pro Pro Ser Arg Asp Glu Leu Thr Lys Asn Gln Val Ser Leu Thr Cys
                115                 120                 125

Leu Val Lys Gly Phe Tyr Pro Ser Asp Ile Ala Val Glu Trp Glu Ser
        130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
                180                 185                 190

Leu His Asn His Tyr Thr Gln Lys Ser Leu Ser Leu Ser Pro
                195                 200                 205

<210> SEQ ID NO 180
<211> LENGTH: 16
<212> TYPE: PRT
<213> ORGANISM: Artificial Sequence
<220> FEATURE:
<223> OTHER INFORMATION: Synthetic

<400> SEQUENCE: 180

Gly Ser Thr His Thr Cys Pro Pro Cys Pro Ala Pro Glu Leu Leu Gly
 1               5                  10                  15

<210> SEQ ID NO 181
<211> LENGTH: 8
<212> TYPE: PRT
<213> ORGANISM: Artificial Sequence
<220> FEATURE:
<223> OTHER INFORMATION: Synthetic

<400> SEQUENCE: 181

Gly Ala Gly Gly Gly Gly Ser Gly
 1               5

<210> SEQ ID NO 182
<211> LENGTH: 6
<212> TYPE: PRT
<213> ORGANISM: Artificial Sequence
<220> FEATURE:
<223> OTHER INFORMATION: Synthetic

<400> SEQUENCE: 182

Glu Pro Lys Ser Ser Asp
 1               5

<210> SEQ ID NO 183
<211> LENGTH: 21
<212> TYPE: PRT
<213> ORGANISM: Artificial Sequence
<220> FEATURE:
<223> OTHER INFORMATION: Synthetic
```

```
<400> SEQUENCE: 183

Glu Ser Pro Lys Ala Gln Ala Ser Ser Val Pro Thr Ala Gln Pro Gln
1               5                   10                  15

Ala Glu Gly Leu Ala
            20

<210> SEQ ID NO 184
<211> LENGTH: 17
<212> TYPE: PRT
<213> ORGANISM: Artificial Sequence
<220> FEATURE:
<223> OTHER INFORMATION: Synthetic

<400> SEQUENCE: 184

Glu Leu Gln Leu Glu Glu Ser Ala Ala Glu Ala Gln Asp Gly Glu Leu
1               5                   10                  15

Asp

<210> SEQ ID NO 185
<211> LENGTH: 9
<212> TYPE: PRT
<213> ORGANISM: Artificial Sequence
<220> FEATURE:
<223> OTHER INFORMATION: Synthetic

<400> SEQUENCE: 185

Gly Gln Pro Asp Glu Pro Gly Gly Ser
1               5

<210> SEQ ID NO 186
<211> LENGTH: 13
<212> TYPE: PRT
<213> ORGANISM: Artificial Sequence
<220> FEATURE:
<223> OTHER INFORMATION: Synthetic

<400> SEQUENCE: 186

Gly Gly Ser Gly Ser Gly Ser Gly Ser Gly Ser Gly Ser
1               5                   10

<210> SEQ ID NO 187
<211> LENGTH: 17
<212> TYPE: PRT
<213> ORGANISM: Artificial Sequence
<220> FEATURE:
<223> OTHER INFORMATION: Synthetic

<400> SEQUENCE: 187

Glu Leu Gln Leu Glu Glu Ser Ala Ala Glu Ala Gln Glu Gly Glu Leu
1               5                   10                  15

Glu

<210> SEQ ID NO 188
<211> LENGTH: 5
<212> TYPE: PRT
<213> ORGANISM: Artificial Sequence
<220> FEATURE:
<223> OTHER INFORMATION: Synthetic

<400> SEQUENCE: 188

Gly Ser Gly Ser Gly
1               5
```

```
<210> SEQ ID NO 189
<211> LENGTH: 4
<212> TYPE: PRT
<213> ORGANISM: Artificial Sequence
<220> FEATURE:
<223> OTHER INFORMATION: Synthetic

<400> SEQUENCE: 189

Gly Ser Gly Cys
1

<210> SEQ ID NO 190
<211> LENGTH: 7
<212> TYPE: PRT
<213> ORGANISM: Artificial Sequence
<220> FEATURE:
<223> OTHER INFORMATION: Synthetic

<400> SEQUENCE: 190

Ala Gly Gly Gly Gly Ser Gly
1               5

<210> SEQ ID NO 191
<211> LENGTH: 4
<212> TYPE: PRT
<213> ORGANISM: Artificial Sequence
<220> FEATURE:
<223> OTHER INFORMATION: Synthetic

<400> SEQUENCE: 191

Gly Ser Gly Ser
1

<210> SEQ ID NO 192
<211> LENGTH: 8
<212> TYPE: PRT
<213> ORGANISM: Artificial Sequence
<220> FEATURE:
<223> OTHER INFORMATION: Synthetic

<400> SEQUENCE: 192

Gln Pro Asp Glu Pro Gly Gly Ser
1               5

<210> SEQ ID NO 193
<211> LENGTH: 6
<212> TYPE: PRT
<213> ORGANISM: Artificial Sequence
<220> FEATURE:
<223> OTHER INFORMATION: Synthetic

<400> SEQUENCE: 193

Gly Ser Gly Ser Gly Ser
1               5

<210> SEQ ID NO 194
<211> LENGTH: 6
<212> TYPE: PRT
<213> ORGANISM: Artificial Sequence
<220> FEATURE:
<223> OTHER INFORMATION: Synthetic

<400> SEQUENCE: 194

Thr Val Ala Ala Pro Ser
1               5

<210> SEQ ID NO 195
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 195

Lys Ala Gly Gly Gly Gly Ser Gly
1               5

<210> SEQ ID NO 196
<211> LENGTH: 13
<212> TYPE: PRT
<213> ORGANISM: Artificial Sequence
<220> FEATURE:
<223> OTHER INFORMATION: Synthetic

<400> SEQUENCE: 196

Lys Gly Ser Gly Ser Gly Ser Gly Ser Gly Ser Gly Ser
1               5                   10

<210> SEQ ID NO 197
<211> LENGTH: 9
<212> TYPE: PRT
<213> ORGANISM: Artificial Sequence
<220> FEATURE:
<223> OTHER INFORMATION: Synthetic

<400> SEQUENCE: 197

Lys Gln Pro Asp Glu Pro Gly Gly Ser
1               5

<210> SEQ ID NO 198
<211> LENGTH: 18
<212> TYPE: PRT
<213> ORGANISM: Artificial Sequence
<220> FEATURE:
<223> OTHER INFORMATION: Synthetic

<400> SEQUENCE: 198

Lys Glu Leu Gln Leu Glu Glu Ser Ala Ala Glu Ala Gln Asp Gly Glu
1               5                   10                  15

Leu Asp

<210> SEQ ID NO 199
<211> LENGTH: 7
<212> TYPE: PRT
<213> ORGANISM: Artificial Sequence
<220> FEATURE:
<223> OTHER INFORMATION: Synthetic

<400> SEQUENCE: 199

Lys Thr Val Ala Ala Pro Ser
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic

<400> SEQUENCE: 200

Lys Ala Gly Gly Gly Gly Ser Gly Gly
1               5
```

```
<210> SEQ ID NO 201
<211> LENGTH: 14
<212> TYPE: PRT
<213> ORGANISM: Artificial Sequence
<220> FEATURE:
<223> OTHER INFORMATION: Synthetic

<400> SEQUENCE: 201

Lys Gly Ser Gly Ser Gly Ser Gly Ser Gly Ser Gly Ser Gly
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Synthetic

<400> SEQUENCE: 202

Lys Gln Pro Asp Glu Pro Gly Gly Ser Gly
1               5                   10

<210> SEQ ID NO 203
<211> LENGTH: 19
<212> TYPE: PRT
<213> ORGANISM: Artificial Sequence
<220> FEATURE:
<223> OTHER INFORMATION: Synthetic

<400> SEQUENCE: 203

Lys Glu Leu Gln Leu Glu Glu Ser Ala Ala Glu Ala Gln Asp Gly Glu
1               5                   10                  15

Leu Asp Gly

<210> SEQ ID NO 204
<211> LENGTH: 8
<212> TYPE: PRT
<213> ORGANISM: Artificial Sequence
<220> FEATURE:
<223> OTHER INFORMATION: Synthetic

<400> SEQUENCE: 204

Lys Thr Val Ala Ala Pro Ser Gly
1               5

<210> SEQ ID NO 205
<211> LENGTH: 8
<212> TYPE: PRT
<213> ORGANISM: Artificial Sequence
<220> FEATURE:
<223> OTHER INFORMATION: Synthetic

<400> SEQUENCE: 205

Ala Gly Gly Gly Gly Ser Gly Gly
1               5

<210> SEQ ID NO 206
<211> LENGTH: 7
<212> TYPE: PRT
<213> ORGANISM: Artificial Sequence
<220> FEATURE:
<223> OTHER INFORMATION: Synthetic

<400> SEQUENCE: 206

Ala Gly Gly Gly Gly Ser Gly
1               5
```

```
<210> SEQ ID NO 207
<211> LENGTH: 13
<212> TYPE: PRT
<213> ORGANISM: Artificial Sequence
<220> FEATURE:
<223> OTHER INFORMATION: Synthetic

<400> SEQUENCE: 207

Gly Ser Gly Ser Gly Ser Gly Ser Gly Ser Gly Ser Gly
1               5                   10

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Pro Asp Glu Pro Gly Gly Ser Gly
1               5

<210> SEQ ID NO 209
<211> LENGTH: 7
<212> TYPE: PRT
<213> ORGANISM: Artificial Sequence
<220> FEATURE:
<223> OTHER INFORMATION: Synthetic

<400> SEQUENCE: 209

Thr Val Ala Ala Pro Ser Gly
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic

<400> SEQUENCE: 210

Pro Ser Thr Ser Thr Ser Thr
1               5

<210> SEQ ID NO 211
<211> LENGTH: 7
<212> TYPE: PRT
<213> ORGANISM: Artificial Sequence
<220> FEATURE:
<223> OTHER INFORMATION: Synthetic

<400> SEQUENCE: 211

Glu Ile Asp Lys Pro Ser Gln
1               5

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Ser Gly Ser Gly Ser Gly Ser
1               5
```

```
<210> SEQ ID NO 213
<211> LENGTH: 10
<212> TYPE: PRT
<213> ORGANISM: Artificial Sequence
<220> FEATURE:
<223> OTHER INFORMATION: Synthetic

<400> SEQUENCE: 213

Gly Ser Gly Ser Gly Ser Gly Ser Gly Ser
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Synthetic

<400> SEQUENCE: 214

Gly Ser Gly Ser Gly Ser Gly Ser Gly Ser Gly Ser
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Synthetic

<400> SEQUENCE: 215

Gly Ser Gly Ser Gly Ser Gly Ser Gly Ser Gly Ser Gly Ser
1               5                   10

<210> SEQ ID NO 216
<211> LENGTH: 13
<212> TYPE: PRT
<213> ORGANISM: Artificial Sequence
<220> FEATURE:
<223> OTHER INFORMATION: Synthetic

<400> SEQUENCE: 216

Gly Gly Ser Gly Ser Gly Ser Gly Ser Gly Ser Gly Ser
1               5                   10

<210> SEQ ID NO 217
<211> LENGTH: 16
<212> TYPE: PRT
<213> ORGANISM: Artificial Sequence
<220> FEATURE:
<223> OTHER INFORMATION: Synthetic

<400> SEQUENCE: 217

Gly Gly Ser Gly Ser Gly Ser Gly Ser Gly Ser Gly Ser Gly Ser Gly
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic

<400> SEQUENCE: 218

Gly Ser Glu Gly Ser Glu Gly Ser Glu Gly Ser Glu Gly Ser Glu
1               5                   10                  15

<210> SEQ ID NO 219
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 219

Gly Gly Ser Glu Gly Gly Ser Glu
1               5

<210> SEQ ID NO 220
<211> LENGTH: 35
<212> TYPE: PRT
<213> ORGANISM: Artificial Sequence
<220> FEATURE:
<223> OTHER INFORMATION: Synthetic

<400> SEQUENCE: 220

Gly Gly Gly Gly Ser Gly Gly Gly Ser Gly Gly Gly Gly Ser Gly
1               5                  10                  15

Gly Gly Gly Ser Gly Gly Gly Ser Gly Gly Gly Ser Gly Gly
            20                  25                  30

Gly Gly Ser
        35

<210> SEQ ID NO 221
<211> LENGTH: 25
<212> TYPE: PRT
<213> ORGANISM: Artificial Sequence
<220> FEATURE:
<223> OTHER INFORMATION: Synthetic

<400> SEQUENCE: 221

Gly Gly Gly Gly Ser Gly Gly Gly Gly Ser Gly Gly Gly Gly Ser Gly
1               5                  10                  15

Gly Gly Gly Ser Gly Gly Gly Gly Ser
            20                  25

<210> SEQ ID NO 222
<211> LENGTH: 16
<212> TYPE: PRT
<213> ORGANISM: Artificial Sequence
<220> FEATURE:
<223> OTHER INFORMATION: Synthetic

<400> SEQUENCE: 222

Gly Gly Gly Gly Ser Gly Gly Gly Gly Ser Gly Gly Gly Gly Ser Gly
1               5                  10                  15

<210> SEQ ID NO 223
<211> LENGTH: 7
<212> TYPE: PRT
<213> ORGANISM: Artificial Sequence
<220> FEATURE:
<223> OTHER INFORMATION: Synthetic

<400> SEQUENCE: 223

Gly Pro Gly Pro Gly Pro Gly
1               5

<210> SEQ ID NO 224
<211> LENGTH: 11
<212> TYPE: PRT
<213> ORGANISM: Artificial Sequence
<220> FEATURE:
<223> OTHER INFORMATION: Synthetic
```

<400> SEQUENCE: 224

Gly Pro Gly Pro Gly Pro Gly Pro Gly Pro Gly
1               5                   10

<210> SEQ ID NO 225
<211> LENGTH: 6
<212> TYPE: PRT
<213> ORGANISM: Artificial Sequence
<220> FEATURE:
<223> OTHER INFORMATION: Synthetic

<400> SEQUENCE: 225

Pro Ala Pro Ala Pro Ala
1               5

<210> SEQ ID NO 226
<211> LENGTH: 12
<212> TYPE: PRT
<213> ORGANISM: Artificial Sequence
<220> FEATURE:
<223> OTHER INFORMATION: Synthetic

<400> SEQUENCE: 226

Pro Ala Pro Ala Pro Ala Pro Ala Pro Ala Pro Ala
1               5                   10

<210> SEQ ID NO 227
<211> LENGTH: 18
<212> TYPE: PRT
<213> ORGANISM: Artificial Sequence
<220> FEATURE:
<223> OTHER INFORMATION: Synthetic

<400> SEQUENCE: 227

Pro Ala Pro Ala Pro Ala Pro Ala Pro Ala Pro Ala Pro Ala Pro Ala
1               5                   10                  15

Pro Ala

<210> SEQ ID NO 228
<211> LENGTH: 106
<212> TYPE: PRT
<213> ORGANISM: Artificial Sequence
<220> FEATURE:
<223> OTHER INFORMATION: Synthetic

<400> SEQUENCE: 228

Met Gly Val Ser Asp Val Pro Arg Asp Leu Glu Val Val Ala Ala Thr
1               5                   10                  15

Pro Thr Ser Leu Leu Ile Ser Trp Val Ser Pro Arg Gly Arg Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Gly Arg Gly Ser Thr Ala Thr Ile Ser Gly Leu
        50                  55                  60

Lys Pro Gly Val Asp Tyr Thr Ile Thr Val Tyr Ala Val Thr Ile Tyr
65                  70                  75                  80

Arg Asp Gly Met Ser His His Asp Pro Ile Ser Ile Asn Tyr Arg Thr
                85                  90                  95

Gly Ser Gly Cys His His His His His His
            100                 105

```
<210> SEQ ID NO 229
<211> LENGTH: 107
<212> TYPE: PRT
<213> ORGANISM: Artificial Sequence
<220> FEATURE:
<223> OTHER INFORMATION: Synthetic

<400> SEQUENCE: 229
```

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Ala Gly His Val
            20                  25                  30

Asn Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Leu
65                  70                  75                  80

Thr Lys Ser Gln Met Ile His Tyr Met Pro Ile Ser Ile Asn Tyr Arg
                85                  90                  95

Thr Gly Ser Gly Cys His His His His His
            100                 105

```
<210> SEQ ID NO 230
<211> LENGTH: 108
<212> TYPE: PRT
<213> ORGANISM: Artificial Sequence
<220> FEATURE:
<223> OTHER INFORMATION: Synthetic

<400> SEQUENCE: 230
```

Met Gly Val Ser Asp Val Pro Arg Asp Leu Glu Val Val Ala Ala Thr
1               5                   10                  15

Pro Thr Ser Leu Leu Ile Ser Trp Thr Leu Pro His Ala Gly Arg Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Thr Thr Thr Ser Val Ile Leu Tyr Lys Pro Ile Ser Ile Asn Tyr Arg
                85                  90                  95

Thr Glu Gly Ser Gly Cys His His His His His
            100                 105

```
<210> SEQ ID NO 231
<211> LENGTH: 108
<212> TYPE: PRT
<213> ORGANISM: Artificial Sequence
<220> FEATURE:
<223> OTHER INFORMATION: Synthetic

<400> SEQUENCE: 231
```

Met Gly Val Ser Asp Val Pro Arg Asp Leu Glu Val Val Ala Ala Thr
1               5                   10                  15

Pro Thr Ser Leu Leu Ile Ser Trp Tyr Leu Pro Tyr Pro Ala His Met
            20                  25                  30

Asn Tyr Tyr Arg Ile Thr Tyr Gly Glu Thr Gly Gly Asn Ser Pro Val
        35                  40                  45

Gln Glu Phe Thr Val Pro Gly Arg Gly Leu Thr Ala Thr Ile Ser Gly
        50                  55                  60

Leu Lys Pro Gly Val Asp Tyr Thr Ile Thr Val Tyr Ala Val Thr Leu
 65                  70                  75                  80

Thr Lys Ser Gln Ile Leu His His Arg Pro Ile Ser Ile Asn Tyr Arg
                 85                  90                  95

Thr Glu Gly Ser Gly Cys His His His His His
            100                 105

<210> SEQ ID NO 232
<211> LENGTH: 108
<212> TYPE: PRT
<213> ORGANISM: Artificial Sequence
<220> FEATURE:
<223> OTHER INFORMATION: Synthetic

<400> SEQUENCE: 232

Met Gly Val Ser Asp Val Pro Arg Asp Leu Glu Val Val Ala Ala Thr
 1               5                  10                  15

Pro Thr Ser Leu Leu Ile Ser Trp Ser Leu Pro Tyr Ala Gly His Leu
                20                  25                  30

Asn Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
        50                  55                  60

Leu Lys Pro Gly Val Asp Tyr Thr Ile Thr Val Tyr Ala Val Thr Leu
 65                  70                  75                  80

Thr Lys Ser Gln Leu Ile His Tyr Met Pro Ile Ser Ile Asn Tyr Arg
                 85                  90                  95

Thr Glu Gly Ser Gly Cys His His His His His
            100                 105

<210> SEQ ID NO 233
<211> LENGTH: 108
<212> TYPE: PRT
<213> ORGANISM: Artificial Sequence
<220> FEATURE:
<223> OTHER INFORMATION: Synthetic

<400> SEQUENCE: 233

Met Gly Val Ser Asp Val Pro Arg Asp Leu Glu Val Val Ala Ala Thr
 1               5                  10                  15

Pro Thr Ser Leu Leu Ile Ser Trp Thr Leu Pro His Ala Gly Arg Ala
                20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
        50                  55                  60

Leu Lys Pro Gly Val Asp Tyr Thr Ile Thr Val Tyr Ala Val Thr Val
 65                  70                  75                  80

Thr Thr Thr Lys Val Ile His Tyr Lys Pro Ile Ser Ile Asn Tyr Arg
                 85                  90                  95

Thr Glu Gly Ser Gly Cys His His His His His
            100                 105

<210> SEQ ID NO 234
<211> LENGTH: 108
<212> TYPE: PRT

<213> ORGANISM: Artificial Sequence
<220> FEATURE:
<223> OTHER INFORMATION: Synthetic

<400> SEQUENCE: 234

```
Met Gly Val Ser Asp Val Pro Arg Asp Leu Glu Val Val Ala Ala Thr
1               5                   10                  15

Pro Thr Ser Leu Leu Ile Ser Trp Thr Leu Pro His Ala Gly Arg Ala
            20                  25                  30

His Tyr Tyr Arg Ile Thr Tyr Gly Glu Thr Gly Gly Asn Ser Pro Val
        35                  40                  45

Gln Glu Phe Thr Val Pro Gly Arg Gly Val Thr Ala Thr Ile Ser Gly
50                  55                  60

Leu Lys Pro Gly Val Asp Tyr Thr Ile Thr Val Tyr Ala Val Thr Val
65                  70                  75                  80

Thr Thr Thr Lys Val Ile His Tyr Lys Pro Ile Ser Ile Asn Tyr Arg
                85                  90                  95

Thr Glu Gly Ser Gly Cys His His His His His
            100                 105
```

<210> SEQ ID NO 235
<211> LENGTH: 107
<212> TYPE: PRT
<213> ORGANISM: Artificial Sequence
<220> FEATURE:
<223> OTHER INFORMATION: Synthetic

<400> SEQUENCE: 235

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Arg Gly Leu Ala Arg
            20                  25                  30

Tyr Tyr Arg Ile Thr Tyr Gly Glu Thr Gly Gly Asn Ser Pro Val Gln
        35                  40                  45

Glu Phe Thr Val Phe Gly Arg Gly Thr Thr Ala Thr Ile Ser Gly Leu
50                  55                  60

Lys Pro Gly Val Asp Tyr Thr Ile Thr Val Tyr Ala Val Thr Ile Asp
65                  70                  75                  80

Arg Asp Gly Thr Arg Ser Phe Asp Pro Ile Ser Ile Asn Tyr Arg Thr
                85                  90                  95

Glu Gly Ser Gly Cys His His His His His
            100                 105
```

<210> SEQ ID NO 236
<211> LENGTH: 107
<212> TYPE: PRT
<213> ORGANISM: Artificial Sequence
<220> FEATURE:
<223> OTHER INFORMATION: Synthetic

<400> SEQUENCE: 236

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Gly Leu Ala Arg
            20                  25                  30

Tyr Tyr Arg Ile Thr Tyr Gly Glu Thr Gly Gly Asn Ser Pro Val Gln
        35                  40                  45

Glu Phe Thr Val Val Gly Arg Gly Asn Thr Ala Thr Ile Ser Gly Leu
50                  55                  60
```

```
Lys Pro Gly Val Asp Tyr Thr Ile Thr Val Tyr Ala Val Thr Ile Phe
 65                  70                  75                  80

Arg Asp Gly Pro Val Thr Trp Asp Pro Ile Ser Ile Asn Tyr Arg Thr
                 85                  90                  95

Glu Gly Ser Gly Cys His His His His His
            100                 105
```

<210> SEQ ID NO 237
<211> LENGTH: 107
<212> TYPE: PRT
<213> ORGANISM: Artificial Sequence
<220> FEATURE:
<223> OTHER INFORMATION: Synthetic

<400> SEQUENCE: 237

```
Met Gly Val Ser Asp Val Pro Arg Asp Leu Glu Val Val Ala Ala Thr
 1               5                  10                  15

Pro Thr Ser Leu Leu Ile Ser Trp Asp Ala Pro Lys Gly Leu Ala Arg
                 20                  25                  30

Tyr Tyr Arg Ile Thr Tyr Gly Glu Thr Gly Gly Asn Ser Pro Val Gln
             35                  40                  45

Glu Phe Thr Val Val Gly Arg Gly Asn Thr Ala Thr Ile Ser Gly Leu
 50                  55                  60

Lys Pro Gly Val Asp Tyr Thr Ile Thr Val Tyr Ala Val Thr Ile Phe
 65                  70                  75                  80

Arg Asp Gly Pro Val Thr Trp Asp Pro Ile Ser Ile Asn Tyr Arg Thr
                 85                  90                  95

Glu Gly Ser Gly Cys His His His His His
            100                 105
```

<210> SEQ ID NO 238
<211> LENGTH: 108
<212> TYPE: PRT
<213> ORGANISM: Artificial Sequence
<220> FEATURE:
<223> OTHER INFORMATION: Synthetic

<400> SEQUENCE: 238

```
Met Gly Val Ser Asp Val Pro Arg Asp Leu Glu Val Val Ala Ala Thr
 1               5                  10                  15

Pro Thr Ser Leu Leu Ile Ser Trp Ser Leu Pro Asn Pro Gly Asn Ala
                 20                  25                  30

His Tyr Tyr Arg Ile Thr Tyr Gly Glu Thr Gly Gly Asn Ser Pro Val
             35                  40                  45

Gln Glu Phe Thr Val Pro Gly Arg Gly Val Thr Ala Thr Ile Ser Gly
 50                  55                  60

Leu Lys Pro Gly Val Asp Tyr Thr Ile Thr Val Tyr Ala Val Thr Val
 65                  70                  75                  80

Thr Asp Thr Gly Phe Ile Thr Tyr Lys Pro Ile Ser Ile Asn Tyr Arg
                 85                  90                  95

Thr Glu Gly Ser Gly Cys His His His His His
            100                 105
```

<210> SEQ ID NO 239
<211> LENGTH: 108
<212> TYPE: PRT
<213> ORGANISM: Artificial Sequence
<220> FEATURE:
<223> OTHER INFORMATION: Synthetic

<400> SEQUENCE: 239

Met Gly Val Ser Asp Val Pro Arg Asp Leu Glu Val Val Ala Ala Thr
1               5                   10                  15

Pro Thr Ser Leu Leu Ile Ser Trp Ser Leu Pro His Gln Gly Lys Ala
            20                  25                  30

Asn Tyr Tyr Arg Ile Thr Tyr Gly Glu Thr Gly Asn Ser Pro Val
        35                  40                  45

Gln Glu Phe Thr Val Pro Gly Arg Gly Val Thr Ala Thr Ile Ser Gly
    50                  55                  60

Leu Lys Pro Gly Val Asp Tyr Thr Ile Thr Val Tyr Ala Val Thr Val
65                  70                  75                  80

Thr Asp Thr Gly Tyr Leu Lys Tyr Lys Pro Ile Ser Ile Asn Tyr Arg
                85                  90                  95

Thr Glu Gly Ser Gly Cys His His His His His His
                100                 105

<210> SEQ ID NO 240
<211> LENGTH: 318
<212> TYPE: DNA
<213> ORGANISM: Artificial Sequence
<220> FEATURE:
<223> OTHER INFORMATION: Synthetic

<400> SEQUENCE: 240
atgggagttt ctgatgtgcc gcgcgacctg gaagtggttg ctgccacccc caccagcctg    60
ctgatcagct gggtttctcc gcgtggtcgt gctcgatatt accgcatcac ttacggcgaa   120
acaggaggca atagccctgt ccaggagttc actgtgcctg gtcgtggttc tacagctacc   180
atcagcggcc ttaaacctgg cgttgattat accatcactg tgtatgctgt cactatctac   240
cgtgacggta tgtctcatca tgacccaatt tccattaatt accgcacagg tagcggttgc   300
caccatcacc accatcac                                                 318

<210> SEQ ID NO 241
<211> LENGTH: 321
<212> TYPE: DNA
<213> ORGANISM: Artificial Sequence
<220> FEATURE:
<223> OTHER INFORMATION: Synthetic

<400> SEQUENCE: 241
atgggagttt ctgatgtgcc gcgcgacctg gaagtggttg ctgccacccc caccagcctg    60
ctgatcagct ggtctctgcc gcatgctggt catgtgaact attaccgcat cacttacggc   120
gaaacaggag gcaatagccc tgtccaggag ttcactgtgc ctggtcgtgg tgttacagct   180
accatcagcg gccttaaacc tggcgttgat tataccatca ctgtgtatgc tgtcactctg   240
actaaatctc agatgatcca ttacatgcca atttccatta attaccgcac aggtagcggt   300
tgccaccatc accaccatca c                                             321

<210> SEQ ID NO 242
<211> LENGTH: 324
<212> TYPE: DNA
<213> ORGANISM: Artificial Sequence
<220> FEATURE:
<223> OTHER INFORMATION: Synthetic

<400> SEQUENCE: 242
atgggagttt ctgatgtgcc gcgcgacctg gaagtggttg ctgccacccc caccagcctg    60

-continued

```
ctgatcagct ggactttgcc gcatgctggt cgtgcgcact attaccgcat cacttacggc    120
gaaacaggag gcaatagccc tgtccaggag ttcactgtgc ctgggcgggg tgttacagct    180
accatcagcg gccttaaacc tggcgttgat tataccatca ctgtgtatgc tgtcactgtg    240
acgacaactt cggtgatcct ttacaagcca atttccatta attaccgcac agaaggtagc    300
ggttgccacc atcaccacca tcac                                          324
```

<210> SEQ ID NO 243
<211> LENGTH: 324
<212> TYPE: DNA
<213> ORGANISM: Artificial Sequence
<220> FEATURE:
<223> OTHER INFORMATION: Synthetic
<400> SEQUENCE: 243

```
atgggagttt ctgatgtgcc gcgcgacctg gaagtggttg ctgccacccc caccagcctg     60
ctgatcagct ggtacctccc gtatcctgcg catatgaact attaccgcat cacttacggc    120
gaaacaggag gcaatagccc tgtccaggag ttcactgtgc ctgggcgggg tctgacagct    180
accatcagcg gccttaaacc tggcgttgat tataccatca ctgtgtatgc tgtcactctg    240
acaaaatctc agattctcca tcataggcca atttccatta attaccgcac agaaggtagc    300
ggttgccacc atcaccacca tcac                                          324
```

<210> SEQ ID NO 244
<211> LENGTH: 324
<212> TYPE: DNA
<213> ORGANISM: Artificial Sequence
<220> FEATURE:
<223> OTHER INFORMATION: Synthetic
<400> SEQUENCE: 244

```
atgggagttt ctgatgtgcc gcgcgacctg gaagtggttg ctgccacccc caccagcctg     60
ctgatcagct ggtctcttcc ttatgctggt catctaaact attaccgcat cacttacggc    120
gaaacaggag gcaatagccc tgtccaggag ttcactgtgc ctggtcgtgg tgtgacagct    180
accatcagcg gccttaaacc tggcgttgat tataccatca ctgtgtatgc tgtcactctg    240
actaagtctc agctgataca ttacatgcca atttccatta attaccgcac agaaggtagc    300
ggttgccacc atcaccacca tcac                                          324
```

<210> SEQ ID NO 245
<211> LENGTH: 324
<212> TYPE: DNA
<213> ORGANISM: Artificial Sequence
<220> FEATURE:
<223> OTHER INFORMATION: Synthetic
<400> SEQUENCE: 245

```
atgggtgtta gtgatgttcc gcgtgatctg gaagttgttg cagcaacccc gaccagcctg     60
ctgattagct ggaccctgcc gcatgcaggt cgtgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccgtt    240
accaccacca aagtgattca ttataaaccg atttccatta attaccgcac agaaggtagc    300
ggttgccacc atcaccacca tcac                                          324
```

<210> SEQ ID NO 246

```
<211> LENGTH: 306
<212> TYPE: DNA
<213> ORGANISM: Artificial Sequence
<220> FEATURE:
<223> OTHER INFORMATION: Synthetic

<400> SEQUENCE: 246
atgggtgtta gtgatgttcc gcgtgatctg aagttgttg cagcaacccc gaccagcctg      60
ctgattagct ggaccctgcc gcatgcaggt cgtgcacatt attatcgtat tacctatggt    120
gaaaccggtg gtaatagtcc ggttcaggaa ttcaccgttc cgggtcgtgg tgttaccgca    180
accattagcg gtctgaaacc gggtgttgat tacaccatta ccgtttatgc agttaccgtt    240
accaccacca aagtgattca ttataaaccg atttccatta attaccgaac agaaggtagc    300
ggttgc                                                                306

<210> SEQ ID NO 247
<211> LENGTH: 321
<212> TYPE: DNA
<213> ORGANISM: Artificial Sequence
<220> FEATURE:
<223> OTHER INFORMATION: Synthetic

<400> SEQUENCE: 247
atgggagttt ctgatgtgcc gcgcgacctg gaagtggttg ctgccacccc caccagcctg     60
ctgatcagct gggacgctcc gagaggtctg gctcgatatt accgcatcac ttacggcgaa   120
acaggaggca atagccctgt ccaggagttc actgtgttcg gtcgtggtac cacagctacc   180
atcagcggcc ttaaacctgg cgttgattat accatcactg tgtatgctgt cactatcgac   240
cgtgacggta cccgcagctt cgacccaatt ccattaatt accgcacaga aggtagcggt    300
tgccaccatc accaccatca c                                              321

<210> SEQ ID NO 248
<211> LENGTH: 321
<212> TYPE: DNA
<213> ORGANISM: Artificial Sequence
<220> FEATURE:
<223> OTHER INFORMATION: Synthetic

<400> SEQUENCE: 248
atgggagttt ctgatgtgcc gcgcgacctg gaagtggttg ctgccacccc caccagcctg     60
ctgatcagct gggacgctcc ggctggtctg gctcgatatt accgcatcac ttacggcgaa   120
acaggaggca atagccctgt ccaggagttc actgtggtcg gtcgtggtaa cacagctacc   180
atcagcggcc ttaaacctgg cgttgattat accatcactg tgtatgctgt cactatcttc   240
cgtgacggtc ccgtcacctg ggacccaatt ccattaatt accgcacaga aggtagcggt    300
tgccaccatc accaccatca c                                              321

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
atgggagttt ctgatgtgcc gcgcgacctg gaagtggttg ctgccacccc caccagcctg     60
ctgatcagct gggacgctcc gaagggtctg gctcgatatt accgcatcac ttacggcgaa   120
acaggaggca atagccctgt ccaggagttc actgtggtcg gtcgtggtaa cacagctacc   180
```
atcagcggcc ttaaacctgg cgttgattat accatcactg tgtatgctgt cactatcttc     240
cgtgacggtc ccgtcacctg ggacccaatt tccattaatt accgcacaga aggtagcggt     300
tgccaccatc accaccatca c                                                321

<210> SEQ ID NO 250
<211> LENGTH: 324
<212> TYPE: DNA
<213> ORGANISM: Artificial Sequence
<220> FEATURE:
<223> OTHER INFORMATION: Synthetic

<400> SEQUENCE: 250
atgggagttt ctgatgtgcc gcgcgacctg gaagtggttg ctgccacccc caccagcctg     60
ctgatcagct ggtctctgcc gaatccgggt aacgcccatt attaccgcat cacttacggc     120
gaaacaggag gcaatagccc tgtccaggag ttcactgtgc ctggtcgtgg tgttacagct     180
accatcagcg gccttaaacc tggcgttgat tataccatca ctgtgtatgc tgtcactgtt     240
actgacacag gtttcatcac gtacaaacca atttccatta attaccgcac agaaggtagc     300
ggttgccacc atcaccacca tcac                                             324

<210> SEQ ID NO 251
<211> LENGTH: 324
<212> TYPE: DNA
<213> ORGANISM: Artificial Sequence
<220> FEATURE:
<223> OTHER INFORMATION: Synthetic

<400> SEQUENCE: 251
atgggagttt ctgatgtgcc gcgcgacctg gaagtggttg ctgccacccc caccagcctg     60
ctgatcagct ggtctctgcc gcaccaaggt aaagccaatt attaccgcat cacttacggc     120
gaaacaggag gcaatagccc tgtccaggag ttcactgtgc ctggtcgtgg tgttacagct     180
accatcagcg gccttaaacc tggcgttgat tataccatca ctgtgtatgc tgtcactgtt     240
actgatacag ggtacctcaa gtacaaacca atttccatta attaccgcac agaaggtagc     300
ggttgccacc atcaccacca tcac                                             324

<210> SEQ ID NO 252
<211> LENGTH: 336
<212> TYPE: PRT
<213> ORGANISM: Artificial Sequence
<220> FEATURE:
<223> OTHER INFORMATION: Synthetic

<400> SEQUENCE: 252

Glu Pro Lys Ser Ser Gly Ser Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Gly Gly Gly Ser Gly Gly Gly Val
225                 230                 235                 240

Ser Asp Val Pro Arg Asp Leu Glu Val Val Ala Ala Thr Pro Thr Ser
                245                 250                 255

Leu Leu Ile Ser Trp Ser Leu Pro Tyr Ala Gly His Leu Asn Tyr Tyr
            260                 265                 270

Arg Ile Thr Tyr Gly Glu Thr Gly Gly Asn Ser Pro Val Gln Glu Phe
        275                 280                 285

Thr Val Pro Gly Arg Gly Val Thr Ala Thr Ile Ser Gly Leu Lys Pro
    290                 295                 300

Gly Val Asp Tyr Thr Ile Thr Val Tyr Ala Val Thr Leu Thr Lys Ser
305                 310                 315                 320

Gln Leu Ile His Tyr Met Pro Ile Ser Ile Asn Tyr Arg Thr Glu Ile
                325                 330                 335

<210> SEQ ID NO 253
<211> LENGTH: 330
<212> TYPE: PRT
<213> ORGANISM: Artificial Sequence
<220> FEATURE:
<223> OTHER INFORMATION: Synthetic

<400> SEQUENCE: 253

Gly Val Ser Asp Val Pro Arg Asp Leu Glu Val Val Ala Ala Thr Pro
1               5                   10                  15

Thr Ser Leu Leu Ile Ser Trp Thr Leu Pro His Ala Gly Arg Ala His
            20                  25                  30

Tyr Tyr Arg Ile Thr Tyr Gly Glu Thr Gly Gly Asn Ser Pro Val Gln
        35                  40                  45

Glu Phe Thr Val Pro Gly Arg Gly Val Thr Ala Thr Ile Ser Gly Leu
    50                  55                  60

Lys Pro Gly Val Asp Tyr Thr Ile Thr Val Tyr Ala Val Thr Val Thr
65                  70                  75                  80

Thr Thr Lys Val Ile His Tyr Lys Pro Ile Ser Ile Asn Tyr Arg Thr
            85                  90                  95

Glu Ile Glu Pro Lys Ser Ser Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 254
<211> LENGTH: 325
<212> TYPE: PRT
<213> ORGANISM: Artificial Sequence
<220> FEATURE:
<223> OTHER INFORMATION: Synthetic

<400> SEQUENCE: 254

Gly Val Ser Asp Val Pro Arg Asp Leu Glu Val Val Ala Ala Thr Pro
1               5                   10                  15

Thr Ser Leu Leu Ile Ser Trp Thr Leu Pro His Ala Gly Arg Ala His
            20                  25                  30

Tyr Tyr Arg Ile Thr Tyr Gly Glu Thr Gly Gly Asn Ser Pro Val Gln
        35                  40                  45

Glu Phe Thr Val Pro Gly Arg Gly Val Thr Ala Thr Ile Ser Gly Leu
50                  55                  60

Lys Pro Gly Val Asp Tyr Thr Ile Thr Val Tyr Ala Val Thr Val Thr
65                  70                  75                  80

Thr Thr Lys Val Ile His Tyr Lys Pro Ile Ser Ile Asn Tyr Arg Thr
            85                  90                  95

Glu Ile Asp Lys Thr His Thr Cys Pro Pro Cys Pro Ala Pro Glu Leu
                100                 105                 110

Leu Gly Gly Pro Ser Val Phe Leu Phe Pro Pro Lys Pro Lys Asp Thr
            115                 120                 125

Leu Met Ile Ser Arg Thr Pro Glu Val Thr Cys Val Val Val Asp Val
130                 135                 140

Ser His Glu Asp Pro Glu Val Lys Phe Asn Trp Tyr Val Asp Gly Val
145                 150                 155                 160
```

```
Glu Val His Asn Ala Lys Thr Lys Pro Arg Glu Glu Gln Tyr Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Ala Leu Pro Ala
        195                 200                 205

Pro Ile Glu Lys Thr Ile Ser Lys Ala Lys Gly Gln Pro Arg Glu Pro
    210                 215                 220

Gln Val Tyr Thr Leu Pro Pro Ser Arg Asp Glu Leu Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
                325

<210> SEQ ID NO 255
<211> LENGTH: 345
<212> TYPE: PRT
<213> ORGANISM: Artificial Sequence
<220> FEATURE:
<223> OTHER INFORMATION: Synthetic

<400> SEQUENCE: 255

Gly Val Ser Asp Val Pro Arg Asp Leu Glu Val Val Ala Ala Thr Pro
1               5                   10                  15

Thr Ser Leu Leu Ile Ser Trp Thr Leu Pro His Ala Gly Arg Ala His
            20                  25                  30

Tyr Tyr Arg Ile Thr Tyr Gly Glu Thr Gly Gly Asn Ser Pro Val Gln
        35                  40                  45

Glu Phe Thr Val Pro Gly Arg Gly Val Thr Ala Thr Ile Ser Gly Leu
    50                  55                  60

Lys Pro Gly Val Asp Tyr Thr Ile Thr Val Tyr Ala Val Thr Val Thr
65                  70                  75                  80

Thr Thr Lys Val Ile His Tyr Lys Pro Ile Ser Ile Asn Tyr Arg Thr
                85                  90                  95

Glu Ile Glu Ser Pro Lys Ala Gln Ala Ser Ser Val Pro Thr Ala Gln
            100                 105                 110

Pro Gln Ala Glu Gly Leu Ala Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190
```

Gln Tyr Asn Ser Thr Tyr Arg Val Val Ser Val Leu Thr Val Leu His
            195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
            245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
            275                 280                 285

Tyr Lys Thr Thr Pro Pro Val Leu Asp Ser Asp Gly Ser Phe Phe Leu
            290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 256
<211> LENGTH: 331
<212> TYPE: PRT
<213> ORGANISM: Artificial Sequence
<220> FEATURE:
<223> OTHER INFORMATION: Synthetic

<400> SEQUENCE: 256

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Ala Gly Gly Gly Ser Gly Gly Val Ser Asp Val Pro Arg
225                 230                 235                 240

Asp Leu Glu Val Val Ala Ala Thr Pro Thr Ser Leu Leu Ile Ser Trp
            245                 250                 255

Thr Leu Pro His Ala Gly Arg Ala His Tyr Tyr Arg Ile Thr Tyr Gly
            260                 265                 270

Glu Thr Gly Gly Asn Ser Pro Val Gln Glu Phe Thr Val Pro Gly Arg
        275                 280                 285

Gly Val Thr Ala Thr Ile Ser Gly Leu Lys Pro Gly Val Asp Tyr Thr
290                 295                 300

Ile Thr Val Tyr Ala Val Thr Val Thr Thr Lys Val Ile His Tyr
305                 310                 315                 320

Lys Pro Ile Ser Ile Asn Tyr Arg Thr Glu Ile
                325                 330

<210> SEQ ID NO 257
<211> LENGTH: 340
<212> TYPE: PRT
<213> ORGANISM: Artificial Sequence
<220> FEATURE:
<223> OTHER INFORMATION: Synthetic

<400> SEQUENCE: 257

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Glu Leu Gln Leu Glu Glu Ser Ala Ala Glu Ala Gln Asp Gly Glu
225                 230                 235                 240

```
Leu Asp Gly Val Ser Asp Val Pro Arg Asp Leu Glu Val Val Ala Ala
            245                 250                 255

Thr Pro Thr Ser Leu Leu Ile Ser Trp Thr Leu Pro His Ala Gly Arg
            260                 265                 270

Ala His Tyr Tyr Arg Ile Thr Tyr Gly Glu Thr Gly Gly Asn Ser Pro
            275                 280                 285

Val Gln Glu Phe Thr Val Pro Gly Arg Gly Val Thr Ala Thr Ile Ser
            290                 295                 300

Gly Leu Lys Pro Gly Val Asp Tyr Thr Ile Thr Val Tyr Ala Val Thr
305                 310                 315                 320

Val Thr Thr Thr Lys Val Ile His Tyr Lys Pro Ile Ser Ile Asn Tyr
            325                 330                 335

Arg Thr Glu Ile
            340

<210> SEQ ID NO 258
<211> LENGTH: 332
<212> TYPE: PRT
<213> ORGANISM: Artificial Sequence
<220> FEATURE:
<223> OTHER INFORMATION: Synthetic

<400> SEQUENCE: 258

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gln Pro Asp Glu Pro Gly Gly Ser Gly Val Ser Asp Val Pro
225                 230                 235                 240

Arg Asp Leu Glu Val Val Ala Ala Thr Pro Thr Ser Leu Leu Ile Ser
                245                 250                 255
```

Trp Thr Leu Pro His Ala Gly Arg Ala His Tyr Tyr Arg Ile Thr Tyr
            260                 265                 270

Gly Glu Thr Gly Gly Asn Ser Pro Val Gln Glu Phe Thr Val Pro Gly
        275                 280                 285

Arg Gly Val Thr Ala Thr Ile Ser Gly Leu Lys Pro Gly Val Asp Tyr
        290                 295                 300

Thr Ile Thr Val Tyr Ala Val Thr Val Thr Thr Lys Val Ile His
305                 310                 315                 320

Tyr Lys Pro Ile Ser Ile Asn Tyr Arg Thr Glu Ile
                325                 330

<210> SEQ ID NO 259
<211> LENGTH: 336
<212> TYPE: PRT
<213> ORGANISM: Artificial Sequence
<220> FEATURE:
<223> OTHER INFORMATION: Synthetic

<400> SEQUENCE: 259

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Ser Gly Ser Gly Ser Gly Ser Gly Ser Gly Ser Gly Val
225                 230                 235                 240

Ser Asp Val Pro Arg Asp Leu Glu Val Val Ala Ala Thr Pro Thr Ser
                245                 250                 255

Leu Leu Ile Ser Trp Thr Leu Pro His Ala Gly Arg Ala His Tyr Tyr
            260                 265                 270

Arg Ile Thr Tyr Gly Glu Thr Gly Gly Asn Ser Pro Val Gln Glu Phe
        275                 280                 285

```
Thr Val Pro Gly Arg Gly Val Thr Ala Thr Ile Ser Gly Leu Lys Pro
    290                 295                 300
Gly Val Asp Tyr Thr Ile Thr Val Tyr Ala Val Thr Val Thr Thr Thr
305                 310                 315                 320
Lys Val Ile His Tyr Lys Pro Ile Ser Ile Asn Tyr Arg Thr Glu Ile
                325                 330                 335

<210> SEQ ID NO 260
<211> LENGTH: 339
<212> TYPE: PRT
<213> ORGANISM: Artificial Sequence
<220> FEATURE:
<223> OTHER INFORMATION: Synthetic

<400> SEQUENCE: 260

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
    115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
    195                 200                 205
His Glu Ala Leu His Asn His Tyr Thr Gln Lys Ser Leu Ser Leu Ser
210                 215                 220
Pro Glu Leu Gln Leu Glu Glu Ser Ala Ala Glu Ala Gln Asp Gly Glu
225                 230                 235                 240
Leu Asp Gly Val Ser Asp Val Pro Arg Asp Leu Glu Val Val Ala Ala
                245                 250                 255
Thr Pro Thr Ser Leu Leu Ile Ser Trp Asp Ala Pro Arg Gly Leu Ala
            260                 265                 270
Arg Tyr Tyr Arg Ile Thr Tyr Gly Glu Thr Gly Gly Asn Ser Pro Val
    275                 280                 285
Gln Glu Phe Thr Val Phe Gly Arg Gly Thr Ala Thr Ile Ser Gly
290                 295                 300
Leu Lys Pro Gly Val Asp Tyr Thr Ile Thr Val Tyr Ala Val Thr Ile
305                 310                 315                 320
```

```
Asp Arg Asp Gly Thr Arg Ser Phe Asp Pro Ile Ser Ile Asn Tyr Arg
            325                 330                 335

Thr Glu Ile

<210> SEQ ID NO 261
<211> LENGTH: 339
<212> TYPE: PRT
<213> ORGANISM: Artificial Sequence
<220> FEATURE:
<223> OTHER INFORMATION: Synthetic

<400> SEQUENCE: 261

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Glu Leu Gln Leu Glu Glu Ser Ala Ala Glu Ala Gln Asp Gly Glu
225                 230                 235                 240

Leu Asp Gly Val Ser Asp Val Pro Arg Asp Leu Glu Val Val Ala Ala
                245                 250                 255

Thr Pro Thr Ser Leu Leu Ile Ser Trp Asp Ala Pro Ala Gly Leu Ala
            260                 265                 270

Arg Tyr Tyr Arg Ile Thr Tyr Gly Glu Thr Gly Gly Asn Ser Pro Val
        275                 280                 285

Gln Glu Phe Thr Val Val Gly Arg Gly Asn Thr Ala Thr Ile Ser Gly
    290                 295                 300

Leu Lys Pro Gly Val Asp Tyr Thr Ile Thr Val Tyr Ala Val Thr Ile
305                 310                 315                 320

Phe Arg Asp Gly Pro Val Thr Trp Asp Pro Ile Ser Ile Asn Tyr Arg
                325                 330                 335

Thr Glu Ile
```

<210> SEQ ID NO 262
<211> LENGTH: 339
<212> TYPE: PRT
<213> ORGANISM: Artificial Sequence
<220> FEATURE:
<223> OTHER INFORMATION: Synthetic

<400> SEQUENCE: 262

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Glu Leu Gln Leu Glu Glu Ser Ala Ala Glu Ala Gln Asp Gly Glu
225                 230                 235                 240

Leu Asp Gly Val Ser Asp Val Pro Arg Asp Leu Glu Val Val Ala Ala
                245                 250                 255

Thr Pro Thr Ser Leu Leu Ile Ser Trp Asp Ala Pro Lys Gly Leu Ala
            260                 265                 270

Arg Tyr Tyr Arg Ile Thr Tyr Gly Glu Thr Gly Gly Asn Ser Pro Val
        275                 280                 285

Gln Glu Phe Thr Val Val Gly Arg Gly Asn Thr Ala Thr Ile Ser Gly
    290                 295                 300

Leu Lys Pro Gly Val Asp Tyr Thr Ile Thr Val Tyr Ala Val Thr Ile
305                 310                 315                 320

Phe Arg Asp Gly Pro Val Thr Trp Asp Pro Ile Ser Ile Asn Tyr Arg
                325                 330                 335

Thr Glu Ile

<210> SEQ ID NO 263
<211> LENGTH: 340

```
<212> TYPE: PRT
<213> ORGANISM: Artificial Sequence
<220> FEATURE:
<223> OTHER INFORMATION: Synthetic

<400> SEQUENCE: 263

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Glu Leu Gln Leu Glu Glu Ser Ala Ala Glu Ala Gln Asp Gly Glu
225                 230                 235                 240

Leu Asp Gly Val Ser Asp Val Pro Arg Asp Leu Glu Val Val Ala Ala
                245                 250                 255

Thr Pro Thr Ser Leu Leu Ile Ser Trp Ser Leu Pro Asn Pro Gly Asn
            260                 265                 270

Ala His Tyr Tyr Arg Ile Thr Tyr Gly Glu Thr Gly Gly Asn Ser Pro
        275                 280                 285

Val Gln Glu Phe Thr Val Pro Gly Arg Gly Val Thr Ala Thr Ile Ser
290                 295                 300

Gly Leu Lys Pro Gly Val Asp Tyr Thr Ile Thr Val Tyr Ala Val Thr
305                 310                 315                 320

Val Thr Asp Thr Gly Phe Ile Thr Tyr Lys Pro Ile Ser Ile Asn Tyr
                325                 330                 335

Arg Thr Glu Ile
            340

<210> SEQ ID NO 264
<211> LENGTH: 340
<212> TYPE: PRT
<213> ORGANISM: Artificial Sequence
<220> FEATURE:
```

<223> OTHER INFORMATION: Synthetic

<400> SEQUENCE: 264

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Glu Leu Gln Leu Glu Glu Ser Ala Ala Glu Ala Gln Asp Gly Glu
225                 230                 235                 240

Leu Asp Gly Val Ser Asp Val Pro Arg Asp Leu Glu Val Val Ala Ala
                245                 250                 255

Thr Pro Thr Ser Leu Leu Ile Ser Trp Ser Leu Pro His Gln Gly Lys
            260                 265                 270

Ala Asn Tyr Tyr Arg Ile Thr Tyr Gly Glu Thr Gly Gly Asn Ser Pro
        275                 280                 285

Val Gln Glu Phe Thr Val Pro Gly Arg Gly Val Thr Ala Thr Ile Ser
    290                 295                 300

Gly Leu Lys Pro Gly Val Asp Tyr Thr Ile Thr Val Tyr Ala Val Thr
305                 310                 315                 320

Val Thr Asp Thr Gly Tyr Leu Lys Tyr Lys Pro Ile Ser Ile Asn Tyr
                325                 330                 335

Arg Thr Glu Ile
            340

<210> SEQ ID NO 265
<211> LENGTH: 329
<212> TYPE: PRT
<213> ORGANISM: Artificial Sequence
<220> FEATURE:
<223> OTHER INFORMATION: Synthetic

<400> SEQUENCE: 265

Gly Val Ser Asp Val Pro Arg Asp Leu Glu Val Val Ala Ala Thr Pro
1               5                   10                  15

Thr Ser Leu Leu Ile Ser Trp Asp Ala Pro Arg Gly Leu Ala Arg Tyr
            20                  25                  30

Tyr Arg Ile Thr Tyr Gly Glu Thr Gly Gly Asn Ser Pro Val Gln Glu
                35                  40                  45

Phe Thr Val Phe Gly Arg Gly Thr Thr Ala Thr Ile Ser Gly Leu Lys
50                      55                  60

Pro Gly Val Asp Tyr Thr Ile Thr Val Tyr Ala Val Thr Ile Asp Arg
65                  70                  75                  80

Asp Gly Thr Arg Ser Phe Asp Pro Ile Ser Ile Asn Tyr Arg Thr Glu
                85                  90                  95

Ile Glu Pro Lys Ser Ser Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 266
<211> LENGTH: 329
<212> TYPE: PRT
<213> ORGANISM: Artificial Sequence
<220> FEATURE:
<223> OTHER INFORMATION: Synthetic

<400> SEQUENCE: 266

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Gly Leu Ala Arg Tyr
            20                  25                  30

```
Tyr Arg Ile Thr Tyr Gly Glu Thr Gly Gly Asn Ser Pro Val Gln Glu
            35                  40                  45

Phe Thr Val Val Gly Arg Gly Asn Thr Ala Thr Ile Ser Gly Leu Lys
 50                  55                  60

Pro Gly Val Asp Tyr Thr Ile Thr Val Tyr Ala Val Thr Ile Phe Arg
 65                  70                  75                  80

Asp Gly Pro Val Thr Trp Asp Pro Ile Ser Ile Asn Tyr Arg Thr Glu
                 85                  90                  95

Ile Glu Pro Lys Ser Ser Asp Lys Thr His Thr Cys Pro Pro Cys Pro
            100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 267
<211> LENGTH: 329
<212> TYPE: PRT
<213> ORGANISM: Artificial Sequence
<220> FEATURE:
<223> OTHER INFORMATION: Synthetic

<400> SEQUENCE: 267

Gly Val Ser Asp Val Pro Arg Asp Leu Glu Val Val Ala Ala Thr Pro
 1               5                  10                  15

Thr Ser Leu Leu Ile Ser Trp Asp Ala Pro Lys Gly Leu Ala Arg Tyr
                20                  25                  30

Tyr Arg Ile Thr Tyr Gly Glu Thr Gly Gly Asn Ser Pro Val Gln Glu
            35                  40                  45

Phe Thr Val Val Gly Arg Gly Asn Thr Ala Thr Ile Ser Gly Leu Lys
 50                  55                  60
```

```
Pro Gly Val Asp Tyr Thr Ile Thr Val Tyr Ala Val Thr Ile Phe Arg
 65                  70                  75                  80

Asp Gly Pro Val Thr Trp Asp Pro Ile Ser Ile Asn Tyr Arg Thr Glu
                 85                  90                  95

Ile Glu Pro Lys Ser Ser Asp Lys Thr His Thr Cys Pro Pro Cys Pro
            100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 268
<211> LENGTH: 330
<212> TYPE: PRT
<213> ORGANISM: Artificial Sequence
<220> FEATURE:
<223> OTHER INFORMATION: Synthetic

<400> SEQUENCE: 268

Gly Val Ser Asp Val Pro Arg Asp Leu Glu Val Val Ala Ala Thr Pro
 1               5                  10                  15

Thr Ser Leu Leu Ile Ser Trp Ser Leu Pro Asn Pro Gly Asn Ala His
                20                  25                  30

Tyr Tyr Arg Ile Thr Tyr Gly Glu Thr Gly Gly Asn Ser Pro Val Gln
            35                  40                  45

Glu Phe Thr Val Pro Gly Arg Gly Val Thr Ala Thr Ile Ser Gly Leu
         50                 55                  60

Lys Pro Gly Val Asp Tyr Thr Ile Thr Val Tyr Ala Val Thr Val Thr
 65                 70                  75                  80

Asp Thr Gly Phe Ile Thr Tyr Lys Pro Ile Ser Ile Asn Tyr Arg Thr
                85                  90                  95
```

```
Glu Ile Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 269
<211> LENGTH: 330
<212> TYPE: PRT
<213> ORGANISM: Artificial Sequence
<220> FEATURE:
<223> OTHER INFORMATION: Synthetic

<400> SEQUENCE: 269

Gly Val Ser Asp Val Pro Arg Asp Leu Glu Val Val Ala Ala Thr Pro
1               5                   10                  15

Thr Ser Leu Leu Ile Ser Trp Ser Leu Pro His Gln Gly Lys Ala Asn
            20                  25                  30

Tyr Tyr Arg Ile Thr Tyr Gly Glu Thr Gly Gly Asn Ser Pro Val Gln
            35                  40                  45

Glu Phe Thr Val Pro Gly Arg Gly Val Thr Ala Thr Ile Ser Gly Leu
50                  55                  60

Lys Pro Gly Val Asp Tyr Thr Ile Thr Val Tyr Ala Val Thr Val Thr
65                  70                  75                  80

Asp Thr Gly Tyr Leu Lys Tyr Lys Pro Ile Ser Ile Asn Tyr Arg Thr
                85                  90                  95

Glu Ile Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

-continued

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 270
<211> LENGTH: 340
<212> TYPE: PRT
<213> ORGANISM: Artificial Sequence
<220> FEATURE:
<223> OTHER INFORMATION: Synthetic

<400> SEQUENCE: 270

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Glu Leu Gln Leu Glu Glu Ser Ala Ala Glu Ala Gln Glu Gly Glu
225                 230                 235                 240

Leu Glu Gly Val Ser Asp Val Pro Arg Asp Leu Glu Val Val Ala Ala
                245                 250                 255

Thr Pro Thr Ser Leu Leu Ile Ser Trp Thr Leu Pro His Ala Gly Arg
            260                 265                 270

Ala His Tyr Tyr Arg Ile Thr Tyr Gly Glu Thr Gly Gly Asn Ser Pro
        275                 280                 285

Val Gln Glu Phe Thr Val Pro Gly Arg Gly Val Thr Ala Thr Ile Ser
    290                 295                 300

Gly Leu Lys Pro Gly Val Asp Tyr Thr Ile Thr Val Tyr Ala Val Thr
305                 310                 315                 320

Val Thr Thr Thr Lys Val Ile His Tyr Lys Pro Ile Ser Ile Asn Tyr
                325                 330                 335

Arg Thr Glu Ile
            340

<210> SEQ ID NO 271
<211> LENGTH: 339
<212> TYPE: PRT
<213> ORGANISM: Artificial Sequence
<220> FEATURE:
<223> OTHER INFORMATION: Synthetic

<400> SEQUENCE: 271

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Glu Leu Gln Leu Glu Glu Ser Ala Ala Glu Ala Gln Glu Gly Glu
225                 230                 235                 240

Leu Glu Gly Val Ser Asp Val Pro Arg Asp Leu Glu Val Val Ala Ala
                245                 250                 255

Thr Pro Thr Ser Leu Leu Ile Ser Trp Asp Ala Pro Ala Gly Leu Ala
            260                 265                 270

Arg Tyr Tyr Arg Ile Thr Tyr Gly Glu Thr Gly Gly Asn Ser Pro Val
        275                 280                 285

Gln Glu Phe Thr Val Val Gly Arg Gly Asn Thr Ala Thr Ile Ser Gly
    290                 295                 300

Leu Lys Pro Gly Val Asp Tyr Thr Ile Thr Val Tyr Ala Val Thr Ile
305                 310                 315                 320

Phe Arg Asp Gly Pro Val Thr Trp Asp Pro Ile Ser Ile Asn Tyr Arg
                325                 330                 335

Thr Glu Ile

<210> SEQ ID NO 272
<211> LENGTH: 339
<212> TYPE: PRT
<213> ORGANISM: Artificial Sequence
<220> FEATURE:
<223> OTHER INFORMATION: Synthetic

<400> SEQUENCE: 272

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Glu Leu Gln Leu Glu Glu Ser Ala Ala Glu Ala Gln Glu Gly Glu
225                 230                 235                 240

Leu Glu Gly Val Ser Asp Val Pro Arg Asp Leu Glu Val Val Ala Ala
                245                 250                 255

Thr Pro Thr Ser Leu Leu Ile Ser Trp Asp Ala Pro Lys Gly Leu Ala
                260                 265                 270

Arg Tyr Tyr Arg Ile Thr Tyr Gly Glu Thr Gly Gly Asn Ser Pro Val
                275                 280                 285

Gln Glu Phe Thr Val Val Gly Arg Gly Asn Thr Ala Thr Ile Ser Gly
    290                 295                 300

Leu Lys Pro Gly Val Asp Tyr Thr Ile Thr Val Tyr Ala Val Thr Ile
305                 310                 315                 320

Phe Arg Asp Gly Pro Val Thr Trp Asp Pro Ile Ser Ile Asn Tyr Arg
                325                 330                 335

Thr Glu Ile

<210> SEQ ID NO 273
<211> LENGTH: 340
<212> TYPE: PRT
<213> ORGANISM: Artificial Sequence
<220> FEATURE:
<223> OTHER INFORMATION: Synthetic

<400> SEQUENCE: 273

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
```

```
            210                 215                 220
Pro Glu Leu Gln Leu Glu Ser Ala Ala Glu Ala Gln Glu Gly Glu
225                 230                 235                 240

Leu Glu Gly Val Ser Asp Val Pro Arg Asp Leu Glu Val Val Ala Ala
                    245                 250                 255

Thr Pro Thr Ser Leu Leu Ile Ser Trp Ser Leu Pro His Gln Gly Lys
                260                 265                 270

Ala Asn Tyr Tyr Arg Ile Thr Tyr Gly Glu Thr Gly Gly Asn Ser Pro
            275                 280                 285

Val Gln Glu Phe Thr Val Pro Gly Arg Gly Val Thr Ala Thr Ile Ser
        290                 295                 300

Gly Leu Lys Pro Gly Val Asp Tyr Thr Ile Thr Val Tyr Ala Val Thr
305                 310                 315                 320

Val Thr Asp Thr Gly Tyr Leu Lys Tyr Lys Pro Ile Ser Ile Asn Tyr
                325                 330                 335

Arg Thr Glu Ile
            340

<210> SEQ ID NO 274
<211> LENGTH: 230
<212> TYPE: PRT
<213> ORGANISM: Artificial Sequence
<220> FEATURE:
<223> OTHER INFORMATION: Synthetic

<400> SEQUENCE: 274

Glu Pro Lys Ser Ser Gly Ser Thr His Thr Cys Pro Pro Cys Pro Ala
1               5                   10                  15

Pro Glu Leu Leu Gly Gly Ser Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro
```

```
225                 230

<210> SEQ ID NO 275
<211> LENGTH: 98
<212> TYPE: PRT
<213> ORGANISM: Artificial Sequence
<220> FEATURE:
<223> OTHER INFORMATION: Synthetic

<400> SEQUENCE: 275

Gly Val Ser Asp Val Pro Arg Asp Leu Glu Val Ala Ala Thr Pro
1               5                   10                  15

Thr Ser Leu Leu Ile Ser Trp Thr Leu Pro His Ala Gly Arg Ala His
                20                  25                  30

Tyr Tyr Arg Ile Thr Tyr Gly Glu Thr Gly Gly Asn Ser Pro Val Gln
            35                  40                  45

Glu Phe Thr Val Pro Gly Arg Gly Val Thr Ala Thr Ile Ser Gly Leu
    50                  55                  60

Lys Pro Gly Val Asp Tyr Thr Ile Thr Val Tyr Ala Val Thr Val Thr
65                  70                  75                  80

Thr Thr Lys Val Ile His Tyr Lys Pro Ile Ser Ile Asn Tyr Arg Thr
                85                  90                  95

Glu Ile

<210> SEQ ID NO 276
<211> LENGTH: 225
<212> TYPE: PRT
<213> ORGANISM: Artificial Sequence
<220> FEATURE:
<223> OTHER INFORMATION: Synthetic

<400> SEQUENCE: 276

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
```

His Glu Ala Leu His Asn His Tyr Thr Gln Lys Ser Leu Ser Leu Ser
    210                 215                 220

Pro
225

<210> SEQ ID NO 277
<211> LENGTH: 97
<212> TYPE: PRT
<213> ORGANISM: Artificial Sequence
<220> FEATURE:
<223> OTHER INFORMATION: Synthetic

<400> SEQUENCE: 277

Gly Val Ser Asp Val Pro Arg Asp Leu Glu Val Val Ala Ala Thr Pro
1               5                   10                  15

Thr Ser Leu Leu Ile Ser Trp Asp Ala Pro Arg Gly Leu Ala Arg Tyr
            20                  25                  30

Tyr Arg Ile Thr Tyr Gly Glu Thr Gly Gly Asn Ser Pro Val Gln Glu
        35                  40                  45

Phe Thr Val Phe Gly Arg Gly Thr Thr Ala Thr Ile Ser Gly Leu Lys
    50                  55                  60

Pro Gly Val Asp Tyr Thr Ile Thr Val Tyr Ala Val Thr Ile Asp Arg
65                  70                  75                  80

Asp Gly Thr Arg Ser Phe Asp Pro Ile Ser Ile Asn Tyr Arg Thr Glu
                85                  90                  95

Ile

<210> SEQ ID NO 278
<211> LENGTH: 97
<212> TYPE: PRT
<213> ORGANISM: Artificial Sequence
<220> FEATURE:
<223> OTHER INFORMATION: Synthetic

<400> SEQUENCE: 278

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Gly Leu Ala Arg Tyr
            20                  25                  30

Tyr Arg Ile Thr Tyr Gly Glu Thr Gly Gly Asn Ser Pro Val Gln Glu
        35                  40                  45

Phe Thr Val Val Gly Arg Gly Asn Thr Ala Thr Ile Ser Gly Leu Lys
    50                  55                  60

Pro Gly Val Asp Tyr Thr Ile Thr Val Tyr Ala Val Thr Ile Phe Arg
65                  70                  75                  80

Asp Gly Pro Val Thr Trp Asp Pro Ile Ser Ile Asn Tyr Arg Thr Glu
                85                  90                  95

Ile

<210> SEQ ID NO 279
<211> LENGTH: 97
<212> TYPE: PRT
<213> ORGANISM: Artificial Sequence
<220> FEATURE:
<223> OTHER INFORMATION: Synthetic

<400> SEQUENCE: 279

Gly Val Ser Asp Val Pro Arg Asp Leu Glu Val Val Ala Ala Thr Pro

```
                1               5                   10                  15
            Thr Ser Leu Leu Ile Ser Trp Asp Ala Pro Lys Gly Leu Ala Arg Tyr
                            20                  25                  30

Tyr Arg Ile Thr Tyr Gly Glu Thr Gly Gly Asn Ser Pro Val Gln Glu
                        35                  40                  45

Phe Thr Val Val Gly Arg Gly Asn Thr Ala Thr Ile Ser Gly Leu Lys
                    50                  55                  60

Pro Gly Val Asp Tyr Thr Ile Thr Val Tyr Ala Val Thr Ile Phe Arg
             65                  70                  75                  80

Asp Gly Pro Val Thr Trp Asp Pro Ile Ser Ile Asn Tyr Arg Thr Glu
                                85                  90                  95

Ile
```

<210> SEQ ID NO 280
<211> LENGTH: 98
<212> TYPE: PRT
<213> ORGANISM: Artificial Sequence
<220> FEATURE:
<223> OTHER INFORMATION: Synthetic

<400> SEQUENCE: 280

```
            Gly Val Ser Asp Val Pro Arg Asp Leu Glu Val Val Ala Ala Thr Pro
             1               5                   10                  15

Thr Ser Leu Leu Ile Ser Trp Ser Leu Pro Asn Pro Gly Asn Ala His
                            20                  25                  30

Tyr Tyr Arg Ile Thr Tyr Gly Glu Thr Gly Gly Asn Ser Pro Val Gln
                        35                  40                  45

Glu Phe Thr Val Pro Gly Arg Gly Val Thr Ala Thr Ile Ser Gly Leu
                    50                  55                  60

Lys Pro Gly Val Asp Tyr Thr Ile Thr Val Tyr Ala Val Thr Val Thr
             65                  70                  75                  80

Asp Thr Gly Phe Ile Thr Tyr Lys Pro Ile Ser Ile Asn Tyr Arg Thr
                                85                  90                  95

Glu Ile
```

<210> SEQ ID NO 281
<211> LENGTH: 98
<212> TYPE: PRT
<213> ORGANISM: Artificial Sequence
<220> FEATURE:
<223> OTHER INFORMATION: Synthetic

<400> SEQUENCE: 281

```
            Gly Val Ser Asp Val Pro Arg Asp Leu Glu Val Val Ala Ala Thr Pro
             1               5                   10                  15

Thr Ser Leu Leu Ile Ser Trp Ser Leu Pro His Gln Gly Lys Ala Asn
                            20                  25                  30

Tyr Tyr Arg Ile Thr Tyr Gly Glu Thr Gly Gly Asn Ser Pro Val Gln
                        35                  40                  45

Glu Phe Thr Val Pro Gly Arg Gly Val Thr Ala Thr Ile Ser Gly Leu
                    50                  55                  60

Lys Pro Gly Val Asp Tyr Thr Ile Thr Val Tyr Ala Val Thr Val Thr
             65                  70                  75                  80

Asp Thr Gly Tyr Leu Lys Tyr Lys Pro Ile Ser Ile Asn Tyr Arg Thr
                                85                  90                  95

Glu Ile
```

<210> SEQ ID NO 282
<211> LENGTH: 98
<212> TYPE: PRT
<213> ORGANISM: Artificial Sequence
<220> FEATURE:
<223> OTHER INFORMATION: Synthetic

<400> SEQUENCE: 282

```
Gly Val Ser Asp Val Pro Arg Asp Leu Glu Val Val Ala Ala Thr Pro
1               5                   10                  15

Thr Ser Leu Leu Ile Ser Trp Ser Leu Pro Tyr Ala Gly His Leu Asn
            20                  25                  30

Tyr Tyr Arg Ile Thr Tyr Gly Glu Thr Gly Gly Asn Ser Pro Val Gln
        35                  40                  45

Glu Phe Thr Val Pro Gly Arg Gly Val Thr Ala Thr Ile Ser Gly Leu
50                  55                  60

Lys Pro Gly Val Asp Tyr Thr Ile Thr Val Tyr Ala Val Thr Leu Thr
65                  70                  75                  80

Lys Ser Gln Leu Ile His Tyr Met Pro Ile Ser Ile Asn Tyr Arg Thr
                85                  90                  95

Glu Ile
```

<210> SEQ ID NO 283
<211> LENGTH: 226
<212> TYPE: PRT
<213> ORGANISM: Artificial Sequence
<220> FEATURE:
<223> OTHER INFORMATION: Synthetic

<400> SEQUENCE: 283

```
Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205
```

Glu Ala Leu His Asn His Tyr Thr Gln Lys Ser Leu Ser Leu Ser Pro
    210                 215                 220

Gly Lys
225

<210> SEQ ID NO 284
<211> LENGTH: 1008
<212> TYPE: DNA
<213> ORGANISM: Artificial Sequence
<220> FEATURE:
<223> OTHER INFORMATION: Synthetic

<400> SEQUENCE: 284
gagcccaaat ctagcgggtc gactcacaca tgcccaccgt gcccagcacc tgaactcctg     60 ggggaagct cagtcttcct cttcccccca aacccaagg acaccctcat gatctcccgg     120 accctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga acaactacaa gaccacgcct     540
cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccc ggcgccggag gcggcggatc cggtggagtt     720
tctgatgtgc cgcgcgacct ggaagtggtt gctgccaccc caccagcct gctgatcagc     780 tggtctcttc cttatgctgg tcatctaaac tattaccgca tcacttacgg cgaaacagga     840
ggcaatagcc ctgtccagga gttcactgtg cctggtcgtg gtgtgacagc taccatcagc     900
ggccttaaac ctggcgttga ttataccatc actgtgtatg ctgtcactct gactaagtct     960
cagctgatac attacatgcc aatttccatt aattaccgga ccgaaatc                  1008

<210> SEQ ID NO 285
<211> LENGTH: 990
<212> TYPE: DNA
<213> ORGANISM: Artificial Sequence
<220> FEATURE:
<223> OTHER INFORMATION: Synthetic

<400> SEQUENCE: 285
ggcgtgagcg acgtgccccg ggatctagaa gtggtggctg ctaccccac aagcttgctg     60 atctcctgga cactgcctca cgctggccgg gctcattact atagaattac ctacggggag     120
acaggcggga actctcccgt gcaggaattc accgtgcctg aaggggcgt gactgccacc     180 atcagtgggc tgaagccagg agtggactac acaattaccg tgtacgctgt gactgtgacc     240
acaactaaag tgatccacta caaacccatc tctattaatt atcggaccga aattgagcct     300
aagagctccg acaaaaccca cacatgccca ccttgtccag ccccgaact gctgggcggc     360 ccttcagtct tcctcttccc cccaaaaccc aaggacaccc tcatgatctc ccggaccct     420 gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600

```
gagtacaagt gcaaggtctc caacaaagcc ctcccagccc ccatcgagaa aaccatctcc    660
aaagccaaag gcagccccg agaaccacag gtgtacaccc tgcccccatc ccgggatgag     720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ttggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tcccgggaaa                                    990
```

<210> SEQ ID NO 286
<211> LENGTH: 975
<212> TYPE: DNA
<213> ORGANISM: Artificial Sequence
<220> FEATURE:
<223> OTHER INFORMATION: Synthetic

<400> SEQUENCE: 286

```
ggcgtgagcg acgtgccccg ggatctagaa gtggtggctg ctaccccac aagcttgctg     60 atctcctgga cactgcctca cgctggccgg gctcattact atagaattac ctacggggag    120
acaggcggga actctcccgt gcaggaattc accgtgcctg aaggggcgt gactgccacc     180 atcagtgggc tgaagccagg agtggactac acaattaccg tgtacgctgt gactgtgacc    240
acaactaaag tgatccacta caaacccatc tctattaatt atcggaccga aattgacaag    300
acccacacat gcccaccttg tccagccccc gagctgctgg gcggcccttc agtcttcctc    360
ttccccccaa aacccaagga caccctcatg atctcccgga cccctgaggt cacatgcgtg    420
gtggtggacg tgagccacga agaccctgag gtcaagttca actggtacgt ggacggcgtg    480
gaggtgcata atgccaagac aaagccgcgg gaggagcagt acaacagcac gtaccgtgtg    540
gtcagcgtcc tcaccgtcct gcaccaggac tggctgaatg gcaaggagta caagtgcaag    600
gtctccaaca aagccctccc agcccccatc gagaaaacca tctccaaagc caagggcag    660 ccccgagaac acaggtgta caccctgccc ccatcccggg atgagctgac caagaaccag    720
gtcagcctga cctgcctggt caaaggcttc tatcccagcg acatcgccgt ggagtgggag    780
agcaatgggc agccggagaa caactacaag accacgcctc ccgtgttgga ctccgacggc    840
tccttcttcc tctacagcaa gctcaccgtg gacaagagca ggtggcagca ggggaacgtc    900
ttctcatgct ccgtgatgca tgaggctctg cacaaccact acacgcagaa gagcctctcc    960
ctgtctcccg ggaaa                                                    975
```

<210> SEQ ID NO 287
<211> LENGTH: 1035
<212> TYPE: DNA
<213> ORGANISM: Artificial Sequence
<220> FEATURE:
<223> OTHER INFORMATION: Synthetic

<400> SEQUENCE: 287

```
ggcgtgagcg acgtgccccg ggatctagaa gtggtggctg ctaccccac aagcttgctg     60 atctcctgga cactgcctca cgctggccgg gctcattact atagaattac ctacggggag    120
acaggcggga actctcccgt gcaggaattc accgtgcctg aaggggcgt gactgccacc     180 atcagtgggc tgaagccagg agtggactac acaattaccg tgtacgctgt gactgtgacc    240
acaactaaag tgatccacta caaacccatc tctattaatt atcggaccga aattgagtct    300
```

```
ccaaaggctc aggccagctc cgtgcctacc gctcagccac aggctgaggg cctggctaag      360
acccacacat gccccccttg tccagctccc gaactgctgg gcgggccttc agtcttcctc      420
ttccccccaa aacccaagga caccctcatg atctcccgga cccctgaggt cacatgcgtg      480
gtggtggacg tgagccacga agaccctgag gtcaagttca actggtacgt ggacggcgtg      540
gaggtgcata atgccaagac aaagccgcgg gaggagcagt acaacagcac gtaccgtgtg      600
gtcagcgtcc tcaccgtcct gcaccaggac tggctgaatg gcaaggagta caagtgcaag      660
gtctccaaca aagccctccc agcccccatc gagaaaacca tctccaaagc caagggcag      720 ccccgagaac cacaggtgta caccctgccc ccatcccggg atgagctgac caagaaccag      780
gtcagcctga cctgcctggt caaaggcttc tatcccagcg acatcgccgt ggagtgggag      840
agcaatgggc agccggagaa caactacaag accacgcctc ccgtgctgga ctccgacggc      900
tccttcttcc tctacagcaa gctcaccgtg gacaagagca ggtggcagca ggggaacgtc      960
ttctcatgct ccgtgatgca tgaggctctg cacaaccact acacgcagaa gagcctctcc     1020
ctgtctcccg ggaaa                                                     1035
```

<210> SEQ ID NO 288
<211> LENGTH: 993
<212> TYPE: DNA
<213> ORGANISM: Artificial Sequence
<220> FEATURE:
<223> OTHER INFORMATION: Synthetic

<400> SEQUENCE: 288

```
gacaaaactc acacatgccc accgtgccca gcacctgaac tcctgggggg accgtcagtc       60
ttcctcttcc ccccaaaacc caaggacacc ctcatgatct cccggacccc tgaggtcaca      120
tgcgtggtgg tggacgtgag ccacgaagac cctgaggtca agttcaactg gtacgtggac      180
ggcgtggagg tgcataatgc caagacaaag ccgcgggagg agcagtacaa cagcacgtac      240
cgtgtggtca gcgtcctcac cgtcctgcac caggactggc tgaatggcaa ggagtacaag      300
tgcaaggtct ccaacaaagc cctcccagcc ccatcgaga aaaccatctc caaagccaaa      360
gggcagcccc gagaaccaca ggtgtacacc ctgcccccat cccgggatga gctgaccaag      420
aaccaggtca gcctgacctg cctggtcaaa ggcttctatc ccagcgacat cgccgtggag      480
tgggagagca atgggcagcc ggagaacaac tacaagacca cgcctcccgt gttggactcc      540
gacggctcct tcttcctcta cagcaagctc accgtggaca agagcaggtg gcagcagggg      600
aacgtcttct catgctccgt gatgcatgag gctctgcaca accactacac gcagaagagc      660
ctctccctgt ctccggcgc cggaggcggc ggatccggtg gcgtgtccga cgtgccccgg      720
gatctagaag tggtggctgc tacccccaca agcttgctga tctcctggac actgcctcac      780
gctggccggg ctcattacta tagaattacc tacggggaga caggcgggaa ctctcccgtg      840
caggaattca ccgtgcctgg aaggggcgtg actgccacca tcagtgggct gaagccagga      900
gtggactaca caattaccgt gtacgctgtg actgtgacca caactaaagt gatccactac      960
aaacccatct ctattaatta tcggaccgaa atc                                 993
```

<210> SEQ ID NO 289
<211> LENGTH: 1020
<212> TYPE: DNA
<213> ORGANISM: Artificial Sequence
<220> FEATURE:
<223> OTHER INFORMATION: Synthetic

<400> SEQUENCE: 289

```
gacaaaactc acacatgccc accgtgccca gcacctgaac tcctgggggg accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc cccatcgaga aaaccatctc caaagccaaa   360
gggcagcccc gagaaccaca ggtgtacacc ctgcccccat cccgggatga gctgaccaag   420
aaccaggtca gcctgacctg cctggtcaaa ggcttctatc ccagcgacat cgccgtggag   480
tgggagagca atgggcagcc ggagaacaac tacaagacca cgcctcccgt gctggactcc   540
gacggctcct tcttcctcta cagcaagctc accgtggaca agagcaggtg gcagcagggg   600
aacgtcttct catgctccgt gatgcatgag gctctgcaca accactacac gcagaagagc   660
ctctccctgt ctcccgagct gcagctggag gaaagcgccg ctgaggctca ggacggagaa   720
ctggatggcg tgagcgacgt gccacgggat ctagaagtgg tggctgctac ccccacaagc   780
ttgctgatct cctggacact gcctcacgct ggccgggctc attactatag aattacctac   840
ggggagacag gcgggaactc tcccgtgcag gaattcaccg tgcctggaag gggcgtgact   900
gccaccatca gtgggctgaa gccaggagtg gactacacaa ttaccgtgta cgctgtgact   960
gtgaccacaa ctaaagtgat ccactacaaa cccatctcta ttaattatcg gaccgaaatt  1020
```

<210> SEQ ID NO 290
<211> LENGTH: 996
<212> TYPE: DNA
<213> ORGANISM: Artificial Sequence
<220> FEATURE:
<223> OTHER INFORMATION: Synthetic

<400> SEQUENCE: 290

```
gacaaaactc acacatgccc accgtgccca gcacctgaac tcctgggggg accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc cccatcgaga aaaccatctc caaagccaaa   360
gggcagcccc gagaaccaca ggtgtacacc ctgcccccat cccgggatga gctgaccaag   420
aaccaggtca gcctgacctg cctggtcaaa ggcttctatc ccagcgacat cgccgtggag   480
tgggagagca atgggcagcc ggagaacaac tacaagacca cgcctcccgt gctggactcc   540
gacggctcct tcttcctcta cagcaagctc accgtggaca agagcaggtg gcagcagggg   600
aacgtcttct catgctccgt gatgcatgag gctctgcaca accactacac gcagaagagc   660
ctctccctgt ctcccggcca gccgacgag cctggcggga gcggcgtgag cgacgtgcca   720
cgggatctag aagtggtggc tgctaccccc acaagcttgc tgatctcctg gacactgcct   780
cacgctggcc gggctcatta ctatagaatt acctacgggg agacaggcgg gaactctccc   840
gtgcaggaat tcaccgtgcc tggaaggggc gtgactgcca ccatcagtgg gctgaagcca   900
ggagtggact acacaattac cgtgtacgct gtgactgtga ccacaactaa agtgatccac   960
tacaaaccca tctctattaa ttatcggacc gaaatt                             996
```

<210> SEQ ID NO 291
<211> LENGTH: 1008
<212> TYPE: DNA
<213> ORGANISM: Artificial Sequence
<220> FEATURE:
<223> OTHER INFORMATION: Synthetic

<400> SEQUENCE: 291

| | | | | | |
|---|---|---|---|---|---|
| gacaaaactc | acacatgccc | accgtgccca | gcacctgaac | tcctgggggg | accgtcagtc | 60 |
| ttcctcttcc | ccccaaaacc | caaggacacc | ctcatgatct | cccggacccc | tgaggtcaca | 120 |
| tgcgtggtgg | tggacgtgag | ccacgaagac | cctgaggtca | agttcaactg | gtacgtggac | 180 |
| ggcgtggagg | tgcataatgc | caagacaaag | ccgcgggagg | agcagtacaa | cagcacgtac | 240 |
| cgtgtggtca | gcgtcctcac | cgtcctgcac | caggactggc | tgaatggcaa | ggagtacaag | 300 |
| tgcaaggtct | ccaacaaagc | cctcccagcc | cccatcgaga | aaaccatctc | caaagccaaa | 360 |
| gggcagcccc | gagaaccaca | ggtgtacacc | ctgcccccat | cccgggatga | gctgaccaag | 420 |
| aaccaggtca | gcctgacctg | cctggtcaaa | ggcttctatc | ccagcgacat | cgccgtggag | 480 |
| tgggagagca | atgggcagcc | ggagaacaac | tacaagacca | cgcctcccgt | gctggactcc | 540 |
| gacggctcct | tcttcctcta | cagcaagctc | accgtggaca | agagcaggtg | gcagcagggg | 600 |
| aacgtcttct | catgctccgt | gatgcatgag | gctctgcaca | accactacac | gcagaagagc | 660 |
| ctctccctgt | ctcccggcgg | cagcgggtct | ggatctggca | gtgggagcgg | ctctggcgtg | 720 |
| agcgacgtgc | cacgggatct | agaagtggtg | gctgctaccc | ccacaagctt | gctgatctcc | 780 |
| tggacactgc | ctcacgctgg | ccgggctcat | tactatagaa | ttacctacgg | ggagacaggc | 840 |
| gggaactctc | ccgtgcagga | attcaccgtg | cctggaaggg | gcgtgactgc | caccatcagt | 900 |
| gggctgaagc | caggagtgga | ctacacaatt | accgtgtacg | ctgtgactgt | gaccacaact | 960 |
| aaagtgatcc | actacaaacc | catctctatt | aattatcgga | ccgaaatt | | 1008 |

<210> SEQ ID NO 292
<211> LENGTH: 917
<212> TYPE: DNA
<213> ORGANISM: Artificial Sequence
<220> FEATURE:
<223> OTHER INFORMATION: Synthetic

<400> SEQUENCE: 292

| | | | | | |
|---|---|---|---|---|---|
| cccggacccc | tgaggtcaca | tgcgtggtgg | tggacgtgag | ccacgaagac | cctgaggtca | 60 |
| agttcaactg | gtacgtggac | ggcgtggagg | tgcataatgc | caagacaaag | ccgcgggagg | 120 |
| agcagtacaa | cagcacgtac | cgtgtggtca | gcgtcctcac | cgtcctgcac | caggactggc | 180 |
| tgaatggcaa | ggagtacaag | tgcaaggtct | ccaacaaagc | cctcccagcc | cccatcgaga | 240 |
| aaaccatctc | caaagccaaa | gggcagcccc | gagaaccaca | ggtgtacacc | ctgcccccat | 300 |
| cccgggatga | gctgaccaag | aaccaggtca | gcctgacctg | cctggtcaaa | ggcttctatc | 360 |
| ccagcgacat | cgccgtggag | tgggagagca | atgggcagcc | ggagaacaac | tacaagacca | 420 |
| cgcctcccgt | gctggactcc | gacggctcct | tcttcctcta | cagcaagctc | accgtggaca | 480 |
| agagcaggtg | gcagcagggg | aacgtcttct | catgctccgt | gatgcatgag | gctctgcaca | 540 |
| accactacac | gcagaagagc | ctctccctgt | ctcccgagct | gcagctggag | gaaagcgccg | 600 |
| ctgaggctca | ggacggagaa | ctggatggcg | tgagcgacgt | gccacgggat | ctagaagtgg | 660 |
| tggctgctac | ccccacaagc | ttgctgatca | gctgggacgc | tccgagaggt | ctggctcgat | 720 |
| attaccgcat | cacttacggc | gaaacaggag | gcaatagccc | tgtccaggag | ttcactgtgt | 780 |

```
tcggtcgtgg taccacagct accatcagcg gccttaaacc tggcgttgat tataccatca    840
ctgtgtatgc tgtcactatc gaccgtgacg gtacccgcag cttcgaccca atttccatta    900
attaccggac cgaaatt                                                    917

<210> SEQ ID NO 293
<211> LENGTH: 1017
<212> TYPE: DNA
<213> ORGANISM: Artificial Sequence
<220> FEATURE:
<223> OTHER INFORMATION: Synthetic

<400> SEQUENCE: 293
gacaaaactc acacatgccc accgtgccca gcacctgaac tcctgggggg accgtcagtc     60
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
gacggctcct tcttcctcta cagcaagctc accgtggaca agagcaggtg gcagcagggg    600
aacgtcttct catgctccgt gatgcatgag gctctgcaca accactacac gcagaagagc    660
ctctccctgt ctcccgagct gcagctggag gaaagcgccg ctgaggctca ggacggagaa    720
ctggatggcg tgagcgacgt gccacgggat ctagaagtgg tggctgctac ccccacaagc    780
ttgctgatca gctgggacgc tccggctggt ctggctcgat attaccgcat cacttacggc    840
gaaacaggag gcaatagccc tgtccaggag ttcactgtgg tcggtcgtgg taacacagct    900
accatcagcg gccttaaacc tggcgttgat tataccatca ctgtgtatgc tgtcactatc    960
ttccgtgacg gtcccgtcac ctgggaccca atttccatta attaccggac cgaaatt     1017

<210> SEQ ID NO 294
<211> LENGTH: 1017
<212> TYPE: DNA
<213> ORGANISM: Artificial Sequence
<220> FEATURE:
<223> OTHER INFORMATION: Synthetic

<400> SEQUENCE: 294
gacaaaactc acacatgccc accgtgccca gcacctgaac tcctgggggg accgtcagtc     60
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
```

| | |
|---|---|
| gacggctcct tcttcctcta cagcaagctc accgtggaca agagcaggtg gcagcagggg | 600 |
| aacgtcttct catgctccgt gatgcatgag gctctgcaca accactacac gcagaagagc | 660 |
| ctctccctgt ctcccgagct gcagctggag gaaagcgccg ctgaggctca ggacggagaa | 720 |
| ctggatggcg tgagcgacgt gccacgggat ctagaagtgg tggctgctac ccccacaagc | 780 |
| ttgctgatca gctgggacgc tccgaagggt ctggctcgat attaccgcat cacttacggc | 840 |
| gaaacaggag gcaatagccc tgtccaggag ttcactgtgg tcggtcgtgg taacacagct | 900 |
| accatcagcg gccttaaacc tggcgttgat tataccatca ctgtgtatgc tgtcactatc | 960 |
| ttccgtgacg gtcccgtcac ctgggaccca atttccatta attaccggac cgaaatt | 1017 |

<210> SEQ ID NO 295
<211> LENGTH: 1020
<212> TYPE: DNA
<213> ORGANISM: Artificial Sequence
<220> FEATURE:
<223> OTHER INFORMATION: Synthetic

<400> SEQUENCE: 295

| | |
|---|---|
| gacaaaactc acacatgccc accgtgccca gcacctgaac tcctgggggg accgtcagtc | 60 |
| ttcctcttcc ccccaaaacc caaggacacc ctcatgatct cccggacccc tgaggtcaca | 120 |
| tgcgtggtgg tggacgtgag ccacgaagac cctgaggtca agttcaactg gtacgtggac | 180 |
| ggcgtggagg tgcataatgc caagacaaag ccgcgggagg agcagtacaa cagcacgtac | 240 |
| cgtgtggtca gcgtcctcac cgtcctgcac caggactggc tgaatggcaa ggagtacaag | 300 |
| tgcaaggtct ccaacaaagc cctcccagcc cccatcgaga aaaccatctc caaagccaaa | 360 |
| gggcagcccc gagaaccaca ggtgtacacc ctgcccccat cccgggatga gctgaccaag | 420 |
| aaccaggtca gcctgacctg cctggtcaaa ggcttctatc ccagcgacat cgccgtggag | 480 |
| tgggagagca atgggcagcc ggagaacaac tacaagacca cgcctcccgt gctggactcc | 540 |
| gacggctcct tcttcctcta cagcaagctc accgtggaca agagcaggtg gcagcagggg | 600 |
| aacgtcttct catgctccgt gatgcatgag gctctgcaca accactacac gcagaagagc | 660 |
| ctctccctgt ctcccgagct gcagctggag gaaagcgccg ctgaggctca ggacggagaa | 720 |
| ctggatggcg tgagcgacgt gccacgggat ctagaagtgg tggctgctac ccccacaagc | 780 |
| ttgctgatca gctggtctct gccgaatccg gtaacgccc attattaccg catcacttac | 840 |
| ggcgaaacag gaggcaatag ccctgtccag gagttcactg tgcctggtcg tggtgttaca | 900 |
| gctaccatca gcggccttaa acctggcgtt gattatacca tcactgtgta tgctgtcact | 960 |
| gttactgaca caggtttcat cacgtacaaa ccaatttcca ttaattaccg gaccgaaatt | 1020 |

<210> SEQ ID NO 296
<211> LENGTH: 1020
<212> TYPE: DNA
<213> ORGANISM: Artificial Sequence
<220> FEATURE:
<223> OTHER INFORMATION: Synthetic

<400> SEQUENCE: 296

| | |
|---|---|
| gacaaaactc acacatgccc accgtgccca gcacctgaac tcctgggggg accgtcagtc | 60 |
| ttcctcttcc ccccaaaacc caaggacacc ctcatgatct cccggacccc tgaggtcaca | 120 |
| tgcgtggtgg tggacgtgag ccacgaagac cctgaggtca agttcaactg gtacgtggac | 180 |
| ggcgtggagg tgcataatgc caagacaaag ccgcgggagg agcagtacaa cagcacgtac | 240 |
| cgtgtggtca gcgtcctcac cgtcctgcac caggactggc tgaatggcaa ggagtacaag | 300 |

```
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
gacggctcct tcttcctcta cagcaagctc accgtggaca gagcaggtg gcagcagggg    600 aacgtcttct catgctccgt gatgcatgag gctctgcaca accactacac gcagaagagc    660
ctctccctgt ctcccgagct gcagctggag aaaagcgccg ctgaggctca ggacggagaa    720
ctggatggcg tgagcgacgt gccacgggat ctagaagtgg tggctgctac ccccacaagc    780
ttgctgatca gctggtctct gccgcaccaa ggtaaagcca attattaccg catcacttac    840
ggcgaaacag gaggcaatag ccctgtccag gagttcactg tgcctggtcg tggtgttaca    900
gctaccatca gcggccttaa acctggcgtt gattatacca tcactgtgta tgctgtcact    960
gttactgata cagggtacct caagtacaaa ccaatttcca ttaattaccg gaccgaaatt   1020
```

<210> SEQ ID NO 297
<211> LENGTH: 987
<212> TYPE: DNA
<213> ORGANISM: Artificial Sequence
<220> FEATURE:
<223> OTHER INFORMATION: Synthetic

<400> SEQUENCE: 297

```
ggcgtgagcg acgtgccccg ggatctagaa gtggtggctg ctaccccac aagcttgctg     60 atcagctggg acgtccgag aggtctggct cgatattacc gcatcactta cggcgaaaca    120
ggaggcaata gccctgtcca ggagttcact gtgttcggtc gtggtaccac agctaccatc    180
agcggcctta aacctggcgt tgattatacc atcactgtgt atgctgtcac tatcgaccgt    240
gacggtaccc gcagcttcga cccaatttcc attaattacc ggaccgaaat tgagcctaag    300
agctccgaca aaacccacac atgcccacct tgtccagccc ccgaactgct gggcggccct    360
tcagtcttcc tcttcccccc aaaacccaag gacaccctca tgatctcccg gacccctgag    420
gtcacatgcg tggtggtgga cgtgagccac gaagaccctg aggtcaagtt caactggtac    480
gtggacggcg tggaggtgca taatgccaag acaaagccgc gggaggagca gtacaacagc    540
acgtaccgtg tggtcagcgt cctcaccgtc ctgcaccagg actggctgaa tggcaaggag    600
tacaagtgca aggtctccaa caaagccctc ccagccccca tcgagaaaac catctccaaa    660
gccaaagggc agccccgaga accacaggtg tacaccctgc ccccatcccg ggatgagctg    720
accaagaacc aggtcagcct gacctgcctg gtcaaaggct tctatcccag cgacatcgcc    780
gtggagtggg agagcaatgg gcagccggag aacaactaca agaccacgcc tcccgtgttg    840
gactccgacg gctccttctt cctctacagc aagctcaccg tggacaagag caggtggcag    900
caggggaacg tcttctcatg ctccgtgatg catgaggctc tgcacaacca ctacacgcag    960
aagagcctct ccctgtctcc cgggaaa                                        987
```

<210> SEQ ID NO 298
<211> LENGTH: 987
<212> TYPE: DNA
<213> ORGANISM: Artificial Sequence
<220> FEATURE:
<223> OTHER INFORMATION: Synthetic

<400> SEQUENCE: 298

```
ggcgtgagcg acgtgccccg ggatctagaa gtggtggctg ctaccccac aagcttgctg      60 atcagctggg acgctccggc tggtctggct cgatattacc gcatcactta cggcgaaaca     120
ggaggcaata gccctgtcca ggagttcact gtggtcggtc gtggtaacac agctaccatc     180
agcggcctta aacctggcgt tgattatacc atcactgtgt atgctgtcac tatcttccgt     240
gacggtcccg tcacctggga cccaatttcc attaattacc ggaccgaaat tgagcctaag     300
agctccgaca aaacccacac atgcccacct tgtccagccc ccgaactgct gggcggccct     360
tcagtcttcc tcttcccccc aaaacccaag gacaccctca tgatctcccg gacccctgag     420
gtcacatgcg tggtggtgga cgtgagccac gaagaccctg aggtcaagtt caactggtac     480
gtggacggcg tggaggtgca taatgccaag acaaagccgc gggaggagca gtacaacagc     540
acgtaccgtg tggtcagcgt cctcaccgtc ctgcaccagg actggctgaa tggcaaggag     600
tacaagtgca aggtctccaa caaagccctc ccagccccca tcgagaaaac catctccaaa     660 gccaagggc  agccccgaga ccacaggtg  tacaccctgc ccccatcccg ggatgagctg     720
accaagaacc aggtcagcct gacctgcctg gtcaaaggct tctatcccag cgacatcgcc     780
gtggagtggg agagcaatgg gcagccggag aacaactaca agaccacgcc tcccgtgttg     840
gactccgacg gctccttctt cctctacagc aagctcaccg tggacaagag caggtggcag     900
caggggaacg tcttctcatg ctccgtgatg catgaggctc tgcacaacca ctacacgcag     960
aagagcctct ccctgtctcc gggaaa                                         987
```

<210> SEQ ID NO 299
<211> LENGTH: 987
<212> TYPE: DNA
<213> ORGANISM: Artificial Sequence
<220> FEATURE:
<223> OTHER INFORMATION: Synthetic

<400> SEQUENCE: 299

```
ggcgtgagcg acgtgccccg ggatctagaa gtggtggctg ctaccccac aagcttgctg      60 atcagctggg acgctccgaa gggtctggct cgatattacc gcatcactta cggcgaaaca    120
ggaggcaata gccctgtcca ggagttcact gtggtcggtc gtggtaacac agctaccatc    180
agcggcctta aacctggcgt tgattatacc atcactgtgt atgctgtcac tatcttccgt    240
gacggtcccg tcacctggga cccaatttcc attaattacc ggaccgaaat tgagcctaag    300
agctccgaca aaacccacac atgcccacct tgtccagccc ccgaactgct gggcggccct    360
tcagtcttcc tcttcccccc aaaacccaag gacaccctca tgatctcccg gacccctgag    420
gtcacatgcg tggtggtgga cgtgagccac gaagaccctg aggtcaagtt caactggtac    480
gtggacggcg tggaggtgca taatgccaag acaaagccgc gggaggagca gtacaacagc    540
acgtaccgtg tggtcagcgt cctcaccgtc ctgcaccagg actggctgaa tggcaaggag    600
tacaagtgca aggtctccaa caaagccctc ccagccccca tcgagaaaac catctccaaa    660 gccaagggc  agccccgaga ccacaggtg  tacaccctgc ccccatcccg ggatgagctg    720
accaagaacc aggtcagcct gacctgcctg gtcaaaggct tctatcccag cgacatcgcc    780
gtggagtggg agagcaatgg gcagccggag aacaactaca agaccacgcc tcccgtgttg    840
gactccgacg gctccttctt cctctacagc aagctcaccg tggacaagag caggtggcag    900
caggggaacg tcttctcatg ctccgtgatg catgaggctc tgcacaacca ctacacgcag    960
aagagcctct ccctgtctcc gggaaa                                         987
```

<210> SEQ ID NO 300
<211> LENGTH: 990
<212> TYPE: DNA
<213> ORGANISM: Artificial Sequence
<220> FEATURE:
<223> OTHER INFORMATION: Synthetic

<400> SEQUENCE: 300

```
ggcgtgagcg acgtgccccg ggatctagaa gtggtggctg ctaccccac  aagcttgctg      60
atcagctggt ctctgccgaa tccgggtaac gcccattatt accgcatcac ttacggcgaa     120
acaggaggca atagccctgt ccaggagttc actgtgcctg gtcgtggtgt tacagctacc     180
atcagcggcc ttaaacctgg cgttgattat accatcactg tgtatgctgt cactgttact     240
gacacaggtt tcatcacgta caaaccaatt tccattaatt accggaccga aattgagcct     300
aagagctccg acaaaaccca cacatgccca ccttgtccag cccccgaact gctgggcggc     360
ccttcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg  agaaccacag gtgtacaccc tgcccccatc ccggatgagc     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ttggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggaaa                                       990
```

<210> SEQ ID NO 301
<211> LENGTH: 990
<212> TYPE: DNA
<213> ORGANISM: Artificial Sequence
<220> FEATURE:
<223> OTHER INFORMATION: Synthetic

<400> SEQUENCE: 301

```
ggcgtgagcg acgtgccccg ggatctagaa gtggtggctg ctaccccac  aagcttgctg      60
atcagctggt ctctgccgca ccaaggtaaa gccaattatt accgcatcac ttacggcgaa     120
acaggaggca atagccctgt ccaggagttc actgtgcctg gtcgtggtgt tacagctacc     180
atcagcggcc ttaaacctgg cgttgattat accatcactg tgtatgctgt cactgttact     240
gatacagggt acctcaagta caaaccaatt tccattaatt accggaccga aattgagcct     300
aagagctccg acaaaaccca cacatgccca ccttgtccag cccccgaact gctgggcggc     360
ccttcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg  agaaccacag gtgtacaccc tgcccccatc ccggatgagc     720
ctgaccaaga accaggtcag cctgacctgc ctggtcaaag gcttctatcc cagcgacatc     780
```

```
gccgtggagt gggagagcaa tgggcagccg agaacaact acaagaccac gcctcccgtg    840
ttggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tcccgggaaa                                     990
```

<210> SEQ ID NO 302
<211> LENGTH: 1020
<212> TYPE: DNA
<213> ORGANISM: Artificial Sequence
<220> FEATURE:
<223> OTHER INFORMATION: Synthetic

<400> SEQUENCE: 302

```
gacaaaactc acacatgccc accgtgccca gcacctgaac tcctgggggg accgtcagtc     60
ttcctcttcc cccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360 ggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
gacggctcct tcttcctcta cagcaagctc accgtggaca gagcaggtg gcagcagggg    600 aacgtcttct catgctccgt gatgcatgag gctctgcaca accactacac gcagaagagc    660
ctctccctgt ctcccgagct gcagctggag gaaagcgccg ctgaggctca ggaaggagaa    720
ctggaaggcg tgagcgacgt gccacgggat ctagaagtgg tggctgctac ccccacaagc    780
ttgctgatct cctggacact gcctcacgct ggccgggctc attactatag aattacctac    840
ggggagacag gcgggaactc tcccgtgcag gaattcaccg tgcctggaag gggcgtgact    900
gccaccatca gtgggctgaa gccaggagtg gactacacaa ttaccgtgta cgctgtgact    960
gtgaccacaa ctaaagtgat ccactacaaa cccatctcta ttaattatcg gaccgaaatt   1020
```

<210> SEQ ID NO 303
<211> LENGTH: 1017
<212> TYPE: DNA
<213> ORGANISM: Artificial Sequence
<220> FEATURE:
<223> OTHER INFORMATION: Synthetic

<400> SEQUENCE: 303

```
gacaaaactc acacatgccc accgtgccca gcacctgaac tcctgggggg accgtcagtc     60
ttcctcttcc cccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360 ggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
```

```
gacggctcct tcttcctcta cagcaagctc accgtggaca agagcaggtg gcagcagggg      600
aacgtcttct catgctccgt gatgcatgag gctctgcaca accactacac gcagaagagc      660
ctctccctgt ctcccgagct gcagctggag gaaagcgccg ctgaggctca ggaaggagaa      720
ctggaaggcg tgagcgacgt gccacgggat ctagaagtgg tggctgctac ccccacaagc      780
ttgctgatca gctgggacgc tccggctggt ctggctcgat attaccgcat cacttacggc      840
gaaacaggag gcaatagccc tgtccaggag ttcactgtgg tcggtcgtgg taacacagct      900
accatcagcg gccttaaacc tggcgttgat tataccatca ctgtgtatgc tgtcactatc      960
ttccgtgacg gtcccgtcac ctgggaccca atttccatta attaccggac cgaaatt      1017
```

<210> SEQ ID NO 304
<211> LENGTH: 1017
<212> TYPE: DNA
<213> ORGANISM: Artificial Sequence
<220> FEATURE:
<223> OTHER INFORMATION: Synthetic

<400> SEQUENCE: 304

```
gacaaaactc acacatgccc accgtgccca gcacctgaac tcctgggggg accgtcagtc       60
ttcctcttcc ccccaaaacc caaggacacc ctcatgatct cccggacccc tgaggtcaca      120
tgcgtggtgg tggacgtgag ccacgaagac cctgaggtca agttcaactg gtacgtggac      180
ggcgtggagg tgcataatgc caagacaaag ccgcgggagg agcagtacaa cagcacgtac      240
cgtgtggtca gcgtcctcac cgtcctgcac caggactggc tgaatggcaa ggagtacaag      300
tgcaaggtct ccaacaaagc cctcccagcc cccatcgaga aaaccatctc caaagccaaa      360
gggcagcccc gagaaccaca ggtgtacacc ctgcccccat cccgggatga gctgaccaag      420
aaccaggtca gcctgacctg cctggtcaaa ggcttctatc cagcgacat cgccgtggag       480 tgggagagca atgggcagcc ggagaacaac tacaagacca cgcctcccgt gctggactcc      540
gacggctcct tcttcctcta cagcaagctc accgtggaca agagcaggtg gcagcagggg      600
aacgtcttct catgctccgt gatgcatgag gctctgcaca accactacac gcagaagagc      660
ctctccctgt ctcccgagct gcagctggag gaaagcgccg ctgaggctca ggaaggagaa      720
ctggaaggcg tgagcgacgt gccacgggat ctagaagtgg tggctgctac ccccacaagc      780
ttgctgatca gctgggacgc tccgaagggt ctggctcgat attaccgcat cacttacggc      840
gaaacaggag gcaatagccc tgtccaggag ttcactgtgg tcggtcgtgg taacacagct      900
accatcagcg gccttaaacc tggcgttgat tataccatca ctgtgtatgc tgtcactatc      960
ttccgtgacg gtcccgtcac ctgggaccca atttccatta attaccggac cgaaatt      1017
```

<210> SEQ ID NO 305
<211> LENGTH: 1020
<212> TYPE: DNA
<213> ORGANISM: Artificial Sequence
<220> FEATURE:
<223> OTHER INFORMATION: Synthetic

<400> SEQUENCE: 305

```
gacaaaactc acacatgccc accgtgccca gcacctgaac tcctgggggg accgtcagtc       60
ttcctcttcc ccccaaaacc caaggacacc ctcatgatct cccggacccc tgaggtcaca      120
tgcgtggtgg tggacgtgag ccacgaagac cctgaggtca agttcaactg gtacgtggac      180
ggcgtggagg tgcataatgc caagacaaag ccgcgggagg agcagtacaa cagcacgtac      240
```

```
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
gacggctcct tcttcctcta cagcaagctc accgtggaca agagcaggtg gcagcagggg    600
aacgtcttct catgctccgt gatgcatgag gctctgcaca accactacac gcagaagagc    660
ctctccctgt ctcccgagct gcagctggag aaagcgccg ctgaggctca ggaaggagaa    720
ctggaaggcg tgagcgacgt gccacgggat ctagaagtgg tggctgctac ccccacaagc    780
ttgctgatca gctggtctct gccgcaccaa ggtaaagcca attattaccg catcacttac    840
ggcgaaacag gaggcaatag ccctgtccag gagttcactg tgcctggtcg tggtgttaca    900
gctaccatca gcggccttaa acctggcgtt gattatacca tcactgtgta tgctgtcact    960
gttactgata cagggtacct caagtacaaa ccaatttcca ttaattaccg gaccgaaatt   1020
```

<210> SEQ ID NO 306
<211> LENGTH: 10
<212> TYPE: PRT
<213> ORGANISM: Artificial Sequence
<220> FEATURE:
<223> OTHER INFORMATION: Synthetic

<400> SEQUENCE: 306

Met Gly Val Ser Asp Val Pro Arg Asp Leu
1               5                   10

<210> SEQ ID NO 307
<211> LENGTH: 9
<212> TYPE: PRT
<213> ORGANISM: Artificial Sequence
<220> FEATURE:
<223> OTHER INFORMATION: Synthetic

<400> SEQUENCE: 307

Gly Val Ser Asp Val Pro Arg Asp Leu
1               5

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Val Ser Asp Val Pro Arg Asp Leu
1               5

<210> SEQ ID NO 309
<211> LENGTH: 7
<212> TYPE: PRT
<213> ORGANISM: Artificial Sequence
<220> FEATURE:
<223> OTHER INFORMATION: Synthetic

<400> SEQUENCE: 309

Ser Asp Val Pro Arg Asp Leu
1               5

```
<210> SEQ ID NO 310
<211> LENGTH: 6
<212> TYPE: PRT
<213> ORGANISM: Artificial Sequence
<220> FEATURE:
<223> OTHER INFORMATION: Synthetic

<400> SEQUENCE: 310

Asp Val Pro Arg Asp Leu
1               5

<210> SEQ ID NO 311
<211> LENGTH: 5
<212> TYPE: PRT
<213> ORGANISM: Artificial Sequence
<220> FEATURE:
<223> OTHER INFORMATION: Synthetic

<400> SEQUENCE: 311

Val Pro Arg Asp Leu
1               5

<210> SEQ ID NO 312
<211> LENGTH: 4
<212> TYPE: PRT
<213> ORGANISM: Artificial Sequence
<220> FEATURE:
<223> OTHER INFORMATION: Synthetic

<400> SEQUENCE: 312

Pro Arg Asp Leu
1

<210> SEQ ID NO 313
<211> LENGTH: 7
<212> TYPE: PRT
<213> ORGANISM: Artificial Sequence
<220> FEATURE:
<223> OTHER INFORMATION: Synthetic

<400> SEQUENCE: 313

Glu Ile Glu Pro Lys Ser Ser
1               5

<210> SEQ ID NO 314
<211> LENGTH: 6
<212> TYPE: PRT
<213> ORGANISM: Artificial Sequence
<220> FEATURE:
<223> OTHER INFORMATION: Synthetic

<400> SEQUENCE: 314

Glu Ile Asp Lys Pro Cys
1               5

<210> SEQ ID NO 315
<211> LENGTH: 5
<212> TYPE: PRT
<213> ORGANISM: Artificial Sequence
<220> FEATURE:
<223> OTHER INFORMATION: Synthetic

<400> SEQUENCE: 315

Glu Ile Asp Lys Pro
1               5

<210> SEQ ID NO 316
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 316

Glu Ile Asp Lys
1

<210> SEQ ID NO 317
<211> LENGTH: 6
<212> TYPE: PRT
<213> ORGANISM: Artificial Sequence
<220> FEATURE:
<223> OTHER INFORMATION: Synthetic

<400> SEQUENCE: 317

Glu Ile Asp Lys Pro Ser
1               5

<210> SEQ ID NO 318
<211> LENGTH: 7
<212> TYPE: PRT
<213> ORGANISM: Artificial Sequence
<220> FEATURE:
<223> OTHER INFORMATION: Synthetic

<400> SEQUENCE: 318

Glu Ile Glu Lys Pro Ser Gln
1               5

<210> SEQ ID NO 319
<211> LENGTH: 9
<212> TYPE: PRT
<213> ORGANISM: Artificial Sequence
<220> FEATURE:
<223> OTHER INFORMATION: Synthetic

<400> SEQUENCE: 319

Glu Ile Asp Lys Pro Ser Gln Leu Glu
1               5

<210> SEQ ID NO 320
<211> LENGTH: 12
<212> TYPE: PRT
<213> ORGANISM: Artificial Sequence
<220> FEATURE:
<223> OTHER INFORMATION: Synthetic

<400> SEQUENCE: 320

Glu Ile Glu Asp Glu Asp Glu Asp Glu Asp Glu Asp
1               5                   10

<210> SEQ ID NO 321
<211> LENGTH: 5
<212> TYPE: PRT
<213> ORGANISM: Artificial Sequence
<220> FEATURE:
<223> OTHER INFORMATION: Synthetic

<400> SEQUENCE: 321

Glu Gly Ser Gly Ser
1               5

<210> SEQ ID NO 322
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 322

Glu Ile Asp Lys Pro Cys Gln
1               5

<210> SEQ ID NO 323
<211> LENGTH: 5
<212> TYPE: PRT
<213> ORGANISM: Artificial Sequence
<220> FEATURE:
<223> OTHER INFORMATION: Synthetic

<400> SEQUENCE: 323

Glu Gly Ser Gly Cys
1               5

<210> SEQ ID NO 324
<211> LENGTH: 9
<212> TYPE: PRT
<213> ORGANISM: Artificial Sequence
<220> FEATURE:
<223> OTHER INFORMATION: Synthetic

<400> SEQUENCE: 324

Glu Ile Asp Lys Pro Cys Gln Leu Glu
1               5

<210> SEQ ID NO 325
<211> LENGTH: 13
<212> TYPE: PRT
<213> ORGANISM: Artificial Sequence
<220> FEATURE:
<223> OTHER INFORMATION: Synthetic

<400> SEQUENCE: 325

Glu Ile Asp Lys Pro Ser Gln His His His His His
1               5                   10

<210> SEQ ID NO 326
<211> LENGTH: 10
<212> TYPE: PRT
<213> ORGANISM: Artificial Sequence
<220> FEATURE:
<223> OTHER INFORMATION: Synthetic

<400> SEQUENCE: 326

Gly Ser Gly Cys His His His His His
1               5                   10

<210> SEQ ID NO 327
<211> LENGTH: 11
<212> TYPE: PRT
<213> ORGANISM: Artificial Sequence
<220> FEATURE:
<223> OTHER INFORMATION: Synthetic

<400> SEQUENCE: 327

Glu Gly Ser Gly Cys His His His His His
1               5                   10

<210> SEQ ID NO 328
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 328

His His His His His His
1               5

<210> SEQ ID NO 329
<211> LENGTH: 17
<212> TYPE: PRT
<213> ORGANISM: Artificial Sequence
<220> FEATURE:
<223> OTHER INFORMATION: Synthetic

<400> SEQUENCE: 329

Leu Tyr Phe Asn Gly Lys Glu Gln Ile Ile Tyr Gly Lys Ile Pro Ala
1               5                   10                  15

Met

<210> SEQ ID NO 330
<211> LENGTH: 11
<212> TYPE: PRT
<213> ORGANISM: Artificial Sequence
<220> FEATURE:
<223> OTHER INFORMATION: Synthetic

<400> SEQUENCE: 330

Pro His Thr His Leu Val His Gln Ala Asn Pro
1               5                   10

<210> SEQ ID NO 331
<211> LENGTH: 87
<212> TYPE: PRT
<213> ORGANISM: Artificial Sequence
<220> FEATURE:
<223> OTHER INFORMATION: Synthetic

<400> SEQUENCE: 331

Glu Val Val Ala Ala Thr Pro Thr Ser Leu Leu Ile Ser Trp Ser Leu
1               5                   10                  15

Pro His Gln Gly Lys Ala Asn Tyr Tyr Arg Ile Thr Tyr Gly Glu Thr
                20                  25                  30

Gly Gly Asn Ser Pro Val Gln Glu Phe Thr Val Pro Gly Arg Gly Val
            35                  40                  45

Thr Ala Thr Ile Ser Gly Leu Lys Pro Gly Val Asp Tyr Thr Ile Thr
        50                  55                  60

Val Tyr Ala Val Thr Val Thr Asp Thr Gly Tyr Leu Lys Tyr Lys Pro
65                  70                  75                  80

Ile Ser Ile Asn Tyr Arg Thr
                85
```